United States Patent
Chaoui et al.

(10) Patent No.: US 12,383,334 B2
(45) Date of Patent: Aug. 12, 2025

(54) ORTHOPEDIC SURGICAL PLANNING BASED ON SOFT TISSUE AND BONE DENSITY MODELING

(71) Applicant: HOWMEDICA OSTEONICS CORP., Mahwah, NJ (US)

(72) Inventors: Jean Chaoui, Locmaria Plouzané (FR); Charlotte Le Saint, Brest (FR); Maximilien Mayya, Antibes (FR); Manuel Jean-Marie Urvoy, Brest (FR)

(73) Assignee: Howmedica Osteonics Corp., Mahwah, NJ (US)

( * ) Notice: Subject to any disclaimer, the term of this patent is extended or adjusted under 35 U.S.C. 154(b) by 552 days.

(21) Appl. No.: 17/413,460

(22) PCT Filed: Dec. 11, 2019

(86) PCT No.: PCT/US2019/065799
§ 371 (c)(1),
(2) Date: Jun. 11, 2021

(87) PCT Pub. No.: WO2020/123709
PCT Pub. Date: Jun. 18, 2020

(65) Prior Publication Data
US 2022/0039868 A1 Feb. 10, 2022

Related U.S. Application Data

(60) Provisional application No. 62/826,146, filed on Mar. 29, 2019, provisional application No. 62/826,119, (Continued)

(51) Int. Cl.
*A61B 34/10* (2016.01)
*A61B 5/00* (2006.01)
(Continued)

(52) U.S. Cl.
CPC ............ *A61B 34/10* (2016.02); *A61B 5/1121* (2013.01); *A61B 5/4519* (2013.01);
(Continued)

(58) Field of Classification Search
CPC ......... A61B 34/20; A61B 34/10; A61B 34/25; A61B 5/1121; A61B 5/4528;
(Continued)

(56) References Cited

U.S. PATENT DOCUMENTS 5,590,165 A 12/1996 Gohno et al.
5,594,767 A 1/1997 Hsieh
(Continued)

FOREIGN PATENT DOCUMENTS

CA 3001898 A1 4/2017
CA 3099718 A1 11/2019
(Continued)

OTHER PUBLICATIONS

"Aurora—The Aurora Electromagnetic Tracking System," NDI, Nov. 2013, 8 pp.
(Continued)

*Primary Examiner* — Maurice L. McDowell, Jr.
(74) *Attorney, Agent, or Firm* — Shumaker & Sieffert, P.A.

(57) ABSTRACT

A surgical planning system for use in surgical procedures to repair an anatomy of interest includes a preplanning system to generate a virtual surgical plan and a mixed reality system that includes a visualization device wearable by a user to view the virtual surgical plan projected in a real environment. The virtual surgical plan includes a 3D virtual model of the anatomy of interest. When wearing the visualization device, the user can align the 3D virtual model with the real anatomy of interest, thereby achieving a registration between details of the virtual surgical plan and the real
(Continued)

anatomy of interest. The registration enables a surgeon to implement the virtual surgical plan on the real anatomy of interest without the use of tracking markers.

31 Claims, 50 Drawing Sheets

Related U.S. Application Data filed on Mar. 29, 2019, provisional application No. 62/826,133, filed on Mar. 29, 2019, provisional application No. 62/826,156, filed on Mar. 29, 2019, provisional application No. 62/826,168, filed on Mar. 29, 2019, provisional application No. 62/778,774, filed on Dec. 12, 2018.

(51) Int. Cl.
| | |
|---|---|
| *A61B 5/11* | (2006.01) |
| *A61B 6/03* | (2006.01) |
| *A61B 34/00* | (2016.01) |
| *A61B 34/20* | (2016.01) |
| *A61B 90/00* | (2016.01) |
| *A61F 2/46* | (2006.01) |
| *G06F 3/01* | (2006.01) |
| *G06N 3/045* | (2023.01) |
| *G06T 7/00* | (2017.01) |
| *G06T 7/30* | (2017.01) |
| *G16H 20/40* | (2018.01) |
| *G16H 30/20* | (2018.01) |
| *A61B 6/50* | (2024.01) |
| *A61F 2/40* | (2006.01) |

(52) U.S. Cl.
CPC .......... *A61B 5/4528* (2013.01); *A61B 5/4872* (2013.01); *A61B 6/032* (2013.01); *A61B 34/20* (2016.02); *A61B 34/25* (2016.02); *A61B 90/36* (2016.02); *A61F 2/46* (2013.01); *G06F 3/011* (2013.01); *G06N 3/045* (2023.01); *G06T 7/0012* (2013.01); *G06T 7/30* (2017.01); *G16H 20/40* (2018.01); *G16H 30/20* (2018.01); *A61B 6/505* (2013.01); *A61B 2034/102* (2016.02); *A61B 2034/105* (2016.02); *A61B 2034/108* (2016.02); *A61B 2034/2068* (2016.02); *A61B 2034/252* (2016.02); *A61B 2090/365* (2016.02); *A61F 2002/4018* (2013.01); *A61F 2002/4633* (2013.01); *G06T 2200/24* (2013.01); *G06T 2207/10081* (2013.01); *G06T 2207/20084* (2013.01); *G06T 2207/30008* (2013.01)

(58) Field of Classification Search
CPC ....... A61B 5/4872; A61B 6/032; A61B 90/36; A61B 6/505; A61B 2034/2068; A61B 2034/252; A61B 2090/365; A61B 5/7264; A61B 5/743; A61B 5/0013; A61B 5/055; A61B 5/7246; A61B 5/7275; A61B 5/4509; A61B 17/56; A61B 2017/00207; A61B 2017/00216; A61B 2090/372; A61B 2090/502; A61B 2505/05; A61B 2576/00; A61B 5/4576; G16H 20/40; G16H 30/20; G16H 30/40; G16H 50/30; G06N 3/045; G06N 3/044; G06N 3/048; G06N 3/084; G06N 3/00; A61F 2/46; A61F 2002/4018; A61F 2002/4633; G06F 3/011; G06T 7/0012; G06T 7/30; G06T 2200/24; G06T 2207/10081; G06T 2207/20084; G06T 2207/30008

USPC .......................................................... 703/6
See application file for complete search history.

(56) References Cited

U.S. PATENT DOCUMENTS

| | | |
|---|---|---|
| 6,856,324 B2 | 2/2005 | Sauer et al. |
| 7,492,968 B2 | 2/2009 | Jerebko et al. |
| 7,542,791 B2 | 6/2009 | Mire et al. |
| 8,160,325 B2 | 4/2012 | Zug et al. |
| 8,175,683 B2 | 5/2012 | Roose |
| 8,214,016 B2 | 7/2012 | Lavallee et al. |
| 8,231,634 B2 | 7/2012 | Mahfouz et al. |
| 8,311,306 B2 | 11/2012 | Pavlovskaia et al. |
| 8,382,765 B2 | 2/2013 | Axelson et al. |
| 8,521,255 B2 | 8/2013 | DiSilvestro et al. |
| 8,532,807 B2 | 9/2013 | Metzger |
| 8,617,174 B2 | 12/2013 | Axelson, Jr. et al. |
| 8,634,618 B2 | 1/2014 | Zug et al. |
| 8,764,836 B2 | 7/2014 | De Wilde et al. |
| 8,830,233 B2 | 9/2014 | Friedland et al. |
| 8,870,889 B2 | 10/2014 | Frey |
| 8,884,618 B2 | 11/2014 | Mahfouz |
| 8,903,530 B2 | 12/2014 | Metzger |
| 8,990,052 B2 | 3/2015 | Lavallee et al. |
| 9,095,375 B2 | 8/2015 | Haimerl et al. |
| 9,097,890 B2 | 8/2015 | Miller et al. |
| 9,111,180 B2 | 8/2015 | Rappaport et al. |
| 9,198,678 B2 | 12/2015 | Frey et al. |
| 9,218,524 B2 | 12/2015 | Wang et al. |
| 9,220,570 B2 | 12/2015 | Kim et al. |
| 9,220,572 B2 | 12/2015 | Meridew et al. |
| 9,259,291 B2 | 2/2016 | Gantes |
| 9,301,812 B2 | 4/2016 | Kehres et al. |
| 9,345,548 B2 | 5/2016 | Schoenefeld et al. |
| 9,408,698 B2 | 8/2016 | Miles et al. |
| 9,495,752 B2 | 11/2016 | Wu et al. |
| 9,504,579 B2 | 11/2016 | Mahfouz et al. |
| 9,642,633 B2 | 5/2017 | Frey et al. |
| 9,646,229 B2 | 5/2017 | Sofka et al. |
| 9,649,170 B2 | 5/2017 | Park et al. |
| 9,684,768 B2 | 6/2017 | Lavallee et al. |
| 9,713,539 B2 | 7/2017 | Haimerl et al. |
| 9,717,508 B2 | 8/2017 | Iannotti et al. |
| 9,737,367 B2 | 8/2017 | Steines et al. |
| 9,741,263 B2 | 8/2017 | Iannotti et al. |
| 9,757,238 B2 | 9/2017 | Metzger |
| 9,788,907 B1 | 10/2017 | Alvi et al. |
| 9,814,533 B2 | 11/2017 | Park et al. |
| 9,839,438 B2 | 12/2017 | Eash |
| 9,861,446 B2 | 1/2018 | Lang |
| 9,913,691 B2 | 3/2018 | Brooks |
| 9,956,089 B2 | 5/2018 | Kelman et al. |
| 9,959,486 B2 | 5/2018 | Kiraly et al. |
| 9,987,024 B2 | 6/2018 | Frey et al. |
| 10,019,551 B2 | 7/2018 | Zellner et al. |
| 10,052,170 B2 | 8/2018 | Saget et al. |
| 10,062,014 B2 | 8/2018 | Zhou et al. |
| 10,070,928 B2 | 9/2018 | Frank et al. |
| 10,102,309 B2 | 10/2018 | McKinnon et al. |
| 10,130,378 B2 | 11/2018 | Bryan |
| 10,154,239 B2 | 12/2018 | Casas |
| 10,159,513 B2 | 12/2018 | Pavlovskaia et al. |
| 10,172,715 B2 | 1/2019 | De Wilde et al. |
| 10,182,870 B2 | 1/2019 | Park et al. |
| 10,194,990 B2 | 2/2019 | Amanatullah et al. |
| 10,206,727 B2 | 2/2019 | Ponce et al. |
| 10,262,084 B2 | 4/2019 | Lavallee et al. |
| 10,368,947 B2 | 8/2019 | Lang |
| 10,438,350 B2 | 10/2019 | Patil et al. |
| 10,482,603 B1 | 11/2019 | Fu et al. |
| 10,537,390 B2 | 1/2020 | Varadarajan et al. |
| 10,580,131 B2 | 3/2020 | Mazo |
| 10,582,907 B2 | 3/2020 | Chen et al. |
| 10,600,515 B2 | 3/2020 | Otto et al. |
| 10,667,867 B2 | 6/2020 | Gangwar et al. |
| 10,675,063 B2 | 6/2020 | Pavlovskaia et al. |
| 10,722,310 B2 | 7/2020 | Luby |

(56) References Cited

U.S. PATENT DOCUMENTS

| | | |
|---|---|---|
| 10,762,623 B2 | 9/2020 | Geebelen et al. |
| 10,769,791 B2 | 9/2020 | Song et al. |
| 10,825,168 B2 | 11/2020 | Tegzes et al. |
| 10,864,057 B2 | 12/2020 | Chappuis et al. |
| 10,922,448 B2 | 2/2021 | McKinnon et al. |
| 10,973,486 B2 | 4/2021 | Sjostrand et al. |
| 10,973,535 B2 | 4/2021 | Iannotti et al. |
| 10,973,580 B2 | 4/2021 | Berend et al. |
| 11,033,335 B2 | 6/2021 | Zhang |
| 11,051,830 B2 | 7/2021 | Jaramaz et al. |
| 11,055,851 B2 | 7/2021 | Novikov et al. |
| 11,071,592 B2 | 7/2021 | McGuan et al. |
| 11,083,525 B2 | 8/2021 | Varadarajan et al. |
| 11,090,019 B2 | 8/2021 | Siemionow et al. |
| 11,138,790 B2 | 10/2021 | Haslam et al. |
| 11,158,061 B2 | 10/2021 | De Winde |
| 11,166,764 B2 | 11/2021 | Roh et al. |
| 11,253,323 B2 | 2/2022 | Hughes et al. |
| 11,278,413 B1 | 3/2022 | Lang |
| 11,288,808 B2 | 3/2022 | Abramoff et al. |
| 11,288,837 B2 | 3/2022 | Komissarov et al. |
| 11,288,865 B2 | 3/2022 | Haslam et al. |
| 11,298,188 B2 | 4/2022 | Kehres et al. |
| 11,298,189 B2 | 4/2022 | Kelman et al. |
| 11,337,762 B2 | 5/2022 | McKinnon et al. |
| 11,344,370 B2 | 5/2022 | Park et al. |
| 11,348,257 B2 | 5/2022 | Lang |
| 11,386,988 B2 | 7/2022 | Johnsson et al. |
| 11,410,769 B1 | 8/2022 | Yildirim |
| 11,419,680 B2 | 8/2022 | Knotaxis et al. |
| 11,423,540 B2 | 8/2022 | Heindl et al. |
| 11,426,281 B2 | 8/2022 | Mahfouz |
| 11,432,931 B2 | 9/2022 | Lang |
| 11,436,801 B2 | 9/2022 | Haslam et al. |
| 11,443,428 B2 | 9/2022 | Petersen et al. |
| 11,443,846 B2 | 9/2022 | Schoenefeld et al. |
| 11,449,993 B2 | 9/2022 | Book et al. |
| 11,488,721 B2 | 11/2022 | Otto et al. |
| 11,490,965 B2 | 11/2022 | Bischoff et al. |
| 11,490,966 B2 | 11/2022 | Roche et al. |
| 11,497,557 B2 | 11/2022 | Haslam et al. |
| 11,551,420 B2 | 1/2023 | Haslam et al. |
| 11,596,479 B2 | 3/2023 | McGuan et al. |
| 11,621,086 B2 | 4/2023 | Spanberg et al. |
| 11,622,818 B2 | 4/2023 | Siemionow et al. |
| 11,626,212 B2 | 4/2023 | Crawford et al. |
| 11,653,976 B2 | 5/2023 | Bonny et al. |
| 11,657,508 B2 | 5/2023 | Richter et al. |
| 11,660,197 B1 | 5/2023 | Lang |
| 11,682,117 B2 | 6/2023 | Fuchs et al. |
| 11,715,210 B2 | 8/2023 | Haslam et al. |
| 11,717,412 B2 | 8/2023 | Casey et al. |
| 11,751,946 B2 | 9/2023 | Gangwar et al. |
| 11,763,454 B2 | 9/2023 | Wang et al. |
| 11,766,268 B2 | 9/2023 | Iannotti et al. |
| 11,842,275 B2 | 12/2023 | Vandersmissen |
| 11,847,755 B2 | 12/2023 | Park et al. |
| 2002/0082498 A1 | 6/2002 | Wendt et al. |
| 2006/0142657 A1 | 6/2006 | Quaid et al. |
| 2007/0211939 A1 | 9/2007 | Kaus et al. |
| 2009/0069823 A1 | 3/2009 | Foerster |
| 2009/0089034 A1 | 4/2009 | Penney et al. |
| 2010/0234770 A1 | 9/2010 | Colombet et al. |
| 2011/0093108 A1 | 4/2011 | Ashby et al. |
| 2011/0257653 A1 | 10/2011 | Hughes et al. |
| 2012/0155734 A1 | 6/2012 | Barratt et al. |
| 2012/0209394 A1 | 8/2012 | Bojarski |
| 2013/0191099 A1 | 7/2013 | Krekel |
| 2013/0243290 A1 | 9/2013 | Poonawalla et al. |
| 2014/0086465 A1 | 3/2014 | Wu et al. |
| 2014/0121715 A1 | 5/2014 | May et al. |
| 2014/0303938 A1 | 10/2014 | Schoenefeld et al. |
| 2014/0303990 A1 | 10/2014 | Schoenefeld et al. |
| 2014/0369581 A1 | 12/2014 | Fu et al. |
| 2015/0366628 A1 | 12/2015 | Ingmanson |
| 2016/0063205 A1 | 3/2016 | Moturu et al. |
| 2016/0157751 A1 | 6/2016 | Mahfouz |
| 2016/0256222 A1 | 9/2016 | Walch |
| 2016/0270854 A1* | 9/2016 | Chaoui ............... A61F 2/4081 |
| 2016/0324580 A1 | 11/2016 | Esterberg |
| 2017/0000562 A1 | 1/2017 | Frank et al. |
| 2017/0011164 A1 | 1/2017 | Adoni et al. |
| 2017/0020609 A1 | 1/2017 | Wentorf et al. |
| 2017/0027702 A1 | 2/2017 | Goldstein et al. |
| 2017/0035513 A1 | 2/2017 | Mahfouz et al. |
| 2017/0189119 A1* | 7/2017 | Yildirim ............... G16H 30/40 |
| 2017/0258526 A1* | 9/2017 | Lang ................ A61B 17/1775 |
| 2017/0299864 A1 | 10/2017 | Vallius et al. |
| 2018/0000547 A1 | 1/2018 | Kang et al. |
| 2018/0008418 A1 | 1/2018 | Bonutti |
| 2018/0049622 A1* | 2/2018 | Ryan ..................... A61B 90/37 |
| 2018/0052277 A1 | 2/2018 | Schowengerdt et al. |
| 2018/0085080 A1 | 3/2018 | Requardt et al. |
| 2018/0092699 A1 | 4/2018 | Finley |
| 2018/0125584 A1 | 5/2018 | Lang |
| 2018/0146947 A1 | 5/2018 | Sarnow et al. |
| 2018/0233222 A1 | 8/2018 | Daley et al. |
| 2018/0235762 A1 | 8/2018 | Radermacher et al. |
| 2018/0240235 A1 | 8/2018 | Mazo |
| 2018/0250138 A1 | 9/2018 | Alidousti et al. |
| 2018/0253838 A1* | 9/2018 | Sperling ............... A61B 8/5261 |
| 2018/0256259 A1 | 9/2018 | Crawford |
| 2018/0315188 A1 | 11/2018 | Tegzes et al. |
| 2018/0325526 A1 | 11/2018 | Haddad |
| 2018/0344308 A1 | 12/2018 | Nawana et al. |
| 2019/0021800 A1 | 1/2019 | Crawford et al. |
| 2019/0029757 A1 | 1/2019 | Roh et al. |
| 2019/0090952 A1 | 3/2019 | Bonny et al. |
| 2019/0105009 A1 | 4/2019 | Siemionow et al. |
| 2019/0142519 A1 | 5/2019 | Siemionow et al. |
| 2019/0239973 A9 | 8/2019 | Esterberg et al. |
| 2019/0254750 A1 | 8/2019 | Metz |
| 2019/0365473 A1 | 12/2019 | Kehres et al. |
| 2019/0380792 A1* | 12/2019 | Poltaretskyi .......... G06T 7/0012 |
| 2019/0388153 A1 | 12/2019 | Running et al. |
| 2020/0030034 A1 | 1/2020 | Kontaxis et al. |
| 2020/0030036 A1 | 1/2020 | Forstein |
| 2020/0074748 A1 | 3/2020 | de Almeida Barreto et al. |
| 2020/0085511 A1 | 3/2020 | Oezbek et al. |
| 2020/0113632 A1 | 4/2020 | Varadarajan et al. |
| 2020/0138518 A1 | 5/2020 | Lang |
| 2020/0229869 A1 | 7/2020 | Dorman |
| 2020/0245960 A1 | 8/2020 | Richter et al. |
| 2020/0281728 A1 | 9/2020 | Kulper et al. |
| 2020/0311937 A1 | 10/2020 | Wang et al. |
| 2020/0410687 A1 | 12/2020 | Siemionow et al. |
| 2021/0019889 A1 | 1/2021 | Novikov et al. |
| 2021/0030477 A1 | 2/2021 | Zuhars et al. |
| 2021/0059822 A1 | 3/2021 | Casey et al. |
| 2021/0128179 A1 | 5/2021 | Dupuis et al. |
| 2021/0161613 A1 | 6/2021 | Poltaretskyi et al. |
| 2021/0196290 A1 | 7/2021 | Iannotti et al. |
| 2021/0307833 A1 | 10/2021 | Farley et al. |
| 2021/0315642 A1 | 10/2021 | McGuan et al. |
| 2021/0322130 A1 | 10/2021 | Penney et al. |
| 2021/0330389 A1 | 10/2021 | Varadarajan et al. |
| 2022/0051045 A1 | 2/2022 | Vandersmissen |
| 2022/0054197 A1 | 2/2022 | Plessers et al. |
| 2022/0058809 A1 | 2/2022 | Fuchs et al. |
| 2022/0110685 A1 | 4/2022 | McGuan et al. |
| 2022/0125515 A1 | 4/2022 | McGuan et al. |
| 2022/0130059 A1 | 4/2022 | Avisar et al. |
| 2022/0148454 A1 | 5/2022 | Jaramaz et al. |
| 2022/0183757 A1 | 6/2022 | Caldera et al. |
| 2022/0202497 A1 | 6/2022 | Janna et al. |
| 2022/0249168 A1 | 8/2022 | Besier et al. |
| 2022/0257321 A1 | 8/2022 | Kehres et al. |
| 2022/0270762 A1 | 8/2022 | Crawford et al. |
| 2022/0273450 A1 | 9/2022 | Steines et al. |
| 2022/0346968 A1 | 11/2022 | Pettersson et al. |
| 2022/0351828 A1 | 11/2022 | Chaoui |
| 2022/0370142 A1 | 11/2022 | Schoenefeld et al. |
| 2022/0387110 A1 | 12/2022 | Chaoui |
| 2023/0045575 A1 | 2/2023 | Lang et al. |

(56) References Cited

U.S. PATENT DOCUMENTS

| | | |
|---|---|---|
| 2023/0085093 A1 | 3/2023 | Chaoui et al. |
| 2023/0139531 A1 | 5/2023 | Roche et al. |
| 2023/0181257 A1 | 6/2023 | McGuan et al. |
| 2023/0237740 A1 | 7/2023 | Haslam et al. |
| 2023/0245784 A1 | 8/2023 | Crawford et al. |
| 2023/0248435 A1 | 8/2023 | Bonny et al. |
| 2023/0317298 A1 | 10/2023 | Spanberg et al. |
| 2023/0346397 A1 | 11/2023 | Iannotti et al. |
| 2023/0372018 A1 | 11/2023 | Gangwar et al. |
| 2023/0410317 A1 | 12/2023 | Haslam et al. |

FOREIGN PATENT DOCUMENTS

| | | |
|---|---|---|
| CN | 104050350 A | 9/2014 |
| CN | 106021977 A | 10/2016 |
| CN | 107545598 A | 1/2018 |
| CN | 108334730 A | 7/2018 |
| CN | 108369473 A | 8/2018 |
| CN | 109330677 A | 2/2019 |
| CN | 110796636 A | 2/2020 |
| EP | 2471483 A1 | 7/2012 |
| EP | 1858430 B1 | 10/2013 |
| EP | 2770919 B1 | 8/2017 |
| EP | 2303192 B1 | 11/2018 |
| EP | 3481318 B1 | 9/2022 |
| JP | 2014180490 A | 9/2014 |
| JP | 2017176803 A | 10/2017 |
| JP | 2017221273 A | 12/2017 |
| JP | 2018000949 A | 1/2018 |
| JP | 2018532454 A | 11/2018 |
| WO | 9519817 A1 | 7/1995 |
| WO | 0048509 A1 | 8/2000 |
| WO | 2008015565 A2 | 2/2008 |
| WO | 2012014082 A2 | 2/2012 |
| WO | 2016102025 A1 | 6/2016 |
| WO | 2017041080 A1 | 3/2017 |
| WO | 2017066518 A1 | 4/2017 |
| WO | 2018005907 A1 | 1/2018 |
| WO | 2018067966 A1 | 4/2018 |
| WO | 2018200767 A1 | 11/2018 |
| WO | 2019014278 A1 | 1/2019 |
| WO | 2019014281 A1 | 1/2019 |
| WO | 2019033037 A2 | 2/2019 |
| WO | 2019213777 A1 | 11/2019 |
| WO | 2019245849 A1 | 12/2019 |
| WO | 2021007418 A2 | 1/2021 |
| WO | 2021225840 A1 | 11/2021 |
| WO | 2022037696 A1 | 2/2022 |
| WO | 2022169678 A1 | 8/2022 |
| WO | 2023200562 A1 | 10/2023 |

OTHER PUBLICATIONS

"Blueprint 3d Planning Software + PSI," Wright Medical Group, retrieved from https://www.wright.com/blueprint-3d-planning-psi-system on Oct. 15, 2020, 9 pp.

"HoloLens 2," Microsoft Hololens, retrieved from https://www.microsoft.com/en-us/hololens, on Oct. 15, 2020, 5 pp.

Birkfellner et al., "Chapter 2—Tracking Devices," from Image-Guided Interventions, Springer Science, 2008, 23 pp. (Applicant points out, in accordance with MPEP 609.04(a), that the year of publication, 2008, is sufficiently earlier than the effective U.S. filing date, so that the particular month of publication is not in issue.).

Boissonnat, J.D., "Shape Reconstruction from Planar Cross Sections," Computer Vision, Graphics, and Image Processing, vol. 44, No. 1, Oct. 1988, 29 pp.

Brochure entitled "Torier SIMPLICITI™ Shoulder System," by Wright Medical Group, downloaded from https://www.wright.com/products-upper/simpliciti-shoulder-arthroplasty-system on May 1, 2020, 1 pp.

Brochure entitled "Tornier SIMPLICITI™ Shoulder System," by Wright Medical Group, downloaded from https://www.wright.com/products-upper/simpliciti-shoulder-arthroplasty-system on Nov. 2, 2021, 6 pp.

Brochure entitled "Torier, SIMPLICITI™ Shoulder System—Surgical Technique (CAW-7656_EN_LR_LE)," by Wright Medical Group, downloaded from https://www.wrightemedia.com/ProductFiles/Files/PDFs/CAW-7656_EN_LR_LE.pdf on Nov. 2, 2021, dated Jan. 14, 2016, 24 pp.

Brochure entitled "Zimmer® PSI Shoulder for Trabecular Metal™ Reverse Glenoid," from Zimmer, #97-4309-040-00, Dec. 16, 2013, 6 pp.

Daftry et al., "Flexible and User-Centric Camera Calibration using Planar Fiducial Markers," British Machine Vision Conference, Sep. 9-13, 2013, 13 pp.

Franz et al., "Electromagnetic Tracking in Medicine—A Review of Technology, Validation, and Applications," IEEE Transactions on Medical Imaging, vol. 33, No. 8, Aug. 2014, pp. 1702-1725.

Giannotti et al., "Indices of risk assessment of fracture of the proximal humerus," Clinical cases in mineral and bone metabolism: the official journal of the Italian Society of Osteoporosis, Mineral Metabolism, and Skeletal Diseases, vol. 9, No. 1, Jan. 2012, 3 pp.

Gibby et al., "Head-mounted display augmented reality to guide pedicle screw placement utilizing computed tomography," International Journal of Computer Assisted Radiology and Surgery, vol. 14, No. 3, Jun. 2018, 11 pp.

International Preliminary Report on Patentability of International Application No. PCT/US2019/065799, mailed Jun. 24, 2021, 8 pp.

International Search Report and Written Opinion of International Application No. PCT/US2019/065799, mailed Mar. 25, 2020, 14 pp.

Itk::BSplineScatteredDataPointSetToImageFilter<TInputPointSet, TOutputImage> Class Template Reference, from ITK r.11.0 Insight Segmentation and Registration Toolkit. downloaded from https://itk.org/Doxygen411/html/classitk_1_1BSplineScatteredDataPointSet-ToImageFilter.html on Nov. 10, 2021, 24 pp.

Lee et al., "Multi-modal imaging, model-based tracking, and mixed reality visualisation for orthopaedic surgery," Healthcare Technology Letters, vol. 4, No. 5, Sep. 2017, 6 pp.

Lee et al., "Scattered Data Interpolation with Multilevel B-Splines," IEEE Transactions on Visualization and Computer Science, vol. 3, No. 3, Jul.-Sep. 1997, 17 pp.

Marker et al., "Contour-Based Surface Reconstruction using Implicit Curve Fitting, and Distance Field Filtering and Interpolation," Volume Graphics, Jan. 2006, 9 pp.

Mather et al., "Proximal humerus cortical bone thickness correlates with bone mineral density and can clinically rule out osteoporosis," Journal of Shoulder and Elbow Surgery, vol. 22, No. 6, Jun. 2013, 7 pp.

Nguyen et al., "A new segmentation method for MRI images of the shoulder joint," Fourth Canadian Conference on Computer and Robot Vision (CRV'07), May 2007, 8 pp.

Prophecy Infinity Pre-Operative navigation Guides—Surgical Technique, by Wright Medical Technology, Inc., Oct. 2014, 80 pp.

Tan et al., "6D Object Pose Estimation with Depth Images: A Seamless Approach for Robotic Interaction and Augmented Reality," Sep. 5, 2017, 4 pp.

Tingart et al., "The cortical thickness of the proximal humeral diaphysis predicts bone mineral density of the proximal humerus," The Journal of Bone & Joint Surgery, vol. 85-B, No. 4, May 2003, accepted after revision Sep. 24, 2002, 7 pp.

Tustison et al., "N-D Ck B-Spline Scattered Data Approximation," The Insight Journal, Aug.-Dec. 2005, 13 pp.

U.S. Appl. No. 17/413,414, filed Dec. 11, 2019, naming inventors Chaoui et al.

U.S. Appl. No. 17/413,432, filed Dec. 11, 2019, naming inventors Chaoui et al.

U.S. Appl. No. 17/413,444, filed Dec. 11, 2019, naming inventors Chaoui et al.

U.S. Appl. No. 17/413,453, filed Dec. 11, 2019, naming inventors Chaoui et al.

U.S. Appl. No. 17/435,978, filed Mar. 18, 2020, naming inventors Poltaretskyi et al.

(56) References Cited

OTHER PUBLICATIONS

Verborgt et al., "Accuracy of patient-specific guided implantation of the glenoid component in reversed shoulder arthroplasty," Orthopaedics & Traumatology: Surgery & Research, vol. 104, No. 6, Jan. 2018, 6 pp.
Wright Medical, "BluePrint Video-Wright Medical Announces the Acquisition of IMASCAP SAS", accessed from www.imascap.com/wp-content/uploads/2017/12/blueprintvid.mp4, Dec. 14, 2017, 9 pp.
Wright, "Aequalis Ascend Flex, Convertible Shoulder System," CAW-5396, Tornier, Mar. 2017, 88 pp.
Wright, "Aequalis Perform, Anatomic Glenoid System," CAW-5233, Torier, Jul. 2017, 36 pp.
Wright, "Aequalis Reversed II Shoulder System," Tornier, CAW-2145, May 12, 2016, 52 pp.
Wright, "BluePrint, 3d Planning + PSI," User Manual V2.1, Torier, CAW-8754, Nov. 2017, 18 pp.
Abdelhameed et al., "Neural network-based shoulder instability diagnosis modeling for robot-assisted rehabilitation systems", Systems Science & Control Engineering, vol. 3, No. 1, 2015, pp. 514-523.
Beeler et al., A comparative analysis of fatty infiltration and muscle atrophy in patients with chronic rotator cuff tears and suprascapular neuropathy, Journal of Shoulder and Elbow Surgery, vol. 22, Iss. 11, Nov. 2013, pp. 1537-1546, DOI: https:// doi.org/1 0.1 016/j.jse.2013.01.028, 10 pp.
Bell, Daniel J, Voxel size, Radiopaedia [online], dated Sep. 4, 2018, downloaded Sep. 11, 2023 from https:// radiopaedia.org/articles/voxel-size-1 ?lang=us, 6 pp.
Bell, Daniel J, Voxel, Radiopaedia [online], dated Nov. 19, 2020, downloaded Sep. 11, 2023 from https://radiopaedia.org/ articles/voxel?lang=us, 6 pp.
Computed Tomography (CT) Scanning, TeachMeAnatomy [online], dated as "Last updated: Apr. 25, 2018", downloaded Sep. 11, 2023 from https://teachmeanatomy.info/the-basics/imaging/computed-tomography-ct-scans/, 3 pp.
F. Commandeur et al., "Deep Learning for Quantification of Epicardial and Thoracic Adipose Tissue From Non-Contrast CT," in IEEE Transactions on Medical Imaging, vol. 37, No. 8, pp. 1835-1846, Aug. 2018, doi: 10.11 09/TMI.2018.2804799, downloaded Sep. 13, 2023, 12 pp.
Goutalliear, et al., Fatty Muscle Degeneration in Cuff Ruptures, Clinical Orthopaedics and Related Research, No. 304, pp. 78-83, 1994 J B Lippincott Company, downloaded Sep. 13, 2023 from https://journals.lww.com/clinorthop/Abstract/1994/07000/ Fatty_Muscle_Degeneration_in_Cuff_Ruptures_Pre_.14.aspx, 6 pp.
Imaging and radiology, from National Institute of Health, National Library of Medicine, MedlinePius, undated, downloaded Sep. 11, 2023 from https://medlineplus.gov/ency/article/007451.htm#, 3 pp.
Kuzel et al., Fatty infiltration and rotator cuff atrophy, Journal of the American Academy of Orthopaedic Surgeons, vol. 21, Iss. 1 0, Publisher: American Academy of Orthopaedic Surgeons, DOI: http://dx.doi.org/1 0.5435/JAAOS-21-10-613, dated Oct. 2013, downloaded Sep. 13, 2023, 16 pp.
Office Action from U.S. Appl. No. 17/413,432 dated Sep. 21, 2023, 19 pp.
Office Action from U.S. Appl. No. 17/413,453 dated Sep. 19, 2023, 28 pp.
Final Office Action from U.S. Appl. No. 17/413,432 dated Apr. 1, 2024, 24 pp.
Office Action from U.S. Appl. No. 17/413,444 dated Sep. 9, 2024, 30 pp.
Office Action from U.S. Appl. No. 17/413,453 dated Jul. 24, 2024, 6 pp.
Response to Office Action mailed Jul. 24, 2024, from U.S. Appl. No. 17/413,453, filed Sep. 24, 2024, 4 pp.
Horng, "Performance evaluation of multiple classification of the ultrasonic supraspinatus images by using ML, RBFNN and SVM classifiers", Expert Systems with Applications, vol. 37, No. 6, Jun. 2010, pp. 4146-4155.
Krekel, P. R. (Feb. 10, 2011). Visualisation of articular motion in orthopaedics. Retrieved from https://hdl. handle. net/1887/ 16455 on Feb. 27, 2024 (Year: 2011), 17 pp.
Office Action from U.S. Appl. No. 17/413,453 dated Mar. 4, 2024, 39 pp.
Response to Office Action dated Sep. 19, 2023 from U.S. Appl. No. 17/413,453, filed Jan. 19, 2024, 20 pp.
Response to Office Action dated Sep. 21, 2023 from U.S. Appl. No. 17/413,432, filed Dec. 21, 2023, 15 pp.
Response to Office Action dated Mar. 4, 2024 from U.S. Appl. No. 17/413,453, filed Jun. 4, 2024, 21 pp.
Final Office Action from U.S. Appl. No. 17/413,453 dated Dec. 13, 2024, 44 pp.
Response to Office Action dated Sep. 9, 2024 from U.S. Appl. No. 17/413,444, filed Dec. 9, 2024, 18 pp.
Baldwin, Mark, A, et al. "Development of subject-specific and statistical shape models of the knee using an efficient segmentation and mesh-morphing approach." Computer methods and programs in biomedicine 97.3, Mar. 2010, pp. 232-240. (Year: 2010).
Castro Mateos, Isaac. Statistical anatomical modelling for efficient and personalised spine biomechanical models. Diss. University of Sheffield, Mar. 2016. 210 Pages. (Year: 2016).
Final Office Action from U.S. Appl. No. 17/413,444 dated Jan. 28, 2025, 32 pp.
Girod et al., "Advances in interactive craniofacial surgery planning by 3D simulation and visualization", International Journal of Oral and Maxillofacial Surgery, vol. 24, Feb. 1995, pp. 120-125.
Marmulla et al., "Image-to-patient registration by natural anatomical surfaces of the head", Central European Journal of Medicine, vol. 2, No. 1, Mar. 2007, pp. 89-102.
Moineau et al., "Three-dimensional measurement method of arthritic glenoid cavity morphology: Feasibility and reproducibility", Orthopaedics & Traumatology: Surgery & Research, vol. 98, No. 6, Elsevier, Jun. 22, 2012, S139-S145 pp.
Stephenson et al., "Computerized tomography of soft tissue abnormalities", Computerized Tomography, vol. 4, No. 3, 1980, pp. 181-188, (Applicant points out, in accordance with MPEP 69.04(a), that the year of publication, 1980, is sufficiently earlier than the effective U.S. filing date, so that the particular month of publication is not in issue.).
Subramanian et al., "High-Resolution Computed Tomography Imaging in Coonductive Hearing Loss: What to Look for?", Current Problems in Diagnostic Radiology, vol. 47, No. 2, Mar. 2018, pp. 119-124.
Blanco et al., "Sectional Anatomic and Computed Tomography Features of the Nasal and Oral Cavities of the One-humped Camel (Camelus Dromedarius)", Anatomia, histologia, embryologia, vol. 44, No. 1, Blackwell, Feb. 14, 2014, 9 pp.
Response to Final Office Action dated Dec. 13, 2024 from U.S. Appl. No. 17/413,453, filed Mar. 13, 2025, 22 pp.
Advisory Action from U.S. Appl. No. 17/413,444 dated Apr. 16, 2025, 3 pp.
Office Action from U.S. Appl. No. 17/413,453 dated Apr. 8, 2025, 27 pp.
Response to Final Office Action dated Jan. 28, 2025 from U.S. Appl. No. 17/413,444, filed Apr. 22, 2025, 21 pp.
Notice of Allowance from U.S. Appl. No. 17/413,444 dated May 14, 2025, 11 pp.

\* cited by examiner

ORTHOPEDIC SURGICAL PLANNING BASED ON SOFT TISSUE AND BONE DENSITY MODELING

BACKGROUND

Surgical joint repair procedures involve repair and/or replacement of a damaged or diseased joint. Many times, a surgical joint repair procedure, such as joint arthroplasty as an example, involves replacing the damaged joint with a prosthetic that is implanted into the patient's bone. Proper selection of a prosthetic that is appropriately sized and shaped and proper positioning of that prosthetic to ensure an optimal surgical outcome can be challenging. To assist with positioning, the surgical procedure often involves the use of surgical instruments to control the shaping of the surface of the damaged bone and cutting or drilling of bone to accept the prosthetic.

Today, visualization tools are available to surgeons that use three-dimensional modeling of bone shapes to facilitate preoperative planning for joint repairs and replacements. These tools can assist surgeons with the design and/or selection of surgical guides and implants that closely match the patient's anatomy and can improve surgical outcomes by customizing a surgical plan for each patient.

SUMMARY

This disclosure describes a variety of systems, devices, and techniques for providing patient analysis, preoperative planning, and/or training and education for surgical joint repair procedures. For example, systems described herein may determine soft tissue (e.g., muscles, connective tissue, fatty tissue, etc.) dimensions and/or characteristics from patient imaging data. Characteristics of soft tissue may include a fatty infiltration, an atrophy ratio, a range of motion, or other similar characteristics. The systems may use these soft tissue dimensions and/or characteristics to determine range of motion values for one or more joints of the patient. Based on these range of motion values, the systems may suggest one or more types of surgical intervention that may be appropriate for treating one or more conditions with the one or more joints. In one example, the system may use the soft tissue dimensions to determine whether an anatomical shoulder replacement surgery or a reverse shoulder replacement surgery is appropriate for a particular patient.

The systems described herein may also, or alternatively, determine a bone density metric for at least a portion of a humeral head of a patient based on the patient-specific image data for that patient. For example, a bone density metric may be a single indication of overall density of the humeral head or a portion of the humeral head. As another example, the bone density metric may include bone density values for respective portions of a humeral head of the patient. The bone density metric may not actually indicate the density of bone, but may be a metric representative of bone density (e.g., voxel intensity from image data, standard deviations of voxel intensity from image data, compressibility, etc.) The system may control a user interface to present a graphical representation of the bone density metric and/or generate a recommendation on the implant type for the humeral head based on the bone density metric. For example, a bone density metric indicative of sufficient trabecular bone density in the humeral head may result in the system recommending a stemless humeral implant as opposed to a stemmed humeral implant.

In one example, a system for modeling a soft-tissue structure of a patient includes a memory configured to store patient-specific image data for the patient and processing circuitry configured to receive the patient-specific image data, determine, based on intensities of the patient-specific image data, a patient-specific shape representative of the soft-tissue structure of the patient, and output the patient-specific shape.

In another example, a method for modeling a soft-tissue structure of a patient that includes storing, by a memory, patient-specific image data for the patient, receiving, by processing circuitry, the patient-specific image data, determining, by the processing circuitry and based on intensities of the patient-specific image data, a patient-specific shape representative of the soft-tissue structure of the patient, and outputting, by the processing circuitry, the patient-specific shape.

In another example, a computer readable storage medium comprising instructions that, when executed by processing circuitry, causes the processing circuitry to store, in a memory, patient-specific image data for a patient, receive the patient-specific image data, determine, based on intensities of the patient-specific image data, a patient-specific shape representative of a soft-tissue structure of the patient, and output the patient-specific shape.

In another example, a system for modeling a soft-tissue structure of a patient includes means for storing patient-specific image data for the patient, means for receiving the patient-specific image data, means for determining, based on intensities of the patient-specific image data, a patient-specific shape representative of the soft-tissue structure of the patient, and means for outputting the patient-specific shape.

The details of various examples of the disclosure are set forth in the accompanying drawings and the description below. Various features, objects, and advantages will be apparent from the description, drawings, and claims.

DETAILED DESCRIPTION

Figure 1:
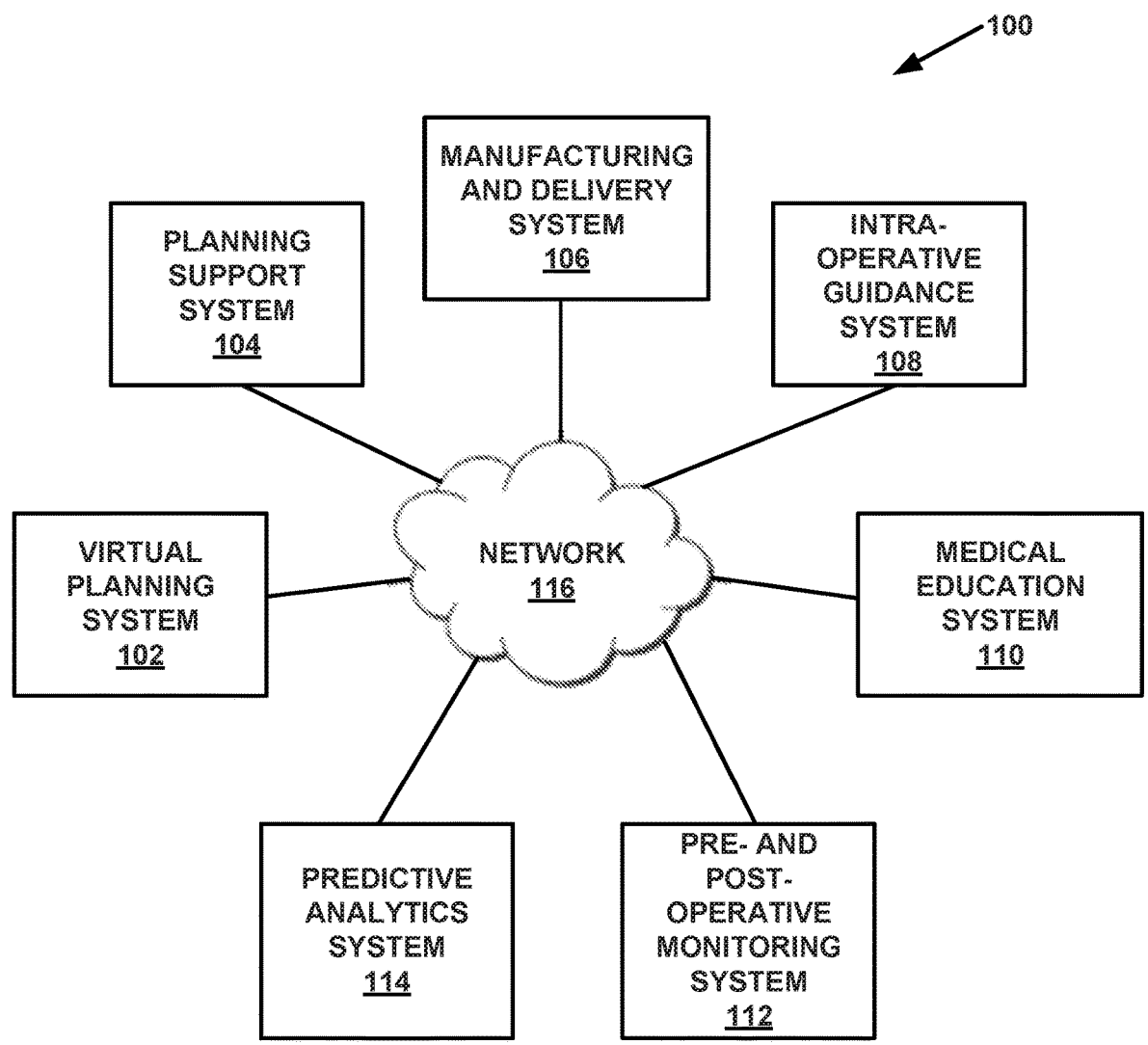
FIG. 1 is a block diagram of an orthopedic surgical system according to an example of this disclosure.

This disclosure describes a variety of systems, devices, and techniques for providing patient analysis, preoperative planning, and/or training and education for surgical joint repair procedures. Orthopedic surgery can involve implanting one or more prosthetic devices to repair or replace a patient's damaged or diseased joint. Virtual surgical planning tools use image data of the diseased or damaged joint to generate an accurate three-dimensional bone model that can be viewed and manipulated preoperatively by the surgeon. These tools can enhance surgical outcomes by allowing the surgeon to simulate the surgery, select or design an implant that more closely matches the contours of the patient's actual bone, and select or design surgical instruments and guide tools that are adapted specifically for repairing the bone of a particular patient.

These planning tools can be used to generate a preoperative surgical plan, complete with an implant and surgical instruments that are selected or manufactured for the individual patient. These systems may rely on bone models for the patient for determining types of procedures and/or specific implants for the individual patient. However, soft tissue structure information (e.g., muscles and/or connective tissue) derived from imaging data for the patient are not available. Without this imaging data for the soft tissues of the patient, the planning tools and the clinician may determine certain aspects of the surgery or implant without the benefit of how the patient's soft tissues may affect the function of the current joint and the joint post-surgery.

As described herein, systems may determine soft tissue (e.g., muscles, tendons, ligaments, cartilage, and/or connective tissue) dimensions and other characteristics from patient imaging data. A system may then be configured to use these soft tissue dimensions and/or other characteristics derived from the patient imaging data to select or suggest certain types of medical interventions, types of surgical treatments, or even types, dimensions, and/or placement of one or more medical implants. In this manner, the system may use the soft tissue information derived from the patient imaging data to determine or assist in the determination of surgical planning for a specific patient. For example, the system may select between an anatomical shoulder replacement surgery or a reverse shoulder replacement surgery, and then output the selection to a user such as a surgeon, e.g., by presentation on a display, based on the soft tissue dimensions and other characteristics derived from the patient imaging data. These recommendations for shoulder replacement described herein may be applied to new replacements or a first replacement of the shoulder or, in other examples, revision surgery in which the patient has already had a shoulder replacement. Typically, a shoulder surgery may be used to restore shoulder function and/or reduce pain for a patient.

In one example, a system may receive patient imaging data (e.g., computed tomography (CT) that includes X-ray images, magnetic resonance imaging (MM) images, or other imaging modality) and construct a three-dimensional (3D) imaging data set. From this imaging data set, the system can identify locations of bones associated with the soft tissue structures of interest and approximate locations of the soft tissue structures themselves. For instance, if the patient may need a shoulder replacement surgery, the system may identify parts of the scapula and humerus and muscles of the rotator cuff. For each of the soft tissue structures (e.g., for each muscle of the rotator cuff), the system may determine a representation of the soft tissue structure from the imaging data. The system may place an initial shape within the estimated location of the soft tissue structure and then fit this initial shape to the imaging data to determine the representation of the actual soft tissue structure. This estimated location may be based on one or more markers or landmarks (e.g., muscle insertion points or muscle origins) on associated bones or other bone structures or portions of bone structures. The initial shape may be a statistical mean shape (SMS) derived from a population of subjects or any geometric shape.

From the initial shape, the system may use vectors normal to the surface of the initial shape to identify voxels outside or inside of the initial shape that exceed an intensity threshold representative of a boundary of the soft tissue structure within the imaging data. In some examples, the boundary of the soft tissue structure may be estimated from a separation zone identified between adjacent soft tissue structures. From the respective locations on the initial shape for each vector, the system may move the surface of the initial shape towards respective voxels of the identified voxels. This movement of the surface of the initial shape may occur over several iterations until the initial shape has been modified to approximate contours of the identified voxels. In other examples, the system may use correspondences from the initial shape to associated bones and/or minimization or maximization algorithms (e.g., a cost function) to fit and scale the initial shape to the patient-specific image data. The final modified shape may then be used as the representation of the soft tissue structure, such as a muscle of the rotator cuff of the patient.

The system may determine one or more characteristics of one or more soft tissue structures from the determined representation. The system may employ these characteristics for surgical planning, for example. In some examples, the system may calculate a volume of the soft tissue structure to be used for other determinations. The system may determine a fatty infiltration values for the soft tissue structure based on thresholding intensities of voxels from the imaging data within the representation of the soft tissue structure, i.e., comparing voxel intensities to threshold intensity values to characterize the voxels as representative of fatty tissue. For example, voxels within the segmented representation of the soft tissue structure having intensities that exceed a threshold intensity value may be considered to be representative of fatty tissue rather than muscle tissue. Voxels, or groups of two or more voxels, that do not exceed the threshold intensity value may be considered to represent non-fatty tissue. Used herein, the term "exceed" may refer to the value being greater than a threshold or being less than a threshold.

The ratio of fatty tissue to total tissue (which includes fatty tissue and non-fatty tissue) within the representation may be determined to be the fatty infiltration value. The system may also calculate an atrophy ratio by dividing the volume of the SMS fit to the bones of the patient (e.g., an estimated pre-morbid tissue volume for the patient) to the volume of the representation of the soft tissue structure. The system can then determine a spring constant (or some other representation of muscle function) of the soft tissue structure and other soft tissue structures associated with a joint to determine a range of motion for that joint. The system can then determine a type of intervention for that joint based on the range of motion and/or other characteristics discussed herein. For example, the system can determine whether an anatomical shoulder replacement or a reverse shoulder replacement is a more appropriate treatment for the patient.

In some examples, a system may determine bone density characteristics of a humeral head of a humerus based on patient-specific image data (e.g., 2D or 3D image data). For example, the system may characterize assign bone density values for voxels or groups of voxels of the trabecular bone within at least a portion of the humeral head. In other examples, the system may determine an overall bone density metric or score indicative of the entire volume of trabecular bone in at least a portion of the humeral head. The system may control a display device to display a user interface that include a representation of the bone density, such as a graphical indication of the bone density. In some examples, the system may generate a recommendation of a type of humeral implant (e.g., stemmed or stemless) based on the determined bone density. In some examples, the recommendation of the type of humeral implant may be based on historical surgical data for humeral implants in which the system has correlated the type of humeral implant used for a patient with bone density values identified in the patient-specific image data for that same patient.

Shoulder replacement surgery is described as one example herein. However, the systems, devices, and techniques described herein may be employed to analyze other anatomical structures or groups of structures of a patient, determine a type of treatment for other joints of the patient (e.g., elbow, hip, knee, etc.), or select a certain type of implant for the particular anatomical condition of the patient. In addition, the techniques described herein for determining soft tissue structures from patient imaging data may be employed to identify other structures, such as bones, in other examples.

In some examples, systems, devices, and methods may employ a mixed reality (MR) visualization system to assist with creation, implementation, verification, and/or modification of a surgical plan before and during a surgical procedure, such as those processes associated to determining why types of treatment to provide to the patient (e.g., a joint replacement surgery such as shoulder replacement). Because MR, or in some instances VR, may be used to interact with the surgical plan, this disclosure may also refer to the surgical plan as a "virtual" surgical plan. Visualization tools other than or in addition to mixed reality visualization systems may be used in accordance with techniques of this disclosure.

A surgical plan or recommendation, e.g., as generated by the BLUEPRINT™ system, available from Wright Medical, Inc., or another surgical planning platform, may include information defining a variety of features of a surgical procedure, such as suggested types of surgical treatment (e.g., anatomical or reverse shoulder surgery) features of particular surgical procedure steps to be performed on a patient by a surgeon according to the surgical plan including, for example, bone or tissue preparation steps and/or steps for selection, modification and/or placement of implant components. Such information may include, in various examples, dimensions, shapes, angles, surface contours, and/or orientations of implant components to be selected or modified by surgeons, dimensions, shapes, angles, surface contours and/or orientations to be defined in bone or soft tissue by the surgeon in bone or tissue preparation steps, and/or positions, axes, planes, angle and/or entry points defining placement of implant components by the surgeon relative to patient bone or other tissue. Information such as dimensions, shapes, angles, surface contours, and/or orientations of anatomical features of the patient may be derived from imaging (e.g., x-ray, CT, MM, ultrasound or other images), direct observation, or other techniques.

Some visualization tools utilize patient image data to generate three-dimensional models of bone contours to facilitate preoperative planning for joint repairs and replacements. These tools may allow surgeons to design and/or select surgical guides and implant components that closely match the patient's anatomy. These tools can improve surgical outcomes by customizing a surgical plan for each patient. An example of such a visualization tool for shoulder repairs is the BLUEPRINT™ system identified above. The BLUEPRINT™ system provides the surgeon with two-dimensional planar views of the bone repair region as well as a three-dimensional virtual model of the repair region. The surgeon can use the BLUEPRINT™ system to select, design or modify appropriate implant components, determine how best to position and orient the implant components and how to shape the surface of the bone to receive the components, and design, select or modify surgical guide tool(s) or instruments to carry out the surgical plan. The information generated by the BLUEPRINT™ system is compiled in a preoperative surgical plan for the patient that is stored in a database at an appropriate location (e.g., on a server in a wide area network, a local area network, or a global network) where it can be accessed by the surgeon or other care provider, including before and during the actual surgery.

Certain examples of this disclosure are described with reference to the accompanying drawings, wherein like reference numerals denote like elements. It should be understood, however, that the accompanying drawings illustrate only the various implementations described herein and are not meant to limit the scope of various technologies described herein. The drawings show and describe various examples of this disclosure.

In the following description, numerous details are set forth to provide an understanding of the present disclosure. However, it will be understood by those skilled in the art that one or more aspects of the present disclosure may be practiced without these details and that numerous variations or modifications from the described examples may be possible.

FIG. 1 is a block diagram of an orthopedic surgical system 100 according to an example of this disclosure. Orthopedic surgical system 100 includes a set of subsystems. In the example of FIG. 1, the subsystems include a virtual planning system 102, a planning support system 104, a manufacturing and delivery system 106, an intraoperative guidance system 108, a medical education system 110, a monitoring system 112, a predictive analytics system 114, and a communications network 116. In other examples, orthopedic surgical system 100 may include more, fewer, or different subsystems. For example, orthopedic surgical system 100 may omit medical education system 110, monitor system 112, predictive analytics system 114, and/or other subsystems. In some examples, orthopedic surgical system 100 may be used for surgical tracking, in which case orthopedic surgical system 100 may be referred to as a surgical tracking system. In other cases, orthopedic surgical system 100 may be generally referred to as a medical device system.

Users of orthopedic surgical system 100 may use virtual planning system 102 to plan orthopedic surgeries. For example, virtual planning system 102 and/or another surgical planning system may analyze patient imaging data (e.g., bone and/or soft tissue) and determine suggested surgical treatments based on bone and/or soft tissue characteristics determined from the imaging data, as discussed herein. Users of orthopedic surgical system 100 may use planning support system 104 to review surgical plans generated using orthopedic surgical system 100. Manufacturing and delivery system 106 may assist with the manufacture and delivery of items needed to perform orthopedic surgeries. Intraoperative guidance system 108 provides guidance to assist users of orthopedic surgical system 100 in performing orthopedic surgeries. Medical education system 110 may assist with the education of users, such as healthcare professionals, patients, and other types of individuals. Pre- and postoperative monitoring system 112 may assist with monitoring patients before and after the patients undergo surgery. Predictive analytics system 114 may assist healthcare professionals with various types of predictions. For example, predictive analytics system 114 may apply artificial intelligence techniques to determine a classification of a condition of an orthopedic joint, e.g., a diagnosis, determine which type of surgery to perform on a patient and/or which type of implant to be used in the procedure, determine types of items that may be needed during the surgery, and so on.

The subsystems of orthopedic surgical system 100 (e.g., virtual planning system 102, planning support system 104, manufacturing and delivery system 106, intraoperative guidance system 108, medical education system 110, pre- and postoperative monitoring system 112, and predictive analytics system 114) may include various systems. The systems in the subsystems of orthopedic surgical system 100 may include various types of computing systems, computing devices, including server computers, personal computers, tablet computers, smartphones, display devices, Internet of Things (IoT) devices, visualization devices (e.g., mixed reality (MR) visualization devices, virtual reality (VR) visualization devices, holographic projectors, or other devices for presenting extended reality (XR) visualizations), surgical tools, and so on. A holographic projector, in some examples, may project a hologram for general viewing by multiple users or a single user without a headset, rather than viewing only by a user wearing a headset. For example, virtual planning system 102 may include a MR visualization device and one or more server devices, planning support system 104 may include one or more personal computers and one or more server devices, and so on. A computing system is a set of one or more computing devices and/or systems configured to operate as a system. In some examples, one or more devices may be shared between the two or more of the subsystems of orthopedic surgical system 100. For instance, in the previous examples, virtual planning system 102 and planning support system 104 may include the same server devices.

Example MR visualization devices include the Microsoft HOLOLENS™ headset, available from Microsoft Corporation of Redmond, Washington, which includes see-through holographic lenses, sometimes referred to as waveguides, that permit a user to view real-world objects through the lens and concurrently view projected 3D holographic objects. The Microsoft HOLOLENS™ headset, or similar waveguide-based visualization devices, are examples of an MR visualization device that may be used in accordance with some examples of this disclosure. Some holographic lenses may present holographic objects with some degree of transparency through see-through holographic lenses so that the user views real-world objects and virtual, holographic objects. In some examples, some holographic lenses may, at times, completely prevent the user from viewing real-world objects and instead may allow the user to view entirely virtual environments. The term mixed reality may also encompass scenarios where one or more users are able to perceive one or more virtual objects generated by holographic projection. In other words, "mixed reality" may encompass the case where a holographic projector generates holograms of elements that appear to a user to be present in the user's actual physical environment. Although MR visualization devices are described as one example herein, display screens such as cathode ray tube (CRT) displays, liquid crystal displays (LCDs), and light emitting diode (LED) displays may be used to present any aspect of the information described herein in other examples.

In the example of FIG. 1, the devices included in the subsystems of orthopedic surgical system 100 may communicate using communication network 116. Communication network 116 may include various types of communication networks including one or more wide-area networks, such as the Internet, local area networks, and so on. In some examples, communication network 116 may include wired and/or wireless communication links.

Figure 2:
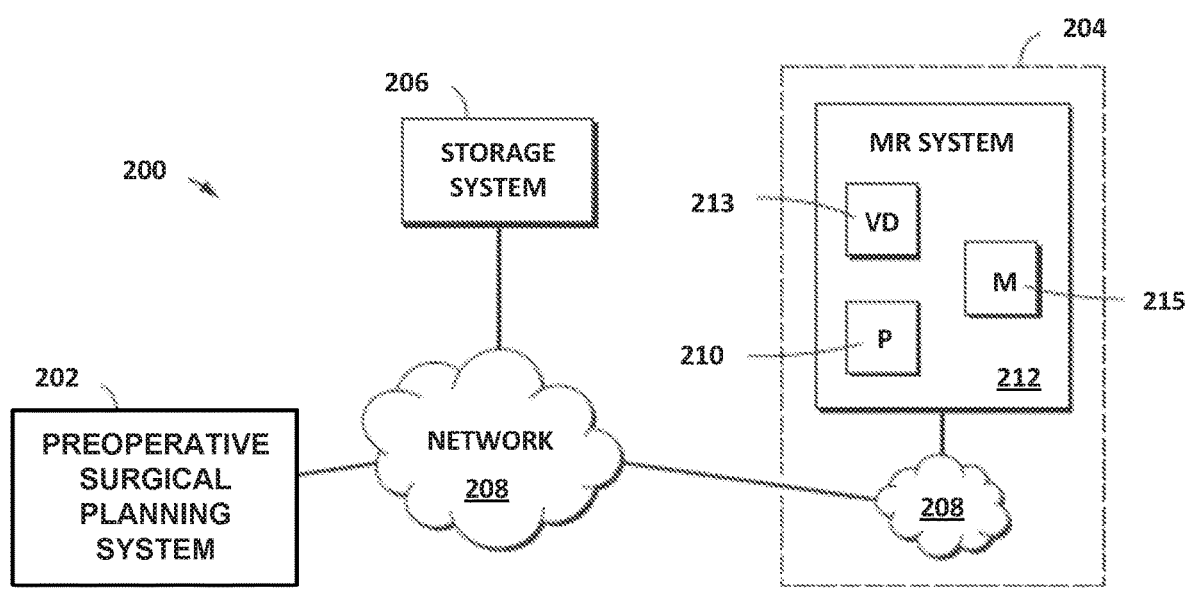
FIG. 2 is a block diagram of an orthopedic surgical system that includes a mixed reality (MR) system, according to an example of this disclosure.

Many variations of orthopedic surgical system 100 are possible. Such variations may include more or fewer subsystems than the version of orthopedic surgical system 100 shown in FIG. 1. For example, FIG. 2 is a block diagram of an orthopedic surgical system 200 that includes one or more mixed reality (MR) systems, according to an example of this disclosure. Orthopedic surgical system 200 may be used for creating, verifying, updating, modifying and/or implementing a surgical plan. In some examples, the surgical plan can be created preoperatively, such as by using a virtual surgical planning system (e.g., the BLUEPRINT™ system), and then verified, modified, updated, and viewed intraoperatively, e.g., using MR visualization or other visualization of the surgical plan. In other examples, orthopedic surgical system 200 can be used to create the surgical plan immediately prior to surgery or intraoperatively, as needed. In some examples, orthopedic surgical system 200 may be used for surgical tracking, in which case orthopedic surgical system 200 may be referred to as a surgical tracking system. In other cases, orthopedic surgical system 200 may be generally referred to as a medical device system.

In the example of FIG. 2, orthopedic surgical system 200 includes a preoperative surgical planning system 202, a healthcare facility 204 (e.g., a surgical center or hospital), a storage system 206 and a network 208 that allows a user at healthcare facility 204 to access stored patient information, such as medical history, image data corresponding to the damaged joint or bone and various parameters corresponding to a surgical plan that has been created preoperatively (as examples). Preoperative surgical planning system 202 may be equivalent to virtual planning system 102 of FIG. 1 and, in some examples, may generally correspond to a virtual planning system similar or identical to the BLUEPRINT™ system.

In the example of FIG. 2, healthcare facility 204 includes a mixed reality (MR) system 212. In some examples of this disclosure, MR system 212 includes one or more processing device(s) (P) 210 to provide functionalities such as presentation of visual information to a user that relates to preoperative planning, intraoperative guidance, or even postoperative review and follow up. Processing device(s) 210 may also be referred to as processor(s). In addition, one or more users of MR system 212 (e.g., a surgeon, nurse, or other care provider) can use processing device(s) (P) 210 to generate a request for a particular surgical plan or other patient information that is transmitted to storage system 206 via network 208. In response, storage system 206 returns the requested patient information to MR system 212. In some examples, the users can use other processing device(s) to request and receive information, such as one or more processing devices that are part of MR system 212, but not part of any visualization device, or one or more processing devices that are part of a visualization device (e.g., visualization device 213) of MR system 212, or a combination of one or more processing devices that are part of MR system 212, but not part of any visualization device, and one or more processing devices that are part of a visualization device (e.g., visualization device 213) that is part of MR system 212. In other words, and example MR visualization device such as the Microsoft HOLOLENS™ device may include all of the components of MR system 212, or utilize one or more external processors and/or memory to perform some or all processing functionality necessary for a passive visualization device 213.

In some examples, multiple users can simultaneously use MR system 212. For example, MR system 212 can be used in a spectator mode in which multiple users each use their own visualization devices so that the users can view the same information at the same time and from the same point of view. In some examples, MR system 212 may be used in a mode in which multiple users each use their own visualization devices so that the users can view the same information from different points of view.

In some examples, processing device(s) 210 can provide a user interface to display data and receive input from users at healthcare facility 204. Processing device(s) 210 may be configured to control visualization device 213 to present a user interface. Furthermore, processing device(s) 210 may be configured to control visualization device 213 (e.g., one or more optical waveguides such as a holographic lens) to present virtual images, such as 3D virtual models, 2D images, surgery plan information, and so on. Processing device(s) 210 can include a variety of different processing or computing devices, such as servers, desktop computers, laptop computers, tablets, mobile phones and other electronic computing devices, or processors within such devices. In some examples, one or more of processing device(s) 210 can be located remote from healthcare facility 204. In some examples, processing device(s) 210 reside within visualization device 213. In some examples, at least one of processing device(s) 210 is external to visualization device 213. In some examples, one or more processing device(s) 210 reside within visualization device 213 and one or more of processing device(s) 210 are external to visualization device 213.

In the example of FIG. 2, MR system 212 also includes one or more memory or storage device(s) (M) 215 for storing data and instructions of software that can be executed by processing device(s) 210. The instructions of software can correspond to the functionality of MR system 212 described herein. In some examples, the functionalities of a virtual surgical planning application, such as the BLUE-PRINT™ system, can also be stored and executed by processing device(s) 210 in conjunction with memory storage device(s) (M) 215. For instance, memory or storage system 215 may be configured to store data corresponding to at least a portion of a virtual surgical plan. In some examples, storage system 206 may be configured to store data corresponding to at least a portion of a virtual surgical plan. In some examples, memory or storage device(s) (M) 215 reside within visualization device 213. In some examples, memory or storage device(s) (M) 215 are external to visualization device 213. In some examples, memory or storage device(s) (M) 215 include a combination of one or more memory or storage devices within visualization device 213 and one or more memory or storage devices external to the visualization device.

Network 208 may be equivalent to network 116. Network 208 can include one or more wide area networks, local area networks, and/or global networks (e.g., the Internet) that connect preoperative surgical planning system 202 and MR system 212 to storage system 206. Storage system 206 can include one or more databases that can contain patient information, medical information, patient image data, and parameters that define the surgical plans. For example, medical images of the patient's diseased or damaged bone and/or soft tissue typically are generated preoperatively in preparation for an orthopedic surgical procedure. The medical images can include images of the relevant bone(s) and/or soft tissue taken along the sagittal plane and the coronal plane of the patient's body. The medical images can include X-ray images, magnetic resonance imaging (MRI) images, computed tomography (CT) images, ultrasound images, and/or any other type of 2D or 3D image that provides information about the relevant surgical area. Storage system 206 also can include data identifying the implant components selected for a particular patient (e.g., type, size, etc.), surgical guides selected for a particular patient, and details of the surgical procedure, such as entry points, cutting planes, drilling axes, reaming depths, etc. Storage system 206 can be a cloud-based storage system (as shown) or can be located at healthcare facility 204 or at the location of preoperative surgical planning system 202 or can be part of MR system 212 or visualization device (VD) 213, as examples.

MR system 212 can be used by a surgeon before (e.g., preoperatively) or during the surgical procedure (e.g., intraoperatively) to create, review, verify, update, modify and/or implement a surgical plan. In some examples, MR system 212 may also be used after the surgical procedure (e.g., postoperatively) to review the results of the surgical procedure, assess whether revisions are required, or perform other postoperative tasks. In this manner, MR system 12 may enable the user to see real-world scenes such as anatomical objects in addition to virtual imagery (e.g., virtual glenoid or humerus images, guidance images, or other text or images) placed at that real-world scene. To that end, MR system 212 may include a visualization device 213 that may be worn by the surgeon and (as will be explained in further detail below) is operable to display a variety of types of information, including a 3D virtual image of the patient's diseased, damaged, or postsurgical joint and details of the surgical plan, such as images of bone and/or soft tissue of the patient derived from patient imaging data, generated models of bone or soft tissue, a 3D virtual image of the prosthetic implant components selected for the surgical plan, 3D virtual images of entry points for positioning the prosthetic components, alignment axes and cutting planes for aligning cutting or reaming tools to shape the bone surfaces, or drilling tools to define one or more holes in the bone surfaces, in the surgical procedure to properly orient and position the prosthetic components, surgical guides and instruments and their placement on the damaged joint, and any other information that may be useful to the surgeon to implement the surgical plan. MR system 212 can generate images of this information that are perceptible to the user of the visualization device 213 before and/or during the surgical procedure.

In some examples, MR system 212 includes multiple visualization devices (e.g., multiple instances of visualization device 213) so that multiple users can simultaneously see the same images and share the same 3D scene. In some such examples, one of the visualization devices can be designated as the master device and the other visualization devices can be designated as observers or spectators. Any observer device can be re-designated as the master device at any time, as may be desired by the users of MR system 212.

Figure 3:
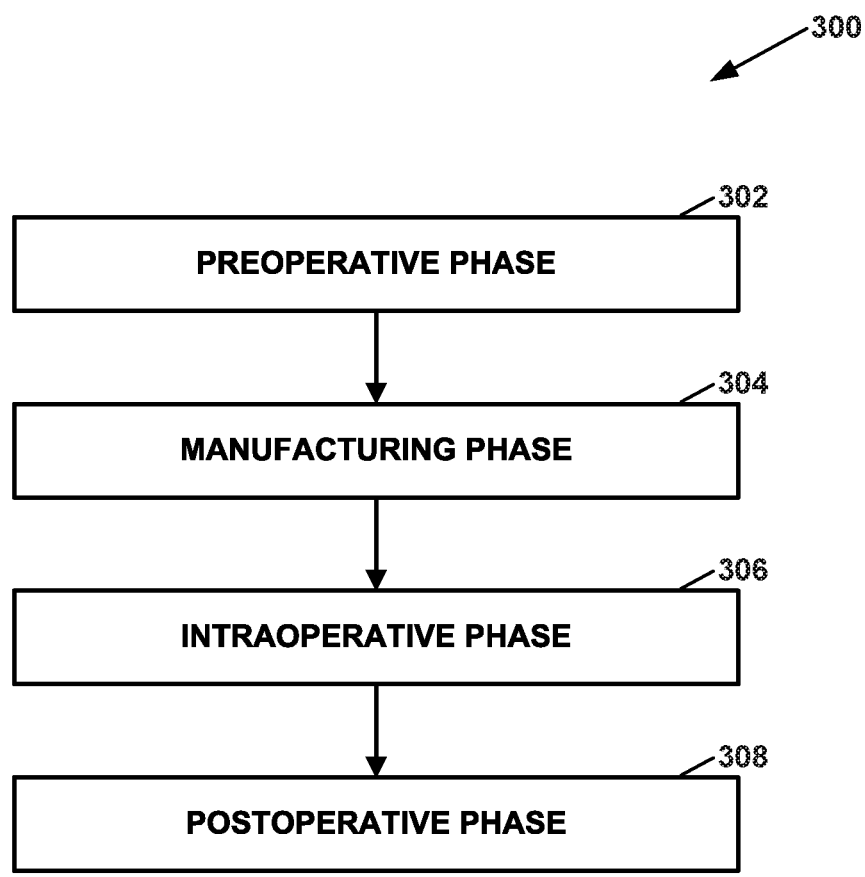
FIG. 3 is a flowchart illustrating example phases of a surgical lifecycle.

FIG. 3 is a flowchart illustrating example phases of a surgical lifecycle 300. In the example of FIG. 3, surgical lifecycle 300 begins with a preoperative phase (302). During the preoperative phase, a surgical plan is developed. The preoperative phase is followed by a manufacturing and delivery phase (304). During the manufacturing and delivery phase, patient-specific items, such as parts and equipment, needed for executing the surgical plan are manufactured and delivered to a surgical site. In some examples, it is unnecessary to manufacture patient-specific items in order to execute the surgical plan. An intraoperative phase follows the manufacturing and delivery phase (306). The surgical plan is executed during the intraoperative phase. In other words, one or more persons perform the surgery on the patient during the intraoperative phase. The intraoperative phase is followed by the postoperative phase (308). The postoperative phase includes activities occurring after the surgical plan is complete. For example, the patient may be monitored during the postoperative phase for complications.

As described in this disclosure, orthopedic surgical system 100 (FIG. 1) may be used in one or more of preoperative phase 302, the manufacturing and delivery phase 304, the intraoperative phase 306, and the postoperative phase 308. For example, virtual planning system 102 and planning support system 104 may be used in preoperative phase 302. In some examples, preoperative phase 302 may include the system analyzing patient imaging data, modeling bone and/ or soft tissue, and/or determining or recommending a type of surgical treatment based on the condition of the patient. Manufacturing and delivery system 106 may be used in the manufacturing and delivery phase 304. Intraoperative guidance system 108 may be used in intraoperative phase 306. Some of the systems of FIG. 1 may be used in multiple phases of FIG. 3. For example, medical education system 110 may be used in one or more of preoperative phase 302, intraoperative phase 306, and postoperative phase 308; pre- and postoperative monitoring system 112 may be used in preoperative phase 302 and postoperative phase 308. Predictive analytics system 114 may be used in preoperative phase 302 and postoperative phase 308. Various workflows may exist within the surgical process of FIG. 3. For example, different workflows within the surgical process of FIG. 3 may be appropriate for different types of surgeries.

Figure 4:
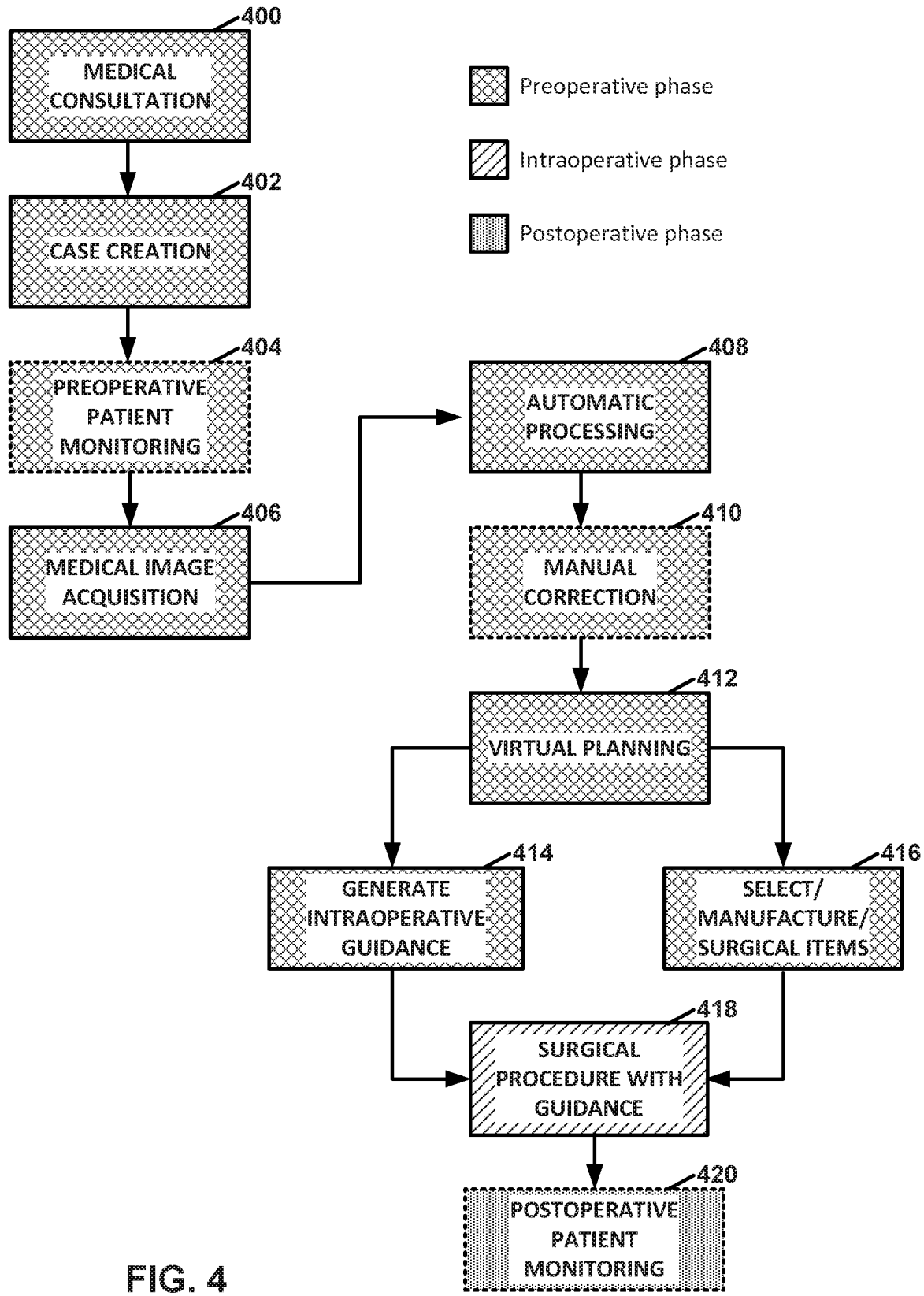
FIG. 4 is a flowchart illustrating preoperative, intraoperative and postoperative workflows in support of an orthopedic surgical procedure.

FIG. 4 is a flowchart illustrating example preoperative, intraoperative and postoperative workflows in support of an orthopedic surgical procedure. In the example of FIG. 4, the surgical process begins with a medical consultation (400). During the medical consultation (400), a healthcare professional evaluates a medical condition of a patient. For instance, the healthcare professional may consult the patient with respect to the patient's symptoms. During the medical consultation (400), the healthcare professional may also discuss various treatment options with the patient. For instance, the healthcare professional may describe one or more different surgeries to address the patient's symptoms.

Furthermore, the example of FIG. 4 includes a case creation step (402). In other examples, the case creation step occurs before the medical consultation step. During the case creation step, the medical professional or other user establishes an electronic case file for the patient. The electronic case file for the patient may include information related to the patient, such as data regarding the patient's symptoms, patient range of motion observations, data regarding a surgical plan for the patient, medical images of the patients, notes regarding the patient, billing information regarding the patient, and so on.

The example of FIG. 4 includes a preoperative patient monitoring phase (404). During the preoperative patient monitoring phase, the patient's symptoms may be monitored. For example, the patient may be suffering from pain associated with arthritis in the patient's shoulder. In this example, the patient's symptoms may not yet rise to the level of requiring an arthroplasty to replace the patient's shoulder. However, arthritis typically worsens over time. Accordingly, the patient's symptoms may be monitored to determine whether the time has come to perform a surgery on the patient's shoulder. Observations from the preoperative patient monitoring phase may be stored in the electronic case file for the patient. In some examples, predictive analytics system 114 may be used to predict when the patient may need surgery, to predict a course of treatment to delay or avoid surgery or make other predictions with respect to the patient's health.

Additionally, in the example of FIG. 4, a medical image acquisition step occurs during the preoperative phase (406). During the image acquisition step, medical images of the patient are generated. The medical images for a specific patient may be generated in a variety of ways. For instance, the images may be generated using a Computed Tomography (CT) process, a Magnetic Resonance Imaging (MRI) process, an ultrasound process, or another imaging process. The medical images generated during the image acquisition step include images of an anatomy of interest of the specific patient. For instance, if the patient's symptoms involve the patient's shoulder, medical images of the patient's shoulder may be generated. The medical images may be added to the patient's electronic case file. Healthcare professionals may be able to use the medical images in one or more of the preoperative, intraoperative, and postoperative phases.

Furthermore, in the example of FIG. 4, an automatic processing step may occur (408). During the automatic processing step, virtual planning system 102 (FIG. 1) may automatically develop a preliminary surgical plan for the patient. For example, virtual planning system 102 may generate a model, or representations of bone and/or soft tissue of the patient. Based on these representations, virtual planning system 102 may determine bone and/or soft tissue characteristics such as soft tissue volume, fatty infiltration of muscle, atrophy ratios of muscles, and range of motion of bones. Virtual planning system 102 may determine what types of treatment should be performed (e.g., whether a shoulder replacement should be an anatomical replacement or a reverse replacement) based on these characteristics. In some examples of this disclosure, virtual planning system 102 may use machine learning techniques to develop the preliminary surgical plan based on information in the patient's virtual case file.

The example of FIG. 4 also includes a manual correction step (410). During the manual correction step, one or more human users may check and correct the determinations made during the automatic processing step. In some examples of this disclosure, one or more users may use mixed reality or virtual reality visualization devices during the manual correction step. In some examples, changes made during the manual correction step may be used as training data to refine the machine learning techniques applied by virtual planning system 102 during the automatic processing step.

A virtual planning step (412) may follow the manual correction step in FIG. 4. During the virtual planning step, a healthcare professional may develop a surgical plan for the patient. In some examples of this disclosure, one or more users may use mixed reality or virtual reality visualization devices during development of the surgical plan for the patient.

Furthermore, in the example of FIG. 4, intraoperative guidance may be generated (414). The intraoperative guidance may include guidance to a surgeon on how to execute the surgical plan. In some examples of this disclosure, virtual planning system 102 may generate at least part of the intraoperative guidance. In some examples, the surgeon or other user(s) may contribute to the intraoperative guidance.

Additionally, in the example of FIG. 4, a step of selecting and manufacturing surgical items is performed (416). During the step of selecting and manufacturing surgical items, manufacturing and delivery system 106 (FIG. 1) may manufacture surgical items for use during the surgery described by the surgical plan. For example, the surgical items may include surgical implants, surgical tools, and other items required to perform the surgery described by the surgical plan.

In the example of FIG. 4, a surgical procedure may be performed with guidance from intraoperative system 108 (FIG. 1) (418). For example, a surgeon may perform the surgery while wearing a head-mounted MR visualization device of intraoperative system 108 that presents guidance information to the surgeon. The guidance information may help guide the surgeon through the surgery, providing guidance for various steps in a surgical workflow, including sequence of steps, details of individual steps, and tool or implant selection, implant placement and position, and bone surface preparation for various steps in the surgical procedure workflow.

Postoperative patient monitoring may occur after completion of the surgical procedure (420). During the postoperative patient monitoring step, healthcare outcomes of the patient may be monitored. Healthcare outcomes may include relief from symptoms, ranges of motion, complications, performance of implanted surgical items, and so on. Pre- and postoperative monitoring system 112 (FIG. 1) may assist in the postoperative patient monitoring step.

The medical consultation, case creation, preoperative patient monitoring, image acquisition, automatic processing, manual correction, and virtual planning steps of FIG. 4 are part of preoperative phase 302 of FIG. 3. The surgical procedures with guidance steps of FIG. 4 is part of intraoperative phase 306 of FIG. 3. The postoperative patient monitoring step of FIG. 4 is part of postoperative phase 308 of FIG. 3.

As mentioned above, one or more of the subsystems of orthopedic surgical system 100 may include one or more mixed reality (MR) systems, such as MR system 212 (FIG. 2). Each MR system may include a visualization device. For instance, in the example of FIG. 2, MR system 212 includes visualization device 213. In some examples, in addition to including a visualization device, an MR system may include external computing resources that support the operations of the visualization device. For instance, the visualization device of an MR system may be communicatively coupled to a computing device (e.g., a personal computer, notebook computer, tablet computer, smartphone, etc.) that provides the external computing resources. Alternatively, adequate computing resources may be provided on or within visualization device 213 to perform necessary functions of the visualization device.

Figure 5A:
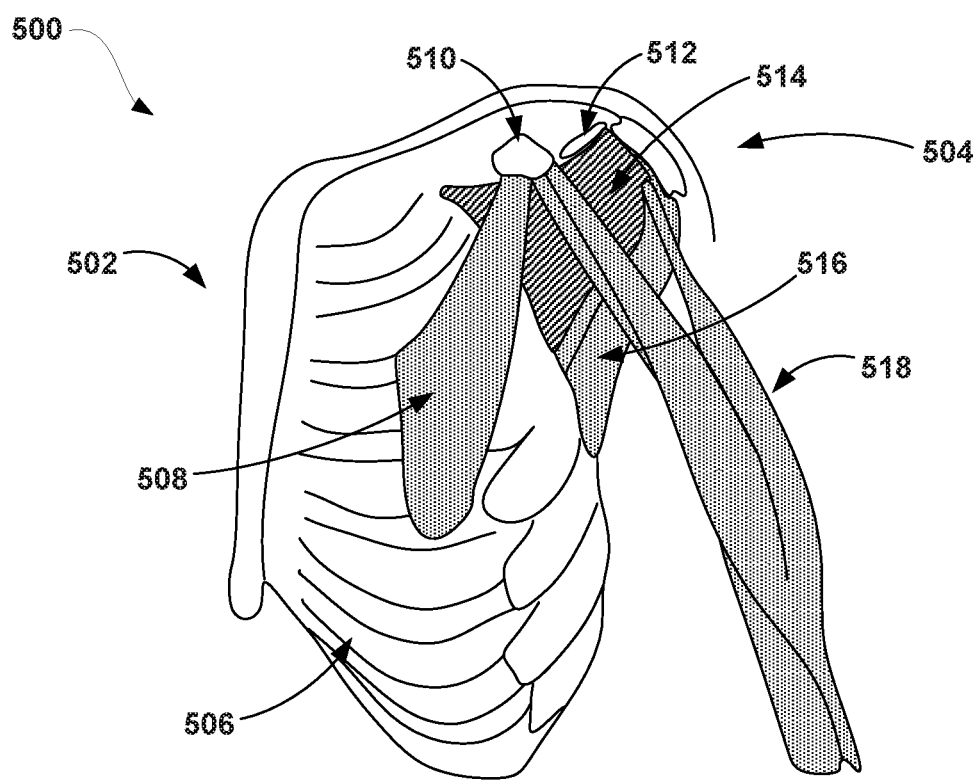
FIGS. 5A and 5B are illustrations of example muscles and bones related to a shoulder of a patient.
Figure 5B:
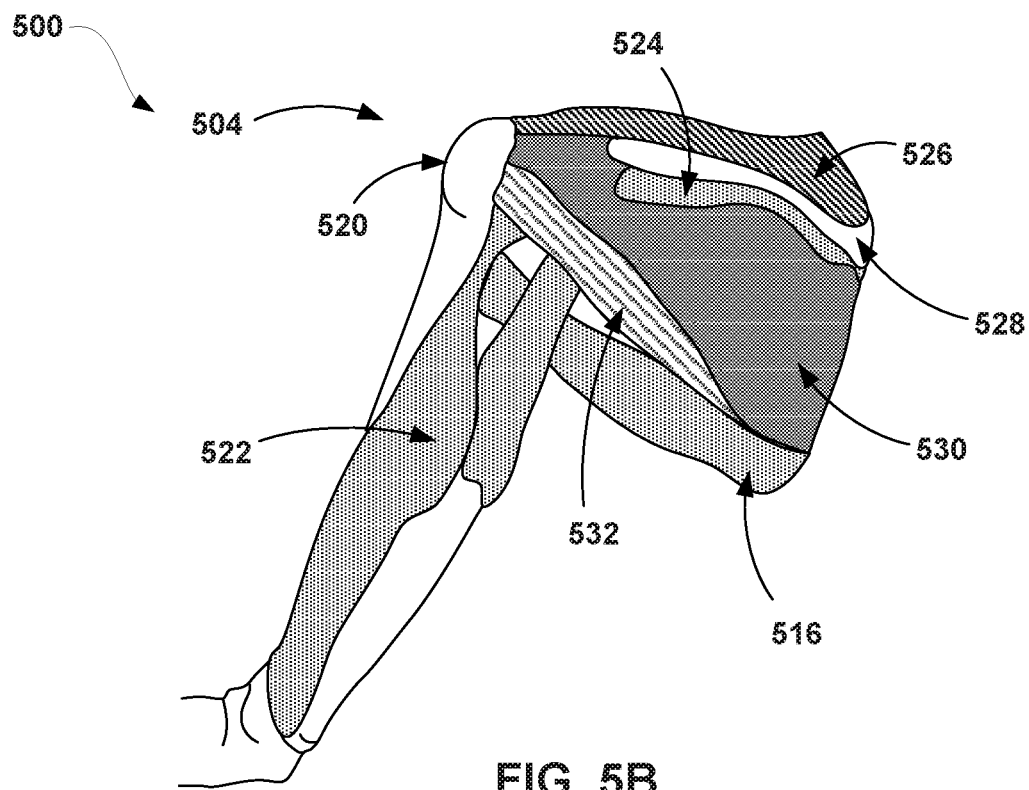

Virtual planning system 102 and/or other systems may analyze patient imaging data that may also be used for planning surgical intervention, such as joint surgery. As discussed herein as an example, shoulder replacement surgery is one type of surgery that may be planned using the system and techniques herein. FIGS. 5A and 5B are illustrations of example muscles and bones related to a shoulder of a patient.

As shown in the example of FIG. 5A, an anterior view of patient 500 includes sternum 502, shoulder 504, and ribs 506. Some bones associated with the structure and function of shoulder 504 include coracoid process 510 and acromion 512 of the scapula (not shown in its entirety). Muscles associated with shoulder 504 include serratus anterior 508, teres major, and biceps 518. Subscapularis 514 is one of the rotator cuff muscles shown in FIG. 5A. The other rotator cuff muscles, supraspinatus 526, infraspinatus 530, and teres minor 532 are shown in the posterior view of patient 500 in the example of FIG. 5B. FIG. 5B also illustrates the bony features of humeral head 520 and spine of scapula 528. Other muscles associated with shoulder 504 include triceps 522 and deltoid 524.

When evaluating shoulder 504 for treatment, such as what type of shoulder treatment or replacement may be appropriate, a system may analyze patient-specific imaging data for bones and soft tissues such as those discussed in FIGS. 5A and 5B. For example, virtual planning system 102 may generate representations of the soft tissue (e.g., muscles) from the patient imaging data and determine various characteristics of the soft tissue. These characteristics may include muscle volumes, fatty infiltration (e.g., fat ratio), muscle atrophy ratios, and range of motion for a joint associated with the muscles.

From this information, virtual planning system 102 may determine recommended types of treatment, such as whether or not the patient would benefit from an anatomical shoulder replacement or a reverse shoulder replacement. In an anatomical shoulder replacement, the humeral head is replaced with an artificial humeral head (e.g., a partial sphere), and the glenoid surface of the scapula is replaced with an artificial curved surface that mates with the artificial humeral head. In a reverse shoulder replacement, an artificial partial sphere is implanted for the glenoid surface and an artificial curved surface (e.g., a cup) that mates with the sphere is implanted in place of the humeral head. Virtual planning system 102 may also suggest dimensions and/or placement of implants based on the patient imaging data and/or the muscle characteristics.

In one example, a system, such as virtual planning system 102, may be configured for modeling a soft-tissue structure of a patient. Virtual planning system 102 may include a memory configured to store patient-specific image data for the patient and processing circuitry. The processing circuitry may be configured to receive the patient-specific image data (e.g., CT data), determine, based on intensities of the patient-specific image data, a patient-specific shape representative of the soft-tissue structure of the patient, and output the patient-specific shape. In this manner, the patient-specific shape may be the model of the actual soft tissue structure of the patient.

Virtual planning system 102 may generate the patient-specific shape of the soft tissue structure using various methods. For example, the processing circuitry may be configured to receive an initial shape (e.g., a geometric shape or statistical mean shape based on a population of patients) and determine a plurality of surface points on the initial shape. Virtual planning system 102 may then register the initial shape to the patient-specific image data (e.g., place the initial shape into the patient-specific image data based on muscle insertion points on adjacent bones) and identify one or more contours in the patient-specific image data representative of a boundary of the soft-tissue structure of the patient. These one or more contours may be voxels or pixels within the patient-specific imaging data with intensities exceeding a threshold that indicate a boundary of the soft tissue structure. In some examples, the contours may be determined by identifying separation zones between adjacent soft tissue structures (e.g., using a Hessian feature image that represents intensity gradients within the patient-specific image data). A hessian feature image identifying separation zones between adjacent structures may improve the precision in which these structure boundaries as opposed to identifying the structure boundaries based on intensities alone which are very similar between muscles, for example, and fatty tissue. Virtual planning system 102 then iteratively moves the plurality of surface points towards respective locations of the one or more contours to change the initial shape to the patient-specific shape representative of the soft-tissue structure of the patient. In this manner, each iteration of the movement causes the modified initial shape to get increasingly more similar to the actual shape of the patient's soft tissue structure as indicated in the image data.

In some examples, virtual planning system 102 may display the patient-specific shape that has been modeled using the imaging data. Virtual planning system 102 may also perform additional determinations as part of the surgical plan. For example, virtual planning system 102 may use the patient-specific imaging data to determine a fat volume ratio for the patient-specific shape, determine an atrophy ratio for the patient-specific shape, determine, based on the fat volume ratio and the atrophy ratio of the patient-specific shape of the soft-tissue structure of the patient, a range of motion of a humerus of the patient, and then determine, based on the range of motion of the humerus, one type of a plurality of types of shoulder treatment procedure for the patient.

Virtual planning system 102 may determine the range of motion of the humerus by determining, based on fat volume ratios and atrophy ratios for one or more muscles of a rotator cuff of the patient, the range of motion of the humerus of the patient. Based on this information, virtual planning system 102 may select the type of shoulder treatment from one of an anatomical shoulder replacement surgery or a reverse shoulder replacement surgery. In some examples, virtual planning system 102 may recommend a reverse shoulder replacement surgery for situations when the bones and/or muscles of the patient cannot support the anatomical shoulder replacement. In this manner, patients determined to have larger fatty infiltration and larger atrophy ratios may be better suited for the reverse shoulder replacement (e.g., as compared to one or more appropriate thresholds). In some examples, planning system 102 may employ a decision tree or neural network and use the fatty infiltration values as an input along with other parameters such as patient age, gender, activity and/or other factors that may indicate whether the patient is better suited for reverse or anatomical shoulder replacement. In some examples, the fatty infiltration value may be a type of quality metric for the soft tissue structure, such as a muscle. In other examples, the quality of the muscle may be represented by another type of value that may or may not incorporate the presence of fat in the muscle.

Figure 6:
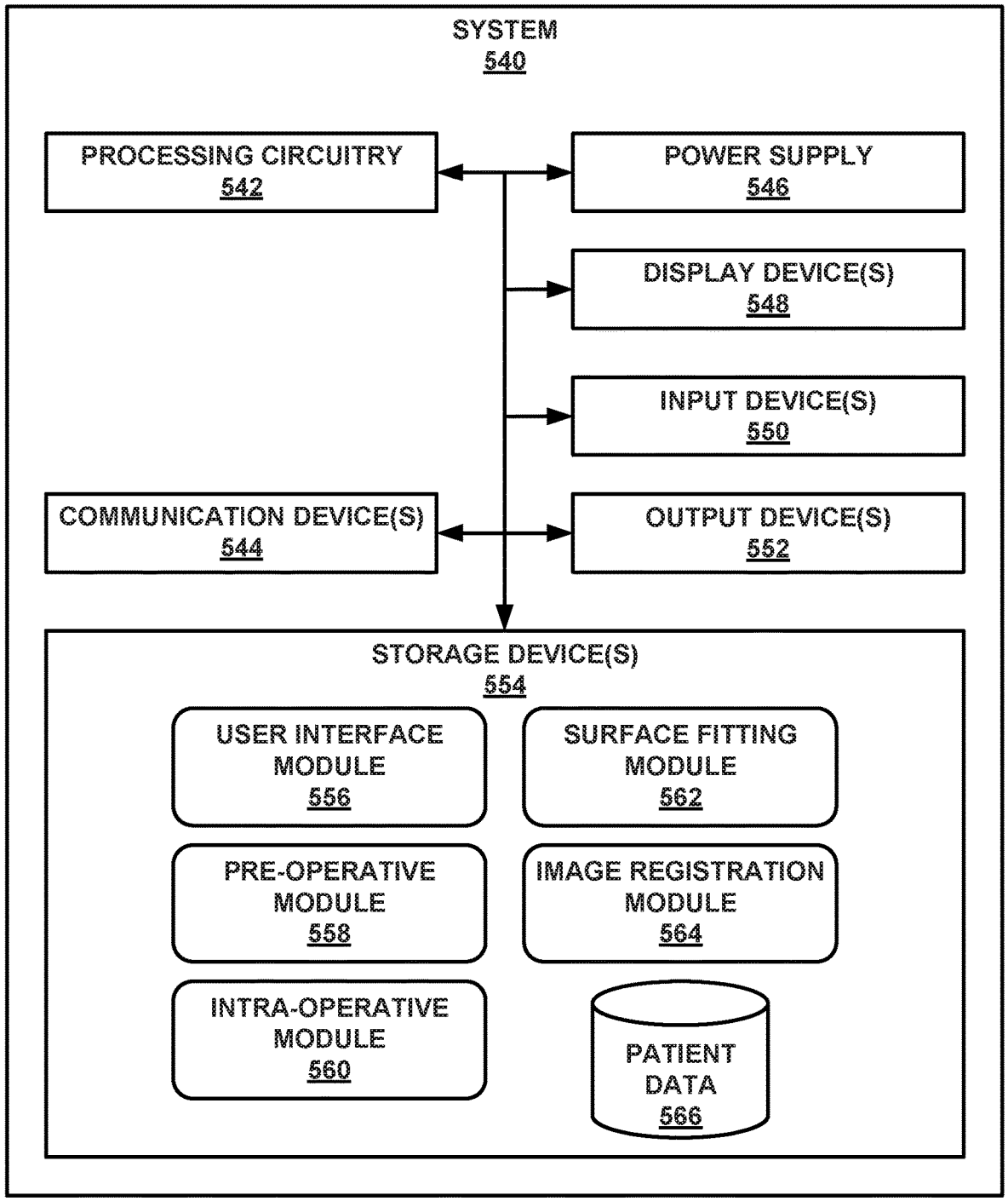
FIG. 6 is a block diagram illustrating example components of a system configured to determine soft tissue structure dimensions and/or characteristics and other information related to surgical intervention associated with a joint, according to an example of this disclosure.

FIG. 6 is a block diagram illustrating example components of system 540 configured to determine soft tissue structure dimensions and other information related to surgical intervention associated with a joint, according to an example of this disclosure. System 540 may be similar to virtual planning system 102 of FIG. 1 and/or systems configured to perform the processes discussed herein. In the example of FIG. 6, system 514 includes processing circuitry 542, a power supply 546, display device(s) 548, input device(s) 550, output device(s) 552, storage device(s) 554, and communication devices 544. In the example of FIG. 6, display device(s) 548 may display imagery to present a user interface to the user, such as opaque or at least partially transparent screens. Display devices 548 may present visual information and, in some examples, audio information or other information presented to a user. For example, display devices 548 may include one or more speakers, tactile devices, and the like. In other examples, output device(s) 552 may include one or more speakers and/or tactile devices. Display device(s) 548 may include an opaque screen (e.g., an LCD or LED display). Alternatively, display device(s) 548 may include an MR visualization device, e.g., including see-through holographic lenses, in combination with projectors, that permit a user to see real-world objects, in a real-world environment, through the lenses, and also see virtual 3D holographic imagery projected into the lenses and onto the user's retinas, e.g., by a holographic projection system such as the Microsoft HOLOLENS™ device. In this example, virtual 3D holographic objects may appear to be placed within the real-world environment. In some examples, display devices 548 include one or more display screens, such as LCD display screens, OLED display screens, and so on. The user interface may present virtual images of details of the virtual surgical plan for a particular patient.

In some examples, a user may interact with and control system 540 in a variety of ways. For example, input devices 550 may include one or more microphones, and associated speech recognition processing circuitry or software, may recognize voice commands spoken by the user and, in response, perform any of a variety of operations, such as selection, activation, or deactivation of various functions associated with surgical planning, intra-operative guidance, or the like. As another example, input devices 550 may include one or more cameras or other optical sensors that detect and interpret gestures to perform operations as described above. As a further example, input devices 550 include one or more devices that sense gaze direction and perform various operations as described elsewhere in this disclosure. In some examples, input devices 550 may receive manual input from a user, e.g., via a handheld controller including one or more buttons, a keypad, a keyboard, a touchscreen, joystick, trackball, and/or other manual input media, and perform, in response to the manual user input, various operations as described above.

Communication devices 544 may include one or more circuits or other components that facilitate data communication with other devices. For example, communication devices 544 may include one or more physical drives (e.g., DVD, blu-ray, or universal serial bus (USB) drives) that allow for transfer of data between system 540 and the drive when physically connected to system 540. In other examples, communication devices 544 may include. Communication devices 544 may also support wired and/or wireless communication with another computing device and/or a network.

Storage devices 544 may include one or more memories and/or repositories that store respective types of data in common and/or separate devices. For example, user interface module 556 may include instructions that define how system 540 controls display devices 548 to present information to a user. Pre-operative module 558 may include instructions regarding analysis of patient data, such as imaging data, and/or determination of treatment options based on patient data. Intra-operative module 560 may include instructions that define how system 540 operates in providing information to a clinician for display such as details regarding the planned surgery and/or feedback regarding the surgical procedure.

Surface fitting module 562 may include instructions defining how processing circuitry 542 determines representations of soft tissue (e.g., patient-specific shapes) from patient-specific imaging data. For example, surface fitting module 562 may specify initial shapes, number of iterations, and other details regarding adjusting the initial shapes to the patient-specific shapes based on the intensities of the patient imaging data. Image registration module 564 may include instructions defining how to register the initial shape or other anatomical structures to patient image data. For example, image registration module 564 may instruct processing circuitry 542 how to register a statistical mean shape (SMS) (e.g., an anatomical shape derived from a population of many people) with the bones of patient imaging data prior to generating the patient-specific shape during the surface fitting process. Patient data 566 may include any type of patient data, such as patient imaging data (e.g., CT scan, X-ray scan, or MRI data), patient characteristics (e.g., age, height, weight), patient diagnoses, patient conditions, prior surgeries or implants, or any other information related to the patient.

As discussed above, surgical lifecycle 300 may include a preoperative phase 302 (FIG. 3). One or more users may use orthopedic surgical system 100 in preoperative phase 302. For instance, orthopedic surgical system 100 may include virtual planning system 102 (with may be similar to system 540) to help the one or more users generate a virtual surgical plan that may be customized to an anatomy of interest of a particular patient. As described herein, the virtual surgical plan may include a 3-dimensional virtual model that corresponds to the anatomy of interest of the particular patient and a 3-dimensional model of one or more prosthetic components matched to the particular patient to repair the anatomy of interest or selected to repair the anatomy of interest. The virtual surgical plan also may include a 3-dimensional virtual model of guidance information to guide a surgeon in performing the surgical procedure, e.g., in preparing bone surfaces or tissue and placing implantable prosthetic hardware relative to such bone surfaces or tissue.

As discussed herein, system 540 may be configured to model a soft-tissue structure of a patient using patient imaging data. For example, system 540 may include a memory (e.g., storage devices 554) configured to store patient-specific image data for the patient (e.g., patient data 566). System 540 also includes processing circuitry 542 configured to receive the patient-specific image data and determine, based on intensities of the patient-specific image data, a patient-specific shape representative of the soft tissue structure of the patient. Processing circuity 542 can then output the patient-specific shape, such as for display or use in further analysis for the patient. For example, processing circuitry 542 may use the patient-specific shape or other characteristics from the patient-specific image data to generate surgical procedure recommendations (e.g., which type of treatment should be performed on a patient) as described herein.

Processing circuitry 542 may determine the patient-specific shape using one or more processes. For example, processing circuitry 542 may receive an initial shape (e.g., a geometric shape or a SMS), determine a plurality of surface points on the initial shape, and register the initial shape to the patient-specific image data. Processing circuitry 542 may register the initial shape by determining one or more muscle insertion points and/or origins on pre-segmented bones in the patient-specific image data or otherwise identifying an approximate location of the soft tissue structure of interest. Processing circuitry 542 may then identify one or more contours in the patient-specific image data representative of a boundary of the soft-tissue structure (which may be based on a separation zone between soft-tissue structures) of the patient and iteratively move the plurality of surface points towards respective locations of the one or more contours to change the initial shape to the patient-specific shape representative of the soft-tissue structure of the patient. In this manner, processing circuitry 542 may generate one or more intermediate shapes as the boundary of the initial shape is iteratively moved towards a closer fit to the contours. The contours may represent a collection of voxels that exceed a certain threshold, or fall within a threshold range, indicative of a boundary of the soft tissue structure.

In some examples, the initial shape and the patient-specific shape are three-dimensional shapes. However, in other examples, the initial shape and/or the patient-specific shape may be defined in two dimensions. A set of several two-dimensional shapes may be used to define an entire volume, or three-dimensional shape, in these examples. In one example, processing circuitry 542 may iteratively move the surface points of the initial shape, and intermediate shapes, in the direction of respective vectors in three dimensions such that processing circuitry 542 processes data in a three-dimensional space. In other examples, processing circuitry 542 may operate in two-dimensional slices to change the initial shape towards the contours in the patient-specific image data. Then, processing circuitry 542 may combine the several two-dimensional slices to generate the full three-dimensional volume of the final patient-specific shape for the patient.

A soft tissue structure may include a muscle, tendon, ligament, or other connective tissue that is not bone. Even though joint replacement treatments may generally involve modification of the bone (e.g., replacing at least a portion of the bone with artificial materials such as metal and/or polymers), soft tissue states may inform what types of replacements may be appropriate for the particular joint being replaced. In this manner, system 540 may analyze the soft tissue of the patient, such as the muscles around the joint, for information that may influence the type of joint replacements. In the case of a shoulder replacement, the soft tissue structures of interest for the joint may include the rotator cuff muscles, such as the subscapularis, supraspinatus, infraspinatus, and teres minor. Other muscles associated with the shoulder, such as the teres major, deltoid, serratus anterior, triceps, and biceps, may be analyzed for shoulder replacement treatment as well. For the purposes of surgical planning, system 540 may determine various characteristics of each soft tissue structure for the purposes of determining to what types of range of motion and/or stresses to which the new repaired joint may be subjected.

In some examples, processing circuitry 542 may determine a type of shoulder treatment for the patient based on various criteria, such as the range of motion of the humerus with respect to the glenoid surface or rest of the scapula. Types of shoulder treatment may include an anatomical shoulder replacement or a reverse shoulder replacement, and processing circuitry 542 may suggest which type of replacement is preferred for the patient based on the soft tissue characteristics. In addition, processing circuity 542 recommend other parameters for the treatment, such as implant placement locations, angles, orientations, type of implant, etc. For example, processing circuitry 542 may determine a fat volume ratio (e.g., fat infiltration value) for the patient-specific shape from the patient-specific image data. Processing circuitry 542 may also determine an atrophy ratio for the patient-specific shape based on an estimated pre-morbid, or previously healthy, state for the soft tissue structure of interest. Processing circuitry 542 can then determine, based on the fat volume ratio and the atrophy ratio of the patient-specific shape of the soft-tissue structure of the patient, a range of motion of a humerus of the patient. For example, higher fat infiltration and atrophy of a muscle may indicate a lower (or narrower) range of motion for the joint. In some examples, the range of motion may be one or more specific angles for respective movements of the joint or a metric or other composite value that represents overall range of motion for the joint. Processing circuitry 542 may determine the range of motion for the joint based on several muscles. For example, processing circuitry 542 may determine one or more range of motion values (e.g., one or more individual angles or one or more composite values representing overall range of motion) of the humerus with respect to the scapula based on fat ratios and atrophy ratios for several respective muscles of the rotator cuff and/or other muscles or connective tissue associated with the shoulder joint. In addition, range of motion may be affected by bone-to-bone collision or other mechanical impingements. From this information, processing circuitry 542 may suggest a type of shoulder treatment for the patient during the preoperative planning phase.

Figure 7:
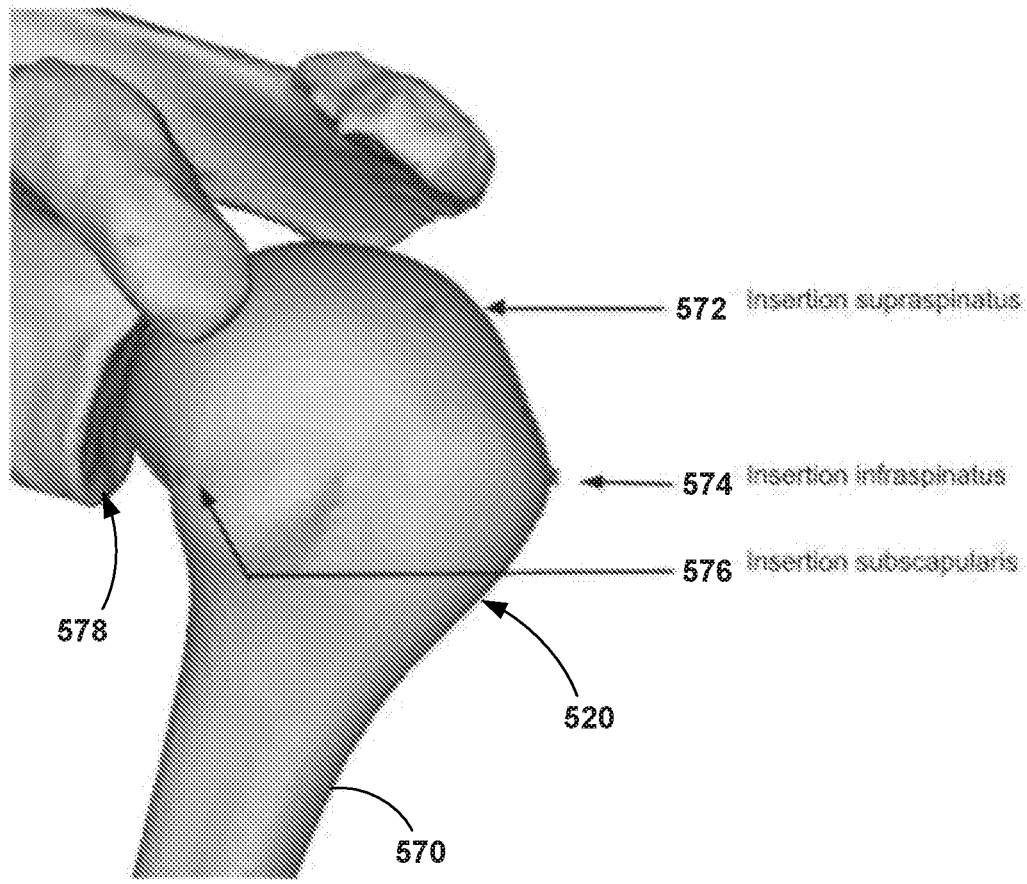
FIG. 7 is an illustration of example insertion points for muscles of a rotator cuff.

FIGS. 7-18B illustrate example steps involved in modeling soft tissue structures of a patient from patient-specific image data. Processing circuitry 542 of system 540 will be described as an example system to perform these processes, but other devices, systems, or combinations thereof may perform similar determinations. FIG. 7 is an illustration of example insertion points for some muscles of a rotator cuff.

As shown in the example of FIG. 7, processing circuitry 542 may initiate soft tissue modeling by registering an initial shape to associated bones of the patient. Glenoid 578 of the scapula is shown in conjunction with humeral head 520 of humerus 570. The bones of the patient may be determined from an automated segmentation process where processing circuitry 542 or another system determines the bones based on intensity values of the patient-specific image data. From these bones, processing circuitry 542 may identify insertion points, or attachment points (or otherwise origins of the muscle), for one or more soft tissue structures of interest for the shoulder joint. In other examples, insertion points or other bone landmarks may be determined directly from the patient-specific image data instead of from bone segmentation. For example, insertion supraspinatus 572 indicates where the supraspinatus muscle is attached to humeral head 520, insertion infraspinatus 574 indicates where the infraspinatus muscle is attached to humeral head 520, and insertion subscapularis 576 indicates where the subscapularis muscle is attached to humeral head 520. Processing circuitry 542 may identify each of these insertion points based on comparison to an anatomical atlas or other instruction based on general human anatomy. In some examples, processing circuitry 542 may determine additional insertion points on the scapula or other bones as additional points for registering the initial shape to the bones of the patient.

As discussed herein, the initial shape that will be transformed and fit to the image data of the patient can start as a geometric shape or a more specific SMS. The SMS may be selected for the general population or selected from a plurality of different SMS based on one or more demographic factors (e.g., sex, age, ethnicity, etc.) for the patient population. In some examples, the SMS may be used because the SMS may more closely match the muscle of the patient. Therefore, processing circuitry 542 may reduce the number of iterations or calculations needed to modify the initial shape and generate the patient-specific shape that fits to the image data. In addition, the SMS may include pre-identified locations which match to the identified insertion points on the associated bones.

Figure 8A:
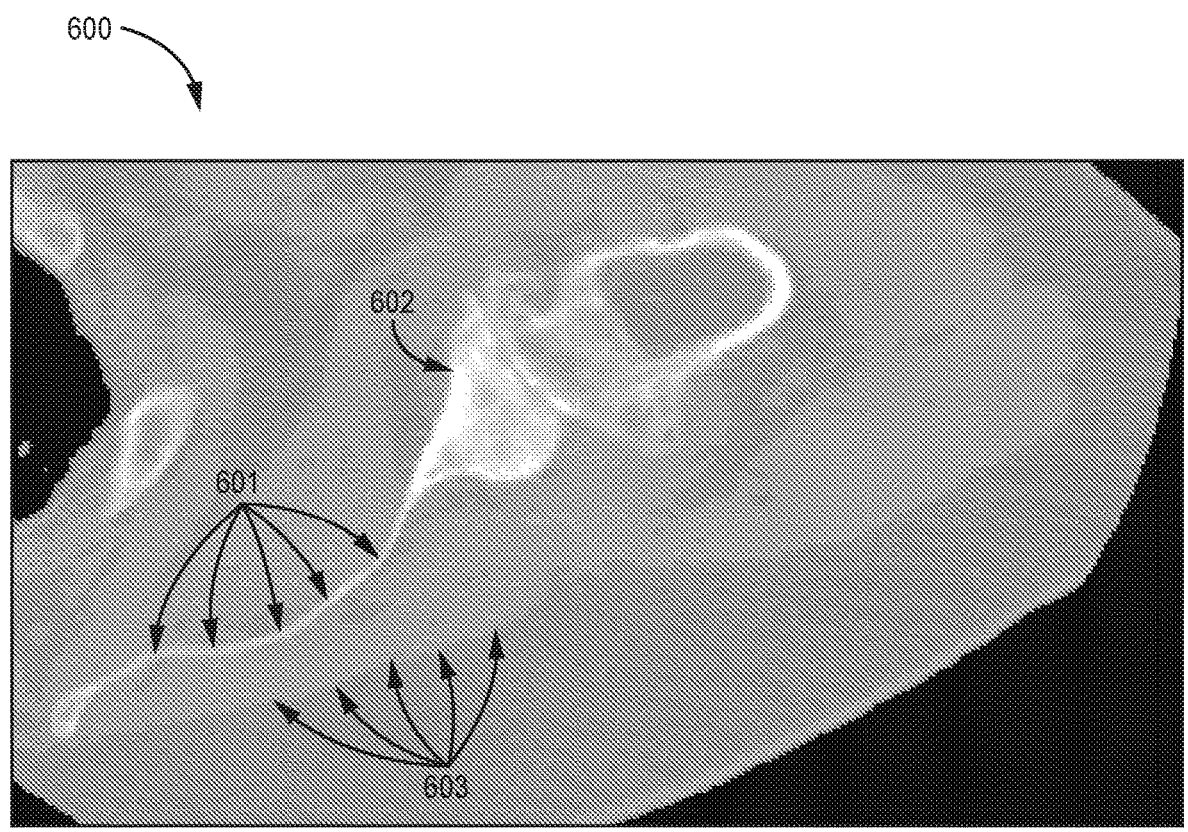
FIG. 8A is a conceptual illustration of example patient-specific image data.

FIG. 8A is a conceptual illustration of example patient-specific image data. As shown in FIG. 8, a two-dimensional image data 600 is shown to illustrate intensities of a CT, or x-ray image. Higher intensities indicate dense tissue that absorbs x-ray energy such as bone in the form of scapula 602. Typically soft tissue structures such as muscle is more difficult to identify in CT data because the tissues absorb x-ray energy at similarly low levels. For example, the infraspinatus muscle may have a boundary partially determined by edge 601 that is an edge of scapula 602 and edge 603 that is the separation zone between the outer edge of the infraspinatus and adjacent fatty tissue layer. Although edge 603 may be difficult to identify from the x-ray data, certain data processing techniques may help to identify edge 603 or separation zones from which edge 603 may be determined.

Figure 8B:
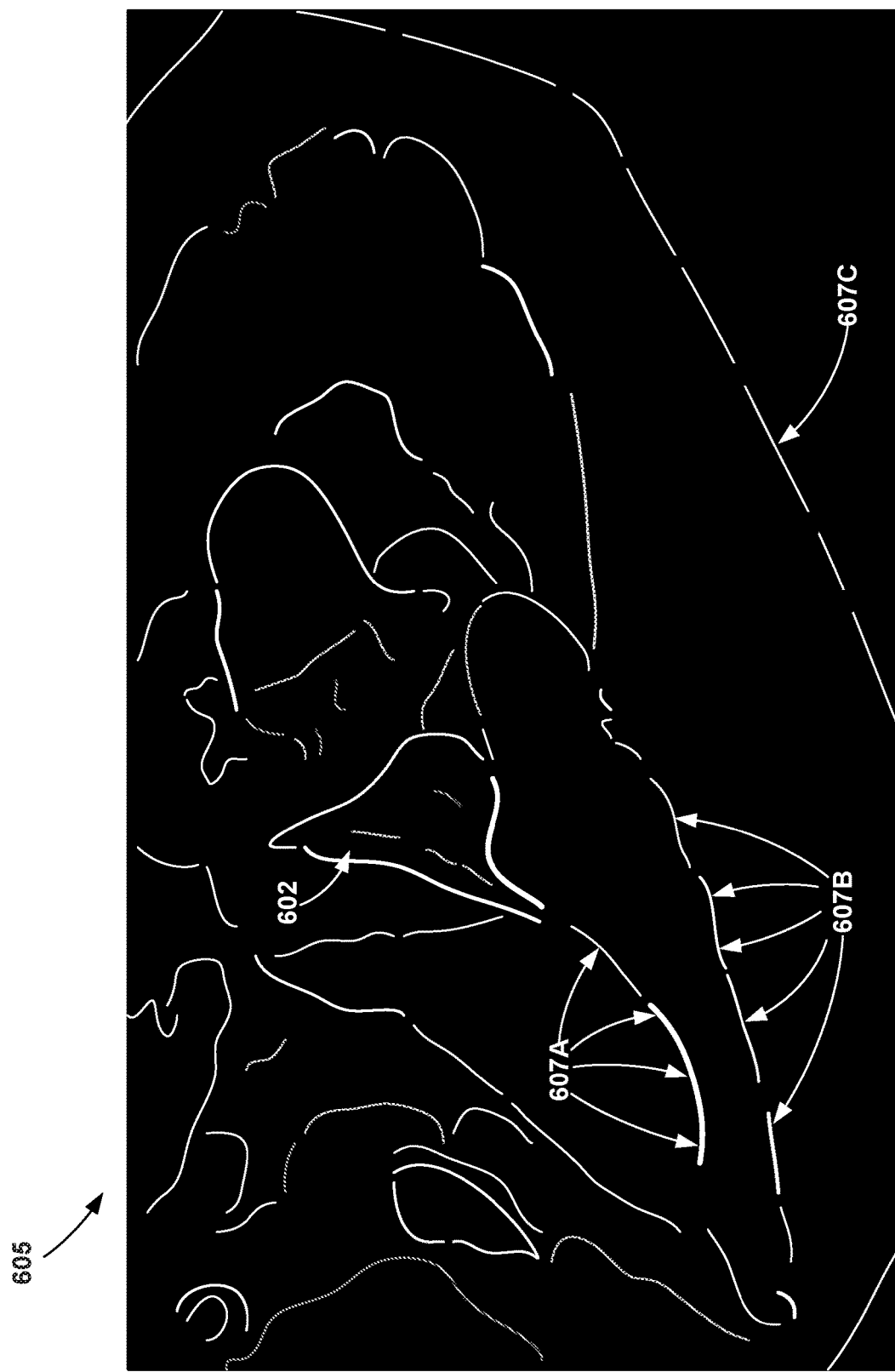
FIG. 8B is a conceptual illustration of a Hessian feature image generated based on the patient-specific image data of FIG. 8A.

FIG. 8B is a conceptual illustration of a Hessian feature image 605 generated based on the patient-specific image data of FIG. 8A. As shown in the example of FIG. 8B, processing circuitry 542 may determine Hessian feature image 605 from the patient-specific CT data, such as image data 600 from FIG. 8A. Hessian feature image 605 is shown as a two-dimensional image, but it may be part of a three-dimensional data field. Hessian feature image 605 indicates regions of the patient-specific CT data comprising higher intensity gradients between two or more voxels in the patient-specific CT data. For example, processing circuitry 542 may compute second derivatives between neighboring voxels, or groups of voxels, to determine the gradients between the voxels or groups of voxels and then generate the Hessian feature image based on the second derivatives. Although the Hessian feature image is described as a three-dimensional image, two-dimensional images may similarly be generated using the same technique.

The Hessian feature image may show separation between two anatomical objects because there is a change in intensity between voxels of these structures, such as between bony objects and soft tissue, between two sets of bony objects that are next to one another, and between two sets of soft tissue that are next one another. Processing circuitry 542 may determine one or more contours, or at least part of a contour, based on the voxel-based separation information (e.g., based on the Hessian feature image).

Although the contour is indicative of separation between anatomical objects, the contour may not provide a complete shape of the anatomical objects. For example, due to imaging imperfections, a lack of intensity gradient between voxels or groups of voxels, or noise, there may be holes, gaps, or other errors that cause discontinuities in the contour representative of the boundary of the anatomical structure (e.g., bone or soft tissue). As one example, the contour may be not be complete and may not be a closed surface representing an anatomical object. In general, the contour may provide an initial estimation of the size, shape, and location of an anatomical object. However, as described in more detail, because the contour is based on image information, and the 2D scans may be imperfect, the contour may be an imprecise indicator of the actual anatomical object (e.g., due holes or other missing portions, as well as protrusions in the contour). Therefore, processing circuitry 542 may use an initial shape that has a closed surface and modify the initial shape to approximate the contour at least partially defined by the Hessian feature image.

Hessian feature image 605 includes several lines of various intensities (e.g., white indicates areas of higher gradients between voxels than dark or black areas). The whiter and broader the line indicates areas of higher gradients. Clavicle 602 can be identified be the lines around the outer surface of clavicle 602 that represent large gradients between voxels having higher intensities from bone and those voxels having lower intensities from soft tissue. As shown in FIG. 8B, the infraspinatus muscle may have a boundary partially determined by contour 607A that is an edge of scapula 602 and contour 607B that is the separation zone between the outer edge of the infraspinatus and adjacent fatty tissue layer. Each of contours 607A and 607B may be identified as running through the middle of the separation zone indicated by the lines of Hessian feature image 605. In this manner, the contours 607A and 607B may indicate correspondences between adjacent structures that may approximate the boundary of each structure.

Each of contours 607A and 607B may be discontinuous, but these contours may be continuous separation zones in other examples. Contours 607A and 607B may then form at least a portion of the contour that represents the boundary of the infraspinatus muscle. In some examples, other separation zones may be used to provide contours for other muscles. For example, Hessian feature image 605 may indicate skin boundaries such as contour 607C that may be used to identify the boundary of those muscles that may typically be located adjacent the skin with minimal fat tissue between the muscle and skin.

Based on Hessian feature image 605, processing circuitry 542 may identify one or more separation zones between the soft-tissue structure and an adjacent soft-tissue structure. In other words, the separation zone may be indicative of intensity gradients between the two soft-tissue structures in the patient-specific image data. Processing circuitry 542 may then determine at least a portion of the one or more contours as passing through the one or more separation zones. The contours may be determined by processing circuitry 542 to pass through the middle of the separation zones or through an intensity-based weighted middle of the separation zones.

Figure 8C:
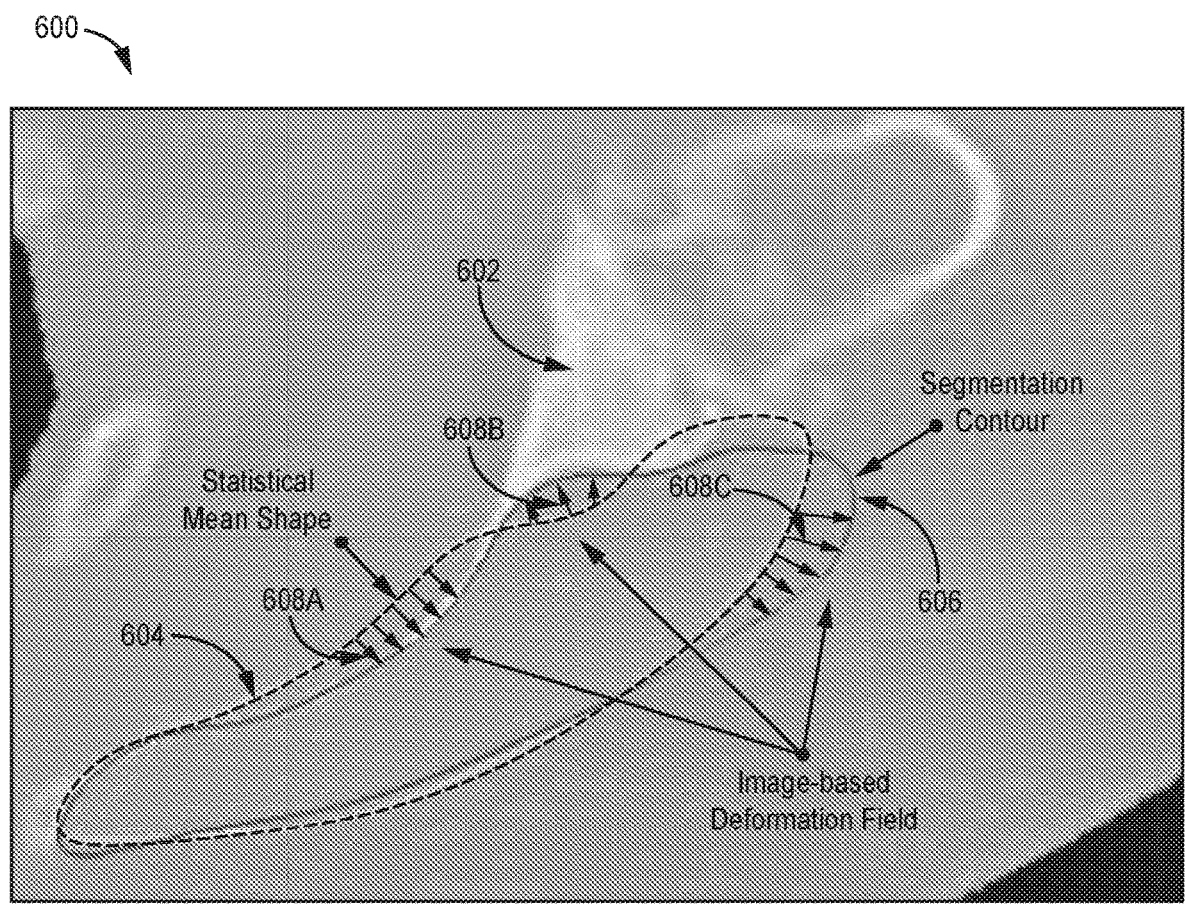
FIG. 8C is a conceptual illustration of an example initial shape and an example contour overlaid on patient-specific image data.

FIG. 8C is a conceptual illustration of an example initial shape 604 and an example segmentation contour overlaid on patient-specific image data. As shown in FIG. 8C, a two-dimensional image data 600 is shown to illustrate the process of modeling a soft tissue structure according to example processes described herein. Although the soft tissue structure of the infraspinatus muscle is shown as an example, the same process may be performed for any soft tissue structure. Although a two-dimensional image is shown in FIG. 8C for illustration purposes, processing circuitry 542 may perform these processes in a three-dimensional space.

An initial shape, such as initial shape 604 illustrated as a broken line, is selected for the soft tissue structure of interest, which is the infraspinatus muscle in this example. Initial shape 604 is then registered to the associated one or more bones, which includes scapula 602. For example, insertion points identified on scapula 602 may be used to match with respective attachment points identified from initial shape 604. Initial shape 604 may be a SMS, which is an anatomical shape representative of the soft tissue structure of a plurality of subjects different than the patient. Since the SMS is specific to the muscle of interest, the initial shape 604 may be similar to the structure of the patient. However, as shown in FIG. 8C, initial shape 604 does not accurately reflect the boundaries of scapula 602 or other intensities of image data 600. Therefore, processing circuitry 542 may deform, or modify, initial shape 604 to fit the image data for that specific patient.

Processing circuitry 542 may, through one or more iterations, move portions of initial shape 604 towards the actual soft tissue structure of the patient as represented by segmentation contour 606 (e.g., similar to the resulting patient-specific shape). As shown by arrow groups 608A, 608B, and 608C (collectively "arrow groups 608"), portions of initial shape 604 are deformed towards the other respective portions of segmentation contour 606. Each of the arrows in respective arrow groups shown in FIG. 8C moves a respective surface point on the surface of initial shape 604 at least a part of the way toward segmentation contour 606 during one iteration. In this manner, after two or more iterations, processing circuitry 542 may deform initial shape 604 to fit with segmentation contour 606. For example, the portion of segmentation contour 606 moved in the direction of arrow group 608B fit to a portion of scapula 602. The portions of initial shape 604 moved in the direction of arrow group 608A and arrow group 608C also now fit the contours of the soft tissue structure as indicated by the intensities of the image data 600. This process may be referred to as closed surface fitting in some examples.

In some examples, processing circuitry 542 may receive segmentation contour 606 which is an initial analysis of the patient-specific image data to generate the representation of the soft tissue structure of interest, such as the infraspinatus muscle. Segmentation contour 606 may be a three-dimensional shape or a plurality of two-dimensional slices, for example. However, segmentation contour 606 may not be a complete model representing the soft tissue structure. For example, various voxels in the image data may be inaccurate or missing, and the resulting segmentation contour 606 may not be complete. For example, segmentation contour 606 may be at least partially determined by contours identified from the separation zones from a Hessian feature image. Therefore, deforming a completely closed SMS or geometric shape to fit to image data 600 may result in a complete model of the soft tissue structure.

Figure 9:
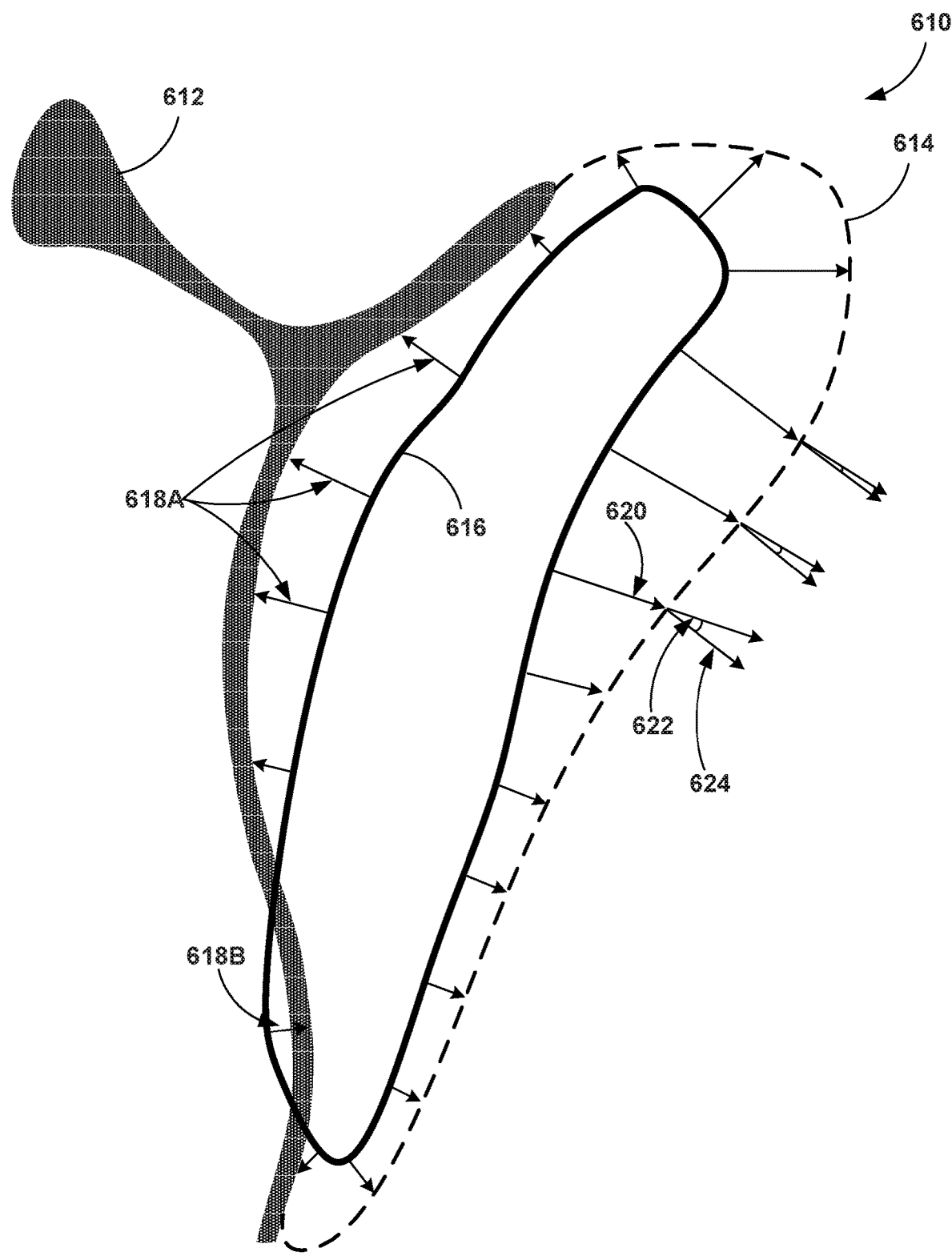
FIG. 9 is a conceptual illustration of an example procedure to alter an initial shape toward a patient-specific shape representative of a soft-tissue structure of a patient.
Figure 10:
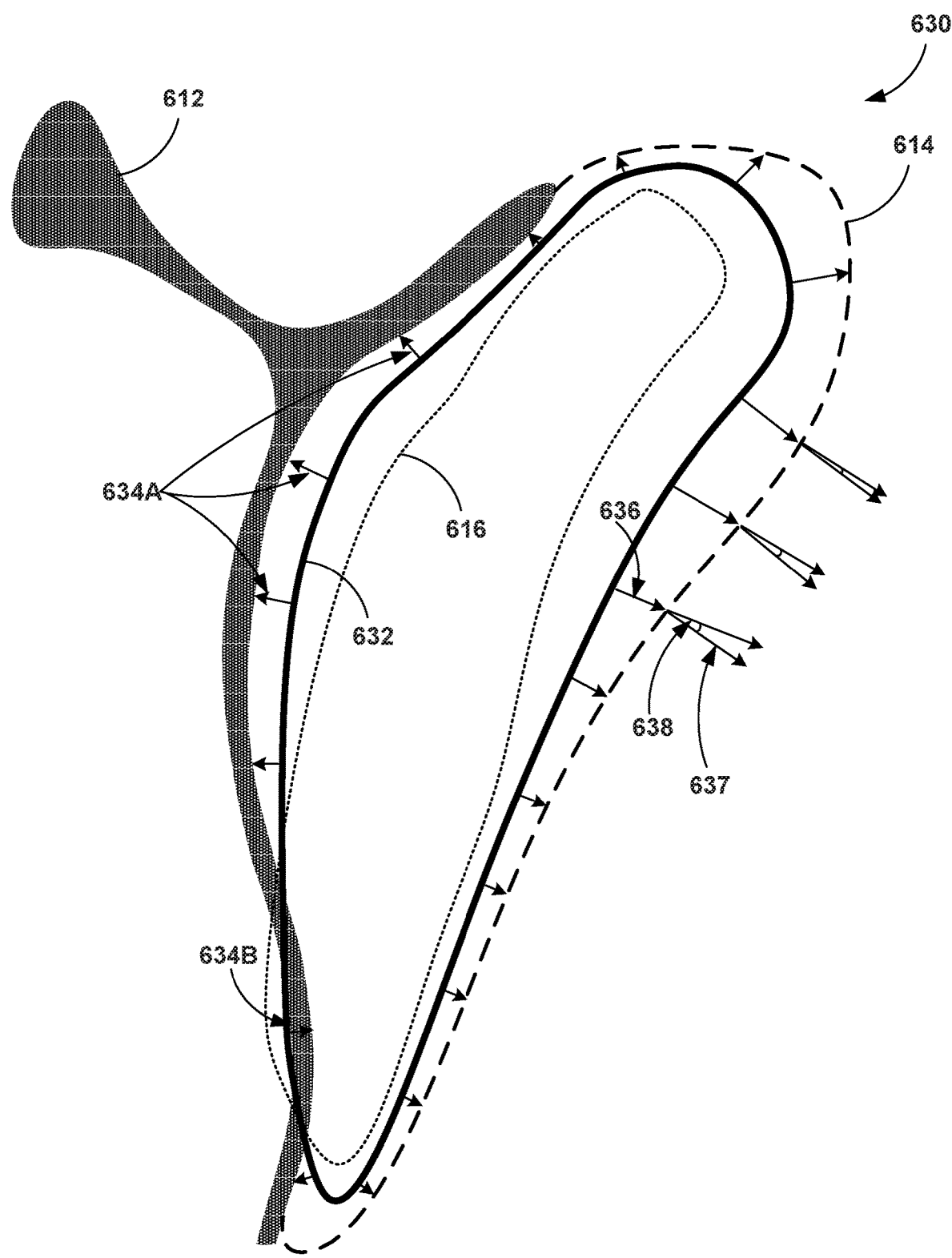
FIG. 10 is a conceptual illustration of an example procedure to alter an intermediate shape toward a patient-specific shape representative of a soft-tissue structure of a patient.
Figure 11:
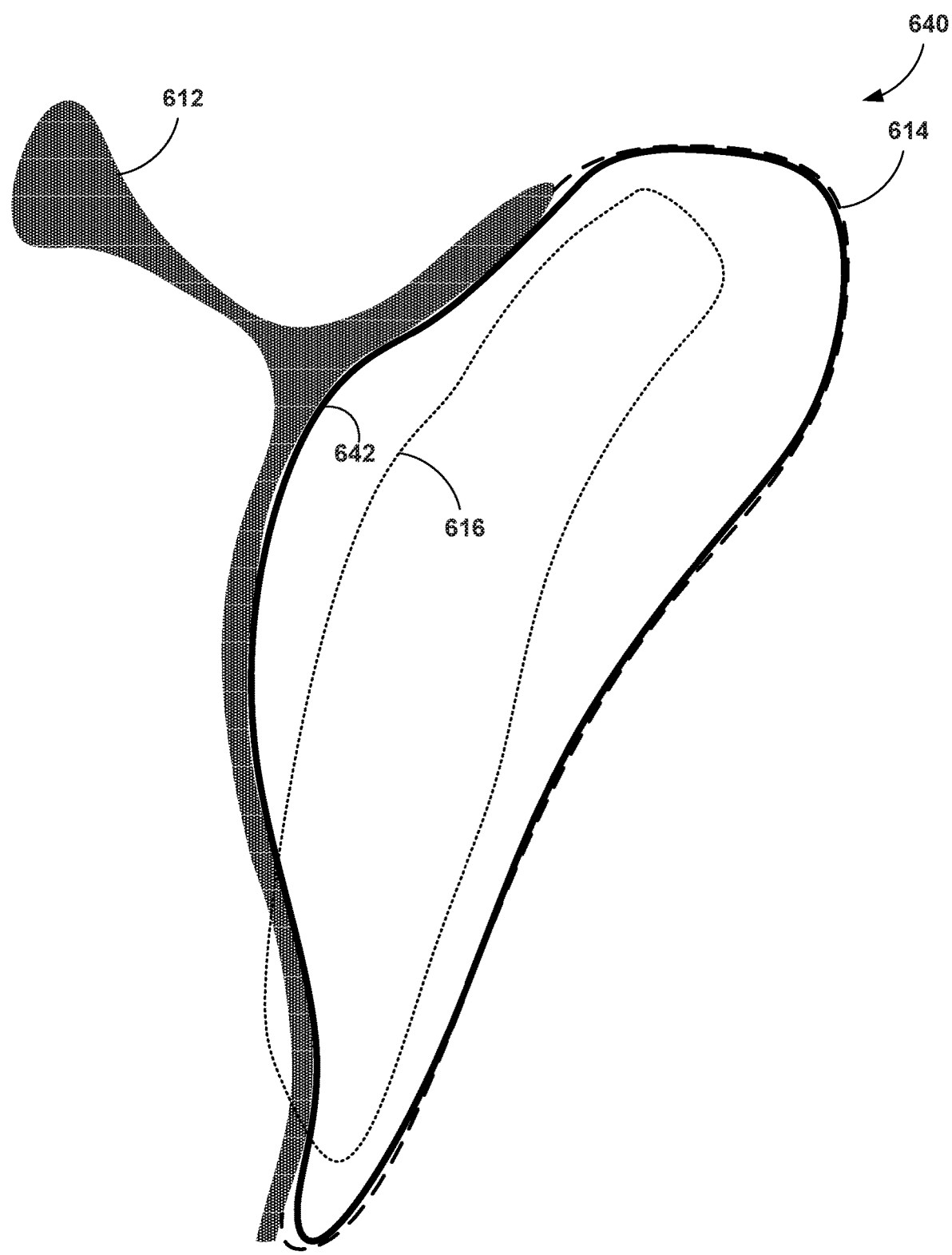
FIG. 11 is a conceptual illustration of an example patient-specific shape representative of a soft-tissue structure of a patient in comparison to actual contours in the patient-specific image data.

In other examples, processing circuitry 542 may not receive any segmentation contour 606 for the soft tissue structure. Instead, processing circuitry 542 may place the initial shape according to insertion points on associated bones within the patient-specific image data. Then, processing circuitry 542 may extend vectors from various locations on the surface of the initial shape towards respective voxels that exceed a threshold intensity, differ from surrounding voxels by a predetermined value or percentage, or otherwise indicate the edge of the soft tissue structure or bone in image data 600. These voxels that exceed the threshold intensity, for example, may together form the one or more contours of the soft tissue structure represented by the patient-specific image data. Or, as discussed herein, the contours representative of the edge of the soft tissue structure may be determined based on the gradients between voxels such as in a Hessian feature image. Therefore, after one or more iterations deforming the initial shape 604 towards the identified voxels that exceed the threshold or exceed a relative change in voxel intensity, the initial shape 604 may then be transformed into the patient-specific shape that represents the soft tissue structure of the patient. The patient-specific shape may thus be a model of that structure for the patient, and various characteristics such as volume, length, etc. may be calculated by processing circuitry 542. FIGS. 9-11 show an example process for determining the patient-specific shape from patient-specific image data by iteratively moving points on the surface of an initial shape.

FIG. 9 is a conceptual illustration of an example procedure to alter an initial shape 616 toward a patient-specific shape 614 representative of a soft-tissue structure of a patient. The example of FIG. 9 indicates sagittal view 610 of patient image data, initial shape 616, and scapula 612. Initial shape 616 may be placed and deformed to represent the soft tissue structure of the subscapularis, which may be similar to contour 614 indicated by the dotted line. Processing circuitry 542 registers initial shape 616 within the image data by registering a plurality of locations on initial shape 616 to corresponding insertion locations on the one or more bones identified in the patient image data. For example, initial shape 616 may be registered to insertion locations on scapula 612. This registration may not require any part of initial shape 616 to actually touch scapula 612, but the registration uses the insertion locations on scapula 612 as guides to where to register initial shape 616 within the patient-specific image data. Initial shape 616 is shown as an SMS to approximate the structure of the patient. In other examples, a geometric shape such as a sphere, ovoid, or other structure may be used as the initial shape 616.

Since initial shape 616 needs to be deformed, or modified, processing circuitry 542 can move portions of initial shape 616 as needed towards voxels of the image data representing a surface of the soft tissue structure. For example, processing circuitry 542 may select a plurality of surface points on initial shape 616. Each of vectors 618A and 618B (collectively "vectors 618") extend from respective surface points on initial shape 616 and in a direction normal from the surface of initial shape 616. Processing circuitry 542 may extend the vectors 618 inside and outside of initial shape 616, which may enable processing circuitry 542 to identify the contours of the soft tissue structure which may reside outside or inside of initial shape 616 depending on where initial shape 616 was initially registered to the imaging data. For example, vector 618B is directed inward from the surface of initial shape 616 because a portion of scapula 612 resides within initial shape 616. Conversely, vectors 618A around the rest of initial shape 616 end up directed outward from the surface of initial shape 616.

Processing circuitry 542 thus can use the vectors 618 to identify the one or more contours corresponding to the edges of the soft tissue structure, as indicated by contour 614 and a surface of scapula 612. For example, processing circuitry 542 may extend, from each surface point (e.g. the point at the base of each of vectors 618) of the plurality of surface points on initial shape 616, a respective vector 618 at least one of outward from or inward from the respective surface point. Processing circuitry 542 then can determine, for the vector from each surface point, a respective location in the patient-specific image data at which voxel intensity exceeds a threshold intensity value. These respective locations for at least one surface point of the plurality of surface points at least partially define the one or more contours. In other words, for each vector of vectors 618, the voxel or pixel that includes an intensity value exceeding the threshold intensity value may be determined to be a part of contour 614 or an adjacent bone to the soft tissue structure. In other examples, processing circuitry 542 may receive contour 614 from prior segmentation of the image data indicating the soft tissue structure of the patient, or the Hessian feature image may be used to determine at least part of contour 614 that may be identified from separation zones in the Hessian feature image. However, processing circuitry 542 may still deform the initial shape 616 towards the known contour in order to generate a fully closed surface model of the soft tissue structure of interest. This fully closed surface model may also be pre-labeled (e.g., the initial shape 616 may be pre-labeled) as which portions should be facing bone or which portions should be adjacent another specific muscle. This labeling may enable or initiate further segmentation of the soft tissue structures.

As discussed above, the location in the patient-specific image that each of vectors 618 may be looking for may be based on the separation zone and contour determined from the Hessian feature image. In other example, processing circuitry 542 may determine the respective location in the patient-specific image data at which voxel intensity exceeds the threshold intensity value by determining the respective location in the patient-specific image data greater than, or less than, a predetermined intensity value. In other words, the intensity may exceed (e.g., become higher than) a high threshold intensity value indicating that the voxel is representative of bone or exceed (e.g., become lower than) a low threshold intensity value indicating the voxel is representative of fluid, fatty tissue, or other tissue indicative of a boundary of the soft tissue structure. For example, the threshold intensity value may be representative of a bone intensity. Once the vector reaches the location of bone, processing circuitry 542 infers that location as the boundary of the soft tissue structure because the soft tissue (e.g., muscle) resides against that bone surface. The threshold intensity value may also be set to a structure other than a muscle to identify that the vector has left the volume of the soft tissue structure. In other examples, the threshold intensity value may be less than the expected intensity values of muscle. For example, once the threshold intensity in the path of the vector is reduced below the threshold intensity value, processing circuitry 542 may interpret that lower intensity value as fluid or other structure different than the soft tissue structure of interest. The threshold intensity value may be a predetermined magnitude in some examples.

In other examples, the threshold intensity value may be a difference value calculated based on where the vector originated and/or previous voxel(s) or pixel(s) recently crossed by the vector. In this manner, processing circuitry 542 can identify relative changes in the intensity of the patient image data (e.g., voxel-to-voxel changes) or a filter mask that may indicate a boundary to the soft tissue structure or other structure that correlates with a portion of contour 614 for the soft tissue structure of interest. For example, processing circuitry 542 may be configured to determine the respective location in the patient-specific image data exceeding the threshold intensity value by determining the respective location in the patient-specific image data greater than a difference threshold between an intensity associated with the respective surface point and an intensity of the respective location in the patient-specific image data. In some examples, processing circuitry 542 may employ one or more of these types of thresholds when analyzing image data for boundaries to the soft tissue structure of interest.

Generally, processing circuitry 542 may identify, for each vector, the respective location in the patient-specific image data which is representative of the boundary to the soft tissue structure. However, in some examples, processing circuitry 542 may not identify a voxel or pixel exceeding the threshold intensity value. This issue may be caused by incomplete information in the patient-specific image data, corruption of the data, patient movement during generation of the data, or any other types of anomalies. Processing circuitry 542 may employ an algorithm to avoid such problems with the deformation process for initial shape 616. For example, processing circuitry 542 may employ a maximum distance in the image data for which to identify the voxel or pixel exceeding the threshold intensity value. The maximum distance may be a predetermined distance or scaled distance from the point on the initial shape 616 from which the vector begins. Maximum distances may be selected in a range from approximately 5 millimeters (mm) to approximately 50 mm. In one example, the maximum distance may be set to approximately 20 mm.

If processing circuitry 542 does not identify a voxel exceeding the threshold intensity value within that distance from an origin of the vector, processing circuitry 542 may remove that vector and a respective point on the surface of initial shape 616 from the deformation process and simply rely on the other points and vectors for deformation. Alternatively, processing circuitry 542 may select a new surface point from the initial shape 616 and extend a new vector from that new surface point in an attempt to find a voxel exceeding the threshold intensity value or to find a voxel that corresponds to the contour or boundary of the soft-tissue structure determined from the Hessian feature image. This new surface point on the surface of initial shape 616 may be within or at a predetermined distance from the removed surface point, at a predetermined distance between the removed surface point and another surface point, or at some other location on initial shape 616 that processing circuitry 542 selects to replace the removed surface point.

Processing circuitry 542 may then use one or more iterations of deforming the surface of initial shape 616 to approach, or fit, the closed initial shape 616 to contour 614 and the portions of scapula 612. During each iteration, processing circuitry 542 may move some or all of the surface points on initial shape 616. For example, processing circuitry 542 may extend, from each surface point of the plurality of surface points, a respective vector 618 from a respective surface point and normal to a surface of initial shape 616 comprising the respective surface point. As discussed above, these vectors may be directed inward and/or outward from the surface of initial shape 616. Processing circuitry 542 may then determine, for the respective vector 618 from each surface point, a respective point in the patient-specific image data exceeding a threshold intensity value. These points exceeding the threshold intensity value may form one or more contours similar to contour 614 and/or a surface of a bone.

At each respective point of contour 614, processing circuitry 542 may determine a plurality of potential locations within an envelope of the respective point and exceeding the threshold intensity value in the patient-specific image data. In this manner, the plurality of potential locations for this single vector at least partially define the surface of contour 614. These potential locations within the envelope indicate the potential direction in which the surface point on initial shape 616 should move. Processing circuitry 542 will select one of these potential locations to guide movement of the respective surface point in order to account for how the surface of the contour at those potential locations is oriented with respect to the surface point on initial shape 616. In other words, processing circuitry 542 may select a potential location with a reduced difference between the orientation of the surface of the initial shape 616 and the orientation of the surface of contour 614 at that potential location.

For example, processing circuitry 542 may determine, for each of the plurality of potential locations, a respective normal vector normal to the surface. For the example of vector 620 from a respective surface point on the surface of initial shape 616, several normal vectors are generated from each of the potential locations. One example normal vector is vector 622 from one of the potential locations. Then, processing circuitry 542 may determine, for each of the respective normal vectors, an angle between the respective normal vector and the vector from the respective surface point. Using the example of vector 624, processing circuitry 542 may determine the angle 622 between vector 624 and vector 620. This angle 622 may be referred to as the cosine angle. Processing circuitry 542 may perform this calculation for each potential location corresponding to the respective vector 618, such as the example vector 620.

Then, processing circuitry 542 may select, for each respective surface point from initial shape 616, one potential location of the plurality of potential locations that has a smallest angle between the vector from the respective surface point (e.g., vector 620) and the respective normal vector from each of the plurality of potential locations (e.g., vector 624). In other words, processing circuitry 542 may identify the location on contour 614 that provides for the appropriate movement of the surface point and deformation of the surface point. Then, processing circuitry 542 can move, for each respective surface point, the respective surface point at least partially towards the selected one potential location. This moving of the respective surface points modifies, or deforms, initial shape 616 towards the patient-specific shape which would correspond to contour 614 and a portion of scapula 612. Processing circuitry 542 may repeat this process for every iteration until initial shape 616 has been deformed to approximate the voxels or pixels exceeding the threshold intensity values or corresponding to previously segmented boundaries of the soft tissue structure of interest.

Processing circuitry 542 may move the respective surface point at least half of a distance between the respective surface point and the selected one potential location corresponding to contour 614. However, the moved distance may vary in other situations or iteration in the process. The surface points may not be moved completely towards the potential locations because the resulting deformation in a single step may not generate an accurate final patient-specific shape. In other words, minor adjustments to the selected locations on contour 614 based on the normal vector for each potential location in each iteration may provide a more closely matched final shape to contour 614. In other words, each surface point on initial shape 616 may not necessarily move in a completely linear direction throughout all of the iterations. This non-linear combination of movements for each surface point may allow the final patient-specific shape to more closely match, or fit, contour 614 and, if appropriate, adjacent bone surfaces.

As shown in the sagittal view 640 of FIG. 10, initial shape 616 from FIG. 9 has been deformed during one iteration to intermediate shape 632, which is closer to contour 614 than initial shape 616. When processing circuitry 542 determines that intermediate shape 632 still does not approximate contour 614 or otherwise requires additional deformation, processing circuitry 542 may perform one or more additional iterations of deformation. For example, processing circuitry 542 may determine vectors 634A and 634B (collectively "vectors 634") from the respective surface points on intermediate shape 632. Vector 634B is directed inward toward the surface of scapula 612, and vectors 634B are directed outward toward portions of scapula 612 and contour 614, similar to vectors 618 described above with respect to FIG. 9.

Processing circuitry 542 then determines another set of potential locations for each of vectors 634 at the point at which the respective vector reaches a voxel or pixel exceeding the threshold intensity value. From each of the potential locations for each vector 634, processing circuitry 542 may select the potential location having a normal vector with a smallest angle when compared with the vector from the surface point. For example, with respect to the example vector 636 from its surface point on intermediate shape 632, processing circuitry 542 may determine a vector 637 as one vector from one of the potential locations in contour 614 within the envelope from the point in contour 614 at which vector 636 reached contour 614. Processing circuitry 542 may select the potential location associated with vector 637 when angle 638 is the smallest angle between the vector from intermediate shape 632 and the normal vectors from the potential locations. In this manner, processing circuitry 542 may select locations on contour 614 that are different than the point at which vectors 634 reach contour 614 for at least some of vector 634. This process enables processing circuitry 542 to more closely approximate contour 614 by moving the surface points on intermediate 632 in a direction other than the direction normal to the surface at that respective surface point.

Processing circuitry 542 may then move the surface points of intermediate shape 632 at least partially towards the selected potential locations on contour 614. For example, processing circuitry 542 may deform intermediate shape 632 into the final patient-specific shape 642 that is fully enclosed as shown in FIG. 11. As shown in FIG. 11, patient-specific shape 642 may approximate the contour 614 and at least some surfaces of scapula 612 against which the soft tissue structure is disposed for the patient. Patient-specific shape 642 may be exactly the same or similar to contour 614 in some examples. Contour 614 may represent an initial segmentation of the soft tissue structure in the patient-specific image data and/or a surface representing the supra-threshold voxels that were identified from each vector. In other examples, processing circuitry 542 may deform the initial shape 616 more than two times before arriving at the final patient-specific shape 642. In some examples, processing circuitry 542 may perform a predetermined number of iterations in order to approximate the contours of the voxels or pixels exceeding the threshold intensity values. In other examples, processing circuitry 542 may continue to perform additional iterations of the deformation of the initial shape until a certain number, certain percentage, or all, of the surface points of the shape are within a predetermined distance of the threshold-exceeding voxels or pixels. In other words, processing circuitry 542 may continue to deform the initial shape, and intermediate shapes thereof, until the deformed shape is within some acceptable allowance, or error, from the contours within the patient-specific image data.

In some examples, processing circuitry 542 may follow the same instructions for the deformation in each iteration. Alternatively, processing circuitry 542 may adjust one or more factors that determine how processing circuitry 542 moves surface points of a shape during an iteration of the deformation process. For example, these factors may specify the number of surface points from the initial shape, or intermediate shape, the number of potential locations identified within the contour, the envelope size from which potential locations can be selected for each vector from surface points, the distance each surface point can move within one iteration, an allowable deviation that each surface point can move with respect to each other within one iteration, or other such factors. These types of factors can limit the extent to which processing circuitry 542 can deform the initial or intermediate shape for a single iteration.

For example, processing circuitry 542 may deform an initial shape in a more uniform manner and deform an intermediate shape in a less uniform manner in order to more closely approximate the actual dimensions of the soft tissue structure as identified in the image data. In one example, processing circuitry 542 may be configured to iteratively move the plurality of surface points towards respective potential locations of the one or more contours (e.g., contour 614) by moving, in a first iteration from initial shape 616, each surface point of the plurality of surface points a first respective distance within a first tolerance of a first modification distance to generate a second shape (e.g., intermediate shape 632). The first tolerance may be selected by processing circuitry 542, a user, or otherwise predetermined, to maintain smoothness of the second shape within respect to the initial shape 616. In other words, the tolerance may be an allowed deviation from a value. The tolerance could be as low as zero such that all surface points must move the same distance. However, the tolerance could be larger to allow processing circuitry 542 to vary the distances each surface point can be moved within the iteration.

Processing circuitry 542 may then move, in a second iteration following the first iteration, each surface point of the plurality of surface points of the second shape a second respective distance within a second tolerance of a second modification distance to generate a third shape (e.g., another intermediate shape or a final shape) from the second shape. In this second iteration, the second tolerance is larger than the first tolerance such that the distances each surface point moves can vary more than the variation allowed in the prior iteration. In this manner, the smaller tolerance may promote smoothness in the deformation of the shape, while larger tolerances may promote more precision in how close the next deformed shape approximates the soft tissue structure. Generally, processing circuitry 542 may increase the tolerance on the modification distance of surface points between iterations. However, in some examples, processing circuitry 542 may switch between increasing or decrease the tolerance, or processing circuitry 542 may maintain the tolerance at the same value for each iteration. Put another way, the elasticity of later iterations may increase such that each surface point can move more closely to their correspondence point (e.g., towards the contour representing the boundary of the soft-tissue structure. In addition, the search distance may decrease for each iteration because the system becomes more confident of the correspondence to the contour 614. For more confident correspondences, such as to portions of contour 614 associated with bone structures, the system may user higher iterations that provide more elastic, or tolerance, movements for each surface point on initial shape 616. In contrast, portions of contour 614 associated with other soft tissue may require initial iterations that have lower elasticity because the correspondences to contour 614 are less confident.

In some examples, this process of registration and modification may be similar to a B-Spline algorithm. The internal parameters of a B-Spline algorithm may include the spline order, the number of control points, and the number of iterations for modification of the shape. The first two parameters of the spline order and number of control points can control the degree of "elasticity" of the algorithm. The higher spline order and number of control points, the more elastic behavior occurs for each surface point on the shape. In other words, later iterations result in more specific solutions for modified shape as long as the confidence of the correspondences to the contour remains high.

In one example, for the first iteration, the algorithm can divide the space of the initial shape 616 into a number of surface points. Processing circuitry 542 may determine a deformation field is based on these surface points and the spline order using a spline relationship. For further iterations, the number of surface points can be duplicated, tripled, and so forth, to enable more specific deformation fields for the changing initial shape 616. Each "iteration" may refer to an inner iteration of the B-Spline algorithm. Processing circuitry 542 may user outer iterations to perform registration of the initial shape, or modified shape, and with "N" inner iterations. "N" may be increased in conjunction with outer iteration in order to enable more elastic output. One example way in which to processing circuitry 542 performs the B-Spline registration is described in Lee et. al "Scattered Data Interpolation with Multilevel B-Splines" IEEE Transactions on Visualization and Computer Graphics, Vol. 3, No. 3, July-September 1997. Additional example ways in which to perform the b-spline registration may be found in https://itk.org/Doxygen411/html/classitk_1_1BSplineScatteredDataPointSetToImageFilter.html and http://www.insight-journal.org/browse/publication/57.

In some examples, processing circuitry 542 may move surface points of the initial shape or intermediate shape a greater distance, or the full distance, towards a contour based on the identified intensity value of the voxel or pixel at that location. For example, high intensity voxels may indicate the presence of bone. Generally, soft tissue structures may be disposed against a portion of bone. Therefore, if the voxel is identified to be bone, processing circuitry 542 may move the respective surface point of the initial shape or intermediate shape directly to, or adjacent to, the identified bone structure. In other examples, processing circuitry 542 may increase the tolerance of the modification distance when bone is identified as part of the contour to enable the next iteration to more precisely approximate the contour of the bone. In other examples, as discussed herein, the contour 614 may be determined based on the Hessian feature image representing separation zones between adjacent structures. In some examples, processing circuitry 542 may track the profile behavior of the Hessian feature image along the vector in order to determine the correspondence to the border of the soft-tissue structure. The Hessian feature image may include a profile similar to a rectangle-like function that provides a voxel for correspondence for the vector. For bone structures, processing circuitry 542 may know the voxel of the bone surface in order to move the surface point directly to that voxel.

Once the final patient-specific shape 642 is determined, processing circuitry 542 may output that patient-specific shape 642. In some examples, processing circuitry 542 may control the patient-specific shape 642 to be displayed to a user. In other examples, processing circuitry 542 may perform additional calculations on patient-specific shape 642. For example, processing circuitry 542 may determine, a volume, linear dimensions, cross-sectional dimensions, or other characteristics of the patient-specific shape 642. Processing circuitry 542 may use these characteristics in other determinations as described herein.

Figure 12:
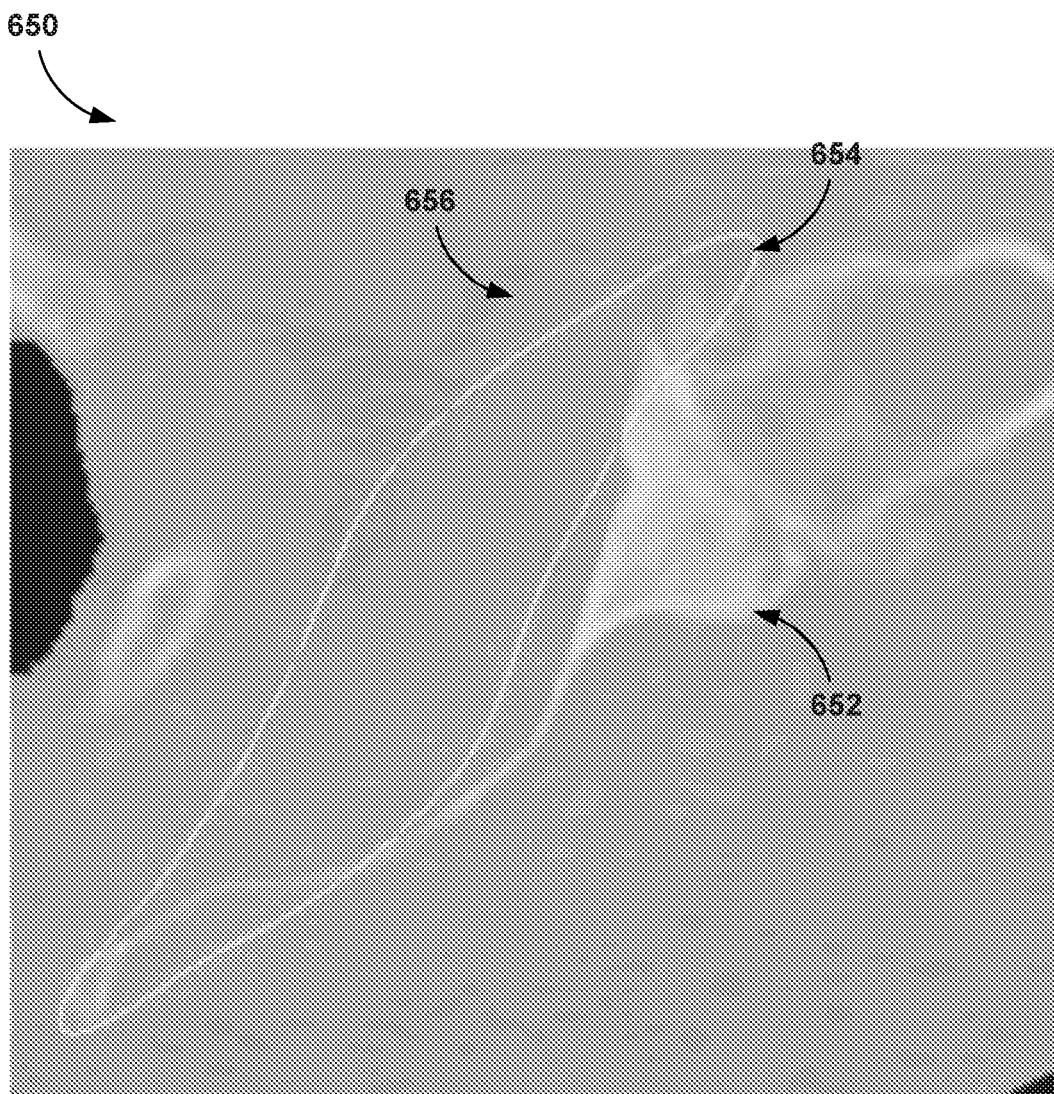
FIG. 12 is a conceptual illustration of an example initial shape and a patient-specific shape representative of a subscapularis muscle overlaid on patient-specific image data.
Figure 13:
FIG. 13 is a conceptual illustration of an example initial shape and a patient-specific shape representative of a supraspinatus muscle overlaid on patient-specific image data.

FIGS. 12-18 illustrate example modeling of rotator cuff muscles based on the deformation processes described herein. In some examples, a system, such as system 540, may display similar images to a user via a user interface. Some views are two-dimensional while other views are three-dimensional of the same modeled structures. FIG. 12 is a conceptual illustration of an example axial view 650 of patient image data, which includes scapula 652. Initial shape 654 represents an SMS for the subscapularis muscle, which has been deformed into patient-specific shape 656 that is representative of the subscapularis muscle of the patient. FIG. 13 is a conceptual illustration of an example sagittal view 660 of patient image data which includes scapula 662. Initial shape 664 represents an SMS for the supraspinatus muscle, which has been deformed into patient-specific shape 666 that is representative of the supraspinatus muscle of the patient.

Figure 14:
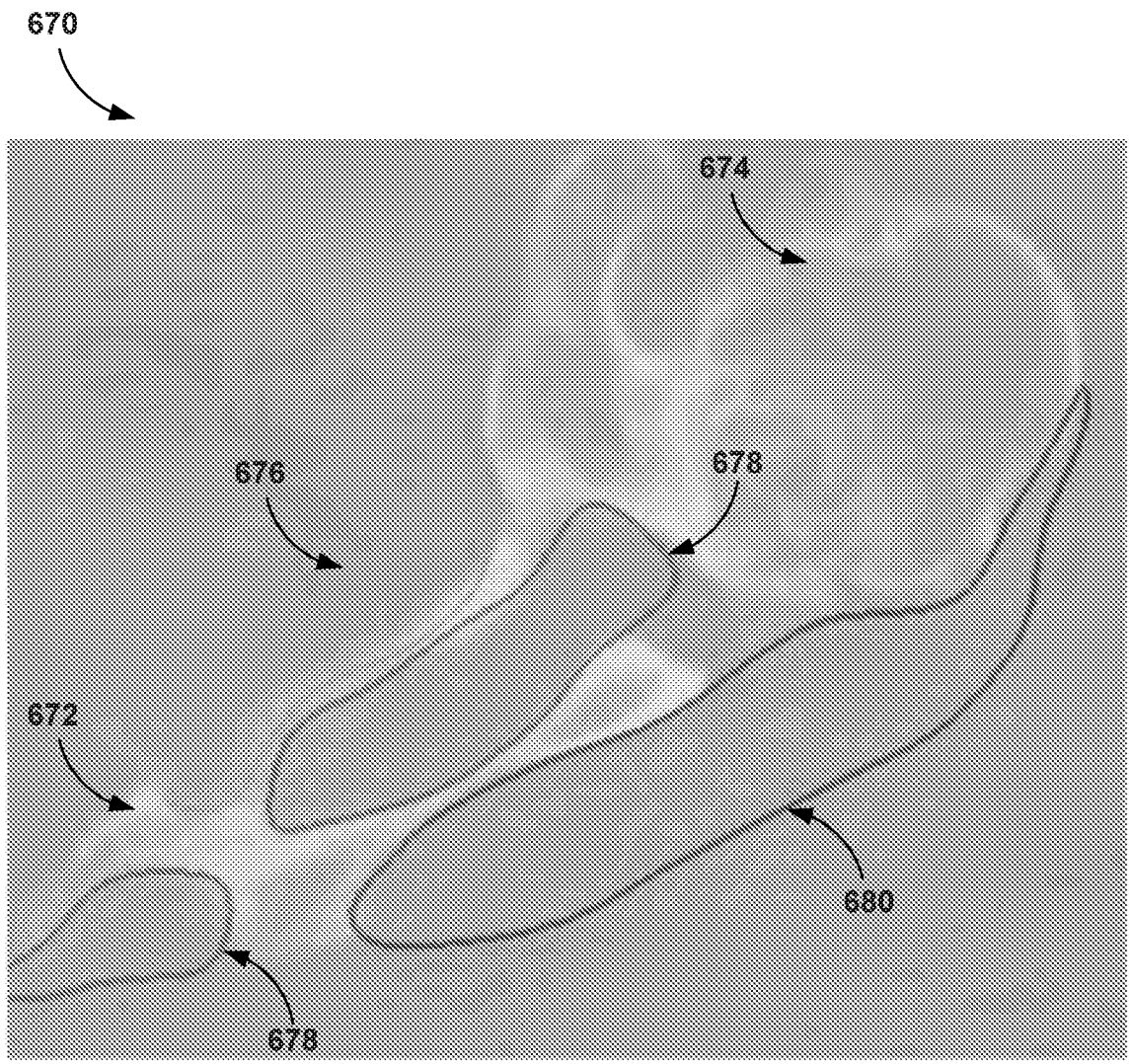
FIG. 14 is a conceptual axial view of example final patient-specific shapes representative of the rotator cuff muscles overlaid on patient-specific image data.
Figure 15:
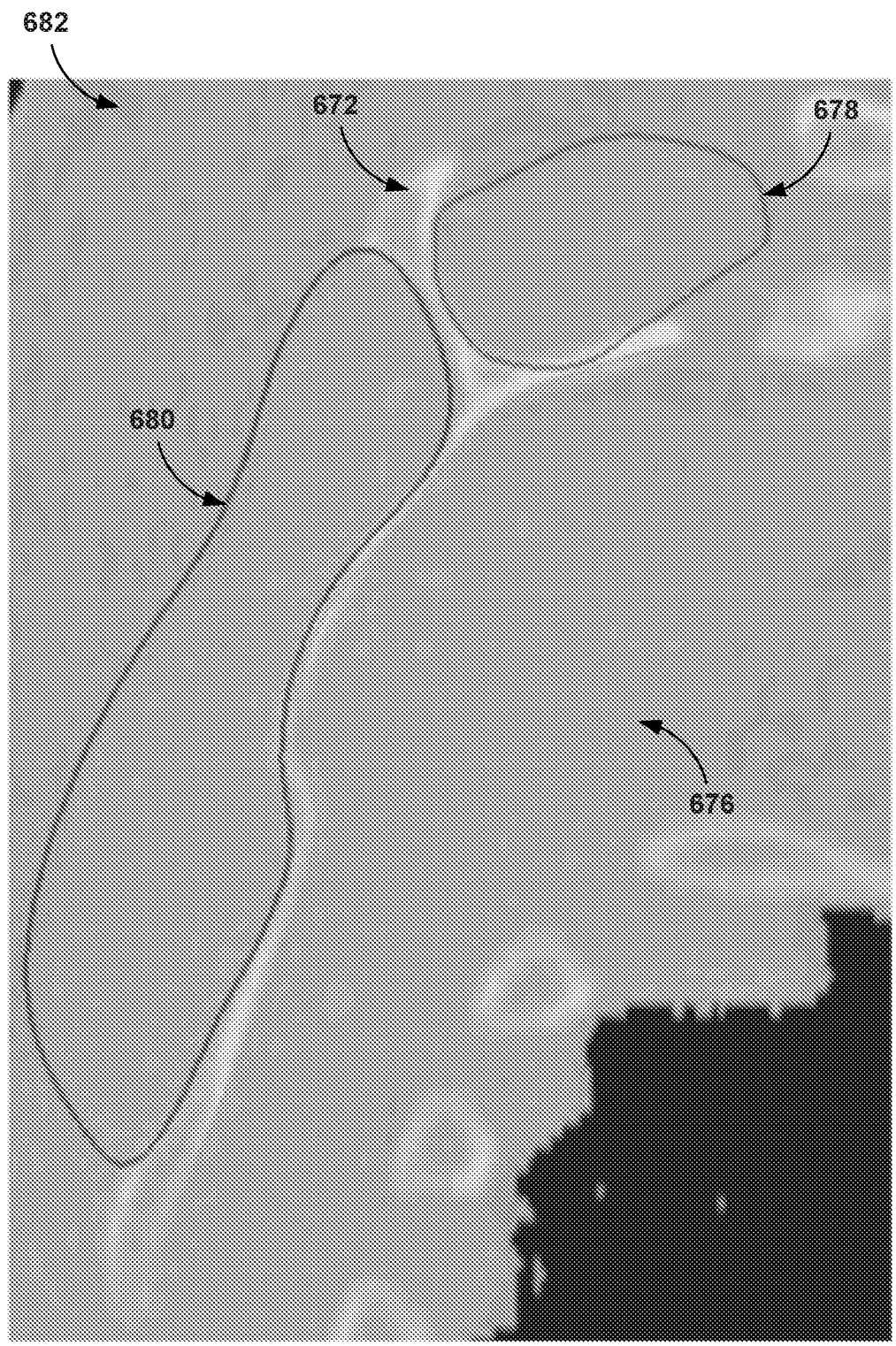
FIG. 15 is a conceptual sagittal view of example final patient-specific shapes representative of the rotator cuff muscles overlaid on patient-specific image data.

FIG. 14 is a conceptual axial view 670 of example final patient-specific shapes 676, 678, and 680 representative of the three rotator cuff muscles overlaid on patient-specific image data. As shown in FIG. 15, scapula 672 is shown with respect to humeral head 674. Specifically, patient-specific shape 676 represents the subscapularis muscle, patient-specific shape 678 represents the supraspinatus muscle, and patient-specific shape 680 represents the infraspinatus muscle. As shown in FIG. 15, sagittal view 682 of the patient image data includes scapula 672 with respect to patient-specific shape 676 (e.g., the subscapularis muscle), patient-specific shape 678 (e.g., the supraspinatus muscle), and patient-specific shape 680 (e.g., the infraspinatus muscle). It is noted that additional rotator muscles, or other muscles associated with the joint of interest, are not shown, but may be determined in other examples.

Figure 16A:
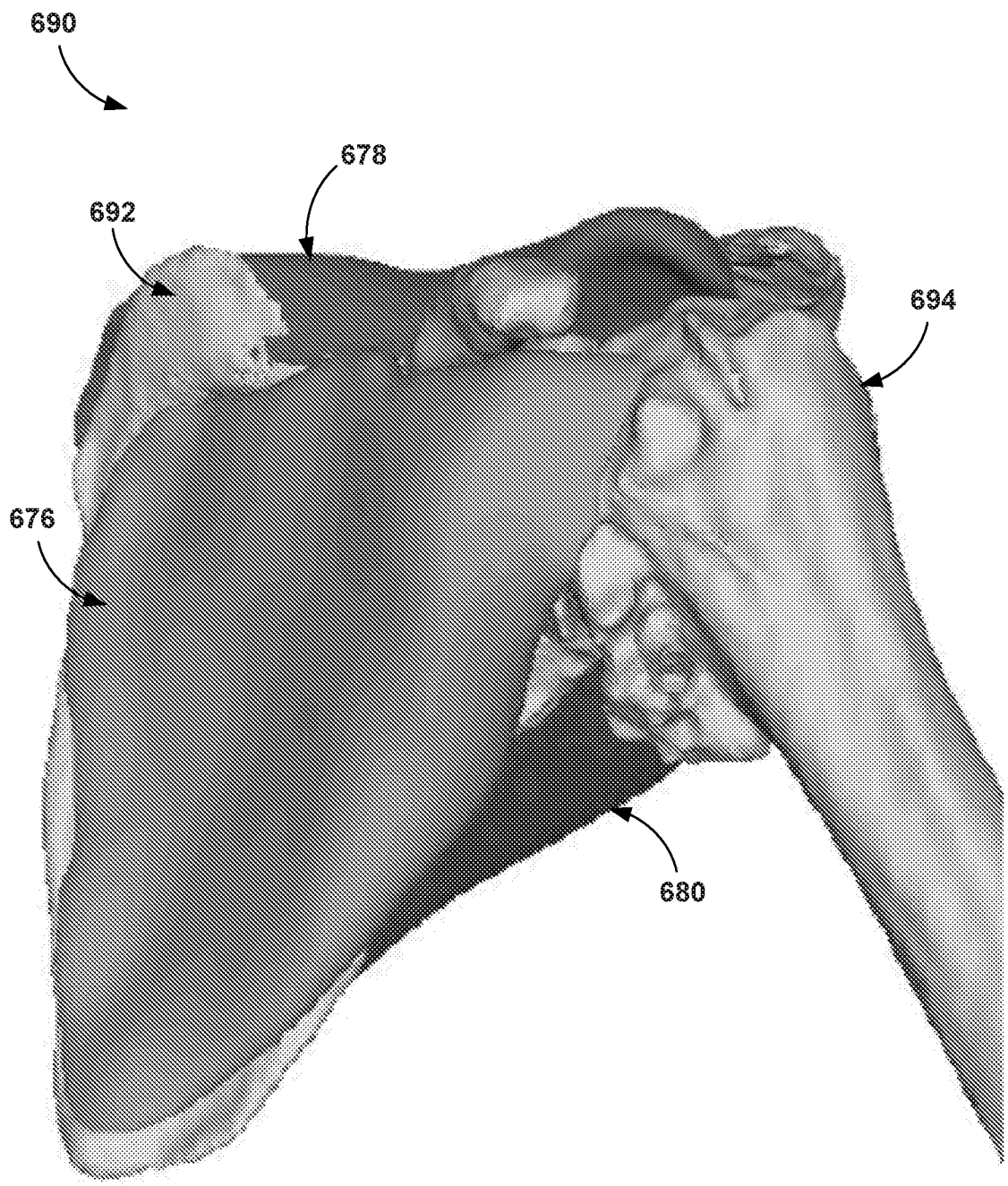
FIG. 16A is a conceptual posterior three-dimensional view of example final patient-specific shapes representative of the rotator cuff muscles together with bones from patient-specific image data.
Figure 16B:
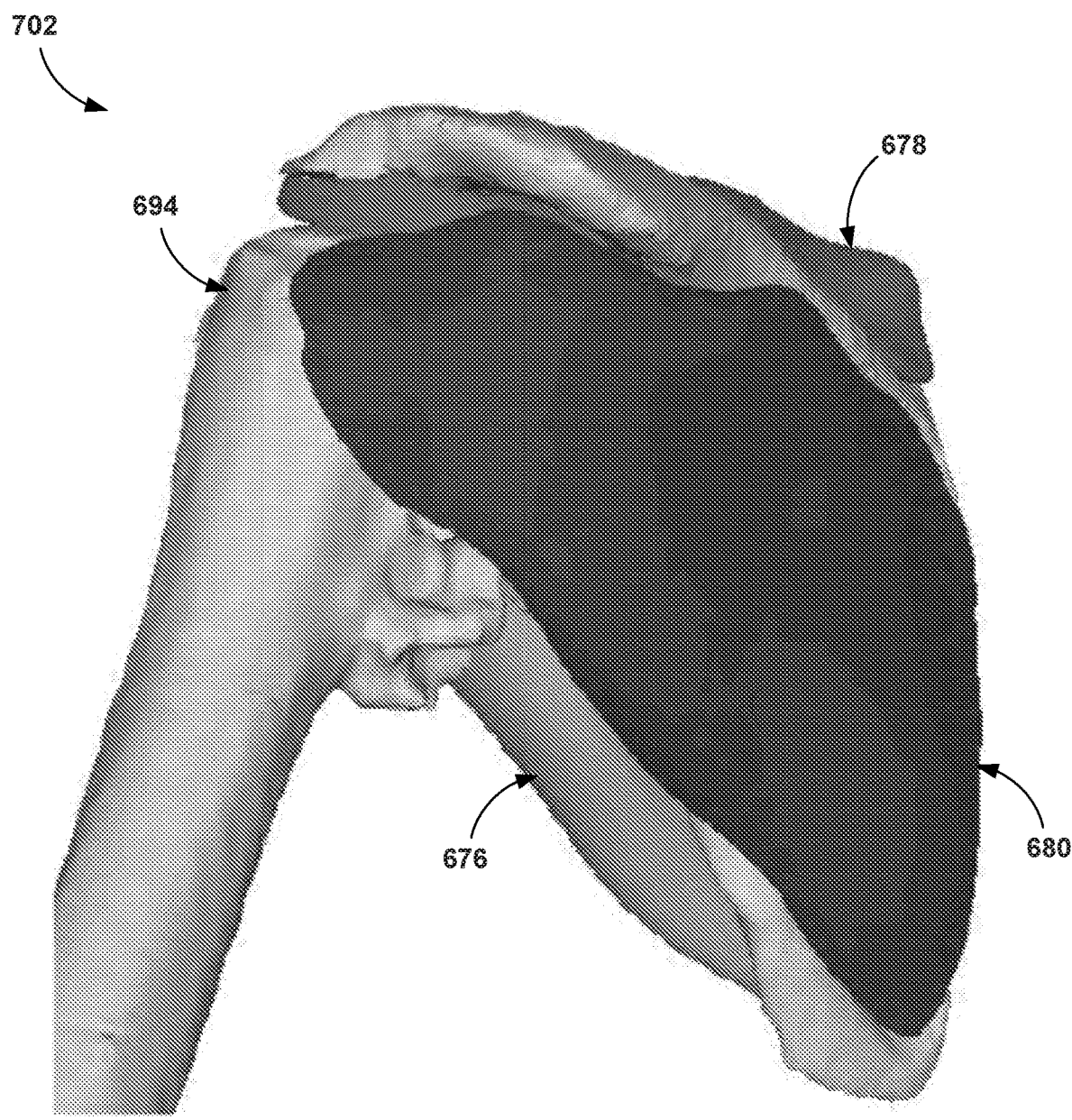
FIG. 16B is a conceptual anterior three-dimensional view of example final patient-specific shapes representative of the rotator cuff muscles together with bones from patient-specific image data.
Figure 17:
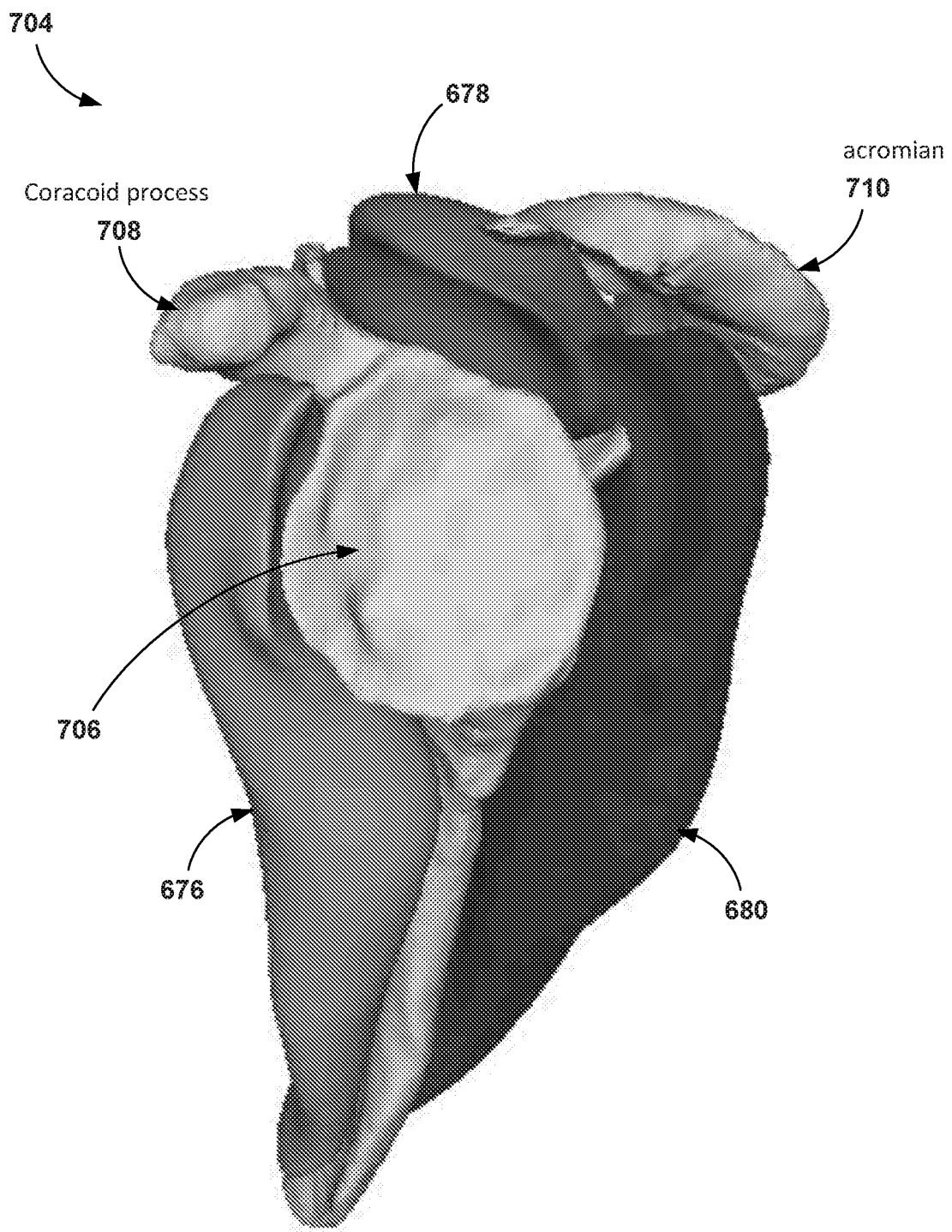
FIG. 17 is a conceptual end-face three-dimensional view of example final patient-specific shapes representative of the rotator cuff muscles together with bones from patient-specific image data.

FIG. 16A is a conceptual posterior three-dimensional view 690 of example final patient-specific shapes representative of the three rotator cuff muscles together with bones from patient-specific image data. As shown in FIG. 16A, the subscapularis muscle represented by patient-specific shape 676 is shown with respect to scapula 692 and humeral head 694. View 690 also illustrates the supraspinatus muscle as patient-specific shape 678 and the infraspinatus muscle as patient-specific shape 680. As shown in FIG. 16B, anterior view 702 is a three-dimensional view of similar structures illustrated in posterior view 690, such as the subscapularis muscle as patient-specific shape 676, the supraspinatus muscle as patient-specific shape 678, and the infraspinatus muscle as patient-specific shape 680. As shown in FIG. 17, end-face view 704 is a three-dimensional view of similar structures illustrated in posterior view 690. End-face view 704 is viewing these shoulder structures in a plane aligned with glenoid surface 706. In this manner, the subscapularis muscle is shown as patient-specific shape 676, the supraspinatus muscle is shown as patient-specific shape 678 between the coracoid process 708 and acromion 710, and the infraspinatus muscle is shown as patient-specific shape 680.

Figure 18A:
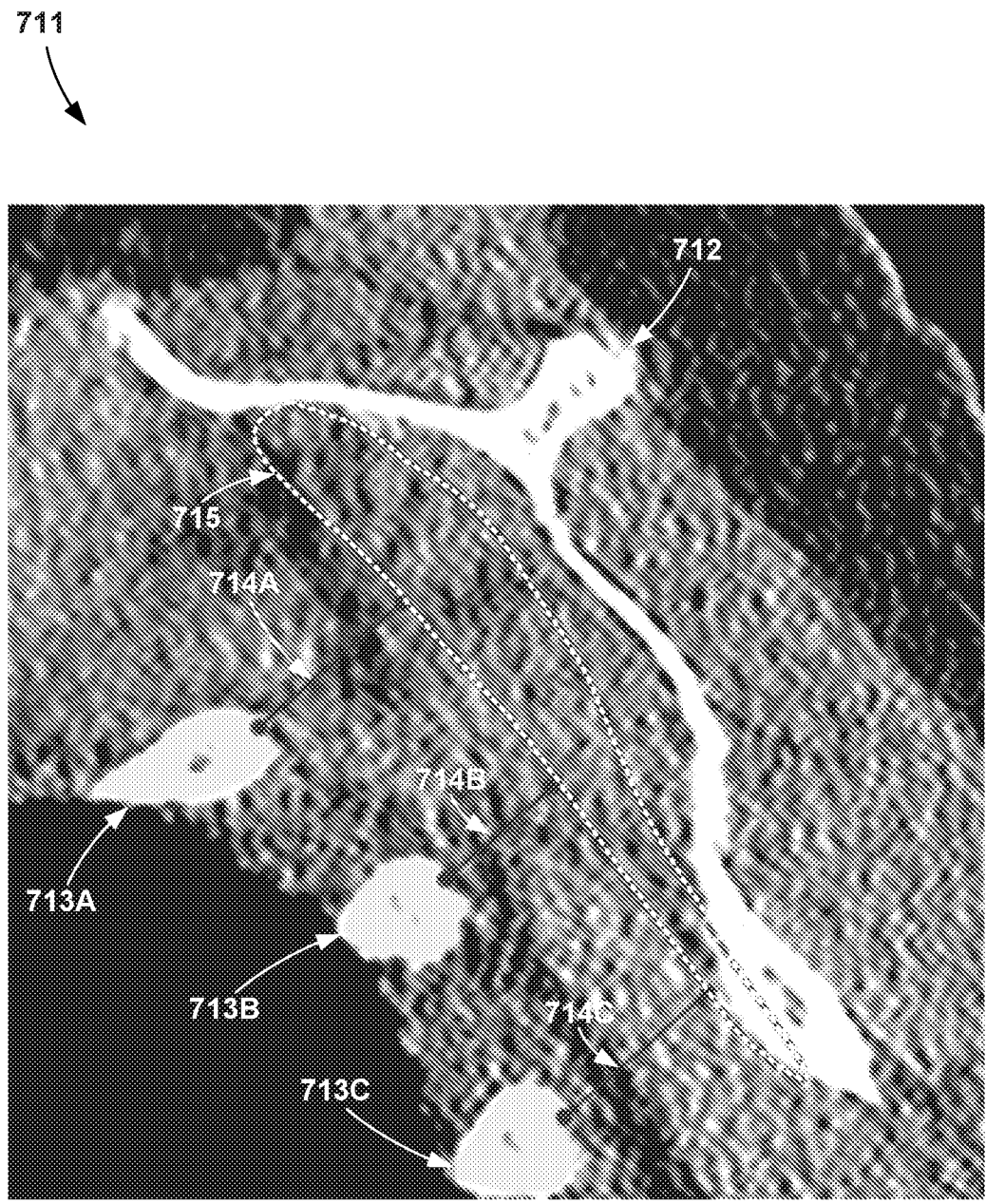
FIGS. 18A and 18B are a conceptual illustrations of example patient-specific CT data in which initial shapes associated with a soft tissue structure are registered to bone structures and modified to patient-specific shapes representative of the soft tissue structure.
Figure 18B:
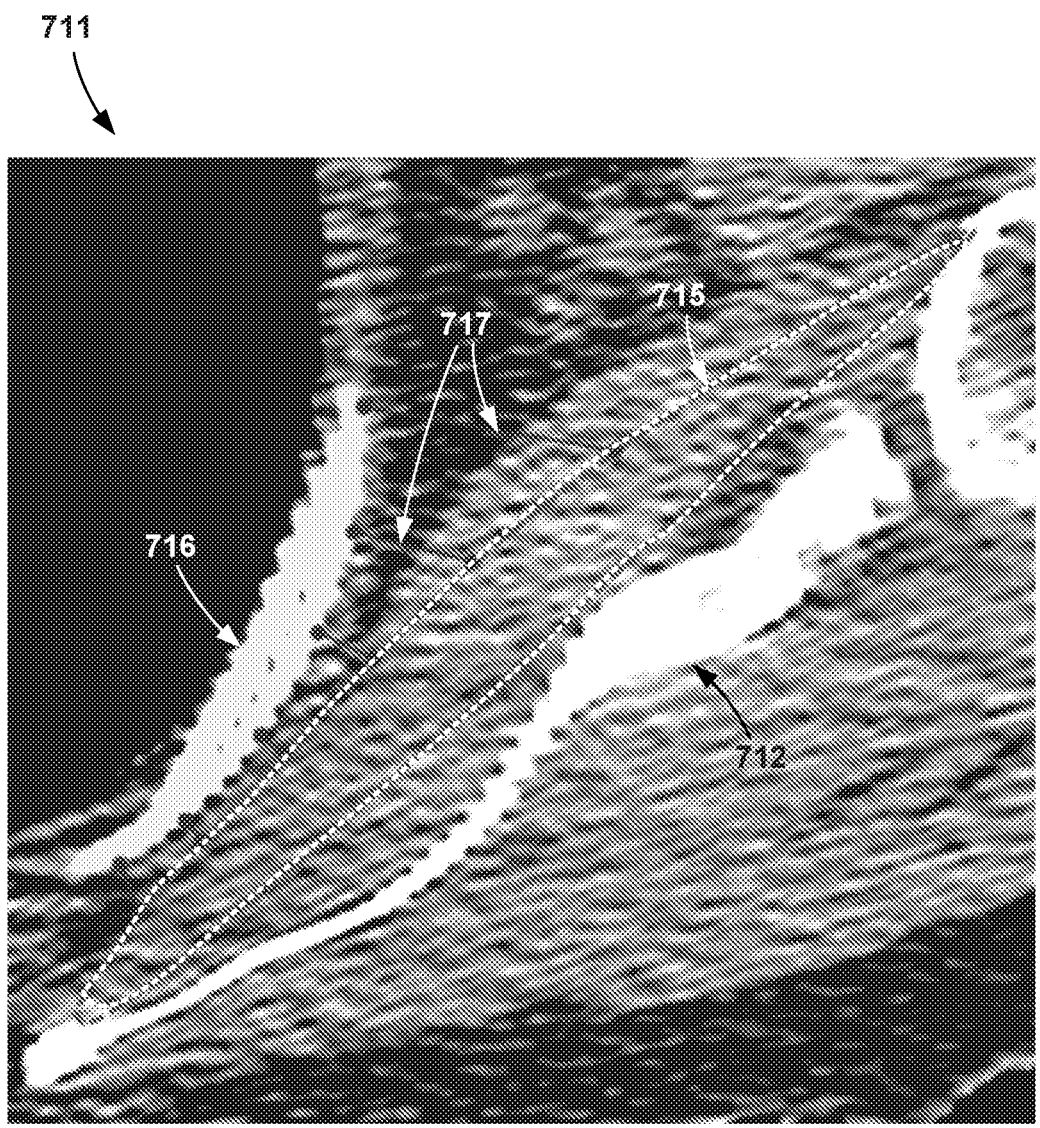

FIGS. 18A and 18B are a conceptual illustrations of example patient-specific CT data in which initial shapes associated with a soft tissue structure are registered to bone structures and modified to patient-specific shapes representative of the soft tissue structure. Processing circuitry 542, for example, may initially identify bone structures within the CT data (e.g., one or more x-ray images) that may be fiducial landmarks for registering an initial shape of a soft-tissue structure and then scaling the initial shape to fit the initial shape to the CT data for the patient.

As shown in the axial slice example of FIG. 18A, processing circuitry 542 may determine a set of fiducial landmarks 713A, 713B, and 713C (collectively "landmarks 713") from the patient image based on the muscle (e.g., a soft tissue structure) being targeted. For example, the sub scapularis muscle is adjacent to the thoracic cage and therefore, the ribs can be segmented and used to locate such landmarks (ribs of landmarks 713). Initial shape 715 may be a statistical mean shape (SMS) of the subscapularis muscle rigidly registered to the patient. Initial shape 715 may be a pathological shape, such as SMS generated from other patients having a similar condition to the patient. Put another way, a healthy SMS may not provide an appropriate model of the patient's soft tissue because the SMS is only registered and scaled. However, in some examples, the registered and/or scaled SMS could further be modified according to the closed-surface modification described with respect to FIGS. 8A-11 herein.

Connections 714A, 714B, and 714C (collectively "connections 714"), indicate correspondences between landmarks 713 and respective points on the SMS of initial shape 715. FIG. 18A is an axial slice of the patient-specific CT data.

FIG. 18B is a sagittal slice of the patient-specific CT data and shows a different view of the ribs and subscapularis muscle. A single rib 716 is a landmark that includes several points that correspond to respective points on initial shape 715, and connections 717 are the lines that indicate those correspondences. FIGS. 18A and 18B are two-dimensional representations of this registration process, by processing circuitry 542 may perform the registration in three dimensions in some examples. The process described with respect to the subscapularis muscle may similarly be performed for other muscles. For example, supraspinatus-related landmarks can be identified on the inferior side of the clavicle and the acromion, and infraspinatus-related landmarks can be identified based on the surrounding skin.

Generally, once the fiducial landmarks (e.g. landmarks 713 and 716), are identified, their closest correspondences on the SMS are located. Processing circuitry 542 may determine an intensity-based profile along the line (e.g., connections 713 and 717) connecting the landmark 'l' with its counterpart point on the SMS 'c'. When a specific variation of the profile is detected at some location 'v', the euclidean distance (d) between 'v' and 'c' is stored as well as the intensity-based value (i) of 'v'. Then, processing circuitry 542 can use the following equation:

$$Cf=\text{fun}(d_n,i_n), n \in \text{landmarks} \quad (1)$$

The intensity-based metric could simply be the intensity value of the CT image data or its gradient. For intensity, the specific variation would be a step going from high (the bone intensity) to low (the soft-tissue structure), while for the gradient example, there would be a positive spike along the profile of the connections indicating the soft-tissue structure boundary. Processing circuitry 542 may utilize a minimization algorithm, such as a cost function, to determine the registration of initial shape 715. The minimization algorithm may refer to a general type of algorithm in which processing circuitry 542 deforms initial shape 715 (e.g., a SMS) by satisfying a threshold of an algorithm to fit the deformed version of the SMS to the bone to muscle dimensions of the soft-tissue structure. For example, the cost function can be a combination of the euclidean distance $d=\|v-c\|$ and i; for, example, $$Cf=\Sigma_n w_1 \times d_n + w_2 \times i_n, \quad (2)$$

where $w_1$ and $w_2$ are weights determined empirically.

The cost function can also have another term that is patient-independent used to smooth the final estimation of the registration. This term, called the regularization term, can provide adaptive weights to the initial shape 715 parameters (based on their relevance and noise in the SMS). This term ($Cf_2$) can be added to the previous "difference" term (now called ($Cf_1$) and the summation is optimized to give:

$$Cf=Cf_1+Cf_2 \quad (3)$$

In order to be comparable, $Cf_1$ may be in the same scale as $Cf_2$. $Cf_2$ may have its values normalized (i.e. between 0 and 1). To scale $Cf_1$ into the same interval, it is normalized using the $Cf_1$ value after the rigid registration (i.e. between the SMS and the patient-specific CT data).

Once initial shape 715 is rigidly registered to the patient, initial shape 715 can be elastically deformed to match the patient soft tissue structure using its finite parametric equation:

$$s=s'+\Sigma_i b_i \sqrt{\lambda_i} \times v_i, \quad (4)$$

where s' is the initial shape (e.g., an SMS), $\lambda_i$ is the eigenvalues and $v_i$ is the eigenvectors of the covariance matrix respectively (e.g., also called modes of variations). The covariance matrix represents the variance in a dataset, such as the variance in the patient-specific patient data. The values of $b_i$ determine the shape of s (e.g., the final patient-specific shape of the soft tissue structure). The term $b_i$ is the scaling factor for the initial shape 715. Processing circuitry 542 may use this process to find the values of $b_i$ so that provide a final shape (s) that estimates the patient-specific structure of the target muscle. For example, this best fit is performed by processing circuitry 542 to minimize a cost function defining the "difference" between s and the patient muscle in the patient-specific CT image (e.g., m). In other words, an optimization algorithm can minimize $Cf=|s-m|$ or maximize $Cf'=|s-m|^{-1}$.

Now defining Cf or Cf' is may be important because based on its convexity, the optimizer would or would not fall into a global or local minimum or maximum. In order to get a good estimate at the end of the optimization process, processing circuitry 542 may determine Cf to reflect the "shape difference" between the modified final object (s) and the target (m). A variation of computing this difference could be related to the euclidean distance of the estimate of final shape (s) to a limited number of fiducial landmarks located on the patient.

Processing circuitry 542 may use an optimization algorithm for the minimization of the cost function by applying a SMS parametric equation in an iterative manner and changing the parameters values based on the value of Cf after each iteration. Processing circuitry 542 may stop this loop when Cf cannot be optimized (minimized or maximized) any further, i.e. arrived to an optimum, or when a maximum number of iterations is reached. At the completion of this optimization algorithm, processing circuitry 542 may finalize the modified initial shape 715 as the final patient-specific shape for the soft tissue structure. The minimization or maximization algorithm may refer to a general type of algorithm in which processing circuitry 542 deforms initial shape 715 (e.g., a SMS) by satisfying a threshold of the algorithm to fit the deformed version of the SMS to the bone to muscle dimensions of the soft-tissue structure. This threshold may be indicative of when the deformed version of the SMS is a best fit, or reduces error, to the soft tissue structure in the patient-specific image data.

Figure 19:
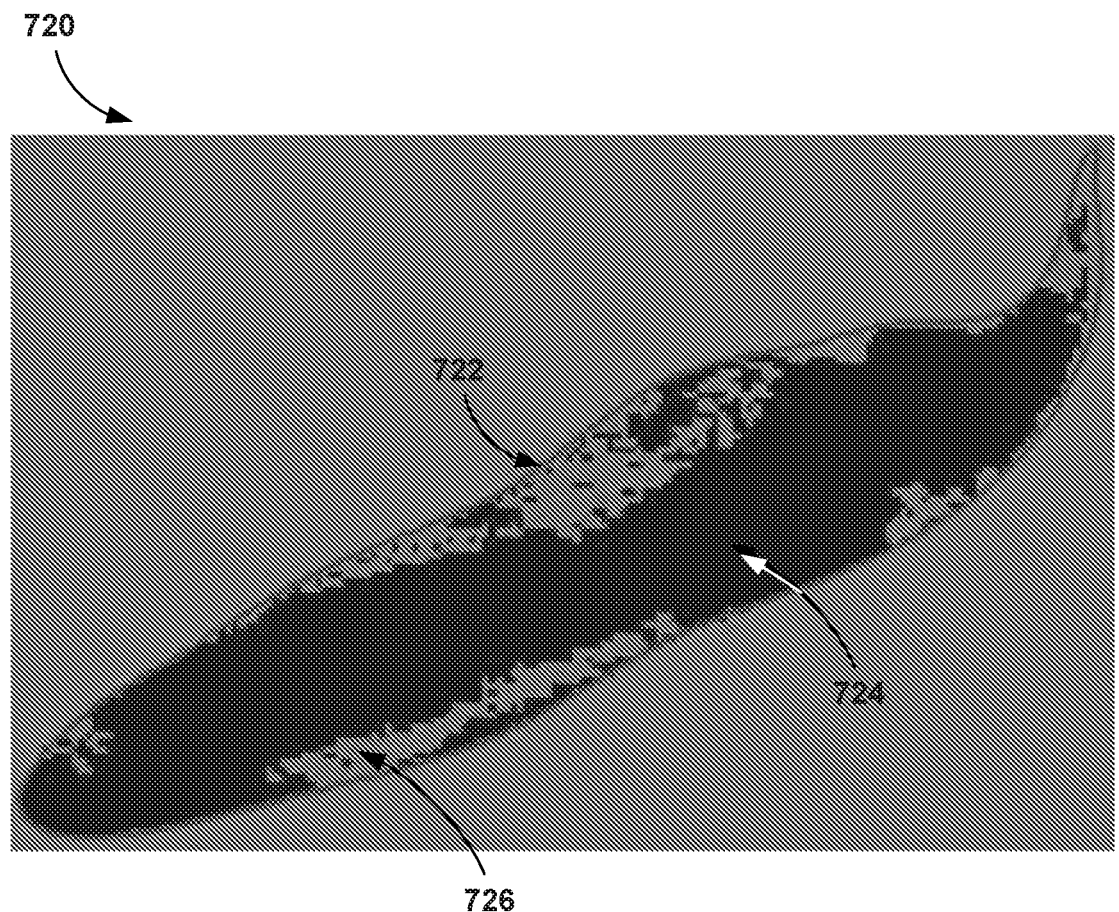
FIG. 19 is a conceptual illustration of an example final patient-specific shape masked and thresholded to determine soft tissue characteristics such as fatty infiltration.

FIG. 19 is a conceptual illustration of an example final patient-specific shape masked and thresholded to determine fatty infiltration. Fatty infiltration, or a value representative of the fat ratio or fat volume within a muscle, may be indicative of a structural and/or functional change from an otherwise healthy muscle. In this manner, the amount of fat within a muscle may be indicative of the health of that muscle. In turn, the health of the muscle may affect what type of joint treatment is appropriate for the patient.

As discussed herein, a system such as system 540 may determine a fatty infiltration value for the modeled soft tissue structure based on thresholding voxels, or groups of voxels, from the patient-specific image data within the representation of the soft tissue structure, with respect to threshold intensity values. The ratio of fatty tissue to total tissue within the representation may be determined to be the fatty infiltration value. System 540 may determine the fatty infiltration value from the pixels of multiple two-dimensional slices of the patient-specific image data or voxels from the three-dimensional image data set. The three-dimensional approach will be described as an example herein, but two-dimensional views are used for illustration purposes. For example CT image data, the thresholds of intensity used for fat may be approximately −29 Hounsfield Units (HU) and 160 HU for muscles. In one example, the fatty infiltration (FI) value may be calculated as: $FI=100*(1-x/X)$, where x is the volume of muscle within the mask and X is the total volume within the mask. In some examples, regions having fat or muscle that are less than a specific threshold (e.g., less than one cubic millimeter) may be considered noise and eliminated.

As shown in FIG. 19, patient image data 720 includes a patient-specific shape 722 that was generated for a muscle of interest with a mask applied to the voxels. The system may first apply a mask to patient-specific shape 722 in order to remove data outside of patient-specific shape 722. Next, the system may apply a threshold to the voxels under the mask. In some examples, the threshold may be applied to groups of voxels or average voxel intensities over two or more voxels in order to avoid noise that may be present in individual voxels. In this manner, a system may analyze intensity and/or spatial characteristics of the patient-specific image data to determine regions of fatty tissue. The black areas indicated by voxels 724 indicate muscle tissue that was above the threshold intensity indicating muscle tissue. In contrast, the lighter voxels 726 are below the threshold, less intensity, and indicate fat tissue. Without the mask as shown, the intensity of fat tissue voxels would be lower than the intensity of the voxels associated with muscle. The system can then determine a fat volume for the soft tissue structure by adding voxels 726 under the threshold. The system then can determine a fatty infiltration value based on the fat volume and a total volume of the patient-specific shape 722 for the soft-tissue structure. For example, system 540 can divide the fat volume by the total volume to determine the fat ratio (e.g., as a percentage) for the soft-tissue structure. System 540 may then output the fat volume ratio for the soft-tissue structure. In some examples, system 540 may use the fat volume ratio as an input when determining what type of joint replacement may be appropriate for the patient. In some examples, system 540 could use muscle quality indicators, such as fatty infiltration, together with range of motion to determine positioning and/or orientation of implant components such as the humeral implant or glenoid implant. For example, system 540 may suggest to move one or more implants laterally or medially in order to improve the range of motion and/or strength of the shoulder for that patient. Since the strength or flexibility of the muscles may depend at least in part on the distance between the glenoid and the humeral head, changing the position of the humeral implant (or choosing a different sized humeral implant) to move the humerus closer to or further from the glenoid may enable a clinician to improve the range of motion and/or strength of the shoulder after implant. In some examples, a bone graft may be used to add to either the humeral head or glenoid to achieve the desired lateralization or medialization of the humerus (with or without a humeral implant).

Figure 20:
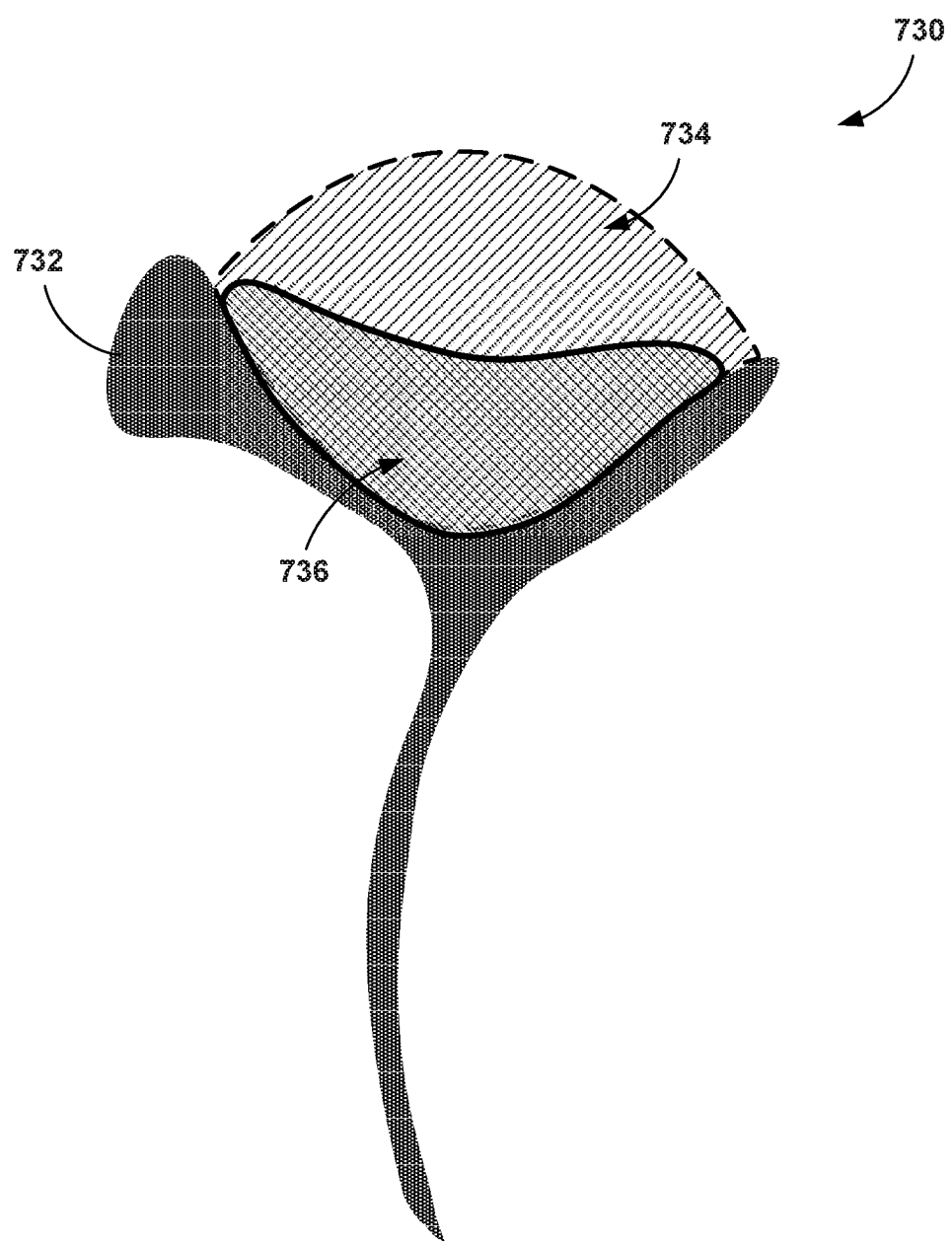
FIG. 20 is a conceptual illustration of an example final patient-specific shape and a pre-morbid estimation of a soft tissue structure.

FIG. 20 is a conceptual illustration of example final patient-specific shape 736 and a pre-morbid prediction 734 of a soft tissue structure. As shown in the example of FIG. 20, sagittal view 730 includes scapula 732 and patient-specific shape 736 for the supraspinatus muscle. Patient-specific shape 736 may be determined based on the closed surface fitting described above. However, it may be informative when selecting a type of joint treatment to understand how the muscle has changed from a healthy or pre-morbid state. In this manner, system 540 may determine an atrophy ratio for the muscle.

For example, processing circuitry 542 of system 540 may be configured to determine bone to muscle dimensions for the soft-tissue structure of the patient. Processing circuitry 542 may determine lengths, widths, and/or volumes of the bones, such as scapula 732, with respect to the dimensions of the muscle according to the patient-specific shape 736. The bone to muscle dimensions may identify specific anatomical sizing for the patient. Processing circuitry 542 may obtain a statistical mean shape (SMS) for the soft-tissue structure. The SMS may be a representation of typical muscle based on calculations from a population of many healthy subjects. However, in some examples, an SMS of pathological structures may be used in some examples.

Next, processing circuitry 542 may deform the SMS using a minimization algorithm to fit the SMS to the bone to muscle dimensions of the soft-tissue structure. For example, processing circuitry 542 may modify the SMS to more closely fit the bone to muscle dimensions of the patient and thus estimate the pre-morbid state for that muscle. The resulting pre-morbid prediction 734 may be used as an estimate of the healthy state of the muscle. Processing circuitry 542 may then determine an atrophy ratio for the soft-tissue structure (e.g., a muscle such as the supraspinatus represented by patient-specific shape 736) by dividing the deformed SMS volume by the soft-tissue structure volume represented by patient-specific shape 736. This result is the atrophy ratio for the soft-tissue structure. In some examples, processing circuitry 542 may output the atrophy ratio for display or for further use in additional calculations during pre-operative planning.

Figure 21:
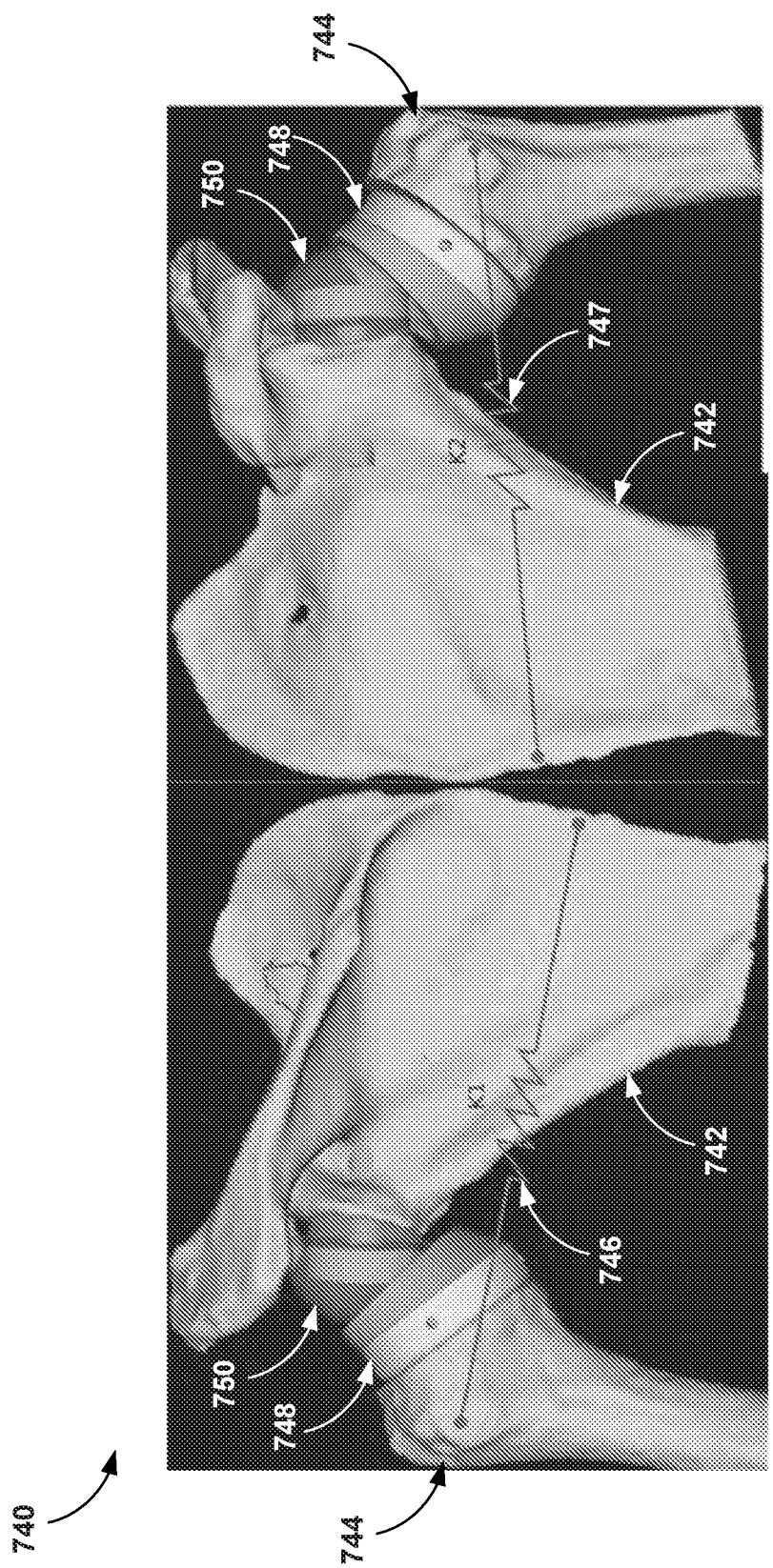
FIGS. 21 and 22 are conceptual illustrations of example springs modeling muscle contribution to range of motion analysis of a shoulder joint.
Figure 22:
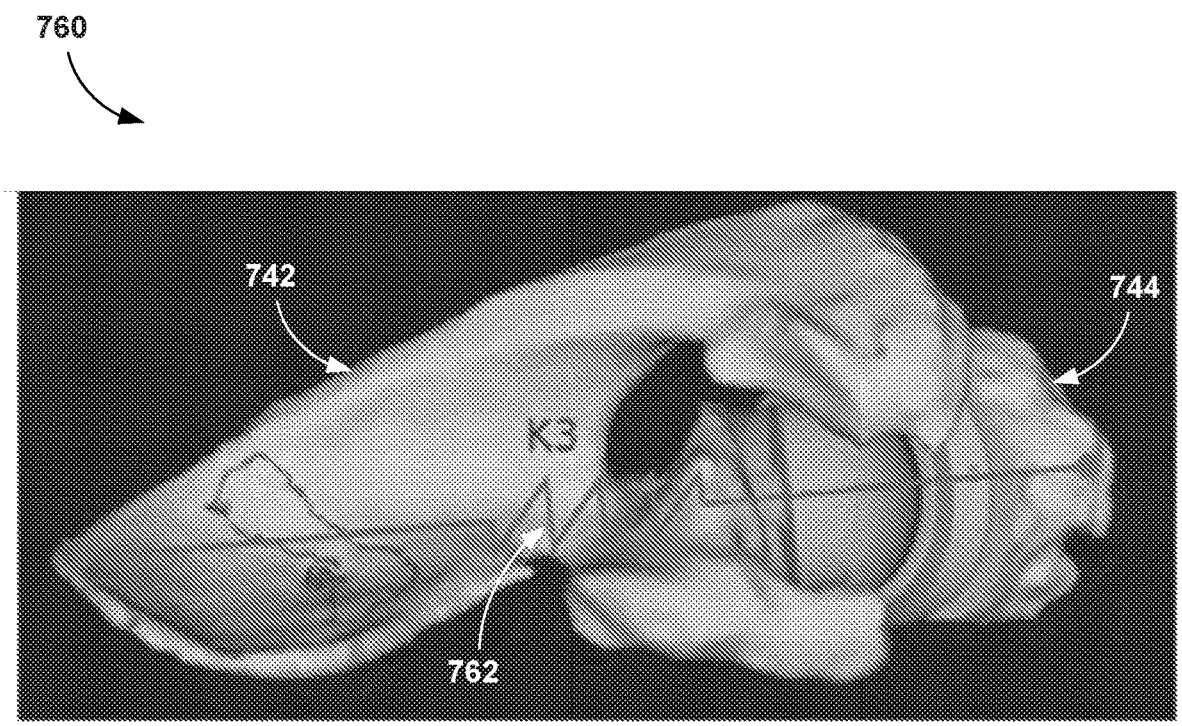

FIGS. 21 and 22 are conceptual illustrations of example springs modeling muscle contribution to range of motion analysis of a shoulder joint. Although FIGS. 21 and 22 illustrate pre-operative planning for a reverse shoulder replacement, an anatomical shoulder replacement may be planned in other examples. As shown in FIG. 21, virtual view 740 includes a posterior view of humeral head 744 and scapula 742 on the left and an anterior view of humeral head 744 and scapula 742 on the right. Humeral head has been fitted with spacer 748 which is configured to mate with glenoid sphere 750 that has been fitted to the glenoid surface. Other components may also be involved in the implants, such as a cup and plate for spacer 748. In an anatomical shoulder replacement, these components are flipped such that the implant sphere is attached to humeral head 744 instead. Some example components may include a reversed glenoid component with a wedge baseplate, a central screw, a glenosphere, and a symmetric graft. A stemless Ascend FLEX reversed humeral component with a standard insert and 1.5 offset tray may also be used in a reverse shoulder replacement.

System 540, for example, may perform a determination as to whether the patient should receive an anatomical or reverse shoulder replacement when the shoulder joint has deteriorated. Part of this determination may include consideration of the contributions of one or more muscles to the movement of the joint. In one example, processing circuitry 542 of system 540 may model three rotator cuff muscles as springs with spring constants K1, K2 and K3. As shown in FIG. 21, the infraspinatus has been modeled as spring 746 and the subscapularis has been modeled as spring 747. Fewer or additional muscles may be modeled as part of this analysis in other examples. As shown in FIG. 22, virtual view 760 illustrates the supraspinatus muscle being modeled as spring 762. Processing circuitry 542 can assign spring constants to each spring, such as spring constants K1, K2, and K3 to springs 746, 747, and 762, respectively.

Processing circuitry 542 may determine each spring constant based on the calculated fat infiltration (e.g., fat volume ratio) and atrophy ratio of the respective muscle that has already been modeled as described herein. For example, processing circuitry 542 may employ an equation such as K=f(R(FI), R(A)), where K is the spring constant, FI is the fat infiltration, and A is the atrophy of the respective muscle, to determine the spring constant of each muscle. In other examples, additional factors may be used when determining the spring constant, such as total volume, length, and/or cross-sectional thickness of the patient-specific shape for the muscle, patient age, patient gender, injury history of the patient, or any other type of factors that may impact the function of the muscle. The attachment points of each spring 746, 747, and 762 may be determined by processing circuitry 542 based on insertion points of the muscle, for example. In some examples, each muscle may be represented by two or more springs, such as different springs representing each attachment point from the muscle to the bone. In other examples, each muscle may be represented by more complex models of muscle function than a spring. In some examples, processing circuitry 542 may determine a load applied to the springs. The load may combine the weight of the bony structure and an external load (such as lifting a standard object). Although springs may be used as some models, a finite element model may be used in other examples.

Processing circuitry 542 may determine the range of motion of the humerus by determining, based on fat volume ratios and atrophy ratios for one or more respective muscle of a rotator cuff of the patient, the range of motion of the humerus of the patient. For example, processing circuitry 542 may calculate the spring constants for each of K1, K2, and K3, and then determine the range of motion of the humerus with respect to the scapula. Processing circuitry 542 may determine the range of motion in one or more planes or in three dimensions, in some examples. The range of motion axes may be predefined, and in some examples, bone collisions may be determined to establish some angles of range of motion when soft tissue is not the limiting factor along those axes. Processing circuitry 542 may perform this calculation for each of the possible types of treatment, such as an anatomical replacement or a reverse replacement. In other examples, processing circuitry 542 may perform the range of motion analysis on the current damaged joint and bones and use this calculation for identifying which type of treatment is appropriate for the patient. In any case, processing circuitry 542 may determine which type of shoulder treatment, such an anatomical shoulder replacement surgery or a reverse shoulder replacement surgery, should be selected for the patient and then output, for display, that selected shoulder treatment type. Processing circuitry 542 may present the analysis for each type of treatment to the user, such as presenting a numerical score or calculation for each type of treatment. The user may then determine, from this presented information for each type of treatment, which type of treatment to provide to the patient.

Figure 23A:
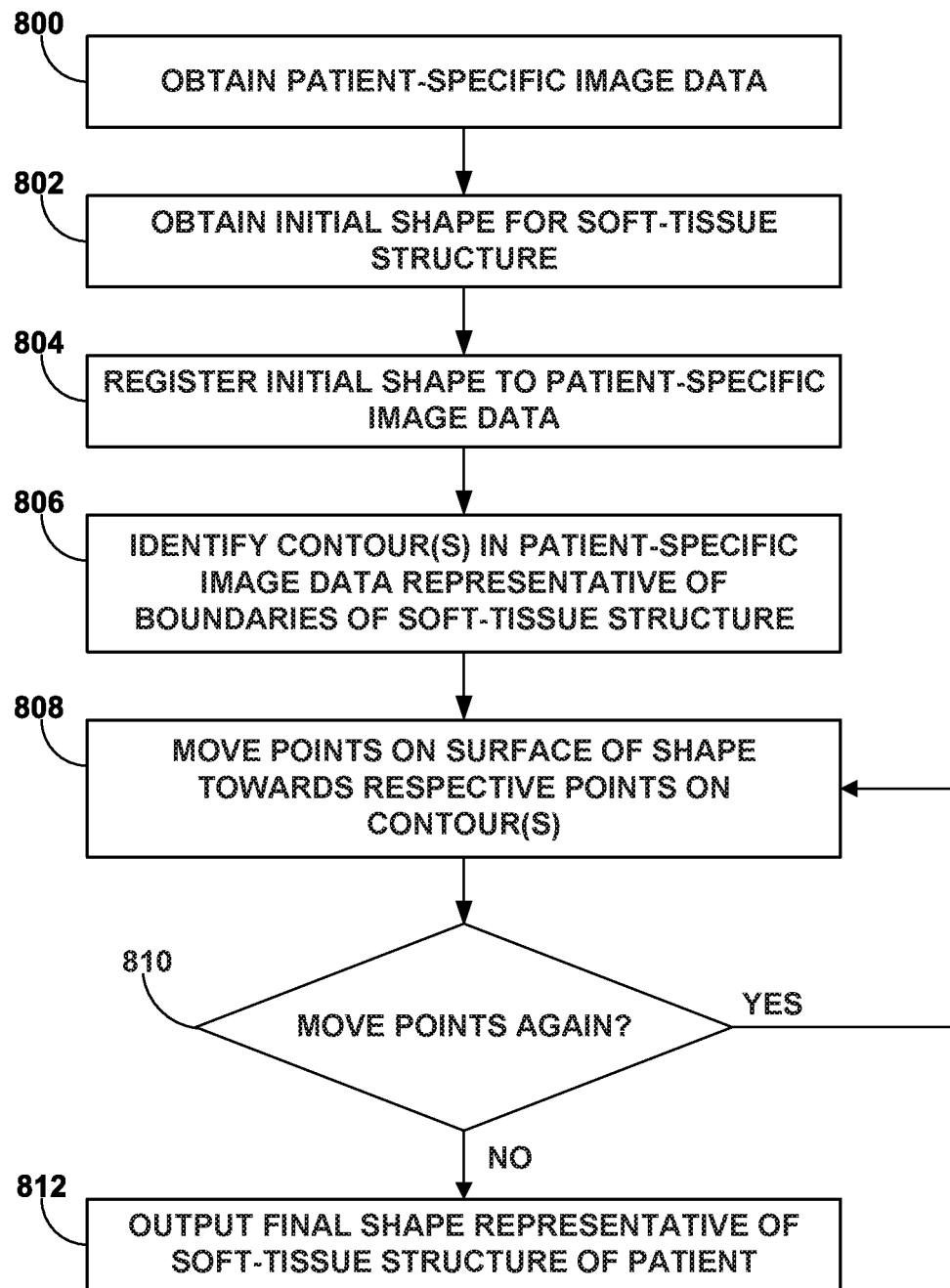
FIG. 23A is a flowchart illustrating an example procedure for modeling a soft tissue structure using patient-specific image data, in accordance with a technique of this disclosure.

FIG. 23A is a flowchart illustrating an example procedure for modeling a soft tissue structure using patient-specific image data, in accordance with a technique of this disclosure. Processing circuitry 542 of system 540 will be described as performing the example of FIG. 23A, but other devices or systems, such as virtual planning system 102, may perform one or more portions of this technique. Furthermore, some portions of this technique may be performed by a combination of two or more devices and/or systems via a distributed system. The example of FIG. 23A may be similar to the illustrations and discussions above with respect to FIGS. 8-11.

As shown in FIG. 23A, processing circuitry 542 may obtain patient-specific image data of the patient of interest (800). This patient-specific image data may be generated from one or more imaging modalities (e.g., x-ray, CT, MM, etc.) and stored in a data storage device. Processing circuitry 542 then obtains an initial shape for a soft-tissue structure of interest (802). The initial shape may be a geometric shape or a statistical mean shape (SMS). This soft-tissue structure may be a muscle or other non-bone structure. However, in other examples, the process of FIG. 23A or other techniques described herein may be performed for bones. Processing circuitry 542 then registers the initial shape to the patient-specific image data (804). This registration may include registering the initial shape to bones and/or bone insertion points identified by already segmented bones in the patient-specific image data. In other examples where a preliminary muscle segmentation has already been performed on the soft tissue structure of interest in the patient-specific image data, processing circuitry 542 may register the initial shape to the preliminary muscle segmentation.

Processing circuitry 542 then identifies one or more contours in the patient-specific image data representative of boundaries of the soft-tissue structure (806). These one or more contours may be identified as voxels associated with already segmented bones and/or the muscle in the patient-specific image data. In other examples, processing circuitry 542 may determine each contour by extending normal vectors from the surface of the initial shape inwards and/or outwards from the initial shape. Voxels or pixels encountered by each vector that exceed a threshold intensity value in the patient-specific image data may be identified as defining at least part of the contour.

Processing circuitry 542 then moves surface points on the surface of the initial shape towards respective points on the one or more contours (808). Movement of these surface points causes the entire surface of the initial shape to be deformed. If processing circuitry 542 determines that the surface points need to be moved again in order to more closely fit the initial shape to the one or more contours ("YES" branch of block 810), processing circuitry 542 again moves the surface points of the deformed surface of the initial shape (808). If processing circuitry 542 determines that the surface points do not need to be moved again and the deformed shape fits the one or more contours ("NO" branch of block 810), processing circuitry 542 outputs the final deformed shape as a patient-specific shape representative of the soft-tissue structure of the patient (812). The patient-specific shape may be presented via a user interface and/or used for further analysis, such as part of pre-operative planning of treatment for the patient.

Figure 23B:
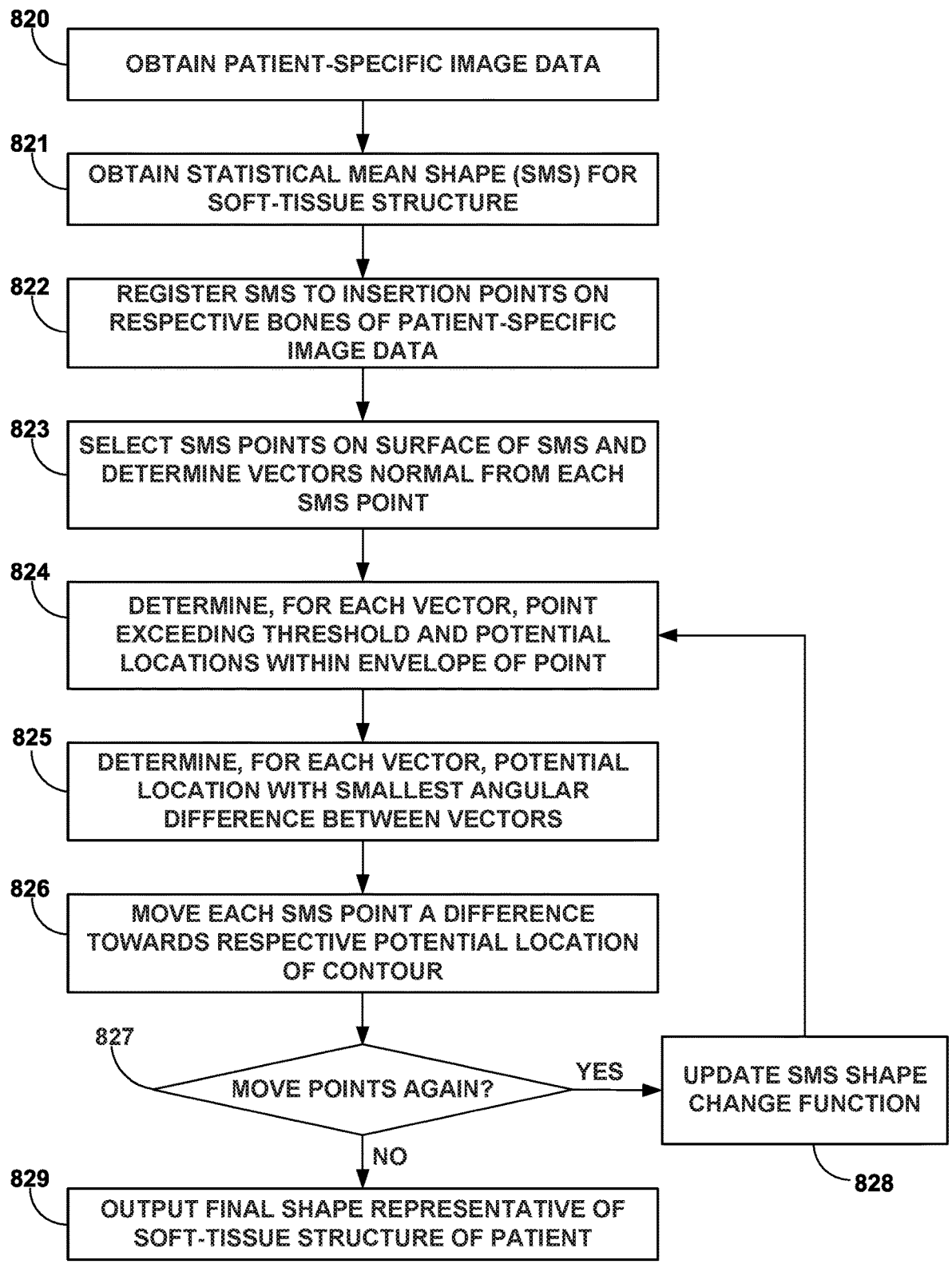
FIG. 23B is a flowchart illustrating another example procedure for modeling a soft tissue structure using patient-specific image data, in accordance with a technique of this disclosure.

FIG. 23B is a flowchart illustrating another example procedure for modeling a soft tissue structure using patient-specific image data, in accordance with a technique of this disclosure. Processing circuitry 542 of system 540 will be described as performing the example of FIG. 23B, but other devices or systems, such as virtual planning system 102, may perform one or more portions of this technique. Furthermore, some portions of this technique may be performed by a combination of two or more devices and/or systems via a distributed system. The example of FIG. 23B may be similar to the illustrations and discussions above with respect to FIGS. 8A-11. The technique of FIG. 23B may also be similar to the technique of FIG. 23A in some aspects.

As shown in FIG. 23B, processing circuitry 542 may obtain patient-specific image data of the patient of interest (820). This patient-specific image data may be generated from one or more imaging modalities (e.g., x-ray, CT, MM, etc.) and stored in a data storage device. Processing circuitry 542 then obtains an initial shape which is a SMS for a soft-tissue structure of interest (821). Processing circuitry 542 then registers the SMS to the insertions points of one or more respective bones of the patient-specific image data (822). In other examples, the registration may include registering the SMS to a preliminary muscle segmentation in the patient-specific image data, which may be in addition to the bone insertion points.

Processing circuitry 542 then selects a plurality of surface points around the surface of the SMS and determines vectors normal to the surface from each surface point (823). The surface points may be distributed evenly around the surface of the SMS at a predetermined density, predetermined spacing, and/or according to other selection factors. In some examples, processing circuitry 542 may direct these normal vectors outward and inward from at least some of the surface points. For each of these vectors, processing circuitry 542 determines a point in the patient-specific image data exceeding a threshold intensity value and potential locations within an envelope of that point (824). The determined point may be a voxel, pixel, or point in space associated with that voxel or pixel. These determined points would correspond with an outer surface (e.g., one or more contours) of the soft tissue structure of interest as identified within the patient-specific image data. The potential locations within the envelope are those locations also exceeding the threshold and part of the one or more contours. The envelope may be determined as a predetermined distance from the point identified by the vector, a number of potential locations adjacent to the point (e.g., the closest eight potential locations from the point) or other such criteria.

These potential locations are analyzed to identify variations in the contour to which the SMS is to be fitted. In other words, the potential locations are analyzed for more precision on the direction in which to move the surface point of the SMS. Processing circuitry 542 determines, for each vector, the potential location with the smallest angular difference between its vector and the vector from the surface point (825). This angle may be referred to as the cosine between the two vectors. Angle 622 of FIG. 9 is an example of this angle between vector 620 from the surface point and vector 624 from the potential location on the contour. After the potential location is selected for each surface point on the SMS, processing circuitry 542 moves each surface point a distance towards the respective potential location of the contour (826). The distance moved may be some portion, or percentage, of the total distance to the potential locations. In one example, the distance is approximately half of the total distance to the potential locations. In this manner, each iteration moves the surface points closer to the one or more contours, but at increasingly smaller distances for each iteration. In other examples, the distance may be less than half of the total distance to the potential locations or more than half of the total distance to the potential locations.

Movement of these surface points causes the entire surface of the SMS to be deformed. If processing circuitry 542 determines that the surface points need to be moved again in order to more closely fit the SMS to the one or more contours ("YES" branch of block 827), processing circuitry 542 updates the SMS shape change function (828) before again determining points exceeding the threshold for each vector and SMS surface point (824). The SMS change function may define how processing circuitry 542 deforms the SMS in that iteration. For example, the SMS change function may define how the deformation of the SMS balances "smoothness" and "precision" for the next shape. For example, early deformations may be smoother, or more uniform, than later deformations that may prioritize precision of the deformation to the one or more contours in the patient-specific image data.

In one example, the SMS change function may utilize a tolerance factor that defines by how much movement of each surface point can deviate from another surface point. For example, a tolerance of zero may indicate that all surface points must move the same distance for that iteration. A larger tolerance may allow the surface points to be moved different distances, which may result in less smoothness in the deformed SMS but a higher precision towards the contours in the patient-specific image data. In some examples, the SMS change function may specify different tolerances for different threshold intensities. For example, if the point in the patient-specific image data exceeds a threshold indicative of bone, the SMS change function may specify a large tolerance which enables processing circuitry 542 to move that surface point much closer to the bone surface because the muscle may be expected to rest against the bone surface. In some examples, processing circuitry 542 may not change the SMS shape change function between two iterations.

If processing circuitry 542 determines that the surface points do not need to be moved again and the deformed SMS shape fits the one or more contours ("NO" branch of block 827), processing circuitry 542 outputs the final deformed shape as a patient-specific shape representative of the soft-tissue structure of the patient (829). The patient-specific shape may be presented via a user interface and/or used for further analysis, such as part of pre-operative planning of treatment for the patient, as described in one or more of the examples of FIGS. 25, 26, and 27.

Figure 24:
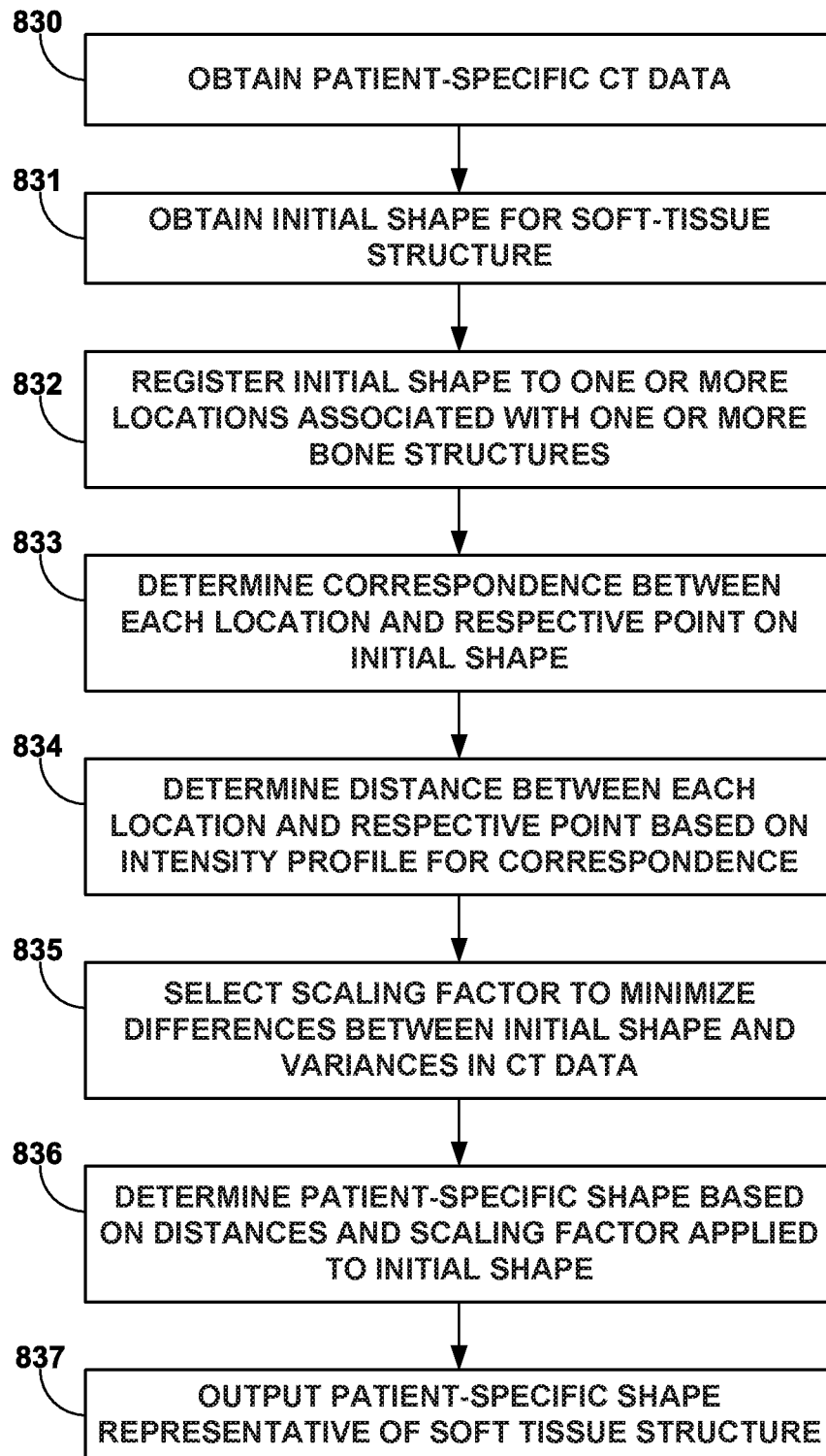
FIG. 24 is a flowchart illustrating an example procedure for modeling a soft tissue structure using patient-specific image data, in accordance with a technique of this disclosure.

FIG. 24 is a flowchart illustrating an example procedure for modeling a soft tissue structure using patient-specific image data, in accordance with a technique of this disclosure. Processing circuitry 542 of system 540 will be described as performing the example of FIG. 24, but other devices or systems, such as virtual planning system 102, may perform one or more portions of this technique. Furthermore, some portions of this technique may be performed by a combination of two or more devices and/or systems via a distributed system. The example of FIG. 24 may be similar to the illustrations and discussions above with respect to FIGS. 18A and 18B.

As shown in FIG. 24, processing circuitry 542 may obtain patient-specific image data of the patient of interest (830). This patient-specific image data may be generated from one or more imaging modalities (e.g., x-ray, CT, MRI, etc.) and stored in a data storage device. Processing circuitry 542 then obtains an initial shape for a soft-tissue structure of interest (831). The initial shape may be a geometric shape or a statistical mean shape (SMS). For example, the SMS may be a pathological shape to capture a condition similar to the patient. This soft-tissue structure may be a muscle or other non-bone structure. Processing circuitry 542 then registers the initial shape to one or more locations associated with one or more bones of the patient-specific CT data (832). This registration may include registering points on the initial shape to corresponding points or locations associated with adjacent bones.

Processing circuitry 542 then determines correspondence between each location of the bones and respective points on the initial shape (833). Processing circuitry 542 then determines a distance between each location and the respective point on the initial shape based on an intensity profile for correspondence (834). For example, an intensity or gradient profile may be used to identify boundaries of the soft tissue structure in the patient-specific CT data. Processing circuitry 542 may employ a cost function to fit the initial shape to all of the available fiducial locations of the bones.

Processing circuitry 542 may then select a scaling factor that minimizes differences between the initial shape and variances in the patient-specific CT data (835). For example, processing circuitry 542 may analyze different scaling factors and use a cost function to obtain the best fit for the initial shape to the patient-specific CT data. Processing circuitry 542 may then output the final patient-specific shape representative of the soft tissue structure of the patient. Processing circuitry 542 may perform this analysis for several muscles, for example, associated with the shoulder to be replaced.

Figure 25:
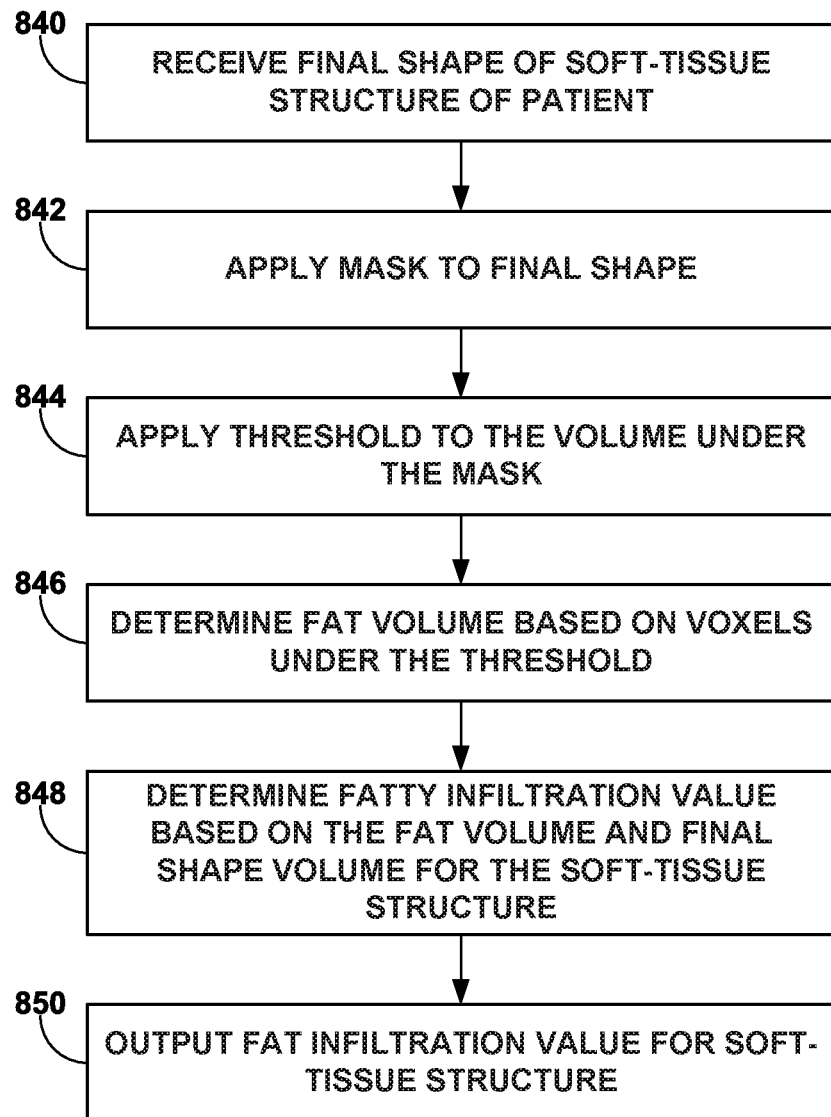
FIG. 25 is a flowchart illustrating an example procedure for determining fatty infiltration values for soft tissue structures of a patient, in accordance with a technique of this disclosure.

FIG. 25 is a flowchart illustrating an example procedure for determining fatty infiltration values for soft tissue structures of a patient, in accordance with a technique of this disclosure. Processing circuitry 542 of system 540 will be described as performing the example of FIG. 25, but other devices or systems, such as virtual planning system 102, may perform one or more portions of this technique. Furthermore, some portions of this technique may be performed by a combination of two or more devices and/or systems via a distributed system. The example of FIG. 25 may be similar to the illustrations and discussions above with respect to FIG. 19. The process of FIG. 25 is described with respect to three-dimensional data sets, but several two-dimension slices of data may be analyzed in a similar manner in other examples.

As shown in FIG. 25, processing circuitry 542 may obtain or receive the final patient-specific shape of the soft tissue structure for the patient (840). Processing circuitry 542 then applies a mask to the patient-specific shape (842). This mask may remove data outside of patient-specific shape. Next, processing circuitry 542 may apply a threshold to the voxels, or volume, under the mask (844). In some examples, processing circuitry 542 may apply the threshold to a group of two or more voxels and/or an averaged intensity over the group of voxels, in order to determine if that group of voxels should be identified as fat tissue or not. This grouping of voxels may reduce the impact of noise from whether or not a voxel is determined to be fatty tissue. Processing circuitry 542 then determines a fat volume for the soft tissue structure by adding the voxels having intensity values that were determined to be under the threshold (846). In other words, voxels under the threshold were determined to be fatty tissue and voxels over the threshold were determined to be muscle. Processing circuitry 542 then determines a fatty infiltration value based on the fat volume (i.e., the number of voxels having intensity values under the intensity threshold, representing the fat volume) and a total volume of the patient-specific shape for the soft-tissue structure (848) (i.e., the total represented by all voxels in the masked patient-specific shape, including the number of voxels having intensity values under the intensity threshold and the number of voxels having intensity values at or above the intensity threshold). For example, processing circuitry 542 can divide the fat volume by the total volume of the patient-specific shape to determine the fat ratio for the soft-tissue structure. Processing circuitry 542 may calculate the total volume of the patient-specific shape or obtain that volume that was previously calculated. Processing circuitry 542 may then output the fat volume ratio for the soft-tissue structure as the fat infiltration value (850). The fat volume ratio may be presented via a user interface and/or used for additional analysis.

Figure 26:
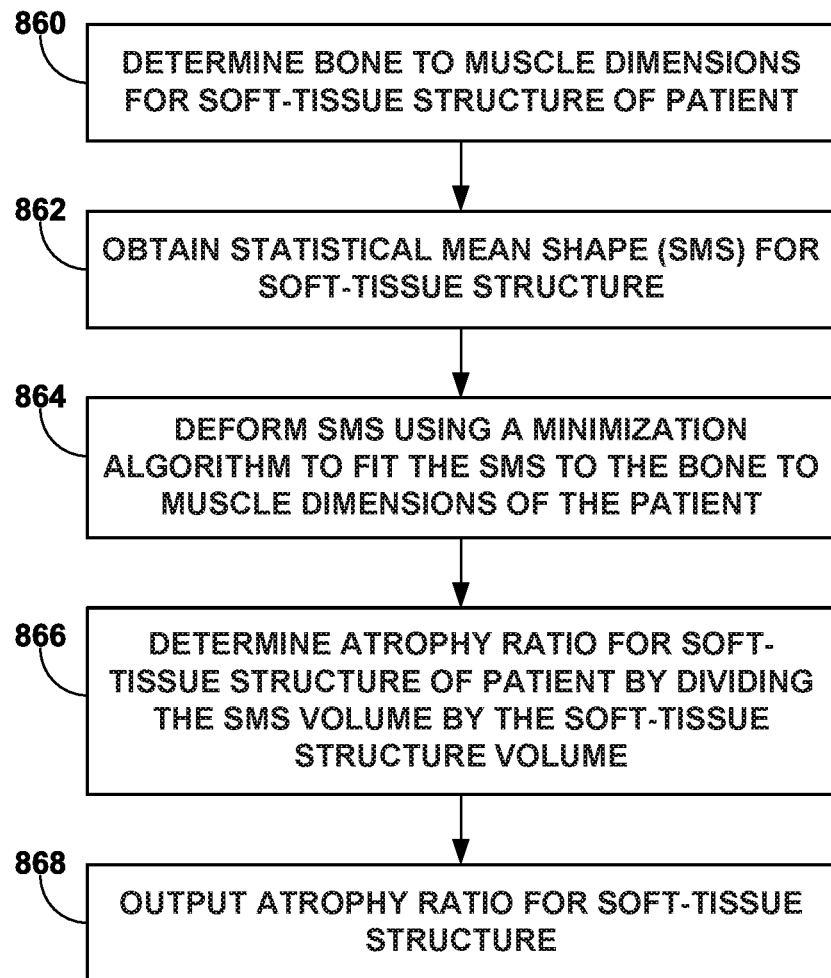
FIG. 26 is a flowchart illustrating an example procedure for determining an atrophy ratio for soft tissue structures of a patient, in accordance with a technique of this disclosure.

FIG. 26 is a flowchart illustrating an example procedure for determining an atrophy ratio for soft tissue structures of a patient, in accordance with a technique of this disclosure. Processing circuitry 542 of system 540 will be described as performing the example of FIG. 26, but other devices or systems, such as virtual planning system 102, may perform one or more portions of this technique. Furthermore, some portions of this technique may be performed by a combination of two or more devices and/or systems via a distributed system. The example of FIG. 26 may be similar to the illustrations and discussions above with respect to FIG. 20. The process of FIG. 26 is described with respect to three-dimensional data sets, but several two-dimension slices of data may be analyzed in a similar manner in other examples.

As shown in the example of FIG. 26, processing circuitry 542 first determines the bone to muscle dimensions for the soft-tissue structure of the patient (860). Processing circuitry 542 may determine lengths, widths, and/or volumes of the bones, such as a scapula, with respect to the dimensions of the muscle according to the patient-specific shape. The bone to muscle dimensions may identify specific anatomical sizing for the patient. Processing circuitry 542 then obtains a statistical mean shape (SMS) for the soft-tissue structure (862). The SMS may be representation of typical muscle dimensions based on calculations from a population of many subjects. This SMS may be based on health populations. In some examples, the SMS may be based on patients with a race, gender, age, height, or other factors similar to the patient.

Next, processing circuitry 542 deforms the SMS using a minimization algorithm to fit the SMS to the bone to muscle dimensions of the soft-tissue structure (864). For example, processing circuitry 542 may modify the SMS to more closely fit the bone to muscle dimensions of the patient and thus estimate the pre-morbid state for that muscle. A variety of different types of minimization algorithms may be employed to fit the SMS to the patient anatomy. The resulting pre-morbid prediction for that muscle may be used as an estimate of the dimensions of the healthy state of the muscle. Processing circuitry 542 then determines an atrophy ratio for the soft-tissue structure by dividing the deformed SMS volume by the soft-tissue structure volume represented by patient-specific shape (866). This result is the atrophy ratio for the soft-tissue structure, i.e., the ratio of the volume of healthy tissue to the volume of the actual tissue. The atrophy ratio may be calculated based on other dimensional comparisons between the healthy and current state of the soft-tissue structure in other examples. Processing circuitry 542 then outputs the atrophy ratio for display to a user or for further use in additional calculations during pre-operative planning (868). For example, processing circuitry 542 may output the present tissue or patient-specific shape overlaid on the pre-morbid, or healthy, estimate of the same soft tissue structure. Processing circuitry 542 may perform this atrophy ratio calculation for each muscle of interest when performing pre-operative planning for the joint of interest (e.g., rotator cuff muscles for a shoulder joint of interest).

Figure 27:
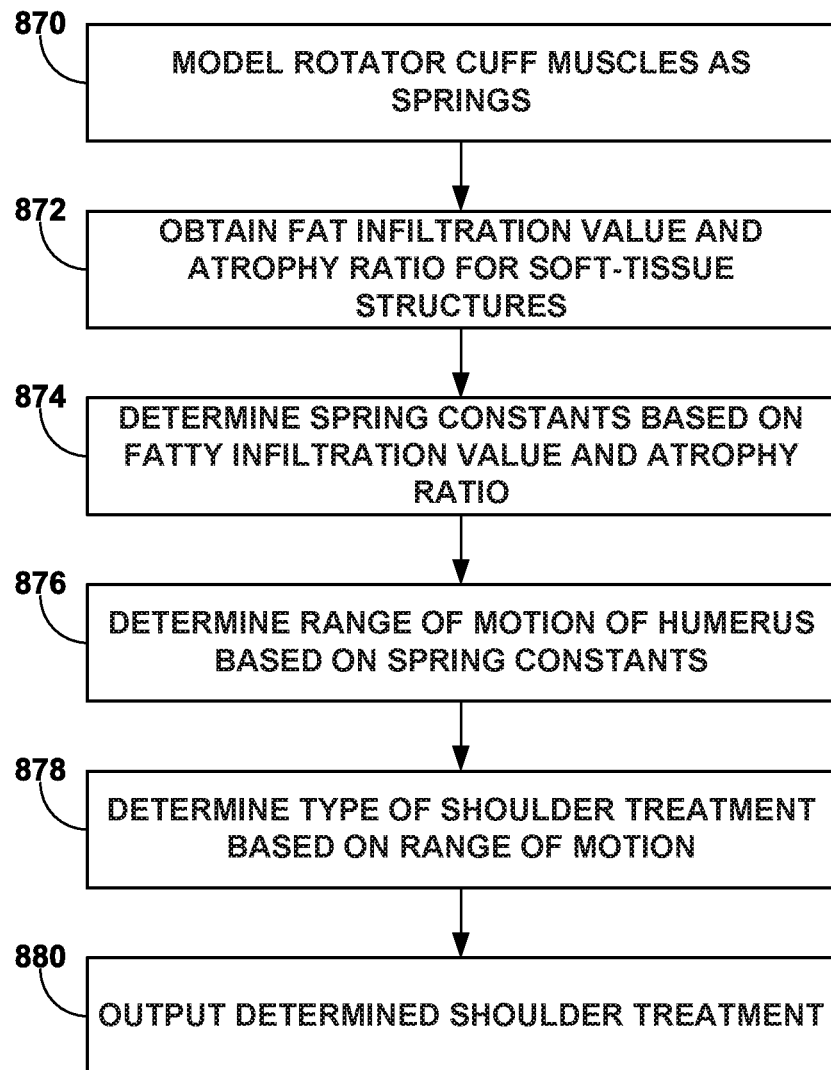
FIG. 27 is a flowchart illustrating an example procedure for determining a type of shoulder treatment based on determined soft tissue structures of a patient, in accordance with a technique of this disclosure.

FIG. 27 is a flowchart illustrating an example procedure for determining a type of shoulder treatment based on determined soft tissue structures of a patient, in accordance with a technique of this disclosure. Processing circuitry 542 of system 540 will be described as performing the example of FIG. 27, but other devices or systems, such as virtual planning system 102, may perform one or more portions of this technique. Furthermore, some portions of this technique may be performed by a combination of two or more devices and/or systems via a distributed system. The process of FIG. 26 is described with respect to three-dimensional data sets, but several two-dimension slices of data may be analyzed in a similar manner in other examples.

As shown in the example of FIG. 27, processing circuitry 542 may model one or more rotator cuff muscles, and/or other muscles associated with the shoulder joint, as springs (870). Processing circuitry 542 then obtains the fat infiltration value and the atrophy ratio for each of the soft tissue structures (872). Processing circuitry 542 then, for each muscle, determines a spring constant based on the fat infiltration value and the atrophy ratio (874). Processing circuitry 542 can then determine a range of motion of the humerus in the shoulder joint based on the spring constants of the one or more muscles (876). Processing circuitry 542 then determines the type of shoulder treatment based on the determined range of motion (878). For example, processing circuitry 542 may select between an anatomical shoulder replacement surgery or a reverse shoulder replacement surgery. In some examples, pathologies such as concentric osteo-arthritis or rotator cuff massive tears, muscle quality indicators, age, and glenoid deformity state may also influence whether an anatomical or reverse shoulder replacement is appropriate for the patient. In some examples, processing circuitry 542 may determine other aspects of surface from this information, such as sizes of implants, locations of implants, or other related information. In some examples, processing circuitry 542 may use one or more decision trees or neural networks in order to determine the type of shoulder treatment. The recommended shoulder treatment may also be based on other patient information such as age, gender, activity, or any other aspect.

Processing circuitry 542 may control a user interface to display the recommended shoulder replacement surgery. In response to a clinician selecting, accepting, or confirming the recommendation, processing circuitry 542 may launch other pre-operative planning for the patient and the selected type of shoulder replacement surgery. For example, processing circuitry 542, or other system such as virtual planning system 102 of FIG. 1, may generate a surgical plan for the selected shoulder replacement surgery. Processing circuitry 542 may control the user interface to guide the clinician through additional customization steps for the patient, such as needed implants, cutting planes, anchor locations, reaming axis, screw drilling and/or placement, sizing, implant placement, specific steps to the surgery, and any other aspects of the selected surgery. The clinician may also interact with the surgical planning by viewing system generated visualization of the procedure, anatomy, and/or implants for the patient. These types of processes may apply to surgeries on other joints, such as ankles, elbows, wrists, hips, knees, etc. In addition, the process of FIG. 27 may be used to determine locations or rotational angles of one or more implants associated with the shoulder treatment. For example, processing circuitry 542 may determine whether to medialize (e.g., move the humeral head implant closer to the scapula or move the glenoid closer to the patient's midline) or lateralize (e.g., move the humeral head implant further from the scapula or move the glenoid closer to the humerus) in order to improve range of motion based on the spring constants. In some examples, processing circuitry 542 may suggest a size and/or location of a bone graft (removal or addition of bone) to the humeral head and/or glenoid in order to achieve the desired location of the humerus with respect to the scapula. Stiffness of the shoulder muscles (e.g., spring constants when used to model the muscles), may be used by processing circuitry to determine an appropriate position of the humeral head in order to achieve appropriate range of motion and/or strength of the shoulder.

Figure 28:
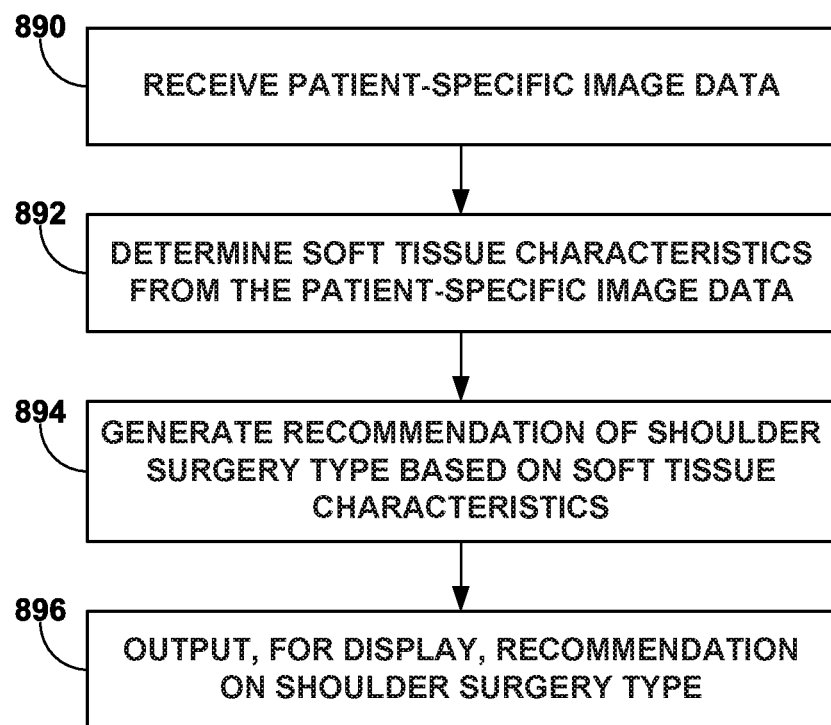
FIG. 28 is a flowchart illustrating an example procedure for determining a type of shoulder treatment based on patient-specific image data, in accordance with a technique of this disclosure.

As described herein, processing circuitry 542 and/or other systems can determine a plurality of measurements of morphological characteristics of the patient using patient-specific imaging data. Such measurements may include distance measurements, angle measurements, and other types of numerical characterizations of measurable relationships of and/or between structures of a patient. For example, the measurements may include any combination of values relating to one or more of:

a glenoid version: an angular orientation of an axis of the glenoid articular surface relative to a transverse axis of the scapula.
a glenoid inclination: the superior/inferior tile of the glenoid relative to the scapula.
a glenoid orientation/direction: the 3-dimensional orientation of the glenoid in a 3-dimensional space.
a glenoid best fit sphere radius: a radius of a best-fit sphere for the patient's glenoid. The best-fit sphere is a conceptual sphere that is sized such that a sector of the sphere would sit flush as possible with the patient's glenoid.
a glenoid best fit sphere root mean square error: the mean square error of the difference between the patient's glenoid and the sector of the best-fit sphere.
a reverse shoulder angle: the tilt of the inferior part of the glenoid.
a critical shoulder angle: the angle between the plane of the glenoid fossa and the connecting line to the most inferolateral point of the acromion.
acromion humeral space: the space between the acromion and the top of the humerus.
glenoid humeral space: the space between the glenoid and the humerus.
humeral version: the angle between the humeral orientation and the epicondylar axis.
humeral neck shaft angle: the angle between the humeral anatomic neck normal vector and the intramedullary axis.
humeral head best fit sphere radius and root mean square error: a radius of a best-fit sphere for the head of the patient's humerus. The best-fit sphere is a conceptual sphere that is sized such that a sector of the sphere matches the surface of the humeral head as much as possible. The root mean square error indicates the error between the best-fit sphere and the patient's actual humeral head.
humeral subluxation: a measure of the subluxation of the humerus relative to the glenoid.
humeral orientation/direction: the orientation of the humeral head in a 3-dimensional space.
a measurement of an epiphysis of the patient's humerus,
a measurement of a metaphysis of the patient's humerus,
a measurement of a diaphysis of the patient's humerus,
retroversion of a bone FIG. 28 is a flowchart illustrating an example procedure for determining a type of shoulder treatment based on patient-specific image data, in accordance with a technique of this disclosure. Processing circuitry 542 of system 540 will be described as performing the example of FIG. 28, but other devices or systems, such as virtual planning system 102, may perform one or more portions of this technique. Furthermore, some portions of this technique may be performed by a combination of two or more devices and/or systems via a distributed system. The process of FIG. 28 is described with respect to three-dimensional data sets, but several two-dimension slices of data may be analyzed in a similar manner in other examples.

As shown in the example of FIG. 28, processing circuitry 542 may receive patient-specific image data for a patient (e.g., CT image data). Processing circuitry 542 then determines one or more soft tissue characteristics from the patient-specific image data for one or more soft tissue structures of the patient (892). Example soft tissue characteristics may include soft tissue shapes and volumes, fatty infiltration values, atrophy rations, range of motion values, or any other such parameters. Processing circuitry 542 then generates a recommendation of a shoulder surgery type based on the determined one or more soft tissue characteristics (894). For example, processing circuitry 542 may select between an anatomical total shoulder replacement or a reverse total shoulder replacement. Then, processing circuitry 542 may output, for display by a user interface, the determined recommendation on the type of shoulder surgery for the patient (896).

One of more of the determinations described herein and related to orthopedic classification and surgery planning may employ artificial intelligence (AI) techniques such as neural networks. In one example, processing circuitry 542 may employ various AI techniques to generate one or more characteristics of tissue, such as an atrophy ratio, fatty infiltration, range of motion, recommendations for types of implants (e.g., a stem size for a humeral implant), and/or recommendations for a particular type of surgical treatment (e.g., anatomical or reverse shoulder replacement). In some examples, such AI techniques may be employed during preoperative phase 302 (FIG. 3) or another phase of a surgical lifecycle. Deep neural networks (DNNs) are a class of artificial neural networks (ANNs) that have shown great promise as classification tools. A DNN includes an input layer, an output layer, and one or more hidden layers between the input layer and the output layer. DNNs may also include one or more other types of layers, such as pooling layers.

Each layer may include a set of artificial neurons, which are frequently referred to simply as "neurons." Each neuron in the input layer receives an input value from an input vector. Outputs of the neurons in the input layer are provided as inputs to a next layer in the DNN. Each neuron of a layer after the input layer may apply a propagation function to the output of one or more neurons of the previous layer to generate an input value to the neuron. The neuron may then apply an activation function to the input to compute an activation value. The neuron may then apply an output function to the activation value to generate an output value for the neuron. An output vector of the DNN includes the output values of the output layer of the DNN.

There have been several challenges associated with application of DNNs to planning orthopedic surgery, particularly with respect to shoulder pathology. For example, some challenges relate to how to structure and train a DNN so that the DNN is able to provide meaningful output regarding shoulder pathology. In another example of a challenge associated with application of DNNs to planning orthopedic surgery, patients and healthcare professionals are understandably reluctant to trust decisions made by a computer, especially when it is unclear how the computer made those decisions. There are therefore problems about how to generate output in a way that helps ensure that patients and healthcare professionals are comfortable in trusting the output of a DNN.

This disclosure describes techniques that may resolve these challenges and provide a DNN structure that provides meaningful output regarding shoulder pathology and/or recommended shoulder treatments based on one or more inputs. For example, an artificial neural network (ANN) has an input layer, an output layer, and one or more hidden layers between the input layer and the output layer. The input layer includes a plurality of input layer neurons. Each input layer neuron in the plurality of input layer neurons corresponds to a different input element in a plurality of input elements. The output layer includes a plurality of output layer neurons.

Each output layer neuron in the plurality of output layer neurons corresponds to a different output element in a plurality of output elements. Each output element in the plurality of output elements corresponds to a different classification in one or more shoulder pathology classification systems. In this example, a computing system may generate a plurality of training datasets from past shoulder surgery cases. Each respective training dataset corresponds to a different training data patient in a plurality of training data patients and comprises a respective training input vector and a respective target output vector.

For each respective training dataset, the training input vector of the respective training dataset comprises a value for each element of the plurality of input elements. For each respective training dataset, the target output vector of the respective training dataset comprises a value for each element of the plurality of output elements. In this example, the computing system may use the plurality of training datasets to train the neural network. Additionally, in this example, the computing system may obtain a current input vector that corresponds to a current patient. The computing system may apply the DNN to the current input vector to generate a current output vector. The computing system may then determine, based on the current output vector, a diagnosis of a shoulder condition of the current patient, which also may be referred to as a shoulder classification.

In this example, by having different output elements in the plurality of output elements correspond to different classes in one or more shoulder pathology classification systems, the DNN may be able to provide meaningful output information that can be used in the diagnosis of shoulder conditions of patients, determination of anatomical characteristics, or recommendations for treatment. For instance, this may be more efficient computationally and in terms of training time than a system in which different values of a neuron in the output layer correspond to different classes. Furthermore, in some examples, the output values of neurons in the output layer indicate measures of confidence that the classified shoulder condition of a patient belongs in the corresponding class in one of the shoulder pathology classification systems. Such confidence values may help users consider the likelihood that the patient may have a different class of shoulder condition than that determined by the computing system using the DNN. Furthermore, it may be computationally efficient for the output of the same output layer neurons to both express confidence levels and be used as the basis for determining a diagnosis (e.g., classification) of a shoulder condition of a patient, certain characteristics of tissue (e.g., fatty infiltration values, atrophy values, range of motion values) or even a recommendation on type of surgery based on one or more of these tissue characteristics.

Figure 29:
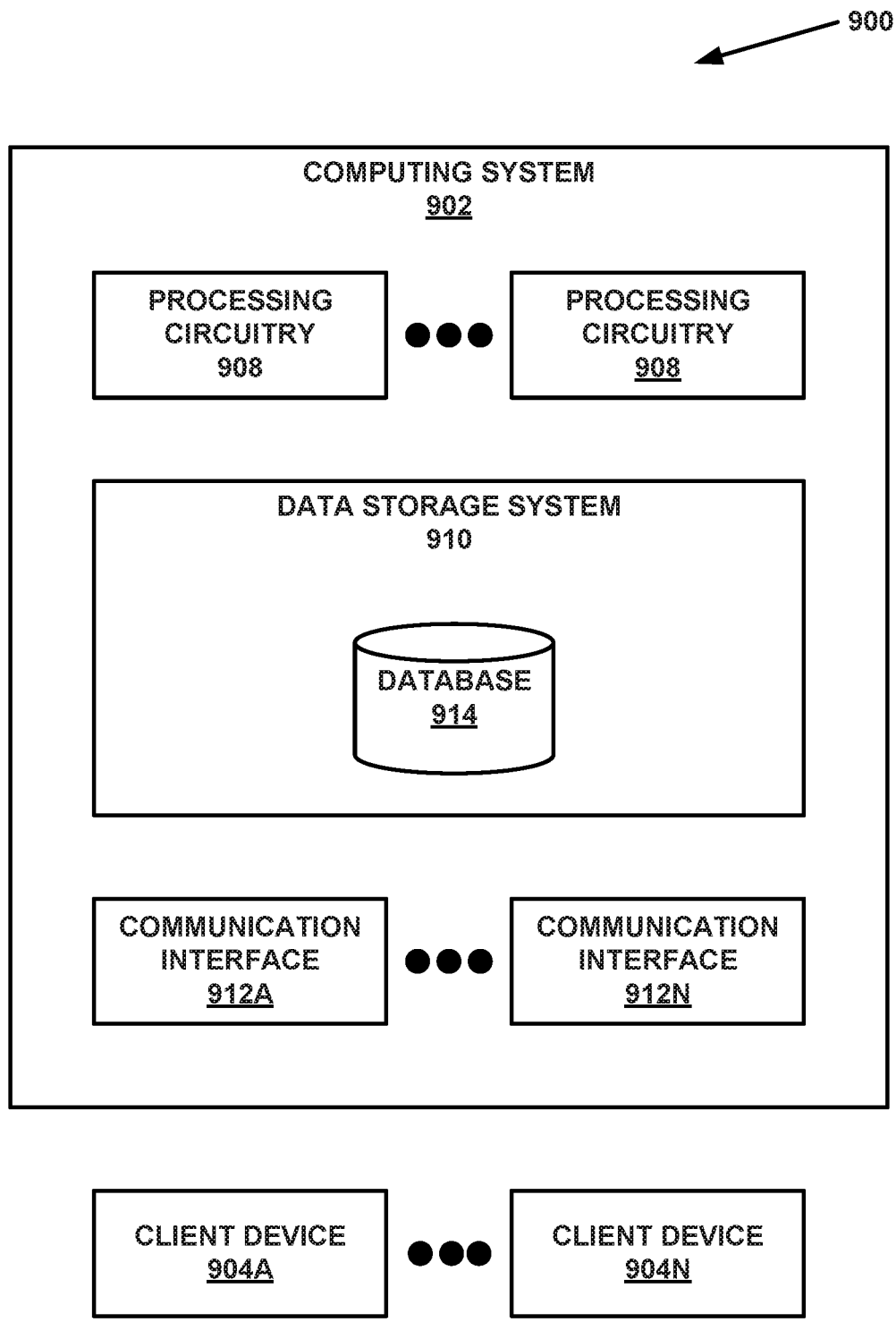
FIG. 29 is a block diagram illustrating an example computing system that implements a deep neural network (DNN) usable for determining one or more aspects of patient anatomy, diagnosis, and/or treatment recommendations, in accordance with a technique of this disclosure.

FIG. 29 is a block diagram illustrating an example computing system 902 that implements a DNN usable for determining one or more aspects of patient anatomy, diagnosis, and/or treatment recommendations, in accordance with a technique of this disclosure. Computing system 902 may be part of orthopedic surgical system 100 (FIG. 1). Computing system 902 may use the DNN to determine a soft tissue characteristic and/or a recommendation on the type of treatment, such as whether the patient would benefit from an anatomical or reverse total shoulder replacement. In some examples, computing system 902 includes a XR visualization device (e.g., an MR visualization device or an XR visualization device) that includes one or more processors that perform operations of computing system 902.

As shown in the example of FIG. 29, system 900 includes a computing system 902, a set of one or more client devices (collectively, "client devices 904"). In other examples, system 900 may include more, fewer, or different devices and systems. In some examples, computing system 902 and client devices 904 may communicate via one or more communication networks, such as the Internet.

Computing system 902 may include one or more computing devices. Computing system 902 and client devices 904 may include various types of computing devices, such as server computers, personal computers, smartphones, laptop computers, and other types of computing devices. In the example of FIG. 29, computing system 902 includes processing circuitry 908, a data storage system 910, and a set of one or more communication interfaces 912A through 912N (collectively, "communication interfaces 912"). Data store 910 is configured to store data. Communication interfaces 912 may enable computing system 902 to communicate (e.g., wirelessly or using wires) to other computing systems and devices, such as client devices 912. For ease of explanation, this disclosure may describe actions performed by processing circuits 906, data store 910, and communication interfaces 912 as being performed by computing system 902 as a whole. One or more sub-systems of orthopedic surgical system 100 (FIG. 1) may include computing system 902 and client devices 904. For example, virtual planning system 102 may include computing system 902 and client devices 904.

Users may use client devices 904 to access information generated by computing system 902. For example, computing system 902 may generate a recommendation for a type of shoulder treatment for the current patient. The recommendation may be represented by a shoulder class among a plurality of shoulder classes in a shoulder treatment classification system. In this example, users may use client devices 904 to access information regarding the recommendation for intervention. Because computing system 902 may be remote from client devices 904, users of client devices 904 may consider computing system 902 to be in a cloud-based computing system. In other examples, some or all the functionality of computing system 902 may be performed by one or more of client devices 904.

Computing system 902 may implement a DNN. Storage system 910 may comprise one or more computer-readable data storage media. Storage system 910 may store parameters of the DNN. For instance, storage system 910 may store weights of neurons of the DNN, bias values of neurons of the DNN, and so on.

Computing system 902 may determine a recommendation for treatment of a shoulder condition of a patient based on output of the DNN. In accordance with a technique of this disclosure, output elements of the DNN include output elements corresponding to different classes in one or more shoulder recommendation classification systems. The shoulder recommendation classification systems may include different classification systems for each of the types of treatments for the patient, or for different classifications for different types of pathologies that may lead to different recommendations. For example, different treatments may include an anatomical shoulder replacement and a reverse shoulder replacement. However, other treatments or surgeries may have respective classification systems. For instance, the Walch classification system and the Favard classification system are two different primary glenohumeral osteoarthritis classification systems. The Warner classification system and the Goutallier classification system are two different rotator cuff classification systems. In some examples, a shoulder pathology classification system may include classes for more general categories of shoulder pathology, such as one or more of: primary glenoid humeral osteoarthritis (PG-HOA), rotator cuff tear arthropathy (RCTA) instability, massive rotator cuff tear (HRCT), rheumatoid arthritis, post-traumatic arthritis, and osteoarthritis. These classification systems may be used to determine a recommendation on treatment.

The Walch classification system, for example, specifies five classes: 1A, 1B, 2A, 2B, and 3. The Favard classification system, as another example, specifies five classes: E0, E1, E2, E3, and E4. The Warner classification system, as a further example, specifies four classes of rotator cuff atrophy: none, mild, moderate, and severe. The Goutallier classification system, as a further example, specifies five classes: 0 (completely normal muscle), I (some fatty streaks), II (amount of muscle is greater than fatty infiltration), III (amount of muscle is equal to fatty infiltration), IV (amount of fatty infiltration is greater than muscle). In other examples, the classification system may use fatty infiltration values or atrophy ratios calculated from the patient-specific image data.

In some examples, computing system 902 may determine the recommendation for treatment based on the diagnosis of the shoulder condition of the patient according to a comparison of the values of the output elements generated by the DNN. For example, the values of the output elements may correspond to confidence values that indicate levels of confidence that the patient's shoulder condition belongs in the classes that correspond to the output layer neurons that generated the values. For instance, the values of the output elements may be the confidence values or computing system 902 may calculate the confidence values based on the values of the output elements.

In some examples, the output function of the output layer neurons generates the confidence values. Furthermore, computing system 902 may identify which of the confidence values is highest. In this example, computing system 902 may determine that the shoulder pathology class corresponding to the highest confidence value is the diagnosis of the shoulder condition of the current patient. In some examples, if none of the confidence values is above a threshold, computing system 902 may generate output indicating that computing system 902 is unable to make a definitive diagnosis. Computing system 902 may thus be unable to determine a recommendation on treatment.

As mentioned above, in some examples, the output elements of the DNN include confidence values. In one such example, a confidence value function outputs confidence values. The confidence value function may be the output function of the output layer neurons of the DNN. In this example, all possible confidence values output by the confidence value function are within a predefined range. Furthermore, in this example, computing system 902 may apply the DNN to an input vector to generate an output vector. As part of applying the DNN, computing system 902 may, for each respective output layer neuron in the plurality of output layer neurons, calculate an output value of the respective output layer neuron.

Computing system 902 may then apply the confidence value function with the output value of the respective output layer neuron as input to the confidence value function. The confidence value function outputs a confidence value for the respective output layer neuron. In this example, for each respective output layer neuron in the plurality of output layer neurons, the output element corresponding to the respective output layer neuron specifies the confidence value for the respective output layer neuron. Furthermore, for each respective output layer neuron in the plurality of output layer neurons, the confidence value for the respective output layer neuron is a measure of confidence that the shoulder condition of the current patient belongs to a class in the one or more shoulder pathology classification systems that corresponds to the output element corresponding to the respective output layer neuron.

Computing system 902 may use various confidence value functions. For example, computing system 902 may apply a hyperbolic tangent function, a sigmoid function, or another type of function that output values that are within a predefined range. The hyperbolic tangent function (tan h) has the form $\gamma(c)=\tan h(c)=(e^c-e^{-c})/(e^c+e^{-c})$. The hyperbolic tangent function takes real-valued arguments, such as output values of output layer neurons, and transforms them to the range $(-1, 1)$. The sigmoid function has the form $\gamma(c)=1/(1+e^{-c})$. The sigmoid function takes real-valued arguments, such as output values of output layer neurons, and transforms them to the range $(0, 1)$.

Computing system 902 may use a plurality of training datasets to train the DNN. Each respective training dataset may correspond to a different training data patient in a plurality of previously-diagnosed training data patients. For instance, a first training dataset may correspond to a first training data patient, a second training dataset may correspond to a second training data patient, and so on. A training dataset may correspond to a training data patient in the sense that the training dataset may include information regarding the patient. The training data patients may be real patients who have diagnosed shoulder conditions. In some examples, the training data patients may include simulated patients.

Each respective training dataset may include a respective training input vector and a respective target output vector. For each respective training dataset, the training input vector of the respective training dataset comprises a value for each element of the plurality of input elements. In other words, the training input vector may include a value for each input layer neuron of the DNN. For each respective training dataset, the target output vector of the respective training dataset may comprise a value for each element of the plurality of output elements. In other words, the target output vector may include a value for each output layer neuron of the DNN.

In some examples, the values in the target output vector are based on confidence values. Such confidence values may, in turn, be based on levels of confidence expressed by one or more trained healthcare professionals, such as orthopedic surgeons. For instance, a trained healthcare professional may be given the information in the training input vector of a training dataset (or information from which the training input vector of the training dataset is derived) and may be asked to provide a confidence level that the training data patient has a shoulder condition belonging to each class in each of the shoulder pathology classification systems.

For instance, in an example where the shoulder pathology classification systems include the Walch classification system, the healthcare professional may indicate that her level of confidence that the training data patient's shoulder condition belongs to class A1 is 0 (meaning she does not at all believe that the training data patient's shoulder condition belongs to class A1), indicate that her level of confidence that the training data patient's shoulder condition belongs to class A2 is 0; indicate that her level of confidence that the training data patient's shoulder condition belongs to class B1 is 0.75 (meaning she is fairly confident that the training data patient's shoulder condition belongs to class B1); indicate that her level of confidence that the training data patient's shoulder condition belongs to class B2 is 0.25 (meaning she believes that there is a smaller chance that the training data patient's shoulder condition belongs to class B2); and may indicate that her level of confidence that the training data patient's shoulder condition belongs to class C is 0. In some examples, computing system 902 may apply the inverse of the confidence value function to the confidence values provided by the healthcare professional to generate values to include in the target output vector. In some examples, the confidence values provided by the healthcare professional are the values included in the target output vector.

Different healthcare professionals may have different levels of confidence that the same training data patient has a shoulder condition belonging to each class in each of the shoulder pathology classification systems. Hence, in some examples, the confidence values upon which the values in the target output vector are based may be averages or otherwise determined from the confidence levels provided by multiple healthcare professionals. Similar confidence values may be calculated for the recommendations on type of treatment based on the identified pathology, or characteristic, determined from the DNN.

In some such examples, the confidence levels of some healthcare professionals may be given greater weight in a weighted average of confidence levels than the confidence levels of other healthcare professionals. For instance, the confidence levels of a preeminent orthopedic surgeon may be given greater weight than the confidence levels of other orthopedic surgeons. In another example, the confidence levels of healthcare professionals or training data patients in particular regions or hospitals may be given greater weight than healthcare professionals or training data patients from other regions or hospitals. Advantageously, such weighted averaging may allow the DNN to be tuned according to various criteria and preferences.

For instance, a healthcare professional may prefer to use a DNN that has been trained such that confidence levels are weighted in particular ways. In some examples where training datasets include training datasets based on a healthcare professional's own cases, the healthcare professional (e.g., an orthopedic surgeon) may prefer to use a DNN trained using training datasets where the healthcare professional's own cases are weighted more heavily or exclusively using the healthcare professional's own cases. In this way, the DNN may generate output tailored to the healthcare professional's own style of practice. Moreover, as mentioned above, healthcare professionals and patients may have difficulty trusting the output of a computing system. Accordingly, in some examples, computing system 902 may provide information indicating that the DNN was trained to emulate the decisions of the healthcare professionals themselves and/or particularly trusted orthopedic surgeons.

In some examples, the confidence levels of different healthcare professionals for the same training data patient may be used in generating different training datasets. For instance, the confidence levels of a first healthcare professional with respect to a particular training data patient may be used to generate a first training dataset and the confidence levels of a second healthcare professional with respect to the same training data patient may be used to generate a second training dataset.

Furthermore, in some examples, computing system 902 may provide confidence values for output to one or more users. For instance, computing system 902 may provide the confidence values to client devices 904 for display to one or more users. In this way, the one or more users may be better able to understand how computing system 902 may have arrived at the diagnosis and/or recommendation for treatment of the shoulder of a patient.

In some examples, to expand the universe of training datasets, computing system 902 may automatically generate confidence values from electronic medical records. For instance, in one example, an electronic medical record for a patient may include data from which computing system 902 may form an input vector and may include data indicating a surgeon's diagnosis of a patient's shoulder condition and the selected shoulder treatment. In this example, computing system 902 may infer a default level of confidence from the diagnosis. The default level of confidence may have various values (e.g., 0.75, 0.8, etc.). While such a default level of confidence may not reflect the surgeon's actual level of confidence, imputing a level of confidence may be help increase the number of available training datasets, which may improve the accuracy of the DNN.

In some examples, the training datasets are weighted based on health outcomes of the training data patients. For example, a training dataset may be given higher weight if the training data patient associated with the training dataset had all positive health outcomes. However, a training dataset may be given a lower weight if the associated training data patient had less positive health outcomes. During training, computing system 902 may use a loss function that weights the training datasets based on the weights given to the training datasets.

In some examples, as part of generating the training datasets, computing system 902 may select the plurality of training datasets from a database of training datasets based on one or more training dataset selection criteria. In other words, computing system 902 may exclude certain training datasets from the training process of the DNN if the training datasets do not satisfy the training dataset selection criteria. In the example of FIG. 122, data storage system 910 stores a database 914 that contains training datasets from past shoulder surgery cases.

There may be a wide variety of training dataset selection criteria. For instance, in one example, the one or more training data set selection criteria may include which surgeon operated on the plurality of training data patients. In some examples, the one or more training dataset selection criteria include a region in which the training data patients live. In some examples, the one or more training dataset selection criteria include a region associated with one or more surgeons (e.g., a region in which the one or more surgeons practice, live, were licensed, were trained, etc.).

In some examples, the one or more training dataset selection criteria include postoperative health outcomes of the training data patients. In such examples, the postoperative health outcomes of the training data patients may include one or more of: postoperative range of motion, presence of postoperative infection, or postoperative pain. Thus, in such examples, the training datasets upon which the DNN is trained may exclude training datasets where adverse health outcomes occurred.

Additional training datasets may be added to the database over time and computing system 902 may use the additional training datasets to train the DNN. Thus, the DNN may continue to improve over time as more training datasets are added to the database.

Computing system 902 may apply one of various techniques to use the training datasets to train the DNN. For example, computing system 902 may use one of the various standard backpropagation algorithms known in the art. For instance, as part of training the DNN, computing system 902 may apply a cost function to determine cost values based on differences between the output vector generated by the DNN and the target output vector. Computing system 902 may then use the cost values in a backpropagation algorithm to update the weights of neurons in the DNN. In this manner, computing system 902 may train the DNN to determine various characteristics of soft tissue a patient (e.g., fatty infiltration, atrophy ratios, range of motion, etc.) based on inputs such as tissue volumes, voxel groupings, pre-morbid shape volumes, etc. In some examples, computing system 902 may train the DNN to determine recommendations for shoulder treatment using inputs from patient-specific image data and/or determined characteristics of soft tissue such as those characteristics that may have been determined from a different DNN. In some examples, computing system 902 may train the DNN to determine recommendations for shoulder treatment using a bone density metric that indicates or is related to the bone density of one or more bones (e.g., the humeral head) that will accept an implant. For example, computing system 902 may train the DNN using patient-specific imaging data (e.g., CT data) associated with a humeral head and the surgeon-selected type of humeral implant (e.g., stemmed, which may or may not include the length of the stem, or stemless humeral implant) for each respective patient. The output of this training would be a recommended type of humeral implant based on the patient-specific image data associated with the humeral head of a new patient. In this manner, the shoulder treatment and/or types of implants may be determined based on the density of trabecular bone, or other characteristic that may be related to density, within the humerus.

Figure 30:
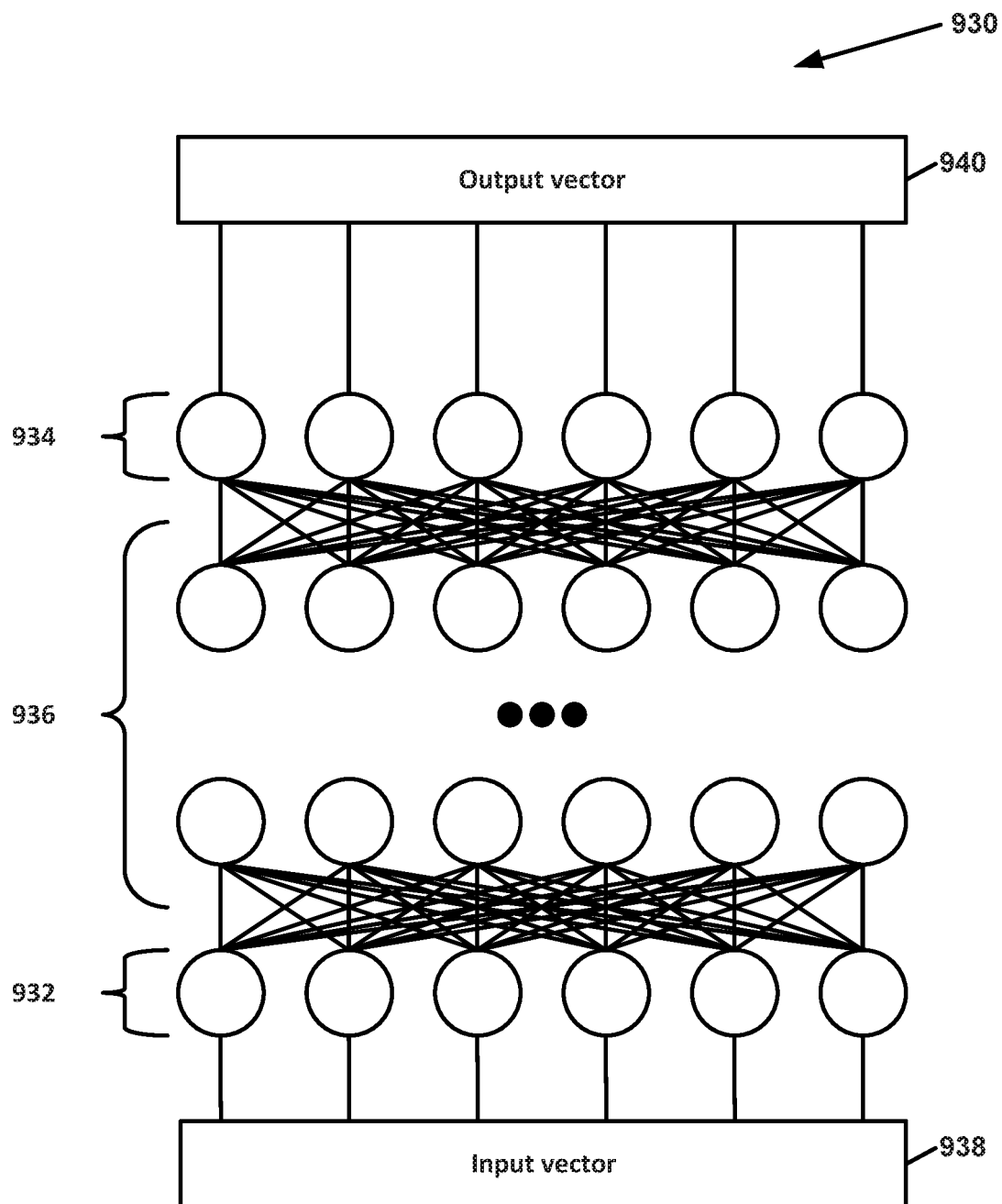
FIG. 30 illustrates an example DNN that may be implemented by the example computing system of FIG. 29.

FIG. 30 illustrates an example DNN 930 that may be implemented by computing system 902 with the system of FIG. 29. In the example of FIG. 30, DNN 930 includes an input layer 932, an output layer 934, and one or more hidden layers 936 between input layer 932 and output layer 934. In the example of FIG. 30, neurons are represented as circles. Although in the example of FIG. 30, each layer is shown as including six neurons, layers in DNN 930 may include more or fewer neurons. Furthermore, although DNN 930 is shown in FIG. 30 as being a fully connected network, DNN 930 may have a different architecture. For instance, DNN 930 may not be a fully connected network, may have one or more convolutional layers, or may otherwise have a different architecture from that shown in FIG. 123.

In some implementations, DNN 930 can be or include one or more artificial neural networks (also referred to simply as neural networks). A neural network can include a group of connected nodes, which also can be referred to as neurons or perceptrons. A neural network can be organized into one or more layers. Neural networks that include multiple layers can be referred to as "deep" networks. A deep network can include an input layer, an output layer, and one or more hidden layers positioned between the input layer and the output layer. The nodes of the neural network can be connected or non-fully connected.

DNN 930 can be or include one or more feed forward neural networks. In feed forward networks, the connections between nodes do not form a cycle. For example, each connection can connect a node from an earlier layer to a node from a later layer.

In some instances, DNN 930 can be or include one or more recurrent neural networks. In some instances, at least some of the nodes of a recurrent neural network can form a cycle. Recurrent neural networks can be especially useful for processing input data that is sequential in nature. In particular, in some instances, a recurrent neural network can pass or retain information from a previous portion of the input data sequence to a subsequent portion of the input data sequence through the use of recurrent or directed cyclical node connections.

In some examples, sequential input data can include time-series data (e.g., sensor data versus time or imagery captured at different times). For example, a recurrent neural network can analyze sensor data versus time to detect or predict a swipe direction, to perform handwriting recognition, etc. Sequential input data may include words in a sentence (e.g., for natural language processing, speech detection or processing, etc.); notes in a musical composition; sequential actions taken by a user (e.g., to detect or predict sequential application usage); sequential object states; etc. Example recurrent neural networks include long short-term (LSTM) recurrent neural networks; gated recurrent units; bi-direction recurrent neural networks; continuous time recurrent neural networks; neural history compressors; echo state networks; Elman networks; Jordan networks; recursive neural networks; Hopfield networks; fully recurrent networks; sequence-to-sequence configurations; etc.

In some implementations, DNN 930 can be or include one or more convolutional neural networks. In some instances, a convolutional neural network can include one or more convolutional layers that perform convolutions over input data using learned filters. Filters can also be referred to as kernels. Convolutional neural networks can be especially useful for vision problems such as when the input data includes imagery such as still images or video. However, convolutional neural networks can also be applied for natural language processing.

DNN 930 may be or include one or more other forms of artificial neural networks such as, for example, deep Boltzmann machines; deep belief networks; stacked autoencoders; etc. Any of the neural networks described herein can be combined (e.g., stacked) to form more complex networks.

In the example of FIG. 30, an input vector 938 includes a plurality of input elements. Each of the input elements may be a numerical value. Input layer 932 includes a plurality of input layer neurons. Each input layer neuron in the plurality of input layer neurons included in input layer 932 may correspond to a different input element in a plurality of input elements. In other words, input layer 932 may include a different neuron for each input element in input vector 938.

Furthermore, in the example of FIG. 30, an output vector 940 includes a plurality of output elements. Each of the output elements may be a numerical value. Output layer 934 includes a plurality of output layer neurons. Each output layer neuron in the plurality of output layer neurons corresponds to a different output element in the plurality of output elements. In other words, each output layer neuron in output layer 934 corresponds to a different output element in output vector 940.

Input vector 938 may include a wide variety of information. For example, input vector 938 may include morphological measurements of the patient. In some examples where input vector 938 includes measurements of the patient's morphology, input vector 938 may determine the measurements based on medical images of the patient, such as CT images, MRI images, or other types of images. For instance, computing system 902 may obtain the medical images of a current patient (e.g., patient-specific image data). For instance, computing system 902 may obtain the medical images from an imaging machine (e.g., a CT machine, MRI machine, or other type of imaging machine), an electronic medical record of the patient, or another data source. In this example, computing system 902 may segment the medical images to identify internal structures of the current patient, such as soft tissue and bone, and, in some examples, generate patient-specific shapes of the bone and/or soft tissue as described herein. Furthermore, in this example, computing system 902 may determine the plurality of measurements based on relative positions of the identified internal structures of the current patient. In this example, the plurality of input elements may include an input element for each measurement in the plurality of measurements. Other inputs may include other determinations from patient-specific image data, such as the fatty infiltration value, atrophy ration, and/or range of motion values for the joint.

As mentioned elsewhere in this disclosure, computing system 902 may include one or more computing devices. Hence, various functions of computing system 902 may be performed by various combinations of the computing devices of computing system 902. For instance, in some examples, a first computing device of computing system 902 may segment the images, a second computing device of computing system 902 may train the DNN, a third computing device of computing system 902 may apply the DNN, and so on. In other examples, a single computing device of computing system 902 may segment the images, train the DNN, and apply the DNN.

In some examples, input vector 938 may include information (e.g., in combination with zero or more other example types of input data described herein) based on a rotator cuff assessment of the patient. For instance, input vector 938 may include information, alone or in combination with morphological inputs described above, regarding fatty infiltration of the rotator cuff, atrophy of the rotator cuff, and/or other information about the patient's rotator cuff. In some examples, fatty infiltration measures and atrophy measures for soft tissue used as inputs to the neural network may be derived, for example, by any of the soft tissue modeling techniques as described in this application. In some examples, the information regarding the patient's rotator cuff may be expressed in terms of a class in a shoulder pathology classification system, such as a Warner classification system or a Goutallier classification system.

In some examples, input vector 938 may include (e.g., in combination with zero or more other example types of input data described herein) patient range of motion information. In some examples, the patient range of motion information may be generated using a motion tracking device, as described elsewhere in this disclosure. In other examples, the range of motion value or values may be determined from analysis of the patient-specific image data, as described herein.

Furthermore, in some examples, input vector 938 may include information (e.g., in combination with zero or more other example types of input data described herein) that specifies a class in one or more shoulder pathology classification systems. In such examples, the output vector may include output elements corresponding to classes in one or more different shoulder recommendations for shoulder treatment. For example, input vector 938 may include information that specifies a class in a rotator cuff classification system and output vector 940 may include output elements corresponding to a recommended type of shoulder treatment (e.g., anatomical or reverse shoulder replacement).

In some examples, input vector 938 may include information (e.g., in combination with zero or more other example types of input data described herein, including morphological inputs and/or rotator cuff inputs) that specifies bone density scores for humerus and/or glenoid. Other information included in input vector 938 may include demographic information, such as patient age, patient activities, patient gender, patient body mass index (BMI), and so on. In some examples, input vector 938 may include information regarding the speed of onset of the symptoms (e.g., gradual or sudden). The plurality of input elements in input vector 938 also may include patient objectives for participation in activities such as particular exercises/sport types, ranges of motion, etc.

In some examples, the output vector may include the plurality of surgery type output elements. Each of the surgery type output elements may correspond to a different type of shoulder surgery. Example types of shoulder surgery types, which may be presented as outputs, may include a stemless standard total shoulder arthroplasty, a stemmed standard total shoulder arthroplasty, a stemless reverse shoulder arthroplasty, a stemmed reverse shoulder arthroplasty, an augmented glenoid standard total shoulder arthroplasty, an augmented glenoid reverse shoulder arthroplasty, and other types of orthopedic shoulder surgery. A shoulder surgery may be "standard" in the sense that, after surgery, the patient's shoulder joint has the standard anatomical configuration where the scapula side of the shoulder joint has a concave surface and the humerus side of the shoulder surgery has a convex surface. A "reverse" shoulder surgery on the other hand results in the opposite configuration where a convex surface is attached to the scapula and a concave surface is attached to the humerus.

Additionally, computing system 902 may determine a recommended type of shoulder surgery for a patient based on the current output vector. For example, computing system 902 may determine which output element in the output vector corresponds to the type of shoulder surgery with the greatest confidence value.

Figure 31:
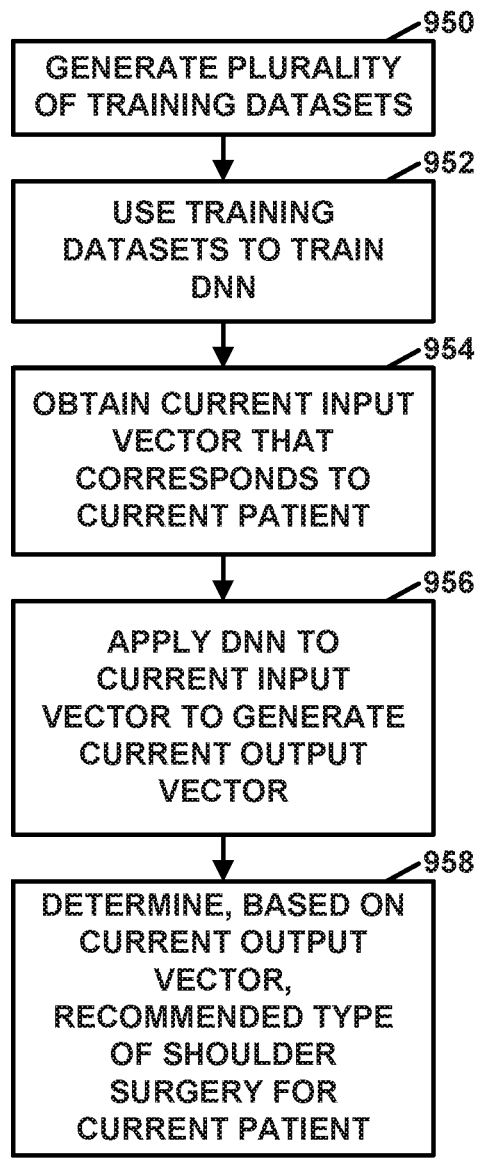
FIG. 31 is a flowchart illustrating an example operation of a computing system that uses a DNN to determine a recommended type of shoulder surgery for a patient, in accordance with a technique of this disclosure.

FIG. 31 is a flowchart illustrating an example operation of a computing system that uses a DNN to determine a recommended type of shoulder surgery for a patient, in accordance with a technique of this disclosure. In the example of FIG. 31, computing system 902 generates a plurality of training datasets (950). In this example, a DNN has an input layer, an output layer, and one or more hidden layers between the input layer and the output layer. The input layer includes a plurality of input layer neurons. Each input layer neuron in the plurality of input layer neurons corresponding to a different input element in a plurality of input elements. The output layer includes a plurality of output layer neurons. Each output layer neuron in the plurality of output layer neurons corresponding to a different output element in a plurality of output elements. The plurality of output elements includes a plurality of surgery type output elements. Each surgery type output element in the plurality of surgery type output elements corresponds to a different type of shoulder surgery in a plurality of types of shoulder surgery. Each respective training dataset corresponds to a different training data patient in a plurality of training data patients and comprises a respective training input vector and a respective target output vector. For each respective training dataset, the training input vector of the respective training dataset comprises a value for each element of the plurality of input elements. For each respective training dataset, the target output vector of the respective training dataset comprises a value for each element of the plurality of output elements.

Furthermore, in the example of FIG. 31, computing system 902 uses the plurality of training datasets to train the DNN (952). Additionally, computing system 902 may obtain a current input vector that corresponds to a current patient (954). Computing system 902 may apply the DNN to the current input vector to generate a current output vector (956). Computing system 902 may determine, based on the current output vector, a recommended type of shoulder surgery for the current patient (958). Computing system 13/208 may perform these activities in accordance with the examples provided elsewhere in this disclosure.

Figure 32:
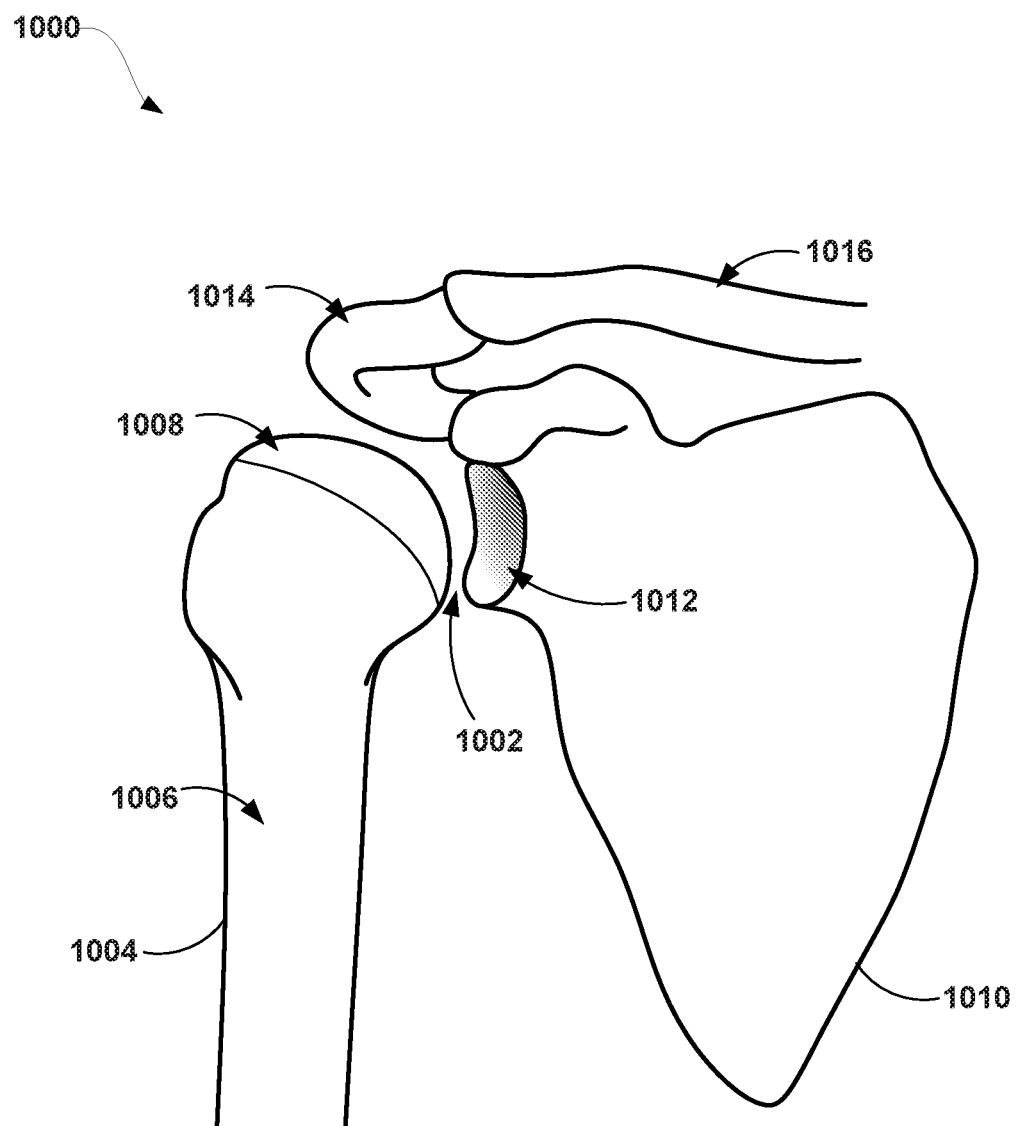
FIG. 32 is an illustration of example bones related to a shoulder of a patient.

FIG. 32 is an illustration of example bones related to a shoulder 1000 of a patient. As shown in the example of FIG. 32, shoulder 1000 includes humerus 1004, scapula 1010, and clavicle 1016. Shaft 1006 of humerus 1004 is connected to humeral head 1008, and humeral head 1008 forms glenohumeral joint 1002 with glenoid 1012. Acromion 1014 of scapula 1010 is attached to clavicle 1016 at the acromioclavicular joint.

Over time, humeral head 1008, glenoid 1012, and/or connective tissue between humeral head 1008 and glenoid 1012 may degrade due to wear and/or disease. In some cases, a patient suffering from degradation to glenohumeral joint 1002 may benefit from shoulder replacement surgery in which at least a portion of humeral head 1008, glenoid 1012, or both, are replaced with artificial implants. For example, humeral head 1008 may be cut to expose less dense trabecular bone within humeral head 1008. A humeral implant may be inserted into the trabecular bone in order to secure the new humeral implant to the shaft 1006 of humerus 1004.

Figure 33:
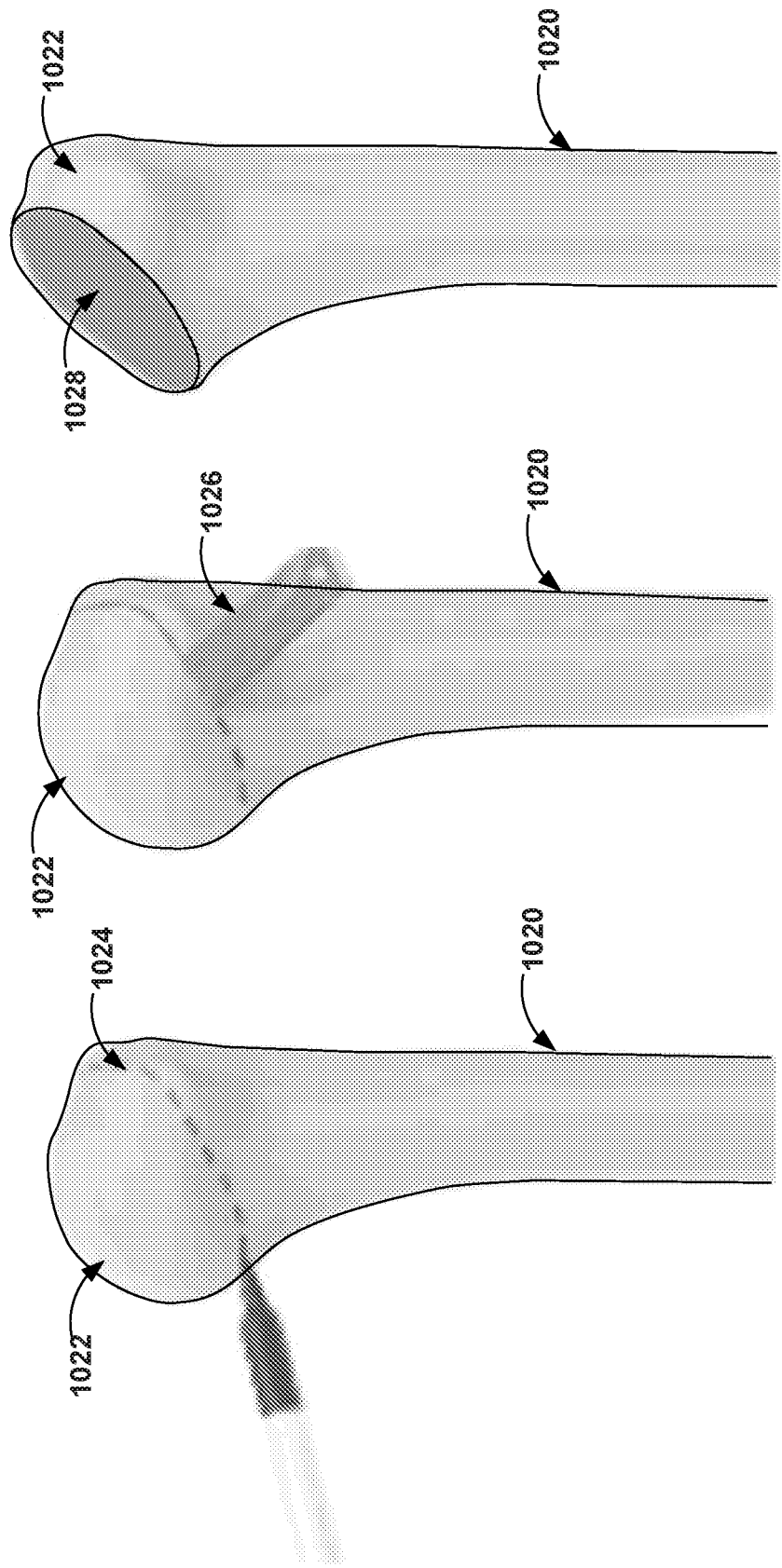
FIGS. 33A, 33B, and 33C are conceptual diagrams of an example humeral head prepared for a humeral implant.

FIGS. 33A, 33B, and 33C are conceptual diagrams of an example humeral head 1022 prepared for a humeral implant. As shown in FIG. 33A, as a part of a shoulder arthroplasty procedure, a clinician may perform a surgical step of resection of humeral head 1022 of humerus 1020 by visually estimating (e.g., "eyeballing") and marking anatomical neck 1024 of humeral head 1020. Anatomical neck 1024 may refer to a plane that bisects a portion of humeral head 1022 to create, or expose, a surface at which a humeral implant can be attached to humerus 1020. As shown in the example of FIG. 33B, the clinician may then perform the resection of humeral head 1022 by guiding cutting tool 1026 (e.g., a blade of an oscillating saw) along the marked anatomical neck 1024 with the clinician's free hand, i.e., without mechanical or visual guidance. After the resection of humeral head 1022 is complete, trabecular bone region 1028 is exposed along the plane corresponding to anatomical neck 1024. Generally, the humeral implant may be inserted into a portion of trabecular bone region 1028 and fixed in place. The density of trabecular bone region 1028, or the variation in density within the volume of trabecular bone region 1028 may, may affect what types of humeral implants can be used for humerus 1020. For example, greater densities of trabecular bone region 1028 may support humeral implants with shorter "stems" of the humeral implant than less dense, or softer, trabecular bone that may require longer stems on the humeral implant.

Figure 34:
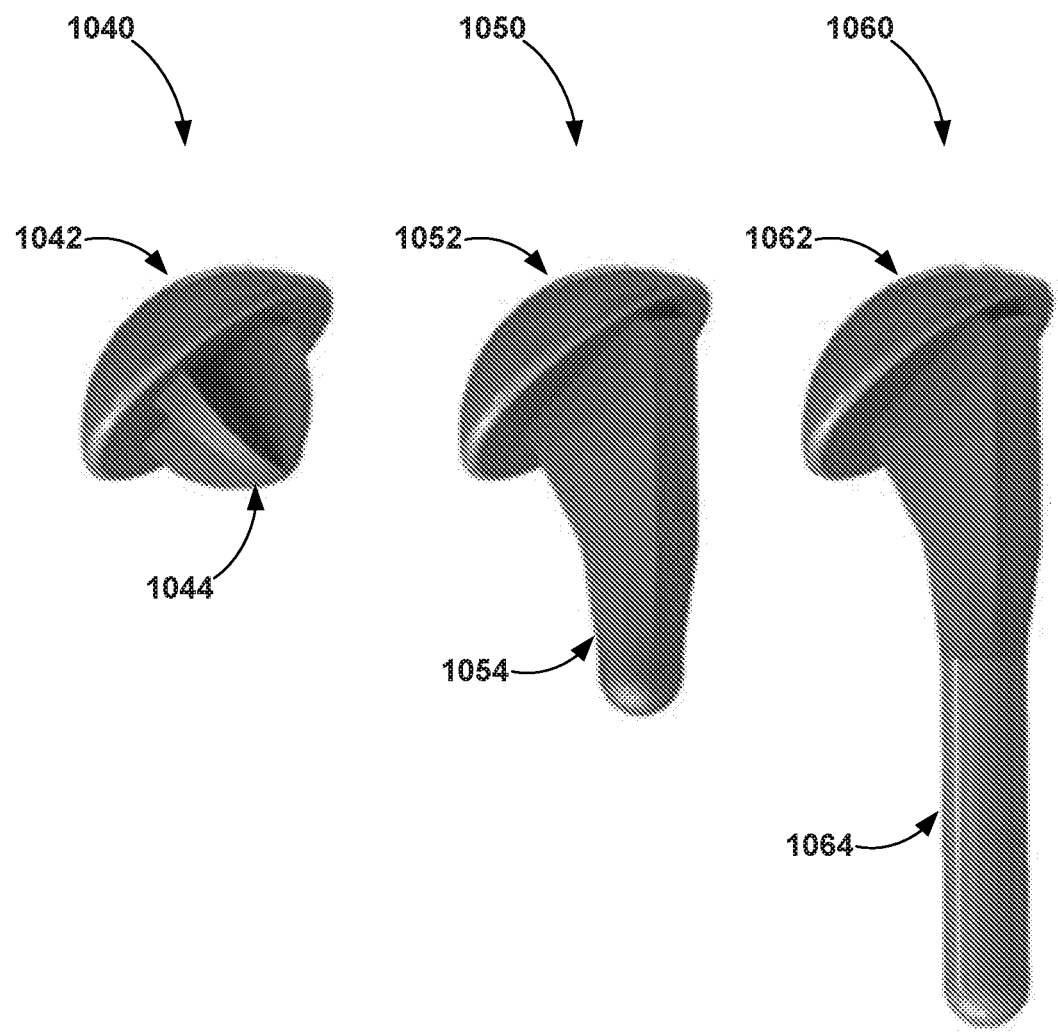
FIG. 34 is a conceptual diagram of example humeral implants.

FIG. 34 is a conceptual diagram of example humeral implants intended for an anatomical shoulder replacement procedure. In total shoulder arthroplasty surgery (e.g., a type of shoulder replacement or shoulder treatment), the humeral implant mechanical fixation strength within the humeral shaft may be primarily determined by the fixation of the diaphyseal stem of the implant. Implantation of the stem can subject the shaft to high mechanical forces during drilling, reaming, broaching, and other blunt impact forces when introducing the stem of the humeral implant. These procedures may result in complications associated w/ intra-operative fractures (humeral diaphysis), and post-operative loosening and stress shielding often leading to revision surgeries. Humeral head implant extraction for revisions can also be difficult, especially when implanted using bone cement.

A stemless humeral implant, or a humeral implant with a shorter stem, can eliminate potential shaft fractures and allow for preservation of native bone stock—which may be beneficial in the event of a revision—by avoiding implantation in the shaft or portions of the shaft of the humerus. Stemless design can also enable the surgeon to restore the gleno-humeral center of rotation independent of the humeral shaft orientation and avoid stem-implantation related complications. Bony fixation of the stemless humeral implant may primarily be achieved within the humeral head and the trabecular bone network therein.

Contra-indications for canal-sparing stemless humeral implants can include poor bone quality (osteopenia, osteoporosis), other metabolic bone diseases (cysts, tumors etc.) or the presence of prior bone fractures that may affect bony support, ingrowth and integration of the metallic component. In this manner, the density of bone within the humeral head, such as the density and/or location of different bone densities, may need to be sufficient to support a shorter stem or a stemless humeral implant type. A surgeon may use a "thumb test" as a primary intra-operative assessment tool whereby compressing the surface of the neck cut (proximal humeral metaphysis) of the humeral head with the thumb can determine substrate viability for implantation. This substrate viability may relate to or be representative of the density of the trabecular bone within the humeral head. In other words, the bone density of the trabecular bone within the humeral head can be assessed with the thumb of the surgeon. Bone that is easily compressible (e.g., low density) with minimal force is considered inacceptable for stemless component implantation. Bone that is not easily compressible, or provides higher resiliency (e.g., high density) may be considered to be acceptable for a stemless type of humeral implant.

In this manner, a surgeon may make a selection of a stemless or stemmed (or even the length of a stem) based on the results of the "thumb test." As described herein, historical data related to humeral head bone quality (such as the density, compressibility, selection of stemmed or stemless implants, or otherwise suitable nature of the humeral head to support an implant) may be correlated with patient-specific imaging data for those patients. For example, the correlations may map intensity thresholds, ranges of Hounsfield Units, or standard deviation of intensities from voxels, in the humeral head from CT data for a specific patient to the type of humeral implant selected by the patient for those respective patients. Once the correlations are complete, the system may use the correlations in order to recommend a specific type of humeral implant based on the CT data mapping to each type of humeral implant. In this manner, as described herein, a system can recommend a specific type of humeral implant (e.g., stemmed, stemless, and/or length of stem) based on the analysis of the patient-specific image data (e.g., the intensity magnitude and/or magnitude location of voxels or groups of voxels).

As shown in the example of FIG. 34, humeral implant 1040 is an example of a "stemless" humeral implant with glide surface 1042 configured to contact a glenoid or glenoid implant. Fixation structure 1044 includes a projection that is configured to be embedded in trabecular bone 1028 to secure humeral implant 1040, but there is no stem that extends down near or into the shaft of the humerus.

Humeral implant 1050 is an example of a "stemmed" humeral implant, but stem fixation structure 1054 includes a short stem that facilitates anchoring humeral implant 1050 into the trabecular bone of the humerus. Humeral implant 1050 includes glide surface 1052 configured to contact a glenoid or glenoid implant. Humeral implant 1060 is an example of a "stemmed" humeral implant, but stem fixation structure 1064 includes a long stem that facilitates anchoring humeral implant 1060 into the trabecular bone of the humerus. Humeral implant 1060 includes glide surface 1062 configured to contact a glenoid or glenoid implant. Humeral implants 1050 and 1060 may be used when the trabecular bone is compromised from healthy bone such that the stem is required to provide sufficient anchoring of the humeral implant. For example, the trabecular bone may not provide sufficient bone density to anchor humeral implant 1040 and therefore a "stemmed" humeral implant like humeral implant 1050 or 1060 may be recommended or selected for the patient instead.

The long stem of fixation structure 1064 may be used for a humerus that has the least dense trabecular bone or otherwise requires more stability. In contrast, humeral implant 1040 may be used when the density of the trabecular bone is high enough to sufficiently anchor the humeral implant with the stemless fixation structure 1044. Benefits of a stemless design similar to that of fixation structure 1044 may be that less trabecular bone in the humerus needs to be removed, as well as quicker healing, and less risk of damage to cortical bone during reaming and/or insertion of a stem into the humerus.

However, clinicians may not be able to determine if the trabecular bone within the humeral head can support a stemless design like humeral implant 1040 until the humeral head has been resected and manually manipulated. As described herein, a system may determine humeral head trabecular bone density metrics using patient-specific image data (e.g., CT data) to assist with shoulder replacement planning prior to surgery. In this way, the example techniques provide for various practical applications for techniques that improve, using computational analysis, ways to determine bone density to reduce surgical times (e.g., determination of which humeral head type to use is already made) and/or improve accuracy of selection of humeral head implant type prior to surgery (e.g., improve pre-operative planning).

Figure 35:
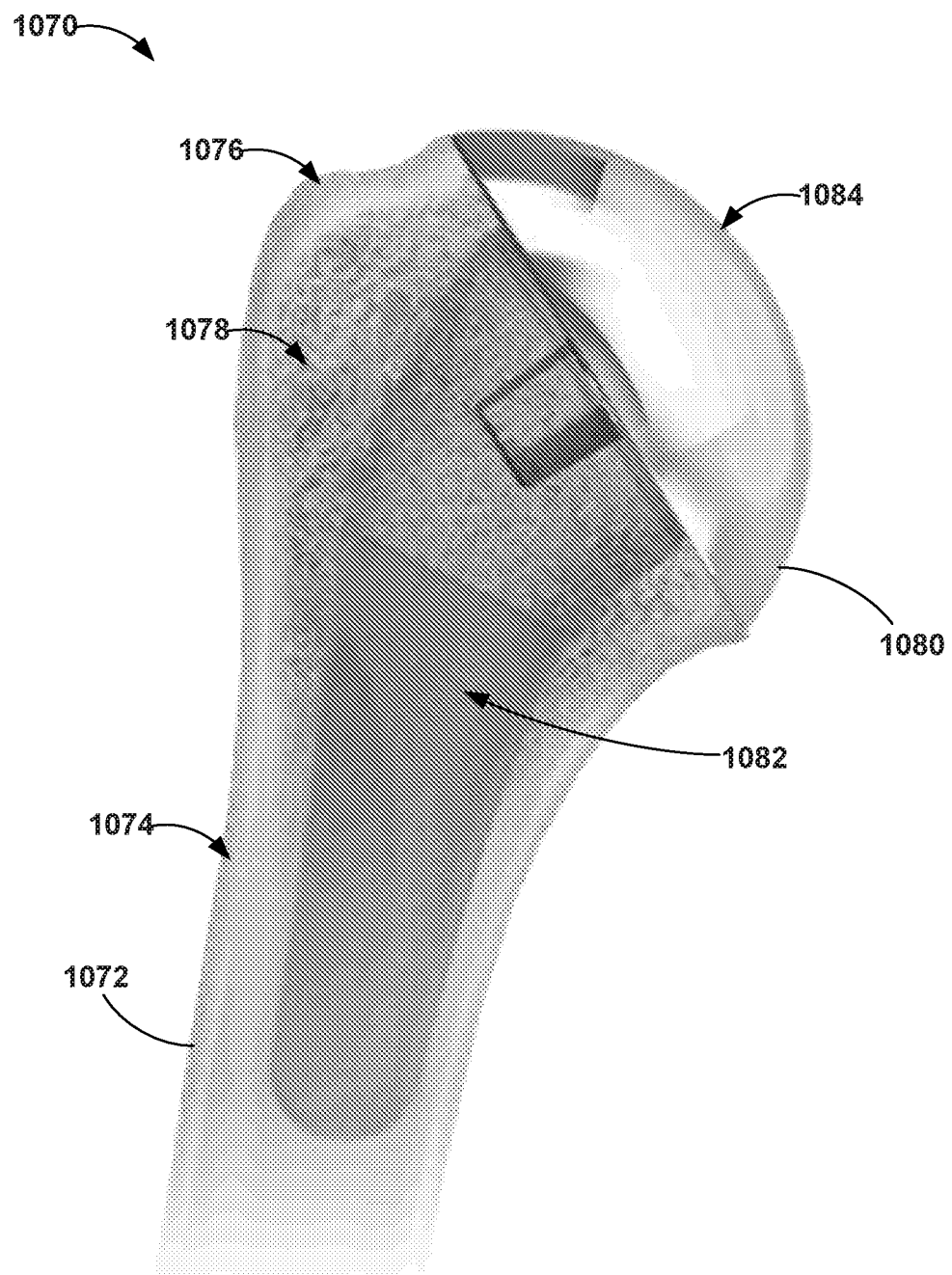
FIG. 35 is a conceptual diagram of an example stemmed humeral implant.

FIG. 35 is a conceptual diagram 1070 of an example stemmed humeral implant 1080 implanted within humerus 1072. As shown in the example of FIG. 35, stemmed humeral implant 1080 includes glide surface 1084 and stem 1080. Stem 1080 has been inserted into trabecular bone 1078 to anchor humeral implant 1080 to humeral head 1076. Although stem 1080 may be a short stem similar to humeral implant 1050 of FIG. 34, stem 1080 may still be inserted at least partially within humeral shaft 1074. The example humeral implant 1080 may be similar to the Aequalis Ascend™ Flex manufactured by Wright Medical Group N.V. of Memphis, Tennessee.

Figure 36:
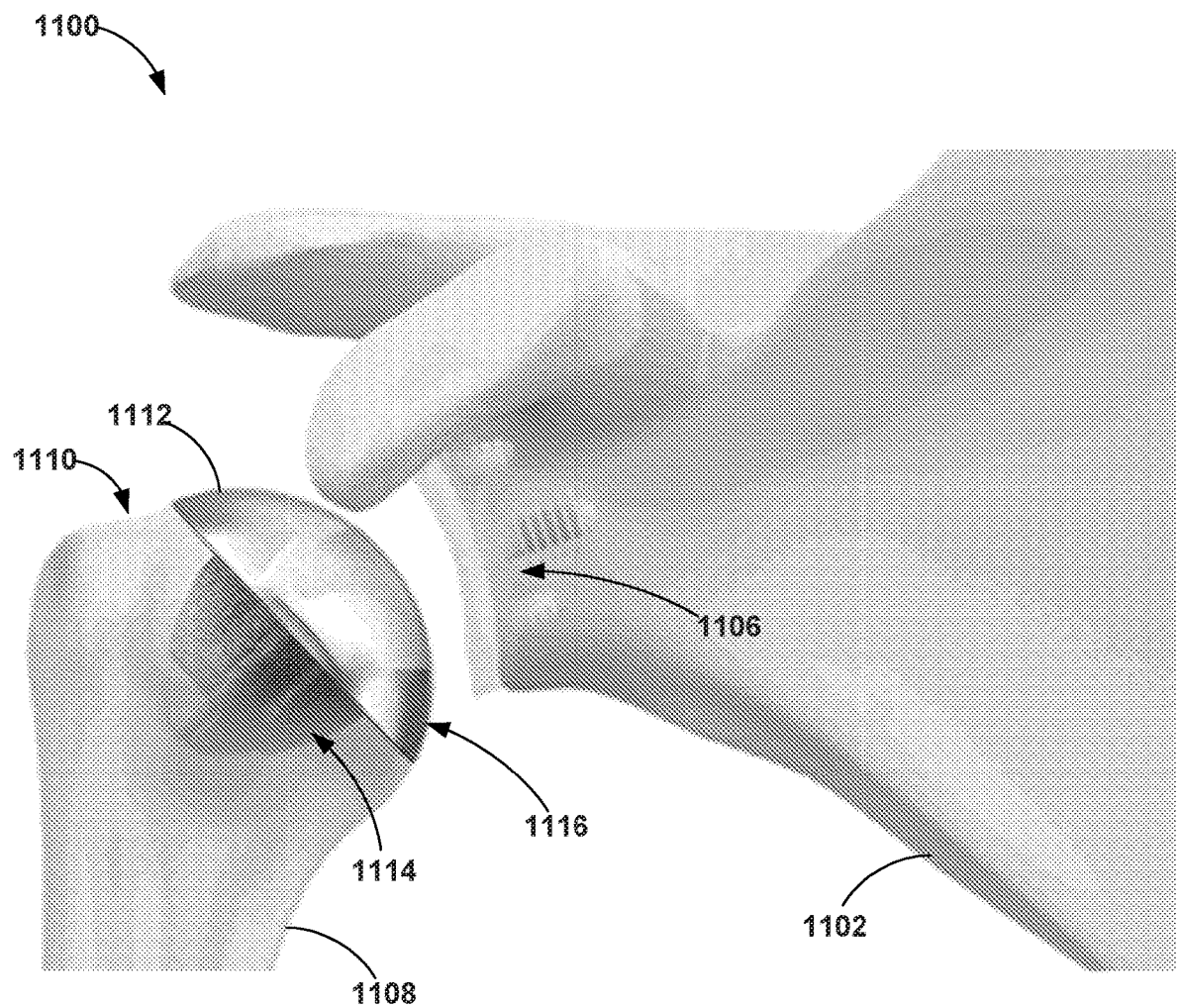
FIG. 36 is a conceptual diagram of an example stemless humeral implant implanted on a humeral head.

FIG. 36 is a conceptual diagram 1100 of an example stemless humeral implant 1112 implanted on humeral head 1110. As shown in the example of FIG. 36, stemless humeral implant 1112 includes glide surface 1116 and fixation structure 1114. Fixation structure 1114 has been embedded into the trabecular bone in humeral head 1110 without a stem. Humeral implant 1112 may be similar to humeral implant 1040 of FIG. 34. The example humeral implant 1112 may be similar to the Simpliciti™ shoulder system manufactured by Wright Medical Group N.V. of Memphis, Tennessee Glide surface 1112 may be configured to contact glenoid implant 1106 implanted in the glenoid surface of scapula 1102. Stemless humeral implant 1112 and glenoid implant 1106 may be part of an anatomical shoulder replacement because humeral implant 1112 includes a spherical surface similar to the spherical surface of a health humeral head.

Figure 37:
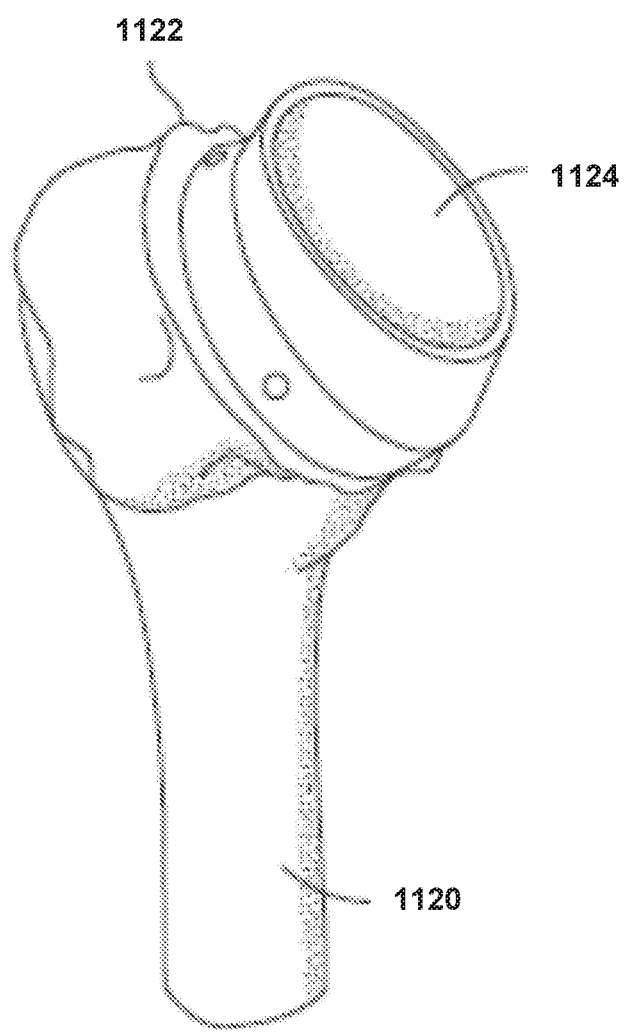
FIG. 37 is a conceptual diagram of an example reverse humeral implant.

FIG. 37 is a conceptual diagram of an example reverse humeral implant 1124. Reverse humeral implant 1124 may be constructed with a stem (similar to humeral implants 1050 or 1060) or as a stemless design (similar to implants 1040) and implanted in humeral head 1122 of humerus 1020. However, reverse humeral implant 1124 has a glide surface that is concave in shape and intended to contact a spherical, or convex, shaped contact surface of a corresponding glenoid implant. A system may recommend a reverse shoulder replacement, which may include a reverse humeral implant 1124, based on characteristics of soft-tissue structures (e.g., one or more muscles of the rotator cuff or other shoulder muscles) and/or bone density of humeral head 1122.

Figure 38:
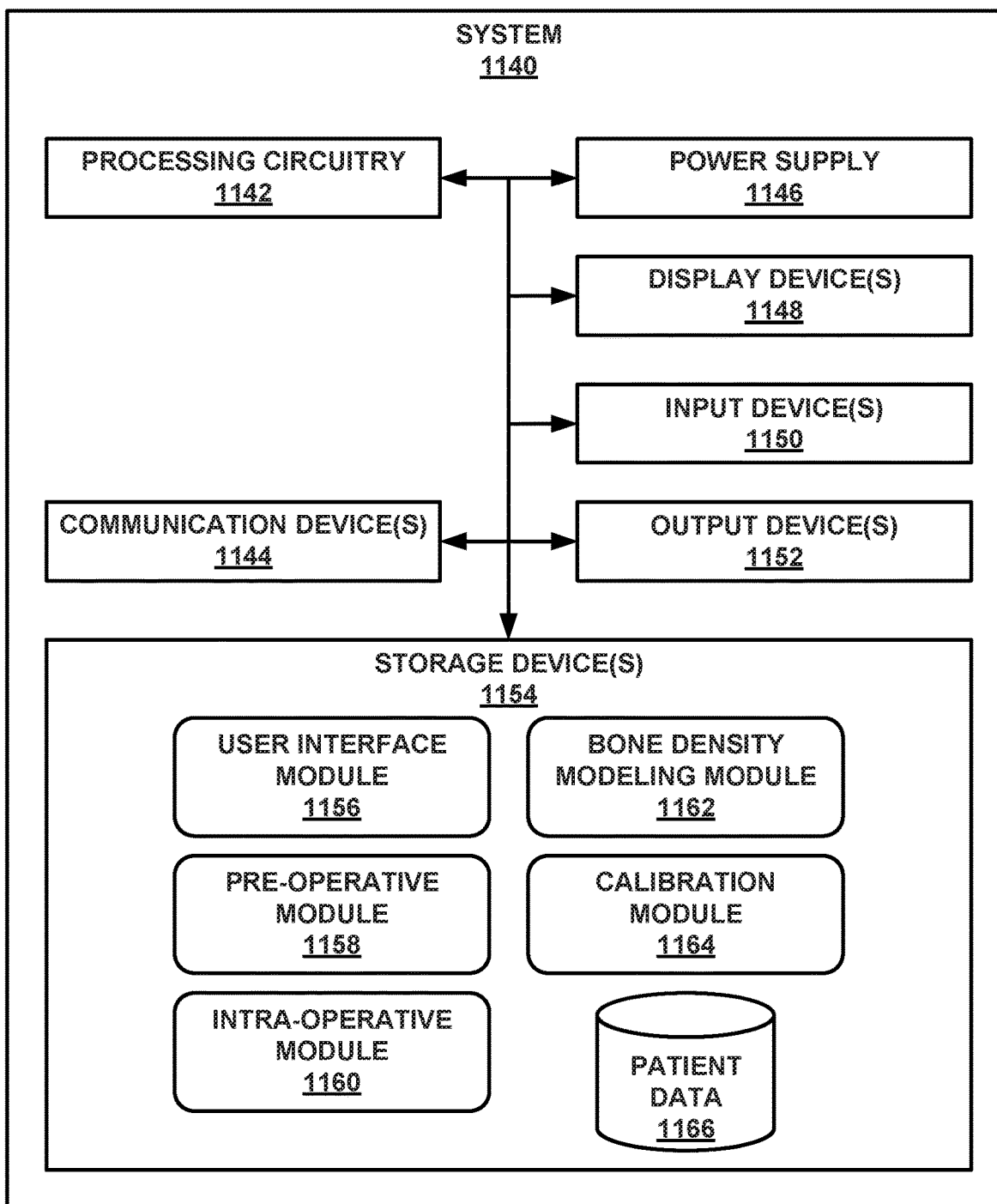
FIG. 38 is a block diagram illustrating example components of a system configured to determine bone density from patient-specific image data, according to an example of this disclosure.

FIG. 38 is a block diagram illustrating example components of system 1140 configured to determine estimated bone density from patient-specific image data, according to an example of this disclosure. System 1140, and the components therein, may be similar to system 540 and components described in FIG. 6 and/or virtual planning system 102 of FIG. 1. In this manner, system 540 or virtual planning system 102 may perform the functions attributed to system 1140 herein.

As shown in the example of FIG. 38, system 1140 may include processing circuitry 1142, a power supply 1146, display device(s) 1148, input device(s) 1150, output device(s) 1152, storage device(s) 1154, and communication devices 1144. Display device(s) 1148 may display imagery to present a user interface to the user, such as opaque or at least partially transparent screens. Display devices 1148 may present visual information and, in some examples, audio information or other information presented to a user. For example, display devices 1148 may include one or more speakers, tactile devices, and the like. In other examples, output device(s) 1152 may include one or more speakers and/or tactile devices. Display device(s) 1148 may include an opaque screen (e.g., an LCD or LED display). Alternatively, display device(s) 1148 may include an MR visualization device, e.g., including see-through holographic lenses, in combination with projectors, that permit a user to see real-world objects, in a real-world environment, through the lenses, and also see virtual 3D holographic imagery projected into the lenses and onto the user's retinas, e.g., by a holographic projection system such as the Microsoft HOLOLENS™ device. In this example, virtual 3D holographic objects may appear to be placed within the real-world environment. In some examples, display devices 1148 include one or more display screens, such as LCD display screens, OLED display screens, and so on. The user interface may present virtual images of details of the virtual surgical plan for a particular patient, such as information related to bone density.

Input devices 1150 may include one or more microphones, and associated speech recognition processing circuitry or software, may recognize voice commands spoken by the user and, in response, perform any of a variety of operations, such as selection, activation, or deactivation of various functions associated with surgical planning, intra-operative guidance, or the like. As another example, input devices 1150 may include one or more cameras or other optical sensors that detect and interpret gestures to perform operations as described above. As a further example, input devices 1150 include one or more devices that sense gaze direction and perform various operations as described elsewhere in this disclosure. In some examples, input devices 1150 may receive manual input from a user, e.g., via a handheld controller including one or more buttons, a keypad, a keyboard, a touchscreen, joystick, trackball, and/or other manual input media, and perform, in response to the manual user input, various operations as described above.

Communication devices 1144 may include one or more circuits or other components that facilitate data communication with other devices. For example, communication devices 1144 may include one or more physical drives (e.g., DVD, blu-ray, or universal serial bus (USB) drives) that allow for transfer of data between system 1140 and the drive when physically connected to system 1140. In other examples, communication devices 1144 may include. Communication devices 1144 may also support wired and/or wireless communication with another computing device and/or a network.

Storage devices 1154 may include one or more memories and/or repositories that store respective types of data in common and/or separate devices. For example, user interface module 1156 may include instructions that define how system 1140 controls display devices 1148 to present information to a user, such as information related to bone density of the humerus or associated recommendations for surgery treatment. Pre-operative module 1158 may include instructions regarding analysis of patient data, such as imaging data, and/or determination of treatment options based on patient data. Intra-operative module 1160 may include instructions that define how system 1140 operates in providing information to a clinician for display such as details regarding the planned surgery and/or feedback regarding the surgical procedure. Patient data 1166 may be a repository that stores the patient-specific image data.

Bone density modeling module 1162 may include instructions defining how processing circuitry 1142 determines one or more bone density metrics for at least a portion of one or more bones, such as the humeral head. For example, bone density modeling module 1162 may determine bone density metrics based on intensity of voxels within patient-specific patient data (e.g., CT image data). Processing circuitry 1142 may execute bone density modeling module 1162 to determine different bone density categories of groups of pixels or voxels according to predetermined ranges of intensity (e.g., Hounsfield units) for individual or groups of pixels or voxels. In some examples, processing circuitry 1142 may generate the bone density metric based on the standard deviation of voxels within the patient-specific image data. The bone density metric may include different bone density values across a two-dimensional or three-dimensional region of the humeral head. In some examples, the bone density metric may be a single value determined based on the average pixel or voxel intensities across the humeral head or in a certain area of the humeral head. In some examples, bone density modeling module 1162 may include instructions that determine why type of humeral implant (e.g., stemmed or stemless) and/or the location at which the humeral implant can be implanted within the humeral head. The bone density metric may not actually indicate the density of bone, but may be a metric representative of bone density. For example, the bone density metric may merely indicate the type of implant (e.g., stemmed or stemless) that corresponds to the analyzed patient-specific image data. As another example, the bone density metric may include voxel intensity from image data, standard deviations of voxel intensity from image data, compressibility, an index, or some other indication that may be related to, or representative of, density without actually providing a measure of the density of the bone.

Processing circuitry 1142 may execute calibration module 1164 to calibrate the bone density metric to patient-specific image data and selected implant types from other patients in historical surgeries (e.g., implant types historically selected based on thumb test information during that surgery). Historically, a clinician may use their thumb to press against the trabecular bone within the humeral head (exposed by the cut head) to determine the stiffness, and thus density, of the trabecular bone. This thumb test may be performed in order to identify what type of stem, if any, is needed for the humeral implant. Calibration module 1164 may use this thumb test data obtained from historical patients to correlate known surgical decisions of humeral implant type made based on thumb test procedures to patient-specific image data of the same respective patient to determine bone density metrics for the current patient. In this manner, calibration module 1164 may be used to identify one or more ranges of bone density metrics that correspond to respective humeral implant types. For instance, with calibration module 1164, processing circuitry 1142 may determine that stemless humeral implant 1040 is for bone density metrics within a first range, short stemmed humeral head 1050 is for bone density metrics within a second range, and long stemmed humeral head 1060 is for bone density metrics within a third range.

As discussed above, surgical lifecycle 300 may include a preoperative phase 302 (FIG. 3). One or more users may use orthopedic surgical system 100 in preoperative phase 302. For instance, orthopedic surgical system 100 may include virtual planning system 102 (with may be similar to system 1140) to help the one or more users generate a virtual surgical plan that may be customized to an anatomy of interest of a particular patient. As described herein, the virtual surgical plan may include a 3-dimensional virtual model that corresponds to the anatomy of interest of the particular patient and a 3-dimensional model of one or more prosthetic components (e.g., implants) matched to the particular patient to repair the anatomy of interest or selected to repair the anatomy of interest. The virtual surgical plan also may include a 3-dimensional virtual model of guidance information to guide a surgeon in performing the surgical procedure, e.g., in preparing bone surfaces or tissue and placing implantable prosthetic hardware relative to such bone surfaces or tissue.

As discussed herein, processing circuitry 1142 may be configured to determine a bone density metric for at least a portion of a humeral head of a patient based on the patient-specific image data for that patient. For example, a bone density metric may be a single indication of overall density of the humeral head or a portion of the humeral head. As another example, the bone density metric may include bone density values for respective portions of a humeral head of the patient. The system may control a user interface via user interface module 1156 to present a graphical representation of the bone density metric (which may be directly or indirectly indicative of bone density) and/or generate a recommendation on the implant type for the humeral head based on the bone density metric. For example, a bone density metric indicative of sufficient trabecular bone density in the humeral head may result in the system recommending a stemless humeral implant as opposed to a stemmed humeral implant.

In one example, processing circuitry 1142 may be configured to identify a humeral head in the patient-specific image data, such as by segmenting the bone or otherwise identifying landmarks or shapes indicative of the humeral head. Processing circuitry 1142 may then determine, based on the patient-specific image data, a bone density metric representing bone density of at least a portion of the humeral head. Based on this bone density metric, processing circuitry 1142 may generate a recommendation of a humeral implant type for the patient. For example, processing circuitry 1142 may recommend a stemmed humeral implant (stemmed implant type) for bone density metrics indicative of less dense bone and processing circuitry 1142 may recommend a stemless humeral implant (stemless implant type) for bone density metrics indicative of higher density bone. Processing circuitry 1142 may then output, for display via a user interface, the recommendation of the humeral implant type for the patient.

In some examples, processing circuitry 1142 may determine a stem length for a humeral implant type that includes a stem. Processing circuitry 1142 may determine that less dense bone requires longer stems to provide sufficient anchoring to the humerus or determine that the locations of lower density trabecular bone within the humerus requires a longer stem. The stem length itself may be identified and presented to the user, or processing circuitry 1142 may recommend certain humeral implants satisfying the recommended length range. In this manner, processing circuitry 1142 may recommend a specific implant or implant type selected between three or more different types of humeral implants based on the bone density metric determined from the patient-specific image data.

In some examples, the bone density metric may represent an overall density score (e.g., a value, index, or category based on voxel or pixel values from image data) for trabecular bone within at least a portion of the humeral head. For example, processing circuitry 1142 may determine an averaged or weighted average density for a region of the humeral head and assign a specific metric value to that region of the humeral head. In other examples, the bone density metric may be determined to be indicative of the lowest density of bone found in the region to establish a lower limit on the bone density in that area. Conversely, the bone density metric may be indictive of the highest density in that region of the humeral head. The bone density metric may include a plurality of bone density values for respective portions within the humeral head. For example, the bone density metric may include a matrix of density values that includes specific bone density values for respective voxels, or groups of voxels, within a region of the humeral head. In this manner, the bone density metric may provide a higher resolution representation of the bone density within the humeral head. In any case, the bone density metric may be indicative of actual bone density values, image data intensities, and/or recommended implant types).

Processing circuitry 1142 may determine the bone density metric using different techniques. In one examples, processing circuitry 1142 may determine the bone density metric by identifying, based on the patient-specific image data, intensities of respective voxels within at least a portion of the humeral head, classifying the intensities of the respective voxels in one of two or more intensity levels, and determining, based on at least one of a number of voxels classified within each of the two or more intensity levels or a location in the humeral head of the voxels classified within each of the two or more intensity levels, the bone density metric. In this manner, processing circuitry 1142 may be configured to classify different intensities in the patient-specific image data as different intensity levels and/or the location of those intensity levels to determine the bone density metric. For example, the location of the intensity levels may be relevant to whether or not the trabecular bone is dense enough to support a stemless humeral implant. If the trabecular bone has a lower overall bone density, but the center of the humeral head is still above a threshold density required to support a stemless humeral implant, processing circuitry 1142 may still determine that the bone density metric is sufficient to support a stemless humeral implant. In other examples, processing circuitry 1142 may determine the bone density metric as indicative of requiring a stemmed humeral implant even with some relatively high bone density levels if pockets of low density trabecular bone are identified in locations at which a stemless humeral implant would be implanted.

In some examples, processing circuitry 1142 may determine the bone density metric for a volume of trabecular bone within the entire humeral head. In other examples, processing circuitry 1142 may determine a plane through a humeral head representative of a humeral cut made in the humerus to prepare the humerus for accepting a humeral implant. This humeral cut would expose the surface of the trabecular bone in which the humeral implant would be implanted. The processing circuitry 1142 would then determine the bone density metric for at least a portion of the humeral head bisected by the plane. In some examples, processing circuitry 1142 may determine the bone density metric for pixels or voxels that correspond to the plane (e.g., are exposed by or bisected by the plane). In other examples, processing circuitry 1142 may determine the bone density metric for a volume of trabecular bone starting at the plane and extending towards the shaft of the humerus. In some examples, the volume of analyzed trabecular bone may extend up to cortical bone that defines the outer surface of the humerus.

The bone density metric may be displayed via a user interface, such as using user interface module 1156, in some examples. Processing circuitry 1142 may output, for display by display devices 1148 or a display device of another system, the user interface comprising a graphical representation of the bone density metric over a representation of at least a portion of the humeral head of the patient. The graphical representation of the bone density metric may include a two or three dimensional graphic that may include one or more shapes or colors that is displayed over or in place of the trabecular bone of the humerus. In one example, the bone density metric may include a heat map of a plurality of colors, where each color of the plurality of colors represents a different range of bone density values. In this manner, different colors may represent different bone density magnitudes to indicate a spatial representation of the variation in bone density within that volume of trabecular bone. The graphical representation of the bone density metric may include a two-dimensional representation of bone density variation within a plane of the humeral head. In other examples, the graphical representation of the bone density metric may include a three-dimensional representation of bone density variation within at last trabecular bone of the humeral head. In some examples, display devices 1148 may include a mixed reality display, and processing circuitry 1142 may control the mixed reality display to present the user interface comprising the graphical representation of the bone density metric.

In some examples, the bone density metric may be associated with bone density data (e.g., image data or other data indicative of bone structure in the humeral head) from other historical patients and the type of humeral implant selected by the clinician for that particular bone density data. The bone density data may be generated for these historical patients using the patient-specific image data for each patient and the resulting type of humeral implant selected by the surgeon for each respective patient (e.g., which may be based on a "thumb test" where the clinician uses their thumb to press against the trabecular bone in the humeral head and classifies the trabecular bone as sufficient or insufficient for a stemless humeral implant). Processing circuitry 1142 may leverage these selected implant types based on the thumb test to classify bone density metrics as suitable or not suitable for stemless humeral implants in future patients. In this manner, processing circuitry 1142 may correlate the bone density metric with type of humeral implant selected by surgeons in previously performed surgeries on other subjects, where the thumb test data is indicative of manually determined density ranges (or compressibility which is representative of bone density) of trabecular bone within respective humeral heads of the other subjects. Based on this correlation, processing circuitry 1142 may determine the recommendation of the humeral implant type for the patient. In some examples, processing circuitry 1142 may employ one or more neural networks to correlate the previous selected implant type and respective patient-specific image data to determine a bone density metric indicative of each type of implant available for future patients. For example, processing circuitry 1142 may use the bone density metric, patient-specific image data, and selected humeral implant type (stemmed, stemless, and/or length of stem) as inputs to the neural network. The outputs of the neural network may be those bone density metrics that correspond to which humeral implant type.

In some examples, processing circuitry 1142 may generate a shoulder surgery recommendation for a patient using soft tissue characteristics and bone density metrics. For example, processing circuitry 1142 may determine, based on the patient-specific imaging data, one or more soft tissue characteristics (e.g., soft tissue volume, fatty infiltration ratio, atrophy ratio and/or range of motion value) and a bone density metric associated with a humerus of the patient. As described herein, processing circuitry 1142 may generate a recommendation of a shoulder surgery type to be performed for the patient (e.g., an anatomical or reverse shoulder surgery) and generate, based on the bone density metric associated with the humerus, a recommendation of a humeral implant type for the patient. Processing circuitry 1142 may then output, for display, the recommendation of the shoulder surgery type and the humeral implant type for the patient. In some examples, the user interface may include the representation of the one or more soft tissue characteristics and/or the bone density metric associated with the humerus as part of a mixed reality user interface.

Figure 39A:
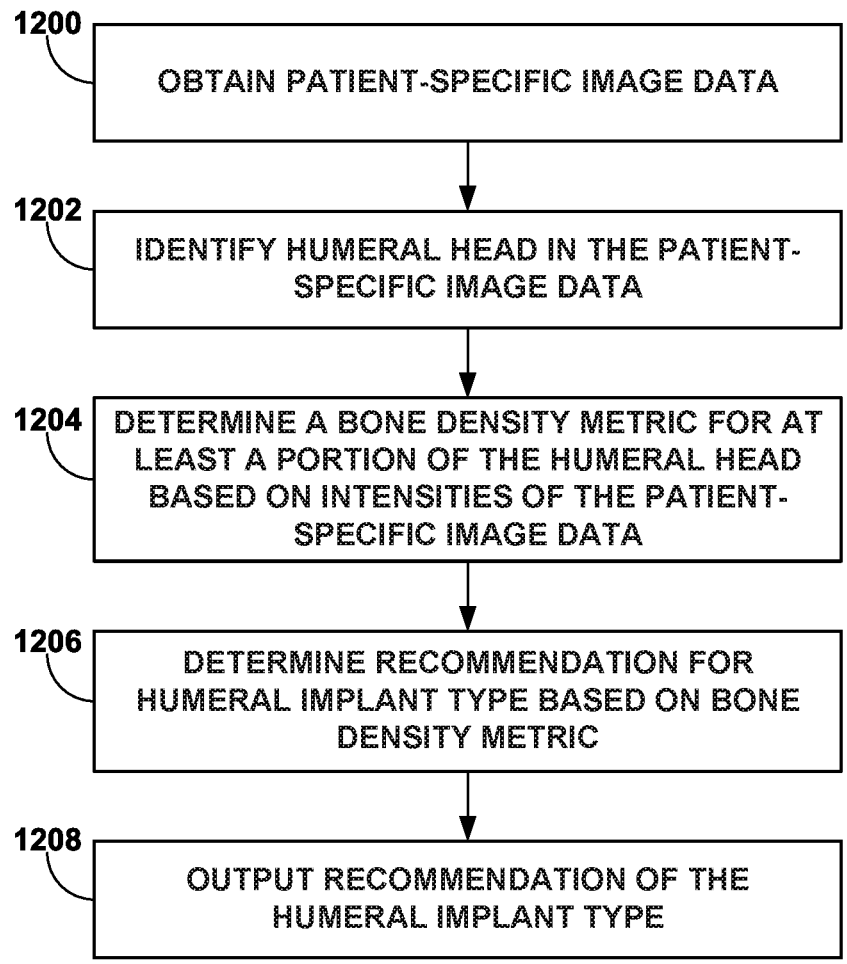
FIG. 39A is a flowchart illustrating an example procedure for determining a type of humeral implant based on bone density.

FIG. 39A is a flowchart illustrating an example procedure for determining a type of humeral implant based on bone density. Processing circuitry 1142 of system 1140 will be described as performing the example of FIG. 39A, but other devices or systems, such as system 542 or virtual planning system 102, may perform one or more portions of this technique. Furthermore, some portions of this technique may be performed by a combination of two or more devices and/or systems via a distributed system. The process of FIG. 39A is described with respect to three-dimensional data sets, but several two-dimension slices of data may be analyzed in a similar manner in other examples.

As shown in the example of FIG. 39A, processing circuitry 1142 may obtain patient-specific image data (e.g., from a memory or other system), such as three-dimensional CT image data (1200). Processing circuitry 1142 may then identify the humeral head in the patient-specific image data (1202). For example, processing circuitry 1142 may segment the bones in order to identify the humeral head or determine landmarks or shapes indicative of the humeral head. Using the patient-specific image data of the humeral head, processing circuitry 1142 may determine a bone density metric for at least a portion of the humeral head based on intensities of the voxels or groups of voxels in the patient-specific image data (1204). The bone density metric may be an overall metric indicative of the overall density of the trabecular bone within the humeral head, or the bone density metric may include values representing density or each voxel of groups of voxels within a region of the humeral head.

Processing circuitry 1142 may then determine a recommendation for the humeral implant type based on the bone density metric (1206). For example, processing circuitry 1142 may determine the recommendation to be a stemless humeral implant when the bone density metric indicates or represents that the density of the trabecular bone is high enough to support a stemless humeral implant. The recommendation may be based on a selection algorithm (e.g., one or more tables, equations, or machine learning algorithm such as a neural network) that is developed, perhaps by processing circuitry 1142, based on historical data related to patients previously receiving a humeral implant. For example, historical data may include patient-specific image data (e.g., CT data) and the type of humeral implant (e.g., stemless or stemmed) that was selected by the surgeon for the respective patient (e.g., via use of a thumb test to determine trabecular bone quality, or density, in the humeral head). In one example, a table may map voxel intensities, or groups of voxel intensities, to recommendations of stemmed or stemless implant types. In another example, a first table may map voxel intensities to density values, and a second table may map density values to recommendations of stemmed or stemless implant types). The system may use this mapping of image data to implant selection to inform the recommendation of implant type for a new patient based on that patient's image data. Processing circuitry 1142 may then output the recommendation of the humeral implant type (1208). The recommendation may be transmitted for use in another recommendation or displayed to a user.

Figure 39B:
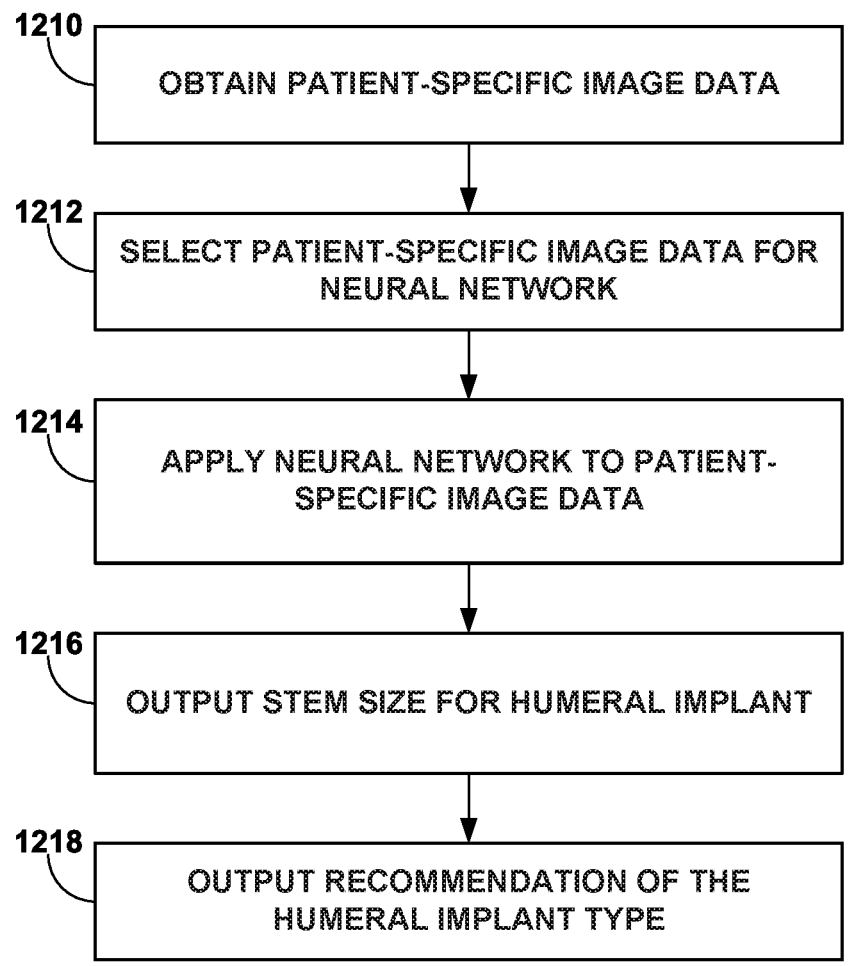
FIG. 39B is a flowchart illustrating an example procedure for applying a neural network to patient-specific image data to determine a stem size for a humeral implant.

FIG. 39B is a flowchart illustrating an example procedure for applying a neural network to patient-specific image data to determine a stem size for a humeral implant. Processing circuitry 1142 of system 1140 will be described as performing the example of FIG. 39B, but other devices or systems, such as system 542 or virtual planning system 102, may perform one or more portions of this technique. Furthermore, some portions of this technique may be performed by a combination of two or more devices and/or systems via a distributed system. The process of FIG. 39B is described with respect to three-dimensional data sets, but several two-dimension slices of data may be analyzed in a similar manner in other examples.

As shown in the example of FIG. 39B, processing circuitry 1142 may obtain patient-specific image data (e.g., from a memory or other system), such as three-dimensional CT image data (1210). Processing circuitry 1142 then selects one or more subsets of the patient-specific image data for application by a neural network (1212). For example, processing circuitry 1142 may select certain portions of the three-dimensional CT image data corresponding to one or more anatomical regions of the humerus. The three-dimensional CT image data may indicate bone density in some examples. Processing circuitry 1142 then applies the neural network to the selected subset of the patient-specific image data (1214).

The neural network may include or be based on a convolutional neural network (CNN). As discussed above, a convolutional neural network can include one or more convolutional layers that perform convolutions over input data using learned filters. Filters can also be referred to as kernels. Convolutional neural networks can be especially useful for vision problems such as when the input data includes still images, such as three-dimensional CT data or other imaging modalities such as Mill data.

An example CNN may include an inception network (e.g., an Inception V Net), a residual neural network (e.g., a ResNet), or other types of networks that include transfer learning techniques applied based on prior data related to prior humerus diagnostic and/or humeral implant data. In some examples, the CNN may be comprised of N convolutional layers, followed by M fully connected layers. Each layer may include one or more filters, and the layers may be stacked convolutional layers. In some examples, one or more filters may be specified for cortical bone while other one or more filters are specified for cancellous (i.e., trabecular) bone. The layers of the CNN may be constructed to assess several bony regions from metaphysis to diaphysis of the humerus.

Processing circuitry 1132 or another processor may train the CNN for humeral stem size prediction may include training a model on dozens, hundreds, or thousands of test images (e.g., CT scan images). The output may be the clinical data collected during or after the surgery such as the stem size and the filling ratio (i.e., the ration of the humeral canal that is filled with the stem of the humeral implant). The stem size may specify a length and/or cross-sectional width or area of the humeral implant. Short stem sizes may be referred to as a stemless humeral implant, while longer stem sizes may be referred to as stemmed humeral implants. The CNN may also include one or more hyperparameters. Several different type of hyperparameters may be used to reduce the average classification rate. One example hyperparameter may include a rectified linear unit (ReLU) for the non-linear part instead of a traditional, slower solutions such as a Tanh or a Sigmond function. The learning rate of the CNN may depend on one or more variants of Gradient Descent Algorithms that are adaptive in nature such as Adagrad, Adadelta, RMSprop, or Adam in which the learning rate adapts based on the type data fed into the CNN. The batch size of the data may be dependent on the learning rate chosen for the CNN. The CNN may utilize momentum values tested according to performance. In one example, the momentum values may be selected from a range of 0.90 through 0.99. However, other momentum values may be chosen in other examples. The CNN may include larger weight values due to relatively small training datasets. However, these weights may be different for other types of training data sets.

The CNN may output the stem size for a humeral implant according to the three-dimensional patient-specific image data to which the CNN was applied (1216). The stem size may include a stem length and/or cross-sectional dimension (e.g., diameter, circumference, area, or other such parameter). In this manner, the determined stem size may be selected to correspond to the specific dimensions and/or bone density of the patient's trabecular bone and/or cancellous bone of the humerus. Based on the stem size, processing circuitry 1132 may output the recommendation of the humeral implant type for the patient (1218). In this manner, processing circuitry 1132 may determine whether a stemmed or stemless humeral implant would be appropriate for treating the patient. In some examples, the CNN may be applied to a bone density metric determined from the patient-specific imaging data. In other examples, the CNN may be used in place of a bone density metric such that the CNN may directly output the stem size of a humeral implant according to the patient-specific imaging data. In some examples, bone density modeling module 1162 may include the CNN and related parameters.

As discussed above, processing circuitry 1132 may train a convolutional neural network and apply the convolutional neural network to patient-specific image data (e.g., 3D imaging data) to generate a recommended stem size for a humeral implant for a patient from which the patient-specific image data was obtained. In one example, a system may include a memory configured to store patient-specific image data for a patient and processing circuitry (e.g., processing circuitry 1132) configured to apply a convolutional neural network to the patient-specific image data (or a subset thereof) and output, based on the convolutional neural networked applied to the patient-specific image data, a stem size for a humeral implant for the patient. The processing circuitry may also be configured to output a recommendation of a humeral implant type that includes the stem size. The patient-specific image data may represent bone density for some or all of one or more bones of the patient, such as the humerus. In some examples, the processing circuitry may also output a representation of a bone density metric representing bone density of at least a portion of the humeral head, but the bone density metric may or may not be employed to generate the stem size recommendation when the CNN is applied to the patient-specific image data.

Figure 39C:
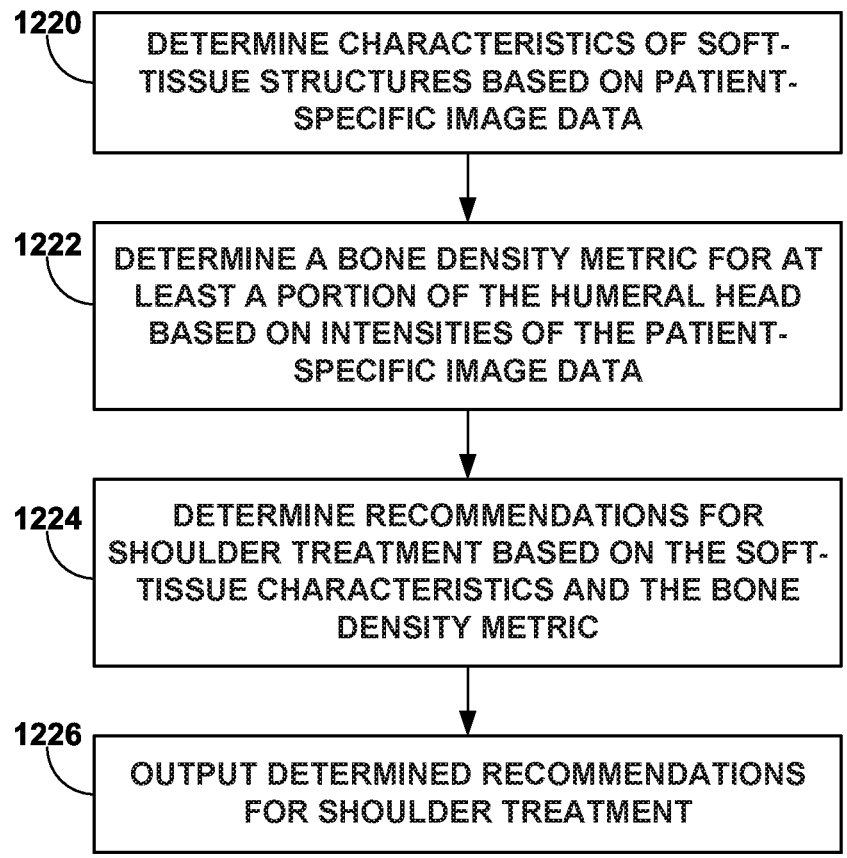
FIG. 39C is a flowchart illustrating an example procedure for determining a recommendation for shoulder treatment based on soft tissue structures and bone density determined from patient-specific image data.

FIG. 39C is a flowchart illustrating an example procedure for determining a recommendation for shoulder treatment based on soft tissue structures and bone density determined from patient-specific image data. Processing circuitry 1142 of system 1140 will be described as performing the example of FIG. 39C, but other devices or systems, such as system 542 or virtual planning system 102, may perform one or more portions of this technique. Furthermore, some portions of this technique may be performed by a combination of two or more devices and/or systems via a distributed system. The process of FIG. 39C is described with respect to three-dimensional data sets, but several two-dimension slices of data may be analyzed in a similar manner in other examples.

As shown in the example of FIG. 39C, processing circuitry 1142 may determine characteristics of one or more soft tissue structures based on patient-specific image data (1220). These characteristics may include a volume, a fatty infiltration ratio, an atrophy ratio, and/or a range of motion of one or more soft tissue structures as described with respect to FIGS. 23A, 23B, 24, 25, 26, and 27, for example. Processing circuitry 1142 may also determine a bone density metric for at least a portion of the humeral head based on intensities of the patient-specific image data (1222), as described herein such as in FIG. 39A.

Processing circuitry 1142 may determine one or more recommendations for shoulder treatment based on the soft-tissue characteristics and the bone density metric (1224). For example, processing circuitry 1142 may determine whether the shoulder replacement should be a reverse or an anatomical replacement based on one or more of the soft-tissue characteristics. In addition, processing circuitry 1142 may determine whether the humeral implant type used in the shoulder replacement should be a stemless or stemmed humeral implant type. In some examples, processing circuitry 1142 may determine the location for at least one of the humeral implant or the glenoid implant based on the soft-tissue characteristics and/or the bone density metric. Processing circuitry 1142 may then output the determined one or more recommendations for the treatment of the patient's shoulder (1226). In this manner, processing circuitry 1142 may use any of the characteristics, metrics, or other information derived from patient-specific image data and other patient information in order to provide recommendations related to shoulder treatment.

Figure 40:
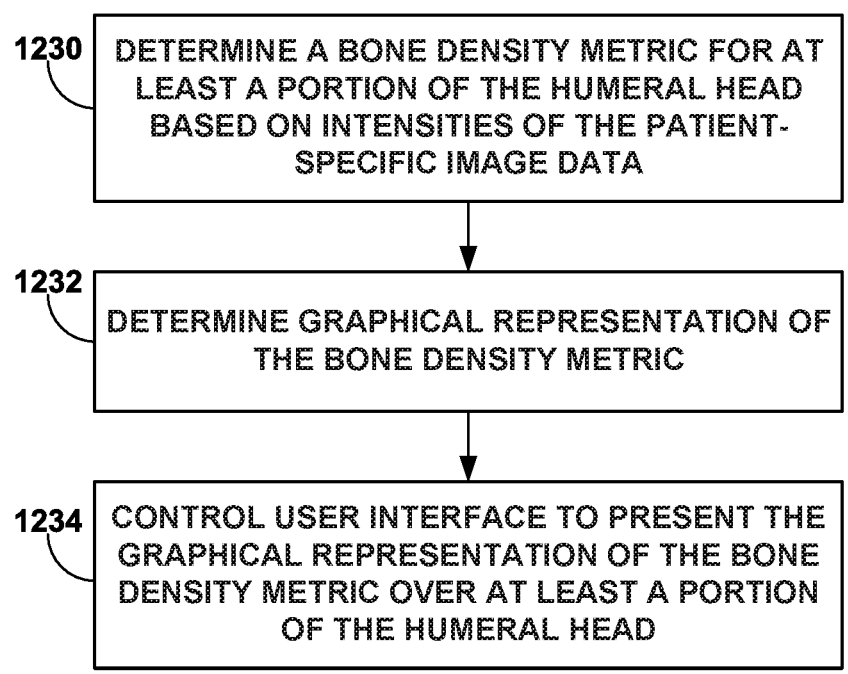
FIG. 40 is a flowchart illustrating an example procedure for displaying bone density information.

FIG. 40 is a flowchart illustrating an example procedure for displaying bone density information. Processing circuitry 1142 of system 1140 will be described as performing the example of FIG. 40, but other devices or systems, such as system 542 or virtual planning system 102, may perform one or more portions of this technique. Furthermore, some portions of this technique may be performed by a combination of two or more devices and/or systems via a distributed system. The process of FIG. 40 is described with respect to three-dimensional data sets, but several two-dimension slices of data may be analyzed in a similar manner in other examples.

As shown in the example of FIG. 40, processing circuitry 1142 may determine a bone density metric for at least a portion of the humeral head based on intensities of the patient-specific image data (1230), such as the process described in FIG. 39A. Processing circuitry 1142 may then determine a graphical representation of the bone density metric (1232). These graphical representations may be similar to the graphical representations of the bone density metrics described in FIGS. 42 and 43. Then, processing circuitry 1142 may control the user interface to present the graphical representation of the bone density metric over at least a portion of the humeral head (1234).

Figure 41:
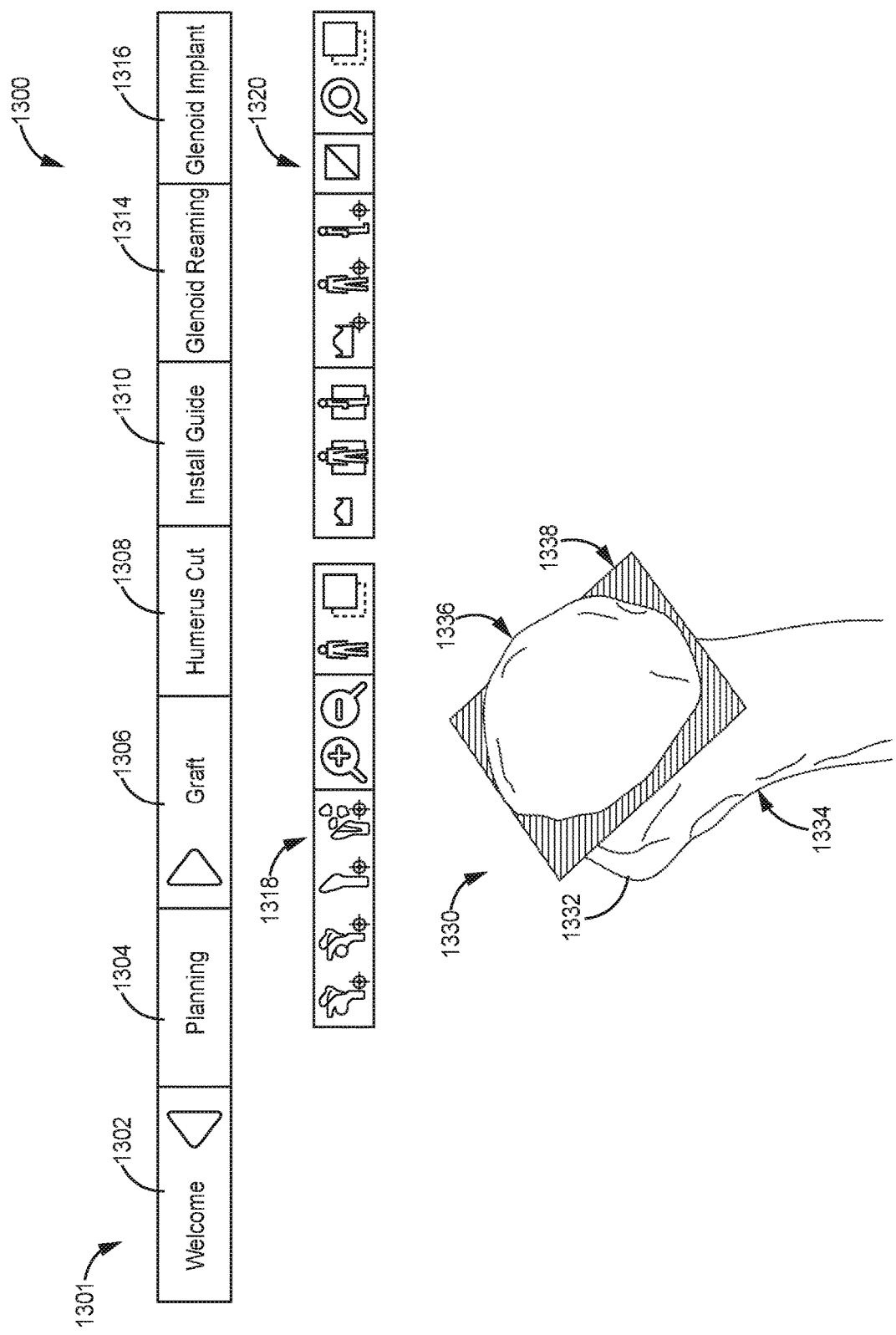
FIG. 41 is a conceptual diagram of an example user interface that includes a humeral head and cutting plane.

FIG. 41 is a conceptual diagram of an example user interface 1300 that includes a humerus 1332 and cut plane 1338. As shown in the example of FIG. 41, user interface 1300 includes navigation bar 1301 and toolbars 1318 and 1320. Navigation bar 1301 may include selectable buttons that, when selected by the user, cause user interface 1300 to change to a different functionality or view of information related to a shoulder treatment, such as planning a shoulder replacement.

Navigation bar 1301 may include a welcome button 1302 that takes the user to a welcome screen showing information related to the patient or possible actions related to types of treatment. Planning button 1304 may change the view of user interface 130 to virtual planning of the shoulder surgery, which may include representations of bones and/or soft tissue structures, such as view 1330 that includes humerus 1332. Graft button 1306 may show a view of potential bone or soft tissue grafts related to surgery, and humerus cut button 1308 may show a representation of humeral head 1332 cut to expose the trabecular bone within. Install guide button 1310 may show possible, or recommended, humeral implants. Glenoid reaming button 1314 may show a view of example reaming to be performed on the glenoid, and glenoid implant button 1316 may show examples of possible, or recommended, glenoid implants that may be implanted for the patient. Toolbar 1318 may include selectable buttons that, when selected, cause user interface 1300 to change the view, rotation, or size of view 1330. Toolbar 1320 may include selectable buttons that, when selected, cause user interface 1300 to change between anatomical planes of the anatomy shown in view 1330, such as ventral or lateral views of the anatomy.

View 1330 includes a perspective view of humerus 1332 which shows shaft 1334 and humeral head 1336. Cut plane 1338 is shown to indicate how humeral head 1336 can be cut prior to implanting the humeral implant. User interface 1300 may enable a user to move cut plane 1338 as desired during the planning process, although user interface 1300 may initially show a recommended position for cut plane 1338. Once the user is satisfied with the position of cut plane 1338, user interface 1300 can remove the top potion of humeral head 1336 to expose a representation of trabecular bone at which a humeral implant may be implanted, as shown in FIGS. 42 and 43.

Figure 42:
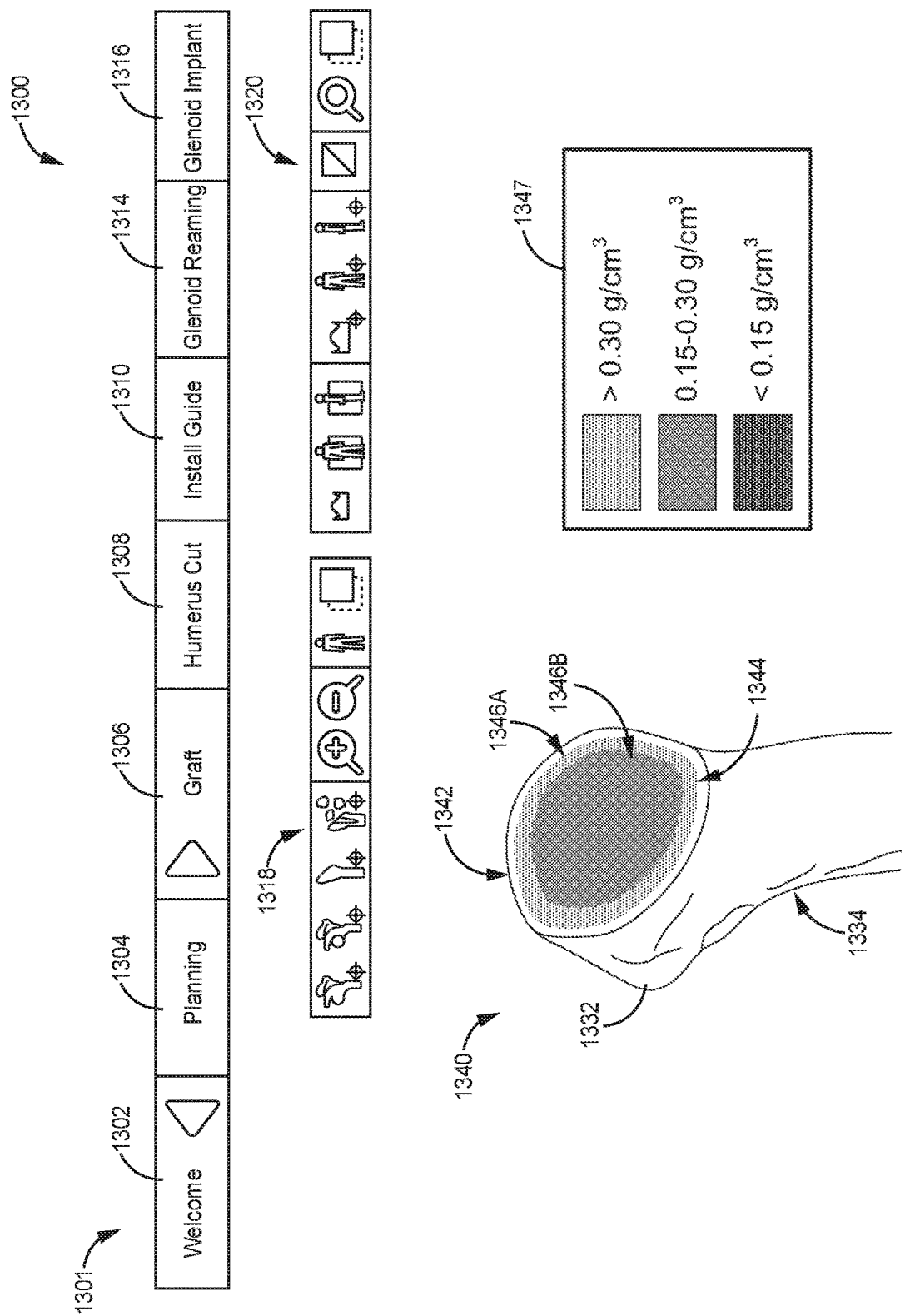
FIG. 42 is a conceptual diagram of an example user interface that includes a humeral head and a representation of internal bone density.
Figure 43:
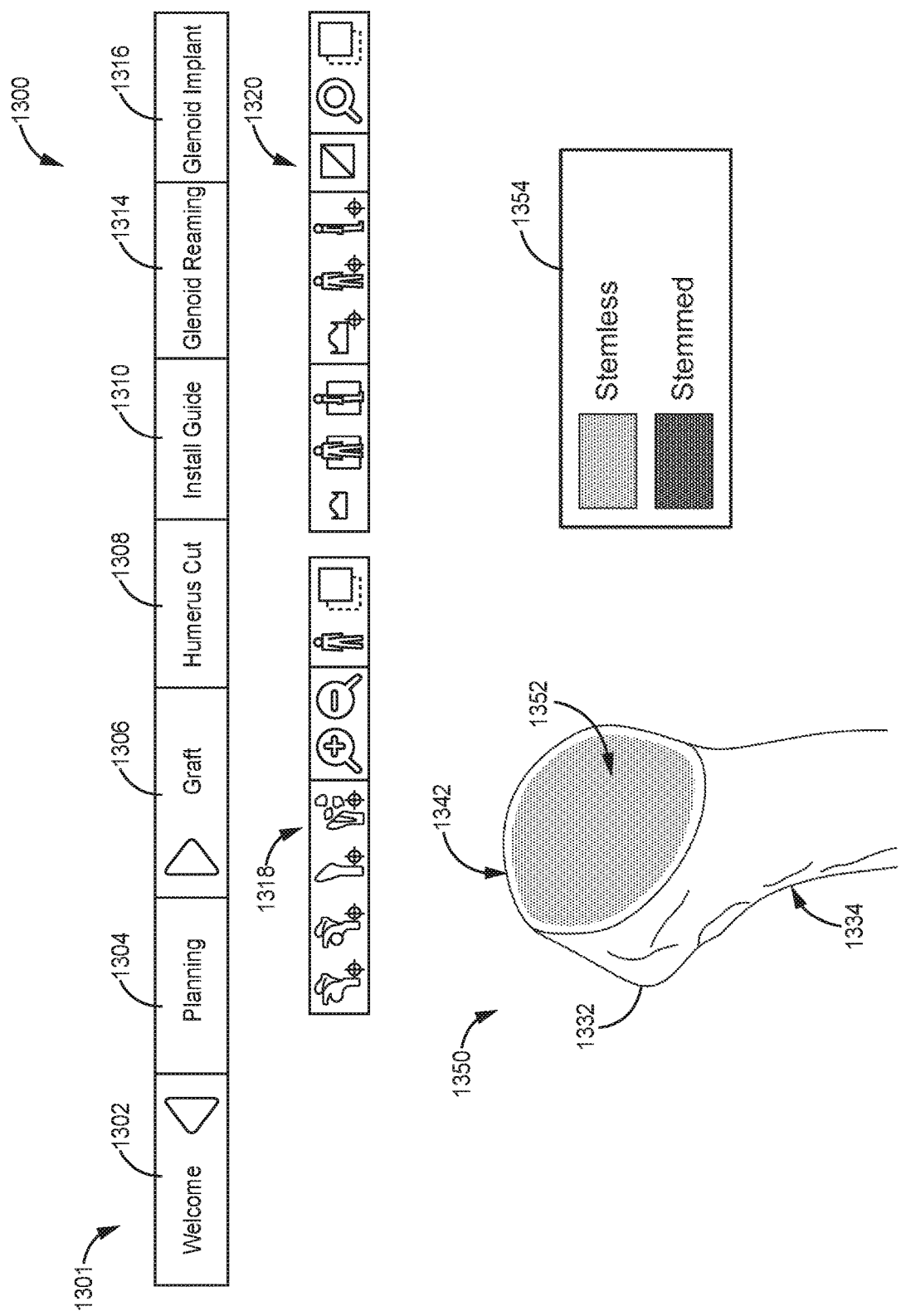
FIG. 43 is a conceptual diagram of an example user interface that includes a humeral head and a representation of internal bone density associated with a type of humeral implant recommendation.

FIG. 42 is a conceptual diagram of an example user interface 1300 that includes a humeral head 1342 and a representation of bone density metric 1344. As shown in the example of FIG. 42, user interface 1300 may include view 1340 in which humeral head 1342 is shown after removal of the top of the humeral head along the cut plane 1338 of FIG. 41. Humeral head 1342 is a representation of the patient's humerus and may be derived from the patient-specific image data. Bone density metric 1344 may be a graphical representation of the bone density metric generated for the trabecular bone of humerus 1332.

Bone density metric 1344 may include different colors that represent voxels of intensity that fall within respective ranges 1346A and 1346B of intensities for each color. In this manner, bone density metric 1344 may include bone density values for different groups of voxels of the trabecular bone within humeral head 1342. For example, range 1346A is representation of bone density greater than 0.30 g/cm$^3$, and range 1346B is a representation of bone density between 0.15 g/cm$^3$ and 0.30 g/cm$^3$. Bone density key 1347 indicates the different colors for possible ranges of bone densities as determined from the patient-specific image data. The three ranges shown in bone density key 1347 are merely examples, and a different number of ranges or ranges having different lower and upper bounds may be used in other examples.

In other examples, view 1340 may present bone density metric 1344 that is an image representing ranges of voxel intensities from the patient-specific image data or a representation of intensities from individual or groups of voxels. As one example, bone density metric 1344 may simply include the voxel intensities from the patient-specific image data that correspond to the same cut plane 1338. In other words, view 1340 may include a picture of the CT data for the 2D plane corresponding to the cut plane 1338 overlaid on the exposed representation of humerus 1332. As another example, view 1340 may include heat map with different colors or patterns, for example, that correspond to different ranges of Hounsfield Units (for the example of CT data). In this manner, although the bone density metric, such as bone density metric 1344, may be related or representative of bone density, the actual bone density metric may not actually reflect a measure of density of bone in that area.

FIG. 43 is a conceptual diagram of an example user interface 1300 that includes a humeral head 1342 and a representation of bone density metric 1352 associated with a type of humeral implant recommendation. As shown in the example of FIG. 43, user interface 1300 may include view 1350 in which humeral head 1342 is shown after removal of the top of the humeral head along the cut plane 1338 of FIG. 41, similar to FIG. 42. Humeral head 1342 is a representation of the patient's humerus and may be derived from the patient-specific image data. Bone density metric 1352 may be a graphical representation of the bone density metric generated for the trabecular bone of humerus 1332.

Bone density metric 1352 indicates the type of humeral implant that could be implanted in the trabecular bone based on the bone density determined for humerus 1332. In this manner, bone density metric 1352 includes the determined bone density from patient-specific patient data as part of a category associated with the type of humeral implant supported by the density of the bone in humerus 1332. Metric key 1354 indicates that colors of bone density metric 1352 that correspond to which types of humeral implant. For example, the lighter color indicates that a stemless humeral implant can be implanted and the darker color indicates that a stemmed humeral implant can be implanted in humerus 1332. As shown in the example of FIG. 43, bone density metric 1352 indicates that the density of the trabecular bone is sufficient to support implantation of a stemless humeral implant. In some examples, bone density metric 1352 may differentiate between different types of humeral implants by different colors, patterns, shapes, or other graphical representations. In one example, bone density metric 1352 may even be a graphical representation of the type of humeral implant itself, such as an image representing the length of the stem, or stemless type, for the humeral implant.

The following examples are described herein. Example 1: A system for modeling a soft-tissue structure of a patient, the system comprising: a memory configured to store patient-specific image data for the patient; and processing circuitry configured to: receive the patient-specific image data; determine, based on intensities of the patient-specific image data, a patient-specific shape representative of the soft-tissue structure of the patient; and output the patient-specific shape.

Example 2: The system of example 1, wherein the processing circuitry is configured to: receive an initial shape; determine a plurality of surface points on the initial shape; register the initial shape to the patient-specific image data; identify one or more contours in the patient-specific image data representative of at least a partial boundary of the soft-tissue structure of the patient; and iteratively move the plurality of surface points towards respective locations of the one or more contours to change the initial shape to the patient-specific shape representative of the soft-tissue structure of the patient.

Example 3: The system of example 2, wherein the processing circuitry is configured to identify the one or more contours by: extending, from each surface point of the plurality of surface points, a vector at least one of outward from or inward from a respective surface point; and determining, for the vector from each surface point, a respective location in the patient-specific image data exceeding a threshold intensity value, wherein the respective locations for at least one surface point of the plurality of surface points at least partially define the one or more contours.

Example 4: The system of any of examples 2 and 3, wherein the processing circuitry is configured to identify the one or more contours by: determining a Hessian feature image from the patient-specific image data, wherein the Hessian feature image indicates regions of the patient-specific image data comprising higher intensity gradients between two or more voxels; identifying, based on the Hessian feature image, one or more separation zones between the soft-tissue structure and an adjacent soft-tissue structure; and determining at least a portion of the one or more contours as passing through the one or more separation zones.

Example 5: The system of any of examples 2 through 4, wherein the processing circuitry is configured to determine the respective location in the patient-specific image data exceeding the threshold intensity value by determining the respective location in the patient-specific image data greater than a predetermined intensity value.

Example 6: The system of example 5, wherein the predetermined threshold intensity value represents bone in the patient-specific image data, and wherein the processing circuitry is configured to, for each respective location in the patient-specific image data exceeding the predetermined threshold intensity value that represents bone, move the surface point to the respective location.

Example 7: The system of any of examples 2 through 6, wherein the processing circuitry is configured to determine the respective location in the patient-specific image data exceeding the threshold intensity value by determining the respective location in the patient-specific image data less than a predetermined intensity value.

Example 8: The system of any of examples 2 through 7, wherein the processing circuitry is configured to determine the respective location in the patient-specific image data exceeding the threshold intensity value by determining the respective location in the patient-specific image data greater than a difference threshold between an intensity associated with the respective surface point and an intensity of the respective location in the patient-specific image data.

Example 9: The system of any of examples 2 through 8, wherein the processing circuitry is configured to iteratively move the plurality of surface points towards respective locations of the one or more contours by, for each iteration of moving the plurality of surface points: extending, from each surface point of the plurality of surface points, a vector from a respective surface point and normal to a surface comprising the respective surface point; determining, for the vector from each surface point, a respective point in the patient-specific image data exceeding a threshold intensity value; determining, for each respective point, a plurality of potential locations within an envelope of the respective point and exceeding the threshold intensity value in the patient-specific image data, wherein the plurality of potential locations at least partially define a surface of the one or more contours; determining, for each of the plurality of potential locations, a respective normal vector normal to the surface; determining, for each of the respective normal vectors, an angle between the respective normal vector and the vector from the respective surface point; selecting, for each respective surface point, one potential location of the plurality of potential locations comprising a smallest angle between the vector from the respective surface point and the respective normal vector from each of the plurality of potential locations; and moving, for each respective surface point, the respective surface point at least partially towards the selected one potential location, wherein moving the respective surface points modifies the initial shape towards the patient-specific shape.

Example 10: The system of example 9, wherein the processing circuitry is configured to move the respective surface point at least half of a distance between the respective surface point and the selected one potential location.

Example 11: The system of any of examples 9 and 10, wherein the processing circuitry is configured to iteratively move the plurality of surface points towards respective potential locations of the one or more contours by: moving, in a first iteration from the initial shape, each surface point of the plurality of surface points a first respective distance within a first tolerance of a first modification distance to generate a second shape, the first tolerance selected to maintain smoothness of the second shape; and moving, in a second iteration following the first iteration, each surface point of the plurality of surface points a second respective distance within a second tolerance of a second modification distance to generate a third shape from the second shape, wherein the second tolerance is larger than the first tolerance.

Example 12: The system of any of examples 2 through 11, wherein the processing circuitry is configured to identify the one or more contours by: determining a Hessian feature image from the patient-specific image data, wherein the Hessian feature image indicates regions of the patient-specific image data comprising higher intensity gradients between two or more voxels; identifying, based on the Hessian feature image, one or more separation zones between the soft-tissue structure and an adjacent soft-tissue structure; and determining at least a portion of the one or more contours as passing through the one or more separation zones.

Example 13: The system of any of examples 2 through 12, wherein the processing circuitry is configured to register the initial shape by registering a plurality of locations on the initial shape to corresponding insertion locations on one or more bones identified in the patient-specific image data.

Example 14: The system of any of examples 2 through 13, wherein the initial shape and the patient-specific shape are three-dimensional shapes.

Example 15: The system of any of examples 1 through 14, wherein the initial shape comprises a geometric shape.

Example 16: The system of any of examples 1 through 15, wherein the initial shape comprises an anatomical shape representative of the soft-tissue structure of a plurality of subjects different than the patient.

Example 17: The system of example 16, wherein the anatomical shape comprises a statistical mean shape generated from the soft-tissue structure imaged for the plurality of subjects.

Example 18: The system of any of examples 1 through 17, wherein the patient-specific image data comprises computed tomography (CT) image data generated from the patient.

Example 19: The system of any of examples 1 through 18, wherein the soft-tissue structure comprises a muscle.

Example 20: The system of example 19, wherein the muscle is associated with a rotator cuff of the patient.

Example 21: The system of any of examples 1 through 20, wherein the patient-specific shape comprises a three-dimensional shape.

Example 22: The system of any of examples 1 through 21, wherein the processing circuitry is configured to: determine a fat volume ratio for the patient-specific shape; determine an atrophy ratio for the patient-specific shape; determine, based on the fat volume ratio and the atrophy ratio of the patient-specific shape of the soft-tissue structure of the patient, a range of motion of a humerus of the patient; and determine, based on the range of motion of the humerus, a type of shoulder treatment for the patient.

Example 23: The system of example 22, wherein the processing circuitry is configured to determine the range of motion of the humerus by determining, based on fat volume ratios and atrophy ratios for each muscle of a rotator cuff of the patient, the range of motion of the humerus of the patient.

Example 24: The system of any of examples 22 and 23, wherein the type of shoulder treatment is selected from one of an anatomical shoulder replacement surgery or a reverse shoulder replacement surgery.

Example 25: The system of any of examples 1 through 24, wherein the processing circuitry is configured to: apply a mask to the patient-specific shape; apply a threshold to the voxels under the mask; determine a fat volume based on the voxels under the threshold; determine a fatty infiltration value based on the fat volume and a volume of the patient-specific shape for the soft-tissue structure; and output a fatty infiltration value for the soft-tissue structure.

Example 26: The system of any of examples 1 through 25, wherein the processing circuitry is configured to: determine bone to muscle dimensions for the soft-tissue structure of the patient; obtain a statistical mean shape (SMS) for the soft-tissue structure; deform the SMS by satisfying a threshold of an algorithm to fit a deformed version of the SMS to the bone to muscle dimensions of the soft-tissue structure; determine an atrophy ratio for the soft-tissue structure by dividing the SMS volume by the soft-tissue structure volume; and output the atrophy ratio for the soft-tissue structure.

Example 27: A method for modeling a soft-tissue structure of a patient, the method comprising: storing, by a memory, patient-specific image data for the patient; receiving, by processing circuitry, the patient-specific image data; determining, by the processing circuitry and based on intensities of the patient-specific image data, a patient-specific shape representative of the soft-tissue structure of the patient; and outputting, by the processing circuitry, the patient-specific shape.

Example 28: The method of example 27, further comprising: receiving an initial shape; determining a plurality of surface points on the initial shape; registering the initial shape to the patient-specific image data; identifying one or more contours in the patient-specific image data representative of a boundary of the soft-tissue structure of the patient; and iteratively moving the plurality of surface points towards respective locations of the one or more contours to change the initial shape to the patient-specific shape representative of the soft-tissue structure of the patient.

Example 29: The method of example 28, wherein identifying the one or more contours by: extending, from each surface point of the plurality of surface points, a vector at least one of outward from or inward from a respective surface point; and determining, for the vector from each surface point, a respective location in the patient-specific image data exceeding a threshold intensity value, wherein the respective locations for at least one surface point of the plurality of surface points at least partially define the one or more contours.

Example 30: The method of any of examples 28 and 29, identifying the one or more contours comprises: determining a Hessian feature image from the patient-specific image data, wherein the Hessian feature image indicates regions of the patient-specific image data comprising higher intensity gradients between two or more voxels;

identifying, based on the Hessian feature image, one or more separation zones between the soft-tissue structure and an adjacent soft-tissue structure; and determining at least a portion of the one or more contours as passing through the one or more separation zones.

Example 31: The method of any of examples 28 through 30, wherein determining the respective location in the patient-specific image data exceeding the threshold intensity value comprises determining the respective location in the patient-specific image data greater than a predetermined intensity value.

Example 32: The method of example 32, wherein the predetermined threshold intensity value represents bone in the patient-specific image data, and wherein the method further comprises, for each respective location in the patient-specific image data exceeding the predetermined threshold intensity value that represents bone, moving the surface point to the respective location.

Example 33: The method of any of examples 28 through 32, wherein determining the respective location in the patient-specific image data exceeding the threshold intensity value comprises determining the respective location in the patient-specific image data less than a predetermined intensity value.

Example 34: The method of any of examples 28 through 33, wherein determining the respective location in the patient-specific image data exceeding the threshold intensity value comprises determining the respective location in the patient-specific image data greater than a difference threshold between an intensity associated with the respective surface point and an intensity of the respective location in the patient-specific image data.

Example 35: The method of any of examples 28 through 34, wherein iteratively moving the plurality of surface points towards respective locations of the one or more contours comprises, for each iteration of moving the plurality of surface points: extending, from each surface point of the plurality of surface points, a vector from a respective surface point and normal to a surface comprising the respective surface point; determining, for the vector from each surface point, a respective point in the patient-specific image data exceeding a threshold intensity value; determining, for each respective point, a plurality of potential locations within an envelope of the respective point and exceeding the threshold intensity value in the patient-specific image data, wherein the plurality of potential locations at least partially define a surface of the one or more contours; determining, for each of the plurality of potential locations, a respective normal vector normal to the surface; determining, for each of the respective normal vectors, an angle between the respective normal vector and the vector from the respective surface point; selecting, for each respective surface point, one potential location of the plurality of potential locations comprising a smallest angle between the vector from the respective surface point and the respective normal vector from each of the plurality of potential locations; and moving, for each respective surface point, the respective surface point at least partially towards the selected one potential location, wherein moving the respective surface points modifies the initial shape towards the patient-specific shape.

Example 36: The method of example 35, further comprising moving the respective surface point at least half of a distance between the respective surface point and the selected one potential location.

Example 37: The method of any of examples 35 and 36, wherein iteratively moving the plurality of surface points towards respective potential locations of the one or more contours comprises: moving, in a first iteration from the initial shape, each surface point of the plurality of surface points a first respective distance within a first tolerance of a first modification distance to generate a second shape, the first tolerance selected to maintain smoothness of the second shape; and moving, in a second iteration following the first iteration, each surface point of the plurality of surface points a second respective distance within a second tolerance of a second modification distance to generate a third shape from the second shape, wherein the second tolerance is larger than the first tolerance.

Example 38: The method of any of examples 28 through 37, wherein the processing circuitry is configured to identify the one or more contours by: determining a Hessian feature image from the patient-specific image data, wherein the Hessian feature image indicates regions of the patient-specific image data comprising higher intensity gradients between two or more voxels; identifying, based on the Hessian feature image, one or more separation zones between the soft-tissue structure and an adjacent soft-tissue structure; and determining at least a portion of the one or more contours as passing through the one or more separation zones.

Example 39: The method of any of examples 28 through 38, wherein registering the initial shape comprises registering a plurality of locations on the initial shape to corresponding insertion locations on one or more bones identified in the patient-specific image data.

Example 40: The method of any of examples 38 through 30, wherein the initial shape and the patient-specific shape are three-dimensional shapes.

Example 41: The method of any of examples 27 through 40, wherein the initial shape comprises a geometric shape.

Example 42: The method of any of examples 27 through 41, wherein the initial shape comprises an anatomical shape representative of the soft-tissue structure of a plurality of subjects different than the patient.

Example 43: The method of example 42, wherein the anatomical shape comprises a statistical mean shape generated from the soft-tissue structure imaged for the plurality of subjects.

Example 44: The method of any of examples 27 through 43, wherein the patient-specific image data comprises computed tomography (CT) image data generated from the patient.

Example 45: The method of any of examples 27 through 44, wherein the soft-tissue structure comprises a muscle.

Example 46: The method of example 45, wherein the muscle is associated with a rotator cuff of the patient.

Example 47: The method of any of examples 27 through 46, wherein the patient-specific shape comprises a three-dimensional shape.

Example 48: The method of any of examples 27 through 47, further comprising: determining a fat volume ratio for the patient-specific shape; determining an atrophy ratio for the patient-specific shape; determining, based on the fat volume ratio and the atrophy ratio of the patient-specific shape of the soft-tissue structure of the patient, a range of motion of a humerus of the patient; and determining, based on the range of motion of the humerus, a type of shoulder treatment for the patient.

Example 49: The method of example 48, wherein determining the range of motion of the humerus comprises determining, based on fat volume ratios and atrophy ratios for each muscle of a rotator cuff of the patient, the range of motion of the humerus of the patient.

Example 50: The method of any of examples 48 and 49, wherein the type of shoulder treatment is selected from one of an anatomical shoulder replacement surgery or a reverse shoulder replacement surgery.

Example 51: The method of any of examples 27 through 50, further comprising: applying a mask to the patient-specific shape; applying a threshold to the voxels under the mask; determining a fat volume based on the voxels under the threshold; determining a fatty infiltration value based on the fat volume and a volume of the patient-specific shape for the soft-tissue structure; and outputting a fat volume ratio for the soft-tissue structure.

Example 52: The method of any of examples 27 through 51, further comprising: determining bone to muscle dimensions for the soft-tissue structure of the patient; obtaining a statistical mean shape (SMS) for the soft-tissue structure; deforming the SMS by satisfying a threshold of an algorithm to fit a deformed version of the SMS to the bone to muscle dimensions of the soft-tissue structure; determining an atrophy ratio for the soft-tissue structure by dividing the SMS volume by the soft-tissue structure volume; and outputting the atrophy ratio for the soft-tissue structure.

Example 53: A computer readable storage medium comprising instructions that, when executed by processing circuitry, causes the processing circuitry to: store, in a memory, patient-specific image data for a patient; receive the patient-specific image data; determine, based on intensities of the patient-specific image data, a patient-specific shape representative of a soft-tissue structure of the patient; and output the patient-specific shape.

Example 54: A system for modeling a soft-tissue structure of a patient, the system comprising: means for storing patient-specific image data for the patient; means for receiving the patient-specific image data; means for determining, based on intensities of the patient-specific image data, a patient-specific shape representative of the soft-tissue structure of the patient; and means for outputting the patient-specific shape.

Example 101: A system for modeling a soft-tissue structure of a patient, the system comprising: a memory configured to store patient-specific computed tomography (CT) data for the patient; and processing circuitry configured to: receive the patient-specific CT data; identify one or more locations associated with one or more bone structures within the patient-specific CT data; register an initial shape to the one or more locations; modify the initial shape to a patient-specific shape representative of the soft-tissue structure of the patient; and output the patient-specific shape.

Example 102: The system of example 101, wherein the one or more locations associated with the one or more bone structures comprises one or more insertion locations of the one or more bone structures identified in the patient-specific CT data.

Example 103: The system of example 102, wherein the processing circuitry is configured to: identify one or more contours in the patient-specific CT data representative of at least a partial boundary of the soft-tissue structure of the patient; and modify, based on the one or more contours, the initial shape to the patient-specific shape representative of the soft-tissue structure of the patient.

Example 104: The system of example 103, wherein the processing circuitry is configured to: determine a plurality of surface points on the initial shape; and modify the initial shape by iteratively moving the plurality of surface points towards respective locations of the one or more contours to change the initial shape to the patient-specific shape representative of the soft-tissue structure of the patient.

Example 105: The system of any of examples 103 and 104, wherein the processing circuitry is configured to modify the initial shape by: extending, from each surface point of the plurality of surface points, a vector at least one of outward from or inward from a respective surface point; determining, for the vector from each surface point, a respective location in the patient-specific CT data exceeding a threshold intensity value, wherein the respective locations for at least one surface point of the plurality of surface points at least partially define the one or more contours.

Example 106: The system of any of examples 103 through 105, wherein the processing circuitry is configured to identify the one or more contours by: determining a Hessian feature image from the patient-specific CT data, wherein the Hessian feature image indicates regions of the patient-specific CT data comprising higher intensity gradients between two or more voxels; identifying, based on the Hessian feature image, one or more separation zones between the soft-tissue structure and an adjacent soft-tissue structure; and determining at least a portion of the one or more contours as passing through the one or more separation zones.

Example 107: The system of any of examples 101 through 106, wherein the processing circuitry is configured to register the initial shape to the one or more locations by: determining a correspondence between each of the one or more locations and a respective point on the initial shape; determining an intensity profile along each of the correspondences in the patient-specific CT data; determining, for each location of the one or more locations and based on the intensity profile for the respective correspondence, a distance between the location and the respective point on the initial shape; and orienting the initial shape within the patient-specific CT data according to the respective distances between the one or more locations and the points on the initial shape.

Example 108: The system of example 107, wherein the processing circuitry is configured to modify the initial shape to the patient-specific shape by scaling the initial shape to minimize differences between the initial shape and variances in the patient-specific CT data representing the soft tissue structure.

Example 109: The system of example 108, wherein the processing circuitry is configured to determine the patient-specific shape (s) according a parametric equation:

$$s=s'+\Sigma_i b_i \sqrt{\lambda_i} \times v_i,$$

wherein s' is the initial shape representative of the soft tissue structure of a plurality of subjects different than the patient, $\lambda_i$ is eigenvalues and $v_i$ is eigenvectors of a covariance matrix representing the variances in the patient-specific CT data, and, $b_i$ is a scaling factor that modifies the initial shape.

Example 110: The system of any of examples 101 through 109, wherein the initial shape comprises an anatomical shape representative of the soft-tissue structure of a plurality of subjects different than the patient.

Example 111: The system of example 110, wherein the anatomical shape comprises a statistical mean shape generated from the soft-tissue structure imaged for the plurality of subjects.

Example 112: The system of any of examples 101 through 111, wherein the soft-tissue structure comprises a muscle.

Example 113: The system of example 112, wherein the muscle is associated with a rotator cuff of the patient.

Example 114: The system of any of examples 101 through 113, wherein the patient-specific shape comprises a three-dimensional shape.

Example 115: The system of any of examples 101 through 114, wherein the processing circuitry is configured to: determine a fat volume ratio for the patient-specific shape; determine an atrophy ratio for the patient-specific shape; determine, based on the fat volume ratio and the atrophy ratio of the patient-specific shape of the soft-tissue structure of the patient, a range of motion of a humerus of the patient; and determine, based on the range of motion of the humerus, a type of shoulder treatment for the patient.

Example 116: The system of example 115, wherein the type of shoulder treatment is selected from one of an anatomical shoulder replacement surgery or a reverse shoulder replacement surgery.

Example 117: A method for modeling a soft-tissue structure of a patient, the method comprising: storing, in a memory, patient-specific computed tomography (CT) data for the patient; receiving, by processing circuitry, the patient-specific CT data; identifying, by the processing circuitry, one or more locations associated with one or more bone structures within the patient-specific CT data; registering, by the processing circuitry, an initial shape to the one or more locations; modifying, by the processing circuitry, the initial shape to a patient-specific shape representative of the soft-tissue structure of the patient; and output, by the processing circuitry, the patient-specific shape.

Example 118: The method of example 117, wherein the one or more locations associated with the one or more bone structures comprises one or more insertion locations of the one or more bone structures identified in the patient-specific CT data.

Example 119: The method of example 118, further comprising: identifying one or more contours in the patient-specific CT data representative of at least a partial boundary of the soft-tissue structure of the patient; and modifying, based on the one or more contours, the initial shape to the patient-specific shape representative of the soft-tissue structure of the patient.

Example 120: The method of example 119, further comprising: determining a plurality of surface points on the initial shape; and modifying the initial shape by iteratively moving the plurality of surface points towards respective locations of the one or more contours to change the initial shape to the patient-specific shape representative of the soft-tissue structure of the patient.

Example 121: The method of any of examples 129 and 120, modifying the initial shape comprises: extending, from each surface point of the plurality of surface points, a vector at least one of outward from or inward from a respective surface point; determining, for the vector from each surface point, a respective location in the patient-specific CT data exceeding a threshold intensity value, wherein the respective locations for at least one surface point of the plurality of surface points at least partially define the one or more contours.

Example 122: The method of any of examples 119 through 121, wherein identifying the one or more contours comprises: determining a Hessian feature image from the patient-specific CT data, wherein the Hessian feature image indicates regions of the patient-specific CT data comprising higher intensity gradients between two or more voxels; identifying, based on the Hessian feature image, one or more separation zones between the soft-tissue structure and an adjacent soft-tissue structure; and determining at least a portion of the one or more contours as passing through the one or more separation zones.

Example 123: The method of any of examples 117 through 122, wherein registering the initial shape to the one or more locations comprises: determining a correspondence between each of the one or more locations and a respective point on the initial shape; determining an intensity profile along each of the correspondences in the patient-specific CT data; determining, for each location of the one or more locations and based on the intensity profile for the respective correspondence, a distance between the location and the respective point on the initial shape; and orienting the initial shape within the patient-specific CT data according to the respective distances between the one or more locations and the points on the initial shape.

Example 124: The method of example 123, wherein modifying the initial shape to the patient-specific shape by scaling the initial shape to minimize differences between the initial shape and variances in the patient-specific CT data representing the soft tissue structure.

Example 125: The method of example 124, wherein determining the patient-specific shape (s) comprises determining the patient-specific shape according a parametric equation:

$$s = s' + \Sigma_i b_i \sqrt{\lambda_i} \times v_i,$$

wherein s' is the initial shape representative of the soft tissue structure of a plurality of subjects different than the patient, $\lambda_i$ is eigenvalues and $v_i$ is eigenvectors of a covariance matrix representing the variances in the patient-specific CT data, and, $b_i$ is a scaling factor that modifies the initial shape.

Example 126: The method of any of examples 117 through 125, wherein the initial shape comprises an anatomical shape representative of the soft-tissue structure of a plurality of subjects different than the patient.

Example 127: The method of example 127, wherein the anatomical shape comprises a statistical mean shape generated from the soft-tissue structure imaged for the plurality of subjects.

Example 128: The method of any of examples 117 through 127, wherein the soft-tissue structure comprises a muscle.

Example 129: The method of example 128, wherein the muscle is associated with a rotator cuff of the patient.

Example 130: The method of any of examples 117 through 129, wherein the patient-specific shape comprises a three-dimensional shape.

Example 131: The method of any of examples 117 through 130, further comprising: determining a fat volume ratio for the patient-specific shape; determining an atrophy ratio for the patient-specific shape; determining, based on the fat volume ratio and the atrophy ratio of the patient-specific shape of the soft-tissue structure of the patient, a range of motion of a humerus of the patient; and determining, based on the range of motion of the humerus, a type of shoulder treatment for the patient.

Example 132: The method of example 131, wherein the type of shoulder treatment is selected from one of an anatomical shoulder replacement surgery or a reverse shoulder replacement surgery.

Example 133: A computer-readable storage medium comprising instructions that, when executed, cause a processor to: store patient-specific computed tomography (CT) data for the patient; receive the patient-specific CT data; identify one or more locations associated with one or more bone structures within the patient-specific CT data; register an initial shape to the one or more locations; modify the initial shape to a patient-specific shape representative of the soft-tissue structure of the patient; and output the patient-specific shape.

Example 201: A system for automatically generating a shoulder surgery type recommendation for a patient, the system comprising: a memory configured to store patient-specific image data for the patient; and processing circuitry configured to: receive the patient-specific image data from the memory; determine one or more soft tissue characteristics from the patient-specific imaging data; generate a recommendation of the shoulder surgery type to be performed for the patient; and output the recommendation of the shoulder surgery type.

Example 202: The system of example 201, wherein the one or more soft tissue characteristics comprises a fatty infiltration ratio for a soft tissue structure of the patient.

Example 203: The system of example 202, wherein the processing circuitry is configured to determine the fatty infiltration ratio by: applying a mask to a patient-specific shape representative of the soft tissue structure; applying a threshold to voxels under the mask; determining a fat volume based on the voxels under the threshold; and determining the fatty infiltration value based on the fat volume and a volume of the patient-specific shape representative of the soft-tissue structure.

Example 204: The system of any of examples 201 through 203, wherein the one or more soft tissue characteristics comprises an atrophy ratio for a soft tissue structure of the patient.

Example 205: The system of example 204, wherein the processing circuitry is configured to determine the atrophy ratio by: determining bone to muscle dimensions for the soft-tissue structure of the patient; obtaining a statistical mean shape (SMS) for the soft-tissue structure; deforming the SMS by satisfying a threshold of an algorithm to fit a deformed version of the SMS to the bone to muscle dimensions of the soft-tissue structure; and determining the atrophy ratio for the soft-tissue structure by dividing the SMS volume by the soft-tissue structure volume.

Example 206: The system of any of examples 201 through 205, wherein the one or more soft tissue characteristics comprises at least one of a fatty infiltration value or an atrophy ratio, and wherein the processing circuitry is configured to generate the recommendation of the shoulder surgery type to be performed for the patient based on at least one of the fatty infiltration value or the atrophy ratio for one or more soft tissue structures of the patient.

Example 207: The system of example 206, wherein the processing circuitry is configured to determine a spring constant for the one or more soft tissue structures based on at least one of the fatty infiltration value or the atrophy ratio.

Example 208: The system of example 207, wherein the processing circuitry is configured to determine the spring constant for the one or more soft tissue structures based on both of the fatty infiltration value and the atrophy ratio.

Example 209: The system of any of examples 207 and 208, wherein the processing circuitry is configured to determine a range of motion of a humerus of the patient based on at least one of the fatty infiltration value, the atrophy ration, or the spring constant for the one or more soft tissue structures.

Example 210: The system of example 209, wherein the one or more soft tissue structures comprise one or more muscles of a rotator cuff of the patient.

Example 211: The system of any of examples 201 through 210, wherein the one or more soft tissue characteristics comprises a range of motion of a humerus.

Example 212: The system of any of examples 201 through 211, wherein the processing circuitry is configured to determine the one or more soft tissue characteristics using a neural network.

Example 213: The system of any of examples 201 through 212, wherein the one or more soft tissue characteristics comprise at least one of a fatty infiltration value, an atrophy value, or a range of motion value for one or more soft tissue structures of the patient, and wherein the processing circuitry is configured to: input at least one of the fatty infiltration value, the atrophy value, or the range of motion value into a neural network; and generate the recommendation of the shoulder surgery type based on an output from the neural network.

Example 214: The system of any of examples 201 through 213, wherein the processing circuitry is configured to determine the one or more soft tissue characteristics from the patient-specific imaging data by: receiving an initial shape for a soft tissue structure of the patient; determining a plurality of surface points on the initial shape; registering the initial shape to the patient-specific image data; identifying one or more contours in the patient-specific image data representative of a boundary of the soft tissue structure of the patient; iteratively moving the plurality of surface points towards respective locations of the one or more contours to change the initial shape to the patient-specific shape representative of the soft tissue structure of the patient; and determining, based on the patient-specific shape, one or more soft tissue characteristics for the soft tissue structure of the patient.

Example 215: The system of any of examples 201 through 214, wherein the processing circuitry is configured to control a user interface to display a representation of the one or more soft tissue characteristics.

Example 216: The system of example 215, wherein the processing circuitry is configured to control the user interface to display the representation of the one or more soft tissue characteristics as part of a mixed reality user interface.

Example 217: The system of any of examples 201 through 216, wherein the shoulder surgery type comprises one of an anatomical shoulder replacement or a reverse shoulder replacement.

Example 218: A method for automatically generating a shoulder surgery type recommendation for a patient, the method comprising: storing, by a memory, a patient-specific image data for the patient; receiving, by processing circuitry, the patient-specific image data from the memory; determining, by the processing circuitry, one or more soft tissue characteristics from the patient-specific imaging data; generating, by the processing circuitry, e a recommendation of the shoulder surgery type to be performed for the patient; and outputting, by the processing circuitry, the recommendation of the shoulder surgery type.

Example 219: A method for determining a fatty infiltration ratio for a soft tissue structure of a patient, the method comprising: receiving patient-specific image data for a patient; determining, from the patient-specific image data, a patient-specific shape representative of the soft tissue structure; applying a mask to the patient-specific shape; applying a threshold to voxels under the mask; determining a fat volume based on the voxels under the threshold; determining the fatty infiltration value based on the fat volume and a volume of the patient-specific shape representative of the soft-tissue structure; and outputting the fatty infiltration value.

Example 220: A method for determining an atrophy ratio for a soft tissue structure of a patient, the method comprising: receiving patient-specific image data for a patient; determining, from the patient-specific image data, a patient-specific shape representative of the soft tissue structure; determining, from the patient-specific image data, bone to muscle dimensions for the soft-tissue structure of the patient; obtaining a statistical mean shape (SMS) for the soft-tissue structure; deforming the SMS by satisfying a threshold of an algorithm to fit a deformed version of the SMS to the bone to muscle dimensions of the soft-tissue structure; determining the atrophy ratio for the soft-tissue structure by dividing the SMS volume by the soft-tissue structure volume; and outputting the atrophy ratio for the soft-tissue structure.

Example 221: A method for determining a range of motion for a humerus of a shoulder of a patient, the method comprising: receiving patient-specific image data for a patient; determining, from the patient-specific image data, one or more patient-specific shapes representative of respective soft tissue structures of a rotator cuff of the patient; determining, based on the one or more patient-specific shapes, at least one of a fatty infiltration ratio or an atrophy ratio for each of the respective soft tissue structures of the rotator cuff; determining, based on the at least one of the fatty infiltration ratio or the atrophy ration, a range of motion of the humerus for the shoulder; and outputting the range of motion of the humerus.

Example 301: A system comprising: a memory configured to store patient-specific image data for the patient; and processing circuitry configured to: identify a humeral head in the patient-specific image data; determine, based on the patient-specific image data, a bone density metric representing bone density of at least a portion of the humeral head; generate, based on the bone density metric, a recommendation of a humeral implant type for the patient; and output the recommendation of the humeral implant type for the patient.

Example 302: The system of example 301, wherein the humeral implant type comprises one of a stemmed implant type or a stemless implant type.

Example 303: The system of any of examples 301 and 302, wherein the recommendation of the humeral implant type comprises a recommendation indicating a length of a stem of a humeral implant.

Example 304: The system of any of examples 301 through 303, wherein the bone density metric represents an overall density score for trabecular bone within at least a portion of the humeral head.

Example 305: The system of any of examples 301 through 304, wherein the bone density metric comprises a plurality of bone density values for respective portions within the humeral head.

Example 306: The system any of examples 301 through 305, wherein the processing circuitry is configured to determine the bone density metric by: identifying, based on the patient-specific image data, intensities of respective voxels within at least a portion of the humeral head; classifying the intensities of the respective voxels in one of two or more intensity levels; and determining, based on at least one of a number of voxels classified within each of the two or more intensity levels or a location in the humeral head of the voxels classified within each of the two or more intensity levels, the bone density metric.

Example 307: The system of any of examples 301 through 306, wherein the processing circuitry is configured to: determine a plane through a humeral head, the plane representative of a humeral cut in the humerus that would prepare the humerus for accepting a humeral implant; and determine the bone density metric for at least a portion of the humeral head exposed by the plane.

Example 308: The system of any of examples 301 through 308, wherein the processing circuitry is configured to output a user interface comprising a graphical representation of the bone density metric over a representation of at least a portion of the humeral head of the patient.

Example 309: The system of example 308, wherein the bone density metric comprises a heat map of a plurality of colors, each color of the plurality of colors representing a different range of bone density values.

Example 310: The system of any of examples 308 and 309, further comprising a mixed reality display, and wherein the processing circuitry is configured to control the mixed reality display to present the user interface comprising the graphical representation of the bone density metric.

Example 311: The system of any of examples 308 through 310, wherein the graphical representation of the bone density metric comprises a two-dimensional representation of bone density variation within a plane of the humeral head.

Example 312: The system of any of examples 308 through 311, wherein the graphical representation of the bone density metric comprises a three-dimensional representation of bone density variation within at last trabecular bone of the humeral head.

Example 313: The system of any of examples 301 through 312, wherein the processing circuitry is configured to apply a convolutional neural network to the patient-specific image data to generate a stem size of the humeral implant, and wherein the recommendation of the humeral implant type for the patient comprises the humeral implant type having the stem size generated from the convolutional neural network.

Example 314: A method comprising: identifying, by processing circuitry, a humeral head in patient-specific image data of a patient; determining, by the processing circuitry and based on the patient-specific image data, a bone density metric representing bone density of at least a portion of the humeral head; generating, by the processing circuitry and based on the bone density metric, a recommendation of a humeral implant type for the patient; and output, by the processing circuitry, the recommendation of the humeral implant type for the patient.

Example 315: The method of example 314, wherein the humeral implant type comprises one of a stemmed implant type or a stemless implant type.

Example 316: The method of any of examples 314 and 315, wherein the recommendation of the humeral implant type comprises a recommendation indicating a length of a stem of a humeral implant.

Example 317: The method of any of examples 314 through 316, wherein the bone density metric represents an overall density score for trabecular bone within at least a portion of the humeral head.

Example 318: The method of any of examples 314 through 317, wherein the bone density metric comprises a plurality of bone density values for respective portions within the humeral head.

Example 319: The method of any of examples 314 through 318, wherein determining the bone density metric comprises: identifying, based on the patient-specific image data, intensities of respective voxels within at least a portion of the humeral head; classifying the intensities of the respective voxels in one of two or more intensity levels; and determining, based on at least one of a number of voxels classified within each of the two or more intensity levels or a location in the humeral head of the voxels classified within each of the two or more intensity levels, the bone density metric.

Example 320: The method of any of examples 314 through 319, further comprising: determining a plane through a humeral head, the plane representative of a humeral cut in the humerus that would prepare the humerus for accepting a humeral implant; and determining the bone density metric for at least a portion of the humeral head exposed by the plane.

Example 321: The method of any of examples 314 through 320, further comprising outputting, for display, a user interface comprising a graphical representation of the bone density metric over a representation of at least a portion of the humeral head of the patient.

Example 322: The method of example 321, wherein the bone density metric comprises a heat map of a plurality of colors, each color of the plurality of colors representing a different range of bone density values.

Example 323: The method of any of examples 321 and 322, further comprising controlling a mixed reality display to present the user interface comprising the graphical representation of the bone density metric.

Example 324: The method of any of examples 321 through 323, wherein the graphical representation of the bone density metric comprises a two-dimensional representation of bone density variation within a plane of the humeral head.

Example 325: The method of any of examples 321 through 324, wherein the graphical representation of the bone density metric comprises a three-dimensional representation of bone density variation within at last trabecular bone of the humeral head.

Example 326: The method of any of examples 314 through 325, further comprising applying a convolutional neural network to the patient-specific image data to generate a stem size of the humeral implant, and wherein the recommendation of the humeral implant type for the patient comprises the humeral implant type having the stem size generated from the convolutional neural network.

Example 327: A computer-readable storage medium comprising instructions that, when executed, cause processing circuitry to: identify a humeral head in patient-specific image data for a patient; determine, based on the patient-specific image data, a bone density metric representing bone density of at least a portion of the humeral head; generate, based on the bone density metric, a recommendation of a humeral implant type for the patient; and output, for display, the recommendation of the humeral implant type for the patient.

Example 328: A system comprising: a memory configured to store patient-specific image data for the patient; and processing circuitry configured to: identify a humeral head in the patient-specific image data; determine, based on the patient-specific image data, a bone density metric representing bone density of at least a portion of the humeral head; and control a user interface to present a graphical representation of the bone density metric over a representation of at least a portion of the humeral head of the patient.

Example 329: The system of example 328, wherein the processing circuitry is configured to: generate, based on the bone density metric, a recommendation of a humeral implant type for the patient; and output, for display, the recommendation of the humeral implant type for the patient.

Example 330: The system of any of examples 328 and 329, wherein the processing circuitry is configured to perform the method of any of examples 313-324.

Example 331: A method comprising: identifying, by processing circuitry, a humeral head in the patient-specific image data for a patient; determining, by the processing circuitry and based on the patient-specific image data, a bone density metric representing bone density of at least a portion of the humeral head; and controlling, by the processing circuitry, a user interface to present a graphical representation of the bone density metric over a representation of at least a portion of the humeral head of the patient.

Example 332: The method of example 331, further comprising: generating, based on the bone density metric, a recommendation of a humeral implant type for the patient; and outputting, for display, the recommendation of the humeral implant type for the patient.

Example 333: A computer-readable storage medium comprising instructions that, when executed, cause processing circuitry to: identify a humeral head in patient-specific image data for a patient; determine, based on the patient-specific image data, a bone density metric representing bone density of at least a portion of the humeral head; and control a user interface to present a graphical representation of the bone density metric over a representation of at least a portion of the humeral head of the patient.

Example 334: The system of example 333, wherein the processing circuitry is configured to: generate, based on the bone density metric, a recommendation of a humeral implant type for the patient; and output, for display, the recommendation of the humeral implant type for the patient.

Example 401: A system for automatically generating a shoulder surgery recommendation for a patient, the system comprising: a memory configured to store patient-specific image data for the patient; and processing circuitry configured to: receive the patient-specific image data from the memory; determine, based on the patient-specific imaging data, one or more soft tissue characteristics and a bone density metric associated with a humerus of the patient; generate, based on the one or more soft tissue characteristics, a recommendation of a shoulder surgery type to be performed for the patient; generate, based on the bone density metric associated with the humerus, a recommendation of a humeral implant type for the patient; and output the recommendation of the shoulder surgery type and the humeral implant type for the patient.

Example 402: The system of example 401, wherein the humeral implant type comprises one of a stemmed implant type or a stemless implant type.

Example 403: The system of any of examples 401 and 402, wherein the recommendation of the humeral implant type comprises a recommendation indicating a length of a stem of a humeral implant.

Example 404: The system of any of examples 401 through 403, wherein the processing circuitry is configured to output, for display, a user interface comprising a graphical representation of the bone density metric over a representation of the humerus of the patient.

Example 405: The system of any of examples 401 through 404, wherein the one or more soft tissue characteristics comprises a fatty infiltration ratio for a soft tissue structure of the patient.

Example 406: The system of example 405, wherein the processing circuitry is configured to determine the fatty infiltration ratio by: applying a mask to a patient-specific shape representative of the soft tissue structure; applying a threshold to voxels under the mask; determining a fat volume based on the voxels under the threshold; and determining the fatty infiltration value based on the fat volume and a volume of the patient-specific shape representative of the soft-tissue structure.

Example 407: The system of any of examples 401 through 406, wherein the one or more soft tissue characteristics comprises an atrophy ratio for a soft tissue structure of the patient.

Example 408: The system of example 407, wherein the processing circuitry is configured to determine the atrophy ratio by: determining bone to muscle dimensions for the soft-tissue structure of the patient; obtaining a statistical mean shape (SMS) for the soft-tissue structure; deforming the SMS by satisfying a threshold of an algorithm to fit a deformed version of the SMS to the bone to muscle dimensions of the soft-tissue structure; and determining the atrophy ratio for the soft-tissue structure by dividing the SMS volume by the soft-tissue structure volume.

Example 409: The system of any of examples 401 through 408, wherein the one or more soft tissue characteristics comprises at least one of a fatty infiltration value or an atrophy ratio, and wherein the processing circuitry is configured to generate the recommendation of the shoulder surgery type to be performed for the patient based on at least one of the fatty infiltration value or the atrophy ratio for one or more soft tissue structures of the patient.

Example 410: The system of example 409, wherein the processing circuitry is configured to determine a spring constant for the one or more soft tissue structures based on at least one of the fatty infiltration value or the atrophy ratio.

Example 411: The system of any of examples 409 and 410, wherein the one or more soft tissue structures comprise one or more muscles of a rotator cuff of the patient.

Example 412: The system of any of examples 401 through 411, wherein the one or more soft tissue characteristics comprises a range of motion of a humerus.

Example 413: The system of any of examples 401 through 412, wherein the processing circuitry is configured to determine at least one of the one or more soft tissue characteristics of the bone density metric associated with the humerus using a neural network.

Example 414: The system of example 413, wherein the one or more soft tissue characteristics comprise at least one of a fatty infiltration value, an atrophy value, or a range of motion value for one or more soft tissue structures of the patient, and wherein the processing circuitry is configured to: input at least one of the fatty infiltration value, the atrophy value, or the range of motion value into a neural network; and generate the recommendation of the shoulder surgery type based on an output from the neural network.

Example 415: The system of any of examples 401 through 414, wherein the processing circuitry is configured to determine the one or more soft tissue characteristics from the patient-specific imaging data by: receiving an initial shape for a soft tissue structure of the patient; determining a plurality of surface points on the initial shape; registering the initial shape to the patient-specific image data; identifying one or more contours in the patient-specific image data representative of a boundary of the soft tissue structure of the patient; iteratively moving the plurality of surface points towards respective locations of the one or more contours to change the initial shape to the patient-specific shape representative of the soft tissue structure of the patient; and determining, based on the patient-specific shape, one or more soft tissue characteristics for the soft tissue structure of the patient.

Example 416: The system of any of examples 401 through 415, wherein the processing circuitry is configured to control a user interface to display a representation of the one or more soft tissue characteristics.

Example 417: The system of example 416, wherein the processing circuitry is configured to control the user interface to display at least one of the representation of the one or more soft tissue characteristics or the bone density metric associated with the humerus as part of a mixed reality user interface.

Example 418: The system of any of examples 401 through 417, wherein the shoulder surgery type comprises one of an anatomical shoulder replacement or a reverse shoulder replacement.

Example 419: A method for automatically generating a shoulder surgery recommendation for a patient, the method comprising: receiving, from a memory, a patient-specific image data; determining, by processing circuitry and based on the patient-specific imaging data, one or more soft tissue characteristics and a bone density metric associated with a humerus of the patient; generating, by the processing circuitry and based on the one or more soft tissue characteristics, a recommendation of a shoulder surgery type to be performed for the patient; generating, by the processing circuitry and based on the bone density metric associated with the humerus, a recommendation of a humeral implant type for the patient; and outputting, by the processing circuitry, the recommendation of the shoulder surgery type and the humeral implant type for the patient.

Example 420: The method of example 419, wherein the humeral implant type comprises one of a stemmed implant type or a stemless implant type.

Example 421: The method of any of examples 419 and 420, wherein the recommendation of the humeral implant type comprises a recommendation indicating a length of a stem of a humeral implant.

Example 422: The method of any of examples 419 through 421, wherein the processing circuitry is configured to output, for display, a user interface comprising a graphical representation of the bone density metric over a representation of the humerus of the patient.

Example 423: The method of any of examples 419 through 422, wherein the one or more soft tissue characteristics comprises a fatty infiltration ratio for a soft tissue structure of the patient.

Example 424: The method of example 423, wherein the processing circuitry is configured to determine the fatty infiltration ratio by: applying a mask to a patient-specific shape representative of the soft tissue structure; applying a threshold to voxels under the mask; determining a fat volume based on the voxels under the threshold; and determining the fatty infiltration value based on the fat volume and a volume of the patient-specific shape representative of the soft-tissue structure.

Example 425: The method of any of examples 419 through 424, wherein the one or more soft tissue characteristics comprises an atrophy ratio for a soft tissue structure of the patient.

Example 426: The method of example 425, wherein the processing circuitry is configured to determine the atrophy ratio by: determining bone to muscle dimensions for the soft-tissue structure of the patient; obtaining a statistical mean shape (SMS) for the soft-tissue structure; deforming the SMS by satisfying a threshold of an algorithm to fit a deformed version of the SMS to the bone to muscle dimensions of the soft-tissue structure; and determining the atrophy ratio for the soft-tissue structure by dividing the SMS volume by the soft-tissue structure volume.

Example 427: The method of any of examples 419 through 426, wherein the one or more soft tissue characteristics comprises at least one of a fatty infiltration value or an atrophy ratio, and wherein the processing circuitry is configured to generate the recommendation of the shoulder surgery type to be performed for the patient based on at least one of the fatty infiltration value or the atrophy ratio for one or more soft tissue structures of the patient.

Example 428: The method of example 427, wherein the processing circuitry is configured to determine a spring constant for the one or more soft tissue structures based on at least one of the fatty infiltration value or the atrophy ratio.

Example 429: The method of any of examples 427 and 428, wherein the one or more soft tissue structures comprise one or more muscles of a rotator cuff of the patient.

Example 430: The method of any of examples 419 through 429, wherein the one or more soft tissue characteristics comprises a range of motion of a humerus.

Example 431: The method of any of examples 419 through 431, wherein the processing circuitry is configured to determine at least one of the one or more soft tissue characteristics of the bone density metric associated with the humerus using a neural network.

Example 432: The method of example 431, wherein the one or more soft tissue characteristics comprise at least one of a fatty infiltration value, an atrophy value, or a range of motion value for one or more soft tissue structures of the patient, and wherein the processing circuitry is configured to: input at least one of the fatty infiltration value, the atrophy value, or the range of motion value into a neural network; and generate the recommendation of the shoulder surgery type based on an output from the neural network.

Example 433: The method of any of examples 419 through 432, wherein the processing circuitry is configured to determine the one or more soft tissue characteristics from the patient-specific imaging data by: receiving an initial shape for a soft tissue structure of the patient; determining a plurality of surface points on the initial shape; registering the initial shape to the patient-specific image data; identifying one or more contours in the patient-specific image data representative of a boundary of the soft tissue structure of the patient; iteratively moving the plurality of surface points towards respective locations of the one or more contours to change the initial shape to the patient-specific shape representative of the soft tissue structure of the patient; and determining, based on the patient-specific shape, one or more soft tissue characteristics for the soft tissue structure of the patient.

Example 434: The method of any of examples 419 through 434, wherein the processing circuitry is configured to control a user interface to display a representation of the one or more soft tissue characteristics.

Example 435: The method of example 434, wherein the processing circuitry is configured to control the user interface to display at least one of the representation of the one or more soft tissue characteristics or the bone density metric associated with the humerus as part of a mixed reality user interface.

Example 436: The method of any of examples 419 through 435, wherein the shoulder surgery type comprises one of an anatomical shoulder replacement or a reverse shoulder replacement.

Example 437: A computer-readable storage medium that, when executed, causes processing circuitry to: receive the patient-specific image data from a memory; determine, based on the patient-specific imaging data, one or more soft tissue characteristics and a bone density metric associated with a humerus of the patient; generate, based on the one or more soft tissue characteristics, a recommendation of a shoulder surgery type to be performed for the patient; generate, based on the bone density metric associated with the humerus, a recommendation of a humeral implant type for the patient; and output, for display, the recommendation of the shoulder surgery type and the humeral implant type for the patient.

Any one or more of these factors may be used in treatment planning for a patient. The techniques described in this disclosure may also be used in the context of other types of treatment. For example, treatment for other joint disorders may be analyzes, such as a total ankle arthroplasty or other joints. While the techniques been disclosed with respect to a limited number of examples, those skilled in the art, having the benefit of this disclosure, will appreciate numerous modifications and variations there from. For instance, it is contemplated that any reasonable combination of the described examples may be performed. It is intended that the appended claims cover such modifications and variations as fall within the true spirit and scope of the invention.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Operations described in this disclosure may be performed by one or more processors, which may be implemented as fixed-function processing circuits, programmable circuits, or combinations thereof, such as one or more digital signal processors (DSPs), general purpose microprocessors, application specific integrated circuits (ASICs), field programmable gate arrays (FPGAs), or other equivalent integrated or discrete logic circuitry. Fixed-function circuits refer to circuits that provide particular functionality and are preset on the operations that can be performed. Programmable circuits refer to circuits that can programmed to perform various tasks and provide flexible functionality in the operations that can be performed. For instance, programmable circuits may execute instructions specified by software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. Accordingly, the terms "processor" and "processing circuitry," as used herein may refer to any of the foregoing structures or any other structure suitable for implementation of the techniques described herein.

What is claimed is:

1. A system for automatically generating a shoulder surgery recommendation for a patient, the system comprising:
    a memory configured to store patient-specific image data for the patient; and
    processing circuitry configured to:
        receive the patient-specific image data from the memory;
        determine, based on the patient-specific image data, one or more soft tissue characteristics and a bone density metric associated with a humerus of the patient, wherein the one or more soft tissue characteristics comprises at least one of a fatty infiltration value or an atrophy ratio for one or more soft tissue structures of the patient;
        generate, based on at least one of the fatty infiltration value or the atrophy ratio for the one or more soft tissue structures of the patient, a recommendation of a shoulder surgery type to be performed for the patient;
        generate, based on the bone density metric associated with the humerus, a recommendation of a humeral implant type for the patient; and
        output the recommendation of the shoulder surgery type and the recommendation of humeral implant type for the patient.

2. The system of claim 1, wherein the humeral implant type comprises one of a stemmed implant type or a stemless implant type.

3. The system of claim 1, wherein the recommendation of the humeral implant type comprises a recommendation indicating a length of a stem of a humeral implant.

4. The system of claim 1, wherein the processing circuitry is configured to output, for display, a user interface comprising a graphical representation of the bone density metric over a representation of the humerus.

5. The system of claim 1, wherein the one or more soft tissue characteristics comprises the fatty infiltration value for the one or more soft tissue structures of the patient.

6. The system of claim 5, wherein the processing circuitry is configured to determine the fatty infiltration value by:
    applying a mask to a patient-specific shape representative of the one or more soft tissue structures;

applying a threshold to voxels under the mask;
determining a fat volume based on the voxels under the threshold; and
determining the fatty infiltration value based on the fat volume and a volume of the patient-specific shape representative of the one or more soft tissue structures.

7. The system of claim 1, wherein the one or more soft tissue characteristics comprises the atrophy ratio for the one or more soft tissue structures.

8. The system of claim 7, wherein the processing circuitry is configured to determine the atrophy ratio by:
determining bone to muscle dimensions for the one or more soft tissue structures;
obtaining a statistical mean shape (SMS) for the one or more soft tissue structures;
deforming the SMS by satisfying a threshold of an algorithm to fit a deformed version of the SMS to the bone to muscle dimensions for the one or more soft tissue structures; and
determining the atrophy ratio for the one or more soft tissue structures by dividing a volume of the deformed SMS by a soft-tissue structure volume.

9. The system of claim 1, wherein the one or more soft tissue characteristics comprises a range of motion of the humerus.

10. The system of claim 1, wherein the processing circuitry is configured to determine at least one of the one or more soft tissue characteristics or the bone density metric associated with the humerus using a neural network.

11. The system of claim 10, wherein the one or more soft tissue characteristics comprise at least one of the fatty infiltration value, the atrophy ratio, or a range of motion value for the one or more soft tissue structures of the patient, and wherein the processing circuitry is configured to:
input at least one of the fatty infiltration value, the atrophy ratio, or the range of motion value into the neural network; and
generate the recommendation of the shoulder surgery type based on an output from the neural network.

12. The system of claim 1, wherein the processing circuitry is configured to determine the one or more soft tissue characteristics from by:
receiving an initial shape for the one or more soft tissue structures, determining a plurality of surface points on the initial shape;
registering the initial shape to the patient-specific image data;
identifying one or more contours in the patient-specific image data representative of a boundary of the one or more soft tissue structures;
iteratively moving the plurality of surface points towards respective locations of the one or more contours to change the initial shape to a patient-specific shape representative of the one or more soft tissue structures; and
determining, based on the patient-specific shape, the one or more soft tissue characteristics for the one or more soft tissue structures.

13. The system of claim 1, wherein the processing circuitry is configured to control a user interface to display a representation of the one or more soft tissue characteristics.

14. The system of claim 13, wherein the processing circuitry is configured to control the user interface to display at least one of the representation of the one or more soft tissue characteristics or the bone density metric associated with the humerus as part of a mixed reality user interface.

15. The system of claim 1, wherein the shoulder surgery type comprises one of an anatomical shoulder replacement or a reverse shoulder replacement.

16. A method for automatically generating a shoulder surgery recommendation for a patient, the method comprising:
receiving, from a memory, patient-specific image data;
determining, by processing circuitry and based on the patient-specific image data, one or more soft tissue characteristics and a bone density metric associated with a humerus of the patient, wherein the one or more soft tissue characteristics comprises at least one of a fatty infiltration value or an atrophy ratio for one or more soft tissue structures of the patient;
generating, by the processing circuitry and based on at least one of the fatty infiltration value or the atrophy ratio for the one or more soft tissue structures, a recommendation of a shoulder surgery type to be performed for the patient;
generating, by the processing circuitry and based on the bone density metric associated with the humerus, a recommendation of a humeral implant type for the patient; and
outputting, by the processing circuitry, the recommendation of the shoulder surgery type and the recommendation of the humeral implant type for the patient.

17. The method of claim 16, wherein the humeral implant type comprises one of a stemmed implant type or a stemless implant type.

18. The method of claim 16, wherein the recommendation of the humeral implant type comprises a recommendation indicating a length of a stem of a humeral implant.

19. The method of claim 16, further comprising outputting, for display, a user interface comprising a graphical representation of the bone density metric over a representation of the humerus.

20. The method of claim 16, wherein the one or more soft tissue characteristics comprises the fatty infiltration value for the one or more soft tissue structures.

21. The method of claim 20, wherein determining the fatty infiltration value comprises:
applying a mask to a patient-specific shape representative of the one or more soft tissue structures;
applying a threshold to voxels under the mask;
determining a fat volume based on the voxels under the threshold; and
determining the fatty infiltration value based on the fat volume and a volume of the patient-specific shape representative of the one or more soft tissue structures.

22. The method of claim 16, wherein the one or more soft tissue characteristics comprises the atrophy ratio for the one or more soft tissue structures.

23. The method of claim 22, wherein determining the atrophy ratio comprises:
determining bone to muscle dimensions for the one or more soft tissue structures;
obtaining a statistical mean shape (SMS) for the one or more soft tissue structures;
deforming the SMS by satisfying a threshold of an algorithm to fit a deformed version of the SMS to the bone to muscle dimensions for the one or more soft tissue structures; and
determining the atrophy ratio for the one or more soft tissue structures by dividing a volume of the deformed SMS by a soft tissue structure volume.

24. The method of claim 16, wherein the one or more soft tissue characteristics comprises a range of motion of the humerus.

25. The method of claim 16, wherein determining at least one of the one or more soft tissue characteristics or the bone density metric associated with the humerus comprises determining at least one of the one or more soft tissue characteristics or the bone density metric associated with the humerus using a neural network.

26. The method of claim 25, wherein the one or more soft tissue characteristics comprise at least one of fatty infiltration value, the atrophy ratio, or a range of motion value for the one or more soft tissue structures of the patient, and wherein the method further comprises:
- inputting at least one of the fatty infiltration value, the atrophy ratio, or the range of motion value into the neural network; and
- generating the recommendation of the shoulder surgery type based on an output from the neural network.

27. The method of claim 16, wherein determining the one or more soft tissue characteristics comprises:
- receiving an initial shape for the one or more soft tissue structures;
- determining a plurality of surface points on the initial shape;
- registering the initial shape to the patient-specific image data;
- identifying one or more contours in the patient-specific image data representative of a boundary of the one or more soft tissue structures;
- iteratively moving the plurality of surface points towards respective locations of the one or more contours to change the initial shape to a patient-specific shape representative of the one or more soft tissue structures; and
- determining, based on the patient-specific shape, the one or more soft tissue characteristics for the one or more soft tissue structures.

28. The method of claim 16, further comprising controlling a user interface to display a representation of the one or more soft tissue characteristics.

29. The method of claim 28, wherein controlling the user interface to display at least one of the representation of the one or more soft tissue characteristics or the bone density metric associated with the humerus comprises controlling the user interface to display at least one of the representation of the one or more soft tissue characteristics or the bone density metric associated with the humerus as part of a mixed reality user interface.

30. The method of claim 16, wherein the shoulder surgery type comprises one of an anatomical shoulder replacement or a reverse shoulder replacement.

31. At least one non-transitory computer-readable storage medium having instructions stored thereon that, when executed, cause processing circuitry to:
- receive patient-specific image data from a memory;
- determine, based on the patient-specific image data, one or more soft tissue characteristics and a bone density metric associated with a humerus of a patient, wherein the one or more soft tissue characteristics comprises at least one of a fatty infiltration value or an atrophy ratio for one or more soft tissue structures of the patient;
- generate, based on at least one of the fatty infiltration value or the atrophy ratio for the one or more soft tissue structures of the patient, a recommendation of a shoulder surgery type to be performed for the patient;
- generate, based on the bone density metric associated with the humerus, a recommendation of a humeral implant type for the patient; and
- output, for display, the recommendation of the shoulder surgery type and the recommendation of the humeral implant type for the patient.

\* \* \* \* \*